US008754085B2

(12) United States Patent
Charlton et al.

(10) Patent No.: US 8,754,085 B2
(45) Date of Patent: Jun. 17, 2014

(54) PYRIDO[2,3-B]PYRAZINE COMPOUNDS USEFUL AS IP RECEPTOR AGONIST

(75) Inventors: Steven John Charlton, Horsham (GB); Catherine Leblanc, Horsham (GB); Stephen Carl McKeown, Hitchin (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/388,819

(22) PCT Filed: Jul. 14, 2011

(86) PCT No.: PCT/EP2011/062028
§ 371 (c)(1),
(2), (4) Date: Feb. 3, 2012

(87) PCT Pub. No.: WO2012/007539
PCT Pub. Date: Jan. 19, 2012

(65) Prior Publication Data
US 2013/0102611 A1    Apr. 25, 2013

Related U.S. Application Data

(60) Provisional application No. 61/364,135, filed on Jul. 14, 2010.

(51) Int. Cl.
*A61K 31/495* (2006.01)

(52) U.S. Cl.
USPC .......................................... 514/249; 544/350

(58) Field of Classification Search
USPC .......................................... 514/249; 544/350
See application file for complete search history.

(56) References Cited

U.S. PATENT DOCUMENTS

| 3,960,876 A | 6/1976 | Curran |
|---|---|---|
| 2008/0027039 A1 | 1/2008 | Arakawa et al. |
| 2008/0064871 A1 | 3/2008 | Hirata et al. |
| 2008/0280041 A1 | 11/2008 | Nishino et al. |
| 2008/0305169 A1 | 12/2008 | Miki et al. |
| 2013/0184282 A1 | 7/2013 | Claire Adcock |

FOREIGN PATENT DOCUMENTS

| EP | 558062 | 9/1993 |
|---|---|---|
| EP | 753528 | 1/1997 |
| EP | 0976732 | 2/2000 |
| EP | 1400518 | 3/2004 |
| EP | 1475368 | 11/2004 |
| EP | 1820515 | 8/2007 |
| WO | WO 92/20642 | 11/1992 |
| WO | WO 95/09872 | 4/1995 |
| WO | WO 96/35713 | 11/1996 |
| WO | WO 98/18796 | 5/1998 |
| WO | WO 00/33838 | 6/2000 |
| WO | WO 00/78724 | 12/2000 |
| WO | WO 01/17959 | 3/2001 |
| WO | WO 01/19788 | 3/2001 |
| WO | WO 01/34602 | 5/2001 |
| WO | WO 01/49675 | 7/2001 |
| WO | WO 01/58441 | 8/2001 |
| WO | WO 03/039544 | 5/2003 |
| WO | WO 2004/083207 | 9/2004 |
| WO | WO 2004/099159 | 11/2004 |
| WO | WO 2005/020926 | 3/2005 |
| WO | WO 2005/051386 | 6/2005 |
| WO | WO 2005/063766 | 7/2005 |
| WO | WO 2006/122156 | 11/2006 |
| WO | WO 2007/017096 | 2/2007 |
| WO | WO 2007/024944 | 3/2007 |
| WO | 2007/088019 A1 | 8/2007 |
| WO | WO 2007/088019 | 8/2007 |
| WO | WO 2008/154221 | 12/2008 |
| WO | WO 2010/008864 | 1/2010 |
| WO | WO 2010/009208 | 1/2010 |
| WO | WO 2010/020366 | 2/2010 |
| WO | WO 2011/111880 | 9/2011 |
| WO | WO 2012/007539 | 1/2012 |
| WO | WO 2013/105057 | 7/2013 |
| WO | WO 2013/105058 | 7/2013 |
| WO | WO 2013/105061 | 7/2013 |
| WO | WO 2013/105063 | 7/2013 |
| WO | WO 2013/105065 | 7/2013 |
| WO | WO 2013/105066 | 7/2013 |

OTHER PUBLICATIONS

Paetzel et al., Journal of Heterocyclic Chemistry 29(5):1067-1068, 1992.
Cosmao et al., Canadian Journal of Chemistry 60(22):2785-2791, 1982.
Armand et al. Canadian Journal of Chemistry 56(13):1804-1816, 1978.
Armand et al. Compte Rendus des Seances de l'Academie des Sciences, Serie C: Sciences Chimiques 281(13):547-549, 1975.
Vinot et al., Bulletin de la Societe Chimique de France (1973), (11, Pt. 2), 3100-3102.
E.Kelly et al., "NaF and Guanine Nucleotides Modulate Adenylate Cyclase Activity in NG108-15 Cells by Interacting with Both $G_s$ and $G_i$," *Br J Pharmacol.* 100(2):223-230 Jun. 1990.
Kuwano et al., "2-{4-[(5,6-Diphenylpyrazin-2-yl)(isopropyl)amino]butoxy}-N-(methylsulfonyl)acetamide (NS-304), an Orally Available and Long-Acting Prostacyclin Receptro Agonist Prodrug" *Journal of Pharmacology and Experimental Therapeutics* 322(3):1181-1188, 2007.
Driscoll et al., "Medical Therapy for Pulmonary Arterial Hypertension" *Expert Opinion on Pharmacotherapy,* 9(1):65-81.
Driscoll et al.; "Medical therapy for pulmonary arterial hypertension"; Expert Opinion on Pharmacotherapy; 9 (1):65-81 (2008).

*Primary Examiner* — Douglas M Willis

(57) ABSTRACT

The present invention provides heterocyclic derivatives which activate the IP receptor. Activating the IP receptor signaling pathway is useful to treat many forms of PAH, pulmonary fibrosis and exert beneficial effects in fibrotic conditions of various organs in animal models and in patients. Pharmaceutical compositions comprising such derivatives are also encompassed. Examples of compounds of the invention include the compounds according to Formula Ia, or a pharmaceutically acceptable salt thereof, and the compounds of the examples.

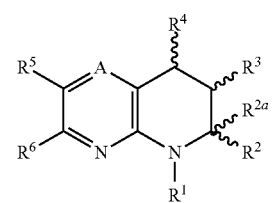

Ia

14 Claims, No Drawings

PYRIDO[2,3-B]PYRAZINE COMPOUNDS USEFUL AS IP RECEPTOR AGONIST

This application is a U.S. National Phase filing of International Serial No. PCT/EP2011/062028 filed Jul. 14, 2011, and claims priority to U.S. Provisional Application Ser. No. 61/364,135 filed Jul. 14, 2010, the contents of which are incorporated herein by reference in their entirety.

BACKGROUND OF THE INVENTION

Prostacyclin (or PGI2) is a member of the family of lipid molecules known as eicosanoids. It is a potent vasodilator, antiproliferative, anti-thrombotic agent that mediates its effects as an agonist of the IP receptor. The IP receptor is a G-protein coupled receptor that, upon activation by prostacyclin, stimulates the formation of cyclic adenosine monophosphate (cAMP). Prostacyclin counteracts the vasoconstrictor and pro-thrombotic activity of endothelin.

Pulmonary arterial hypertension (PAH) is a life-threatening disease characterized by a progressive pulmonary vasculopathy leading to right ventricular hypertrophy. Exogenous administration of an agonist of the IP receptor has become an important strategy in the treatment of PAH. (See, e.g., Tuder et al., Am. J. Respir. Crit. Care. Med., 1999, 159: 1925-1932; Humbert et al, J. Am. Coll. Cardiol., 2004, 43:13S-24S; Rosenzweig, Expert Opin. Emerging Drugs, 2006, 11:609-619; McLaughlin et al, Circulation, 2006, 114:1417-1431; Rosenkranz, Olin. Res. Cardiol., 2007, 96:527-541; Driscoll et al, Expert Opin. Pharmacother., 2008, 9:85-81.).

The prostacyclin analogue epoprostenol (flolan) is at least as effective as transplantation in terms of survival. Despite this, it is not used as frontline therapy due to significant tolerability, convenience and cost issues. Instead, patients with PAH are often treated first with either endothelin receptor antagonists (e.g. bosentan) and/or PDE5 inhibitors (e.g. sildenafil), which are better tolerated but can have limited efficacy. Prostacyclin analogues are used mainly as add-on treatment as severity of the disease progresses and tolerability and convenience become less of an issue.

Two key issues prevent current prostacyclin analogues being used as frontline therapy in PAH. Firstly, they are very unstable with an extremely short half-life, meaning they must be constantly infused via an in-dwelling intra venous (i.v.) catheter that is both inconvenient for the patient and also associated with a significant risk of infection and sepsis. Secondly, they are associated with significant side effects including nausea, jaw pain, headache and other side effects associated with systemic hypotension.

One solution to these issues is iloprost, which is available as a nebulized formulation that has reduced tolerability issues, but the short half life results in a 6-9 times daily dosing regime. More recently, researchers made efforts to generate stable, orally available IP receptor agonists. These ligands would improve patient convenience and compliance, but high levels of systemic drug is required to achieve pharmacodynamic effects in the lung; thus, possibly generating similar side effects to those observed with i.v. flolan.

The present invention describes stable, highly selective IP receptor agonists that are suitable for oral and inhaled delivery. The present invention offers a significant improvement over existing prostacyclin analogues and enables their use in less-severe patients. In addition, long term activation of the IP receptor has been shown to reverse remodeling associated with PAH; therefore, earlier intervention with the present invention may have significant effects on disease progression and potentially may show reversal.

In addition, pharmaceutical research has considerable interest in developing IP receptor agonists for the treatment of pulmonary fibrosis. IP deficient mice have been shown to be more susceptible to bleomycin-induced lung fibrosis than wild-type animals (Lovgren A K et al. (2006) *Am J Physiol Lung Cell Mol Physiol.* 291:L144-56), and the IP receptor agonist iloprost increases survival in bleomycin-treated mice (Zhu et al (2010) Respir Res. 11(1):34).

Furthermore, IP receptor signaling has been shown to exert beneficial effects in fibrotic conditions of various organs in animal models and in patients. Benefits of IP receptor agonist were shown for fibrosis of the heart, lung, skin, pancreas and liver, and in systemic sclerosis. (Gayraud M (2007) *Joint Bone Spine.* 74(1):e1-8; Hirata Y et al (2009) *Biomed Pharmacother.* 63(10):781-6; Kaneshige T et al (2007) *J Vet Med Sci.* 69(12):1271-6; Sahsivar M O et al (2009) *Shock* 32(5): 498-502; Sato N et al (2010) *Diabetes* 59(4):1092-100; Shouval D S et al (2008) *Clin Exp Rheumatol.* 26(3 Suppl 49): S105-7; Spargias K et al (2009) *Circulation.* 120(18):1793-9; Stratton R et al (2001) *J Clin Invest.* 108(2):241-50; Takenaka M et al (2009) *Prostaglandins Leukot Essent Fatty Acids.* 80(5-6):263-7; Watanabe M et al (2009) *Am J Nephrol.* 30(1): 1-11; Yano T et al (2005) *Am J Pathol.* 166(5):1333-42; Zardi E M et al (2007) *Expert Opin Biol Ther.* 7(6):785-90; Zardi E M et al (2006) *In Vivo* 20(3):377-80; Rehberger P et al (2009) *Acta Derm Venereol.* 89(3):245-9). Fibrotic conditions can occur in most organs secondary to chronic inflammation indications throughout the body and are likely to share common causes.

Therefore, antifibrotic agents such as IP receptor agonists of the present invention are of potential benefit in all indications that are associated with fibrotic tissue remodeling.

There is considerable, interest in developing agonists of the IP receptor for use in the treatment of other diseases, such as atherothrombosis, preeclampsia. It is highly desirable to develop a stable, inhaled agonists of the IP receptor, which may lead to improved management of PAH.

The invention pertains to the compounds, methods for using them, and uses thereof as described herein. Examples of compounds of the invention include the compounds according to any of Formula I, Ia, II or IIa, or a pharmaceutically acceptable salt thereof, and the compounds of the examples.

The invention therefore provides a compound of the Formula Ia:

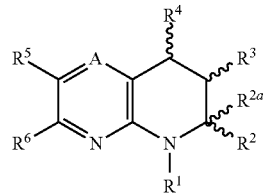

or a pharmaceutically acceptable salt thereof, wherein

A is N or CR';

R' is H, $C_1$-$C_8$ alkyl optionally substituted by one or more halogen atoms;

$R^1$ is H, $C_1$-$C_8$ alkyl optionally substituted by one or more halogen atoms, $C_1$-$C_4$ alkyl, OH, OR', —$NR^{19}R^{21}$, CN or $C_3$-$C_7$ cycloalkyl; or $R^1$ is —X—Y; or $R^1$ is —W—$R^7$—X—Y; or $R^1$ is —S(O)$_2$—W—X—Y; or $R^1$ is —S(O)$_2$—W—$R^7$—X—Y;

$R^2$ is H, $C_1$-$C_8$ alkyl optionally substituted by one or more halogen atoms, $C_1$-$C_4$ alkyl, OH, OR', —$NR^{19}R^{21}$, CN or $C_3$-$C_7$ cycloalkyl; or $R^2$ is —X—Y; or $R^2$ is —W—$R^7$—X—Y; or $R^2$ is —S(O)$_2$—W—X—Y;

$R^2$ is —S(O)$_2$—W—$R^7$—X—Y;

wherein either $R^1$ or $R^2$ is —X—Y, —S(O)$_2$—W—X—Y; or —S(O)$_2$—W—$R^7$—X—Y;

$R^{2a}$ is hydrogen; or $R^2$ and $R^{2a}$ taken together are oxo;

$R^3$ is H, $C_1$-$C_4$ alkoxy, OH, —$NR^{19}R^{21}$CN, halogen, $C_3$-$C_7$ cycloalkyl or $C_1$-$C_8$ alkyl optionally substituted by one or more halogen atoms;

$R^4$ is H, $C_1$-$C_4$ alkoxy, OH, —$NR^{19}R^{21}$CN, halogen, $C_3$-$C_7$ cycloalkyl or $C_1$-$C_8$ alkyl optionally substituted by one or more halogen atoms;

$R^5$ is $C_1$-$C_8$ alkyl optionally substituted by one or more halogen atoms, $C_1$-$C_4$ alkyl, OH, OR', —$NR^{19}R^{21}$, CN or $C_3$-$C_7$ cycloalkyl; $C_1$-$C_8$ alkoxy optionally substituted by one or more halogen atoms; $C_6$-$C_{14}$ aryl; —($C_0$-$C_4$ alkyl)-4 to 14 membered heteroaryl, or —($C_0$-$C_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents;

$R^6$ is $C_6$-$C_{14}$ aryl; —($C_0$-$C_4$ alkyl)-4 to 14 membered heteroaryl, —($C_0$-$C_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents;

W is $C_1$-$C_8$ alkylene optionally substituted by hydroxy, halogens or $C_1$-$C_4$ alkyl;

X is $C_1$-$C_8$ alkylene optionally substituted by hydroxy, halogens or $C_1$-$C_4$ alkyl;

Y is carboxy, alkoxycarbonyl, tetrazolyl, carbamoyl, monoalkylcarbamoyl, dialkylcarbamoyl, or —CONH—S(O)$_q$—$R^x$, wherein $R^x$ is —$C_1$-$C_4$ alkyl or —$NR^{19}R^{21}$;

q is 0, 1 or 2;

$R^7$ is a divalent moiety represented by —O—, —NHC(O)—, —CH$_2$=CH$_2$—, —$C_6$-$C_{14}$ aryl-D-; —3 to 14 membered heterocyclyl-D-, wherein the heterocyclyl contains at least one heteroatom selected from N, O and S, wherein D is O, S, NH or not present;

Z is independently OH, aryl, O-aryl, benzyl, O-benzyl, $C_1$-$C_6$ alkyl optionally substituted by one or more OH groups or NH$_2$ groups, $C_1$-$C_6$ alkyl optionally substituted by one or more halogen atoms, $C_1$-$C_6$ alkoxy optionally substituted by one or more OH groups, $C_1$-$C_6$ alkoxy optionally substituted by one or more halogen, $C_1$-$C_6$ alkoxy optionally substituted by $C_1$-$C_4$ alkoxy, $NR^{18}(SO_2)R^{21}$, $(SO_2)NR^{19}R^{21}$, $(SO_2)R^{21}$, $NR^{18}C(O)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, NO$_2$, halogen or a 3 to 14 membered heterocyclyl, wherein the heterocyclyl contains at least one heteroatom selected from N, O and S;

$R^{18}$ is independently H or $C_1$-$C_6$ alkyl;

$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclyl, the heterocyclyl including one or more heteroatoms selected from N, O and S, optionally substituted by one or more groups selected from halogen, oxo, $C_1$-$C_6$ alkyl and C(O)$C_1$-$C_8$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or C(O)$C_1$-$C_6$ alkyl; wherein the alkyl groups are optionally substituted by one or more halogen atoms, $C_1$-$C_4$ alkoxy, C(O)NH$_2$, C(O)NH$C_1$-$C_6$ alkyl or C(O)N($C_1$-$C_6$ alkyl)$_2$; or $R^{19}$ and $R^{21}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; S(O)$_2$-aryl; S(O)$_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and C(O)OC$_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

Various embodiments of the invention are described herein. It will be recognized that features specified in each embodiment may be combined with other specified features to provide further embodiments.

In an embodiment of the invention as described anywhere herein, A is N.

In an embodiment of the invention as described anywhere herein, A is CR'.

In an embodiment of the invention as described anywhere herein, A is CR', wherein R' is H.

In an embodiment of the invention as described anywhere herein, wherein $R^1$ is H, $C_1$-$C_8$ alkyl optionally substituted by one or more halogen atoms, $C_1$-$C_4$ alkyl, OH, or OR'; or $R^1$ is —X—Y; or $R^1$ is —W—$R^7$—X—Y; or $R^1$ is —S(O)$_2$—X—Y or $R^2$ is —S(O)$_2$—W—$R^7$—X—Y;

$R^2$ is H, $C_1$-$C_8$ alkyl optionally substituted by one or more halogen atoms, $C_1$-$C_4$ alkyl, OH, or OR'; $R^2$ is —X—Y; or $R^2$ is —W—$R^7$—X—Y; or $R^2$ is —S(O)$_2$—X—Y; $R^2$ is —S(O)$_2$—W—$R^7$—X—Y;

wherein either $R^1$ or $R^2$ is —X—Y, —S(O)$_2$—W—X—Y; or —S(O)$_2$—W—$R^7$—X—Y;

W is $C_1$-$C_6$ alkylene optionally substituted by hydroxy, halogens or $C_1$-$C_4$ alkyl;

X is $C_1$-$C_6$ alkylene optionally substituted by hydroxy, halogens or $C_1$-$C_4$ alkyl;

Y is —C(O)OH, —C(O)OR$^x$, tetrazolyl, carbamoyl, monoalkylcarbamoyl, dialkylcarbamoyl, or —CONH—S(O)$_q$—$R^x$, wherein $R^x$ is —$C_1$-$C_4$ alkyl or —$NR^{19}R^{21}$; and q is 2;

R' is H, $C_1$-$C_4$ alkyl optionally substituted by one or more halogen atoms;

$R^7$ is a divalent moiety represented by —$C_6$-$C_{14}$ aryl-D-; —3 to 14 membered heterocyclyl-D-, wherein the heterocyclyl contains at least one heteroatom selected from N, O and S, wherein D is O;

$R^{19}$ and $R^{21}$ are each independently H; $C_1$-$C_8$ alkyl.

In an embodiment of the invention as described anywhere herein, wherein $R^1$ is —X—Y; or —W—$R^7$—X—Y;

$R^2$ is H, $C_1$-$C_8$ alkyl optionally substituted by one or more halogen atoms, $C_1$-$C_4$ alkyl, OH, or OR';

W is $C_1$-$C_6$ alkylene optionally substituted by hydroxy, halogens or $C_1$-$C_4$ alkyl;

X is $C_1$-$C_6$ alkylene optionally substituted by hydroxy, halogens or $C_1$-$C_4$ alkyl;

Y is —C(O)OH, —C(O)OR$^x$, tetrazolyl, carbamoyl, monoalkylcarbamoyl, dialkylcarbamoyl, or —CONH—S(O)$_q$—R$^x$, wherein R$^x$ is —C$_1$-C$_4$ alkyl or —NR$^{19}$R$^{21}$; and
q is 2;
R' is H, C$_1$-C$_4$ alkyl optionally substituted by one or more halogen atoms;
R$^7$ is a divalent moiety represented by —C$_6$-C$_{14}$ aryl-D-; –3 to 14 membered heterocyclyl-D-, wherein the heterocyclyl contains at least one heteroatom selected from N, O and S,
wherein D is O;
R$^{19}$ and R$^{21}$ are each independently H; C$_1$-C$_8$ alkyl.

In an embodiment of the invention as described anywhere herein, wherein
R$^1$ is —X—Y; or —W—R$^7$—X—Y;
R$^2$ is H, C$_1$-C$_4$ alkyl optionally substituted by one or more halogen atoms;
W is C$_1$-C$_6$ alkylene optionally substituted by hydroxy, halogens or C$_1$-C$_4$ alkyl;
X is C$_1$-C$_6$ alkylene optionally substituted by hydroxy, halogens or C$_1$-C$_4$ alkyl;
Y is —C(O)OH;
R$^7$ is a divalent moiety represented by —C$_6$-C$_{14}$ aryl-D-; –3 to 14 membered heterocyclyl-D-, wherein the heterocyclyl contains at least one heteroatom selected from N, O and S, wherein D is O.

In an embodiment of the invention as described anywhere herein, wherein
R$^1$ is C$_1$-C$_4$ alkyl optionally substituted by one or more halogen atoms, —(CH$_2$)$_m$—C(O)OR", or —(CH$_2$)$_m$—R$^7$—(CH$_2$)$_n$—C(O)OR";
R$^2$ is H, C$_1$-C$_4$ alkyl optionally substituted by one or more halogen atoms;
m is 1, 2, 3, 4, 5, 6, 7 or 8;
n is 0, 1, 2 or 3;
R" is H or C$_1$-C$_4$ alkyl optionally substituted by one or more halogen atoms;
R$^7$ is a divalent moiety represented by —C$_6$-C$_{14}$ aryl-D-; –3 to 14 membered heterocyclyl-D-, wherein the heterocyclyl contains at least one heteroatom selected from N, O and S, wherein D is O;

In an embodiment of the invention as described anywhere herein, wherein
R$^1$ is —(CH$_2$)$_m$—C(O)OR", or —(CH$_2$)$_n$—R$^7$—(CH$_2$)$_n$—C(O)OR";
R$^2$ is H, C$_1$-C$_4$ alkyl optionally substituted by one or more halogen atoms;
m is 1, 2, 3, 4, 5, 6, 7 or 8;
n is 0, 1, 2 or 3;
R" is H or C$_1$-C$_4$ alkyl optionally substituted by one or more halogen atoms;
R$^7$ is a divalent moiety represented by —C$_6$-C$_{14}$ aryl-D-; –3 to 14 membered heterocyclyl-D-, wherein the heterocyclyl contains at least one heteroatom selected from N, O and S, wherein D is O.

In an embodiment of the invention as described anywhere herein, wherein
R$^1$ is —(CH$_2$)$_m$—C(O)OR";
R$^2$ is H, C$_1$-C$_4$ alkyl optionally substituted by one or more halogen atoms;
m is 1, 2, 3, 4, 5, 6, 7 or 8;
R" is H or C$_1$-C$_4$ alkyl optionally substituted by one or more halogen atoms.

In an embodiment of the invention as described anywhere herein, wherein
R$^1$ is —(CH$_2$)$_m$—C(O)OR";
R$^2$ is H;
R" is H;
m is 4, 5 or 6.

In an embodiment of the invention as described anywhere herein, wherein

R$^1$ is
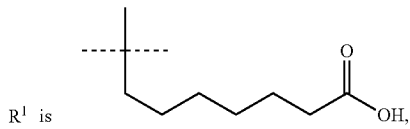
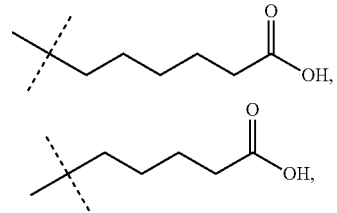
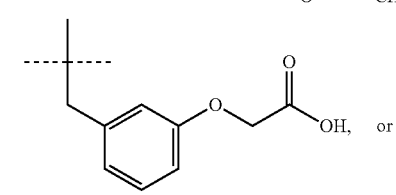
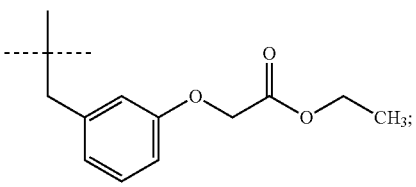
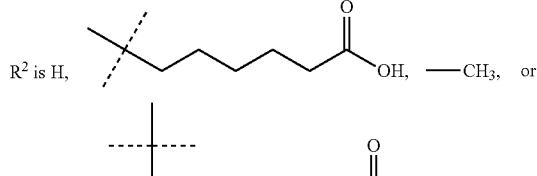

R$^2$ is H, 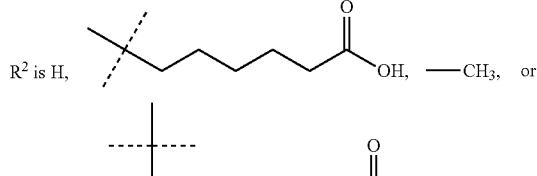 —CH$_3$, or

In an embodiment of the invention as described anywhere herein,

R$^1$ is H,
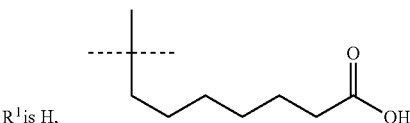
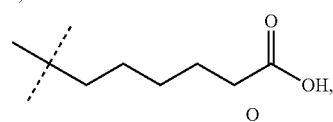
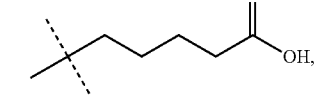

-continued

[chemical structures shown: ethyl ester of a fatty acid chain; methyl group; substituted phenoxyacetic acid; ethyl ester of substituted phenoxyacetate]

$R^2$ is [carboxylic acid chain structures shown: OH-terminated acid and another OH-terminated acid]

In an embodiment of the invention as described anywhere herein, wherein
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms.

In an embodiment of the invention as described anywhere herein, wherein
$R^3$ is H, $C_1$-$C_4$ alkoxy, OH, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, CN, halogen, $C_3$-$C_7$ cycloalkyl or $C_1$-$C_4$ alkyl optionally substituted by one or more halogen atoms.

In an embodiment of the invention as described anywhere herein, wherein
$R^3$ is H, methoxy, OH, CN, halogen, cyclopropyl or methyl;
$R^4$ is H, methoxy, OH, CN, halogen, cyclopropyl or methyl.

In an embodiment of the invention as described anywhere herein, wherein
$R^3$ is H, OH, cyclopropyl or methyl;
$R^4$ is H, OH, cyclopropyl or methyl.

In an embodiment of the invention as described anywhere herein, wherein
$R^3$ is H, or OH;
$R^4$ is H, or OH.

In an embodiment of the invention as described anywhere herein, wherein
$R^5$ is $C_6$-$C_{14}$ aryl; —($C_0$-$C_4$ alkyl)-4 to 14 membered heteroaryl, or —($C_0$-$C_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents; and
$R^6$ is $C_6$-$C_{14}$ aryl; —($C_0$-$C_4$ alkyl)-4 to 14 membered heteroaryl, —($C_0$-$C_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents.

In an embodiment of the invention as described anywhere herein, wherein
$R^5$ is $C_6$-$C_{14}$ aryl; –5 to 6 membered heteroaryl, or –5 to 6 membered heterocyclyl wherein the heteroaryl and heterocyclyl contain at least one heteroatom selected from N, O and S, wherein the aryl, heteroaryl and heterocyclyl are each optionally substituted by one or more Z substituents; and
$R^6$ is $C_6$-$C_{14}$ aryl; –5 to 6 membered heteroaryl, –5 to 6 membered heterocyclyl wherein the heteroaryl and heterocyclyl contain at least one heteroatom selected from N, O and S, wherein the aryl, heteroaryl and heterocyclyl are each optionally substituted by one or more Z substituents.

In an embodiment of the invention as described anywhere herein, wherein
$R^5$ is phenyl; 2-pyridyl, 3-pyridyl, or 4-pyridyl, and
$R^6$ is phenyl; 2-pyridyl, 3-pyridyl, or 4-pyridyl,
wherein the phenyl, 2-pyridyl, 3-pyridyl, and 4-pyridyl are each optionally substituted by one or more Z substituents.

In an embodiment of the invention as described anywhere herein, wherein
$R^5$ is phenyl optionally substituted by OH, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $NR^{19}R^{21}$, $C(O)OR^{19}$, $C(O)R^{19}$, $SR^{19}$, $OR^{19}$, CN, $NO_2$, or halogen; and
$R^6$ is phenyl optionally substituted by OH, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $NR^{19}R^{21}$, $C(O)OR^{19}$, $C(O)R^{19}$, $SR^{19}$, $OR^{19}$, CN, $NO_2$, or halogen.

In an embodiment of the invention as described anywhere herein, wherein
$R^5$ is phenyl optionally substituted by $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy or halogen; and
$R^6$ is phenyl optionally substituted by $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy or halogen.

In an embodiment of the invention as described anywhere herein, wherein
$R^5$ is phenyl optionally substituted by $C_1$-$C_4$ alkyl optionally substituted by one or more halogen atoms, $C_1$-$C_4$ alkoxy or halogen; and
$R^6$ is phenyl optionally substituted by $C_1$-$C_4$ alkyl optionally substituted by one or more halogen atoms, $C_1$-$C_4$ alkoxy or halogen.

In an embodiment of the invention as described anywhere herein, wherein
$R^5$ is phenyl optionally substituted by $C_1$-$C_4$ alkyl optionally substituted by one or more halogen atoms, $C_1$-$C_4$ alkoxy or halogen; and
$R^6$ is phenyl optionally substituted by $C_1$-$C_4$ alkyl optionally substituted by one or more halogen atoms, $C_1$-$C_4$ alkoxy or halogen.

In an embodiment of the invention as described anywhere herein, wherein

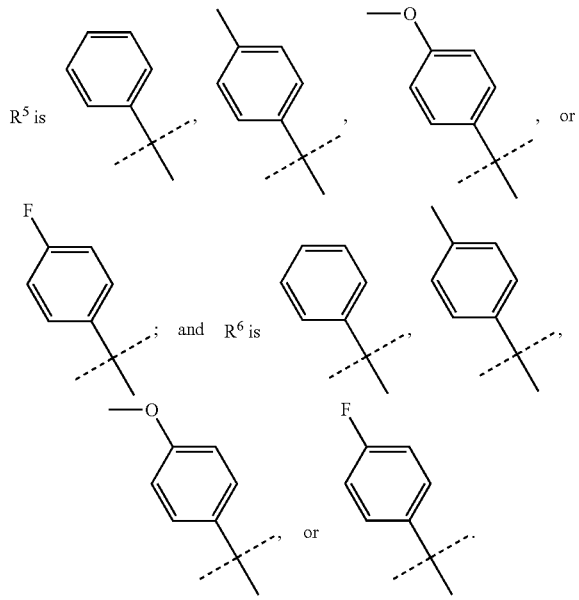

R⁵ is ... , ... , or ... ;

and R⁶ is ... , ... , ... , or ... .

Another embodiment of the invention as defined above provides compounds according to Formula II, represented by

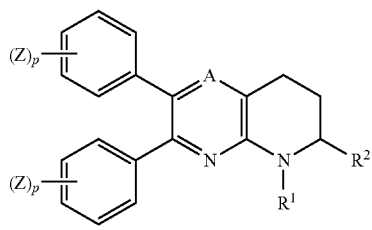

II

In an embodiment of the invention as described in Formula II herein, A is N.

In an embodiment of the invention as described Formula II herein, A is CR'.

In an embodiment of the invention as described Formula II herein, A is CR', wherein R' is H.

In an embodiment of the invention as described Formula II herein, wherein $R^1$ is H, $C_1$-$C_8$ alkyl optionally substituted by one or more halogen atoms, $C_1$-$C_4$ alkyl, OH, or OR'; or $R^1$ is —X—Y; or $R^1$ is —W—$R^7$—X—Y; or $R^1$ is —S(O)₂—X—Y or $R^2$ is —S(O)₂—W—$R^7$—X—Y;

$R^2$ is H, $C_1$-$C_8$ alkyl optionally substituted by one or more halogen atoms, $C_1$-$C_4$ alkyl, OH, or OR'; $R^2$ is —X—Y; or $R^2$ is —W—$R^7$—X—Y; or $R^2$ is —S(O)₂—X—Y; $R^2$ is —S(O)₂—W—$R^7$—X—Y;

wherein either $R^1$ or $R^2$ is —X—Y, —W—$R^7$—X—Y, —S(O)₂—W—X—Y; or —S(O)₂—W—$R^7$—X—Y;

W is $C_1$-$C_6$ alkylene optionally substituted by hydroxy, halogens or $C_1$-$C_4$ alkyl;

X is $C_1$-$C_6$ alkylene optionally substituted by hydroxy, halogens or $C_1$-$C_4$ alkyl;

Y is carboxy, alkoxycarbonyl, tetrazolyl, carbamoyl, monoalkylcarbamoyl, dialkylcarbamoyl, or —CONH—S(O)$_q$—$R^x$, wherein $R^x$ is —$C_1$-$C_4$ alkyl or —N$R^{19}R^{21}$; and q is 2;

R' is H, $C_1$-$C_4$ alkyl optionally substituted by one or more halogen atoms;

$R^7$ is a divalent moiety represented by —$C_6$-$C_{14}$ aryl-D-; –3 to 14 membered heterocyclyl-D-, wherein the heterocyclyl contains at least one heteroatom selected from N, O and S, wherein D is O;

$R^{19}$ and $R^{21}$ are each independently H; $C_1$-$C_8$ alkyl.

In an embodiment of the invention as described Formula II herein, wherein $R^1$ is —X—Y; or —W—$R^7$—X—Y;

$R^2$ is H, $C_1$-$C_8$ alkyl optionally substituted by one or more halogen atoms, $C_1$-$C_4$ alkyl, OH, or OR';

W is $C_1$-$C_6$ alkylene optionally substituted by hydroxy, halogens or $C_1$-$C_4$ alkyl;

X is $C_1$-$C_6$ alkylene optionally substituted by hydroxy, halogens or $C_1$-$C_4$ alkyl;

Y is —C(O)OH, —C(O)O$R^x$, tetrazolyl, carbamoyl, monoalkylcarbamoyl, dialkylcarbamoyl, or —CONH—S(O)$_q$—$R^x$, wherein $R^x$ is —$C_1$-$C_4$ alkyl or —N$R^{19}R^{21}$; and q is 2;

p is 0, 1, 2, 3, or 4;

R' is H, $C_1$-$C_4$ alkyl optionally substituted by one or more halogen atoms;

$R^7$ is a divalent moiety represented by —$C_6$-$C_{14}$ aryl-D-; –3 to 14 membered heterocyclyl-D-, wherein the heterocyclyl contains at least one heteroatom selected from N, O and S, wherein D is O;

$R^{19}$ and $R^{21}$ are each independently H; $C_1$-$C_8$ alkyl.

In an embodiment of the invention as described Formula II herein, wherein $R^1$ is —X—Y; or —W—$R^7$—X—Y;

$R^2$ is H, $C_1$-$C_4$ alkyl optionally substituted by one or more halogen atoms;

W is $C_1$-$C_6$ alkylene optionally substituted by hydroxy, halogens or $C_1$-$C_4$ alkyl;

X is $C_1$-$C_6$ alkylene optionally substituted by hydroxy, halogens or $C_1$-$C_4$ alkyl;

Y is —C(O)OH;

p is 0, 1, 2, 3, or 4;

$R^7$ is a divalent moiety represented by —$C_6$-$C_{14}$ aryl-D-; –3 to 14 membered heterocyclyl-D-, wherein the heterocyclyl contains at least one heteroatom selected from N, O and S, wherein D is O.

In an embodiment of the invention as described Formula II herein, wherein $R^1$ is —(CH₂)$_m$—C(O)OR'', or —(CH₂)$_m$—$R^7$—(CH₂)$_n$—C(O)OR'';

$R^2$ is H, $C_1$-$C_4$ alkyl optionally substituted by one or more halogen atoms;

m is 1, 2, 3, 4, 5, 6, 7 or 8;

n is 0, 1, 2 or 3;

p is 0, 1, 2, 3, or 4;

R'' is H or $C_1$-$C_4$ alkyl optionally substituted by one or more halogen atoms;

$R^7$ is a divalent moiety represented by —$C_6$-$C_{14}$ aryl-D-; –3 to 14 membered heterocyclyl-D-, wherein the heterocyclyl contains at least one heteroatom selected from N, O and S, wherein D is O;

In an embodiment of the invention as described Formula II herein, wherein $R^1$ is —(CH₂)$_m$—C(O)OR'', or —(CH₂)$_m$—$R^7$—(CH₂)$_n$—C(O)OR'';

$R^2$ is H, $C_1$-$C_4$ alkyl optionally substituted by one or more halogen atoms;

m is 1, 2, 3, 4, 5, 6, 7 or 8;

n is 0, 1, 2 or 3;

p is 0, 1, 2, 3, or 4;

R" is H or $C_1$-$C_4$ alkyl optionally substituted by one or more halogen atoms;

$R^7$ is a divalent moiety represented by —$C_6$-$C_{14}$ aryl-D-; –3 to 14 membered heterocyclyl-D-, wherein the heterocyclyl contains at least one heteroatom selected from N, O and S, wherein D is O.

In an embodiment of the invention as described Formula II herein, wherein $R^1$ is —$(CH_2)_m$—C(O)OR";

$R^2$ is H, $C_1$-$C_4$ alkyl optionally substituted by one or more halogen atoms;

m is 1, 2, 3, 4, 5, 6, 7 or 8;

p is 0, 1, 2, 3, or 4;

R" is H or $C_1$-$C_4$ alkyl optionally substituted by one or more halogen atoms.

In an embodiment of the invention as described Formula II herein, wherein $R^1$ is —$(CH_2)_m$—C(O)OR";

$R^2$ is H;

R" is H;

m is 4, 5 or 6;

p is 0.

In an embodiment of the invention as described Formula II herein, wherein

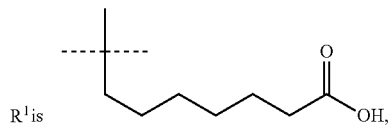

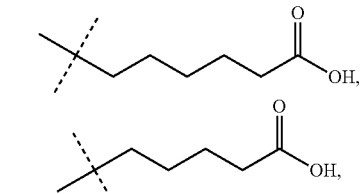

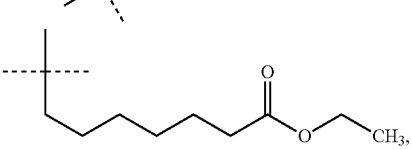

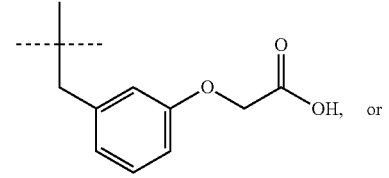

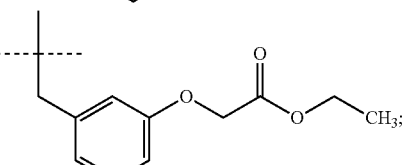

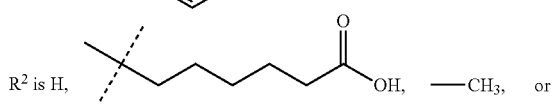

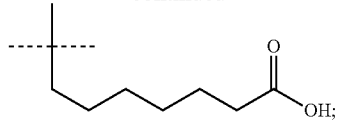

p is 0 or 1.

In an embodiment of the invention as described Formula II herein, wherein

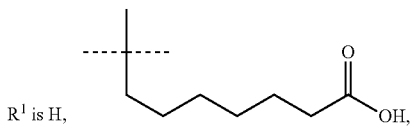

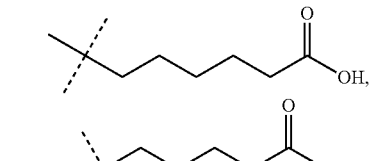

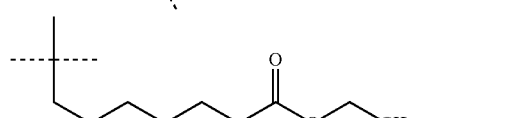

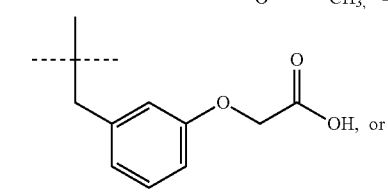

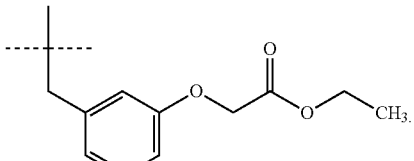

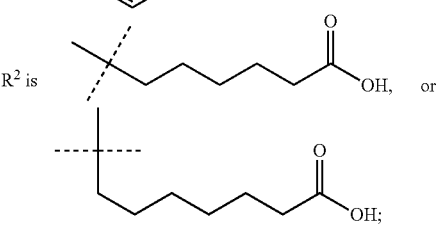

p is 0 or 1.

In an embodiment of the invention as described Formula II herein, wherein $R^3$ and $R^4$ are independently H, OH, $C_1$-$C_6$ alkyl, $C_1$-$C_4$ alkoxy, cyano or halogen.

In an embodiment of the invention as described Formula II herein, wherein $R^3$ and $R^4$ are independently H, OH, $C_1$-$C_4$ alkyl, $C_1$-$C_4$ alkoxy or halogen.

In an embodiment of the invention as described Formula II herein, wherein $R^3$ and $R^4$ are independently H, OH, methyl, ethyl, isopropyl, tert-butyl, methoxy, ethoxy, propoxy, butoxy, fluorine, bromine or chlorine.

In an embodiment of the invention as described anywhere herein, wherein

Z is independently OH, $C_6$-aryl, O—$C_6$-aryl, benzyl, O-benzyl, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $NR^{18}(SO_2)R^{21}$, $(SO_2)NR^{19}R^{21}$, $(SO_2)R^{21}$, $NR^{18}C(O)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, $NO_2$, halogen or a 4 to 6 membered heterocyclyl, wherein the heterocyclyl contains at least one heteroatom selected from N, O and S;

$R^{18}$ is H or $C_1$-$C_4$ alkyl;

$R^{19}$ and $R^{21}$ are each independently H; $C_1$-$C_4$ alkyl; $C_3$-$C_6$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_4$ alkyl, $C_1$-$C_4$ alkoxy and halogen; ($C_0$-$C_4$ alkyl)-4- to 6-membered heterocyclyl, the heterocyclyl including one or more heteroatoms selected from N, O and S, optionally substituted by one or more groups selected from halogen, oxo, $C_1$-$C_4$ alkyl and $C(O)C_1$-$C_4$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or $C(O)C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alky)$_2$; or $R^{19}$ and $R^{21}$ together with the nitrogen atom to which they attached form a 5- to 6-membered heterocyclyl, the heterocyclyl including one or more further heteroatoms selected from N, O and S, the heterocyclyl being optionally substituted by one or more substituents selected from OH; halogen; aryl; 5- to 6-membered heterocyclyl including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_4$ alkoxy optionally substituted by one or more OH groups or $C_1$-$C_4$ alkoxy; and $C(O)OC_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

In an embodiment of the invention as described anywhere herein, wherein

Z is independently OH, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $NR^{19}R^{21}$, $C(O)OR^{19}$, $C(O)R^{19}$, $SR^{19}$, $OR^{19}$, CN, $NO_2$, or halogen;

$R^{19}$ and $R^{21}$ are each independently H; $C_1$-$C_4$ alkyl; $C_3$-$C_6$ cycloalkyl; or $C_1$-$C_4$ alkoxy-$C_1$-$C_4$ alkyl, wherein all alkyls are optionally substituted with halogens.

In an embodiment of the invention as described anywhere herein, wherein

Z is independently OH, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $C(O)OR^{19}$, $C(O)R^{19}$, $OR^{19}$, CN, or halogen;

$R^{19}$ is H; $C_1$-$C_4$ alkyl; $C_3$-$C_6$ cycloalkyl; or $C_1$-$C_4$ alkoxy-$C_1$-$C_4$ alkyl, wherein all alkyl are optionally substituted with halogens.

In an embodiment of the invention as described anywhere herein, wherein

Z is independently, $C_1$-$C_4$ alkyl optionally substituted by one or more halogen atoms, $C_1$-$C_4$ alkoxy or halogen;

It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments. It is understood by those skilled in the art that combinations of substituents where not possible are not an aspect of the present invention.

Another embodiment of the invention as defined above provides compounds according to Formula I and Formula II, represented by 7-(2,3-diphenyl-7,8-dihydropyrido[3,2-b]pyrazin-5(6H)-yl) heptanoic acid;

7-(2,3-bis(4-fluorophenyl)-7,8-dihydropyrido[2,3-b] pyrazin-5(6H)-yl)heptanoic acid;

7-(2,3-d-tolyl-7,8-dihydropyrido[2,3-b]pyrazin-5(6H)-yl) heptanoic acid;

7-(2,3-bis(4-methoxyphenyl)-7,8-dihydropyrido[2,3-b] pyrazin-5(6H)-yl)heptanoic acid;

6-(2,3-diphenyl-7,8-dihydropyrido[3,2-b]pyrazin-5(6H)-yl) hexanoic acid;

5-(2,3-diphenyl-7,8-dihydropyrido[3,2-b]pyrazin-5(6H)-yl) pentanoic acid;

7-(6,7-diphenyl-3,4-dihydro-1,8-naphthyridin-1(2H)-yl) heptanoic acid;

Ethyl 7-(6,7-diphenyl-3,4-dihydro-1,8-naphthyridin-1(2H)-yl)heptanoate;

rac-6-(1-methyl-6,7-diphenyl-1,2,3,4-tetrahydro-1,8-naphthyridin-2-yl)hexanoic acid;

Enantiomer 1 of 7-(2-methyl-6,7-diphenyl-3,4-dihydro-1,8-naphthyridin-1(2H)-yl)heptanoic acid;

Enantiomer 2 of 7-(1-methyl-6,7-diphenyl-1,2,3,4-tetrahydro-1,8-naphthyridin-2-yl)heptanoic acid;

2-(3-((6,7-diphenyl-3,4-dihydro-1,8-naphthyridin-1(2H)-yl) methyl)phenoxy)acetic acid;

Ethyl 2-(3-((6,7-diphenyl-3,4-dihydro-1,8-naphthyridin-1 (2H)-yl)methyl)phenoxy)acetate;

Enantiomer 2 of 7-(2-methyl-6,7-diphenyl-3,4-dihydro-1,8-naphthyridin-1(2H)-yl)heptanoic acid;

Enantiomer 1 and Enantiomer 2 of 6-(1-methyl-6,7-diphenyl-1,2,3,4-tetrahydro-1,8-naphthyridin-2-yl)hexanoic acid;

6-(6,7-diphenyl-3,4-dihydro-1,8-naphthyridin-1(2H)-yl) hexanoic acid; and

Enantiomer 1 of 7-(1-methyl-6,7-diphenyl-1,2,3,4-tetrahydro-1,8-naphthyridin-2-yl)heptanoic acid.

Especially preferred specific compounds of Formula I, Ia, II or IIa or pharmaceutical salts thereof are those described hereinafter in the Examples.

DEFINITIONS

Terms used in the specification have the following meanings:

"Optionally substituted" means the group referred to can be substituted at one or more positions by any one or any combination of the radicals listed thereafter.

"Optionally substituted by one or more Z groups" denotes that the relevant group may include one or more substituents, each independently selected from the groups included within the definition of Z. Thus, where there are two or more Z group substituents, these may be the same or different.

"Halo" or "halogen", as used herein, may be fluorine, chlorine, bromine or iodine.

"$C_1$-$C_8$-Alkyl", as used herein, denotes straight chain or branched alkyl having 1-8 carbon atoms. If a different number of carbon atoms is specified, such as $C_6$ or $C_3$, then the definition is to be amended accordingly, such as "$C_1$-$C_4$-Alkyl" will represent methyl, ethyl, propyl, isopropyl, butyl, isobutyl, sec-butyl and tert-butyl.

"$C_1$-$C_8$-Alkoxy", as used herein, denotes straight chain or branched alkoxy having 1-8 carbon atoms. If a different number of carbon atoms is specified, such as $C_6$ or $C_3$, then the definition is to be amended accordingly, such as "$C_1$-$C_4$-Alkoxy" will represent methoxy, ethoxy, propoxy, isopropoxy, butoxy, isobutoxy, sec-butoxy and tert-butoxy.

"$C_1$-$C_4$-Haloalkyl", as used herein, denotes straight chain or branched alkyl having 1-4 carbon atoms with at least one hydrogen substituted with a halogen. If a different number of carbon atoms is specified, such as $C_6$ or $C_3$, then the definition is to be amended accordingly, such as "$C_1$-$C_4$-Haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2-$, $(CF_3)_2CH-$, $CH_3-CF_2-$, $CF_3CF_2-$, $CF_3$, $CF_2H-$, $CF_3CF_2CHCF_3$ or $CF_3CF_2CF_2CF_2-$.

The term "alkylene" is a straight or branched alkylene (divalent alkyl chain) having 1 to 8 carbon atoms, for example, methylene, ethylene, 1-methylethylene, 2-methylethylene, trimethylene, tetramethylene, pentamethylene, hexamethylene, heptamethylene, and octamethylene.

"$C_3$-$C_{15}$ Cycloalkyl", as used herein, denotes a carbocyclic group having 3- to 15-ring carbon atoms that is saturated or partially saturated, such as a $C_3$-$C_8$-cycloalkyl. Examples of $C_3$-$C_{15}$-carbocyclic groups include but are not limited to cyclopropyl, cyclobutyl, cyclopentyl, cyclohexyl, cycloheptyl or cyclooctyl or a bicyclic group, such as bicyclooctyl, bicyclononyl including indanyl and indenyl and bicyclodecyl. If a different number of carbon atoms is specified, such as $C_6$, then the definition is to be amended accordingly.

"aryl" or "$C_6$-$C_{15}$-Aromatic carbocyclic group", as used herein, denotes an aromatic group having 6- to 15-ring carbon atoms. Examples of $C_6$-$C_{15}$-aromatic carbocyclic groups include, but are not limited to, phenyl, phenylene, benzenetriyl, naphthyl, naphthylene, naphthalenetriol or anthrylene. If a different number of carbon atoms is specified, such as $C_{10}$, then the definition is to be amended accordingly.

"4- to 8-Membered heterocyclyl", "5- to 6-membered heterocyclyl", "3- to 10-membered heterocyclyl", "3- to 14-membered heterocyclyl", "4- to 14-membered heterocyclyl" and "5- to 14-membered heterocyclyl", refers, respectively, to 4- to 8-membered, 5- to 6-membered, 3- to 10-membered, 3- to 14-membered, 4- to 14-membered and 5- to 14-membered heterocyclic rings containing at least one ring heteroatom selected from the group consisting of nitrogen, oxygen and sulphur, which may be saturated, partially saturated or unsaturated (aromatic). The heterocyclyl includes single ring groups, fused ring groups and bridged groups. Examples of such heterocyclyl include, but are not limited to, furan, pyrrole, pyrrolidine, pyrazole, imidazole, triazole, isothiazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, morpholine, triazine, oxazine, tetrahyrofuran, tetrahydrothiophene, tetrahydrothiopyran, tetrahydropyran, 1,4-dioxane, 1,4-oxathiane, indazole, quinoline, indazole, indole, 8-aza-bicyclo[3.2.1]octane, 2,3-dihydrobenzofuran or thiazole.

"Heteroaryl" is a subset of heterocyclyl, wherein the completely unsaturated (aromatic). Examples of such groups are pyridine and pyrazine.

The term "hydroxy" or "hydroxyl" includes groups with an —OH.

The term "heteroatom" includes atoms of any element other than carbon or hydrogen. Preferred heteroatoms are nitrogen, oxygen, sulfur and phosphorus. In one embodiment, "heteroatom" includes nitrogen, sulfur and oxygen.

The term "carboxy" refers to carboxylic acid.

The term "alkoxycarboxy" refers to an ester.

The term "carbamoyl" is —C(O)NH$_2$. The terms "monoalkylcarbamoyl" and "dialkylcarbamoyl" are carbamoyl, wherein the hydrogen or hydrogens on the nitrogen are substituted with $C_1$-$C_8$ alkyl as described above.

A second aspect of the invention provides a compound of Formula I, Ia, II or IIa or pharmaceutical salts thereof as defined anywhere herein for use as a pharmaceutical.

Activating the IP receptor has been shown to have a beneficial effect or treat the following diseases or disorders:

PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH); Raynaud's phenomenon, including Raynaud's disease and Raynaud's syndrome; fibrotic diseases, including pulmonary fibrosis, systemic sclerosis/scleroderma, hepatic fibrosis/cirrhosis, renal fibrosis; thrombotic diseases associated with excessive platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, preeclampsia, inflammation, prophylaxis against unwanted side effects of COX-1, COX-2 and non-selective COX inhibitors, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

A further aspect of the invention provides a compound of Formula I, Ia, II or IIa or pharmaceutical salts thereof for use in the treatment of PAH as described above.

A further aspect of the invention provides a compound of Formula I, Ia, II or IIa or pharmaceutical salts thereof for use in the treatment of a disorder selected from the aforementioned diseases and disorders.

A still further aspect of the present invention provides for the use of a compound of formula I, Ia, II or IIa, as defined in any of the aforementioned embodiments, in free or pharmaceutically acceptable salt form, for the manufacture of a medicament for the treatment of pulmonary arterial hypertension.

An embodiment of the present invention provides for the use of a compound of formula I, Ia, II or IIa, as defined in any of the aforementioned embodiments, in free or pharmaceutically acceptable salt form, for the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH).

An embodiment of the present invention provides method for the prevention or treatment of an IP receptor mediated condition or disease comprising administering an effective amount of at least one compound as described herein to a subject in need of such treatment. Such IP receptor mediated condition or disease are selected from PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH).

Other IP receptor mediated condition or disease are selected from platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, inflammation, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

An embodiment of the present invention provides method for the prevention or treatment of an IP receptor mediated condition or disease comprising administering an effective amount of at least one compound as described herein to a subject in need of such treatment. Such IP receptor mediated condition or disease is PAH.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethanedisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate trifluoroacetate and xinafoate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, 1-hydroxy-2-naphthoic acid and sulfosalicylic acid.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, chlorinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, acetone or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds of the present invention, including their salts, can also be obtained in the form of their hydrates, or include other solvents used for their crystallization.

Compounds of the invention, i.e. compounds of formula I, Ia, II or IIa that contain groups capable of acting as donors and/or acceptors for hydrogen bonds may be capable of forming co-crystals with suitable co-crystal formers. These co-crystals may be prepared from compounds of formula I, Ia, II or IIa by known co-crystal forming procedures. Such procedures include grinding, heating, co-subliming, co-melting, or contacting in solution compounds of formula I, Ia, II or IIa with the co-crystal former under crystallization conditions and isolating co-crystals thereby formed. Suitable co-crystal formers include those described in WO 2004/078163. Hence the invention further provides co-crystals comprising a compound of formula I, Ia, II or IIa.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$, $^{13}C$, and $^{14}C$, are present. Such isotopically labeled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula I, Ia, II or IIa. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of formula I, Ia, II or IIa can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Synthesis

Generally, compounds according to Formula I, Ia, II or IIa or pharmaceutical salts thereof can be synthesized by the routes described in Schemes A-M and the Examples.

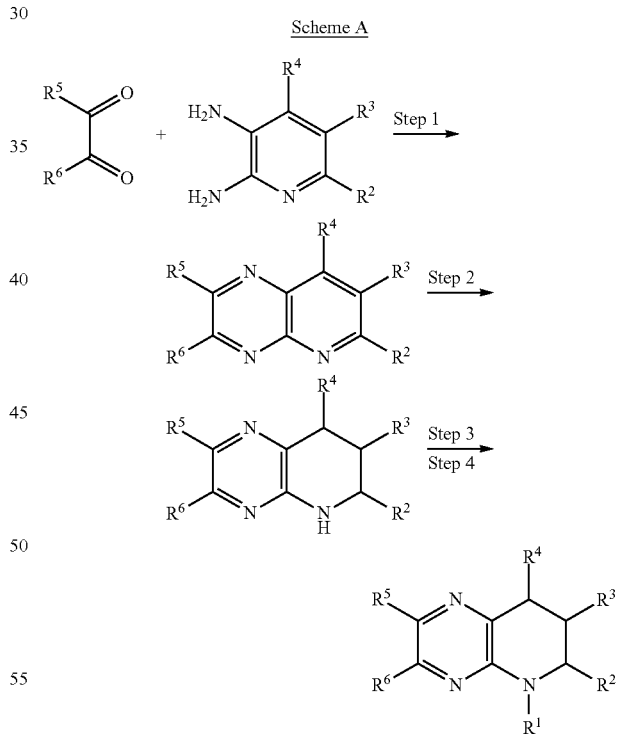

Scheme A

Scheme A begins with a Step 1 reaction taking commercially available starting material or starting material that one skilled in the art can synthesize and condensing the material as shown. Step 2 is a hydrogenation. Step 3 is either an alkylation or reductive amination depending on the desired product. Step 4 of Scheme A is a hydrolysis to form a free acid, if an ester is present. $R^1$, $R^2$, $R^3$, $R^4$, $R^5$ and $R^6$ are as defined herein.

Scheme B

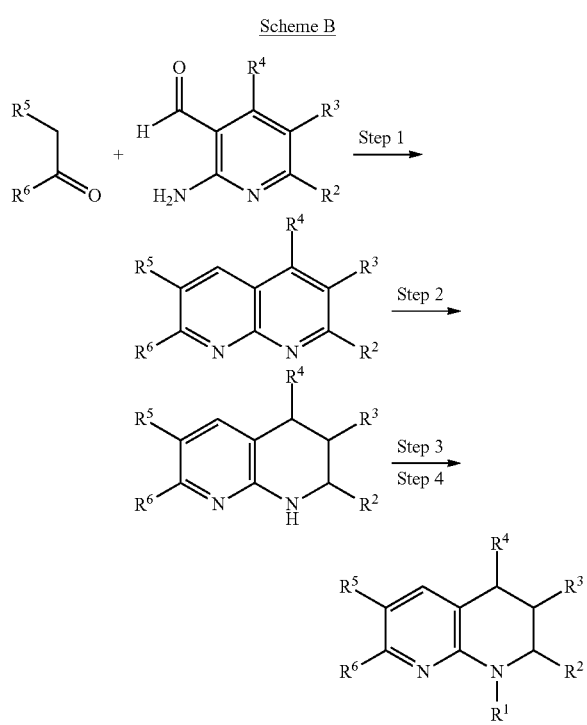

Scheme B begins with a Step 1 reaction taking commercially available starting material or starting material that one skilled in the art can synthesize and condensing the material as shown. Step 2 is a hydrogenation. Step 3 is either an alkylation or reductive amination depending on the desired product. Step 4 of Scheme B is a hydrolysis to form a free acid, if an ester is present. $R^1$, $R^2$, $R^3$, $R^4$, $R^5$ and $R^6$ are as defined herein.

Scheme C

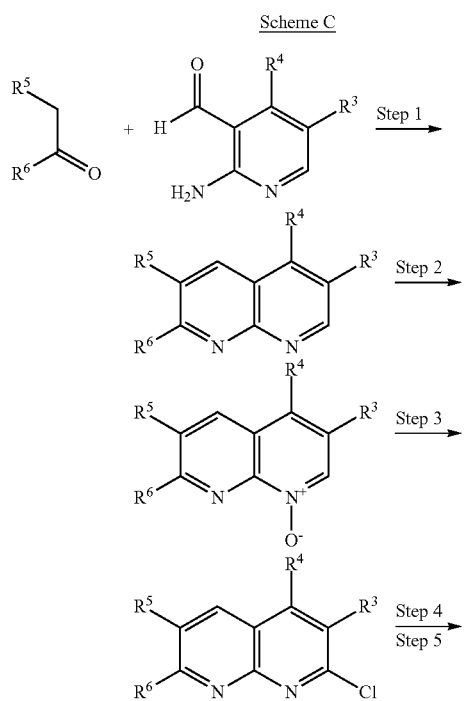

Scheme C begins with a Step 1 reaction taking commercially available starting material or starting material that one skilled in the art can synthesize and condensing the material as shown. Step 2 is the formation of an N-oxide. Step 3 selectively inserts a chlorine. Step 4 is a Negishi cross-coupling at the chlorine on the ring. Step 5 is a hydrogenation. Step 6 is either an alkylation or a reductive amination depending on the desired product. Step 7 is a chiral separation of the compounds mixture using Supercritical Fluid Chromatography to provide the individual enantiomers. Step 8 of Scheme C is a hydrolysis to form a free acid if an ester is present. $R^1$, $R^2$, $R^3$, $R^4$, $R^5$ and $R^6$ are as defined herein.

Scheme D

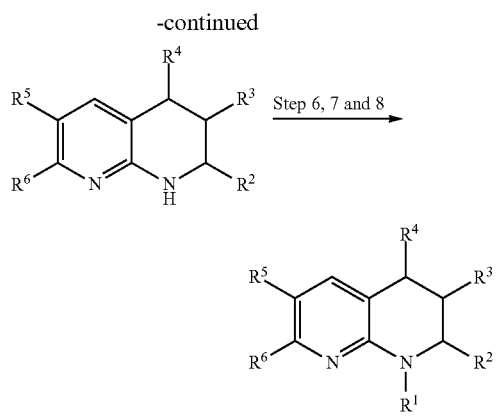

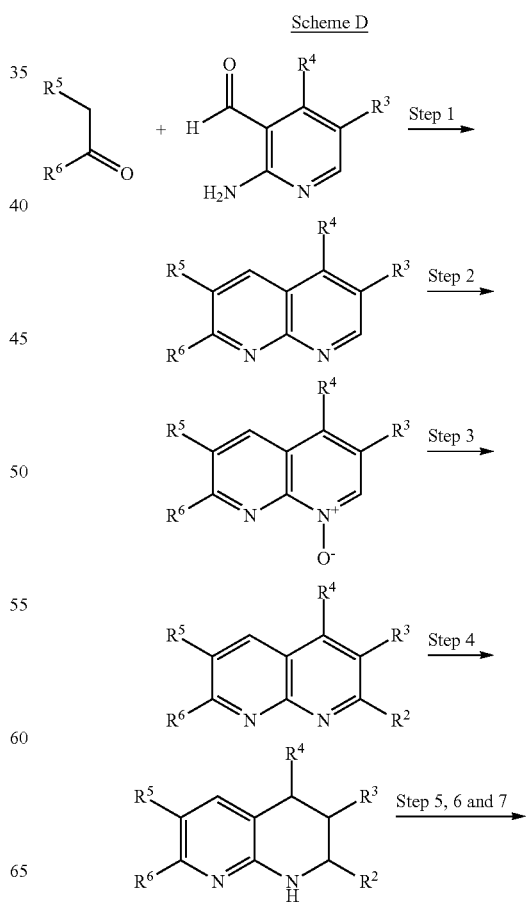

-continued

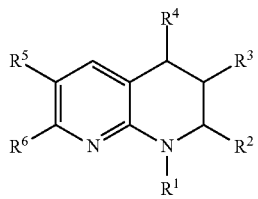

Scheme D begins with a Step 1 reaction taking commercially available starting material or starting material that one skilled in the art can synthesize and condensing the material as shown. Step 2 is the formation of an N-oxide. Step 3 is a chemoselective addition of Grignard reagents to an N-oxide derivative. Step 4 is a hydrogenation. Step 5 is either an alkylation or a reductive amination depending on the desired product. Step 6 is a chiral separation of the compounds mixture using Supercritical Fluid Chromatography to provide the individual enantiomers. Step 7 of Scheme D is a hydrolysis to form a free acid if an ester is present. $R^1$, $R^2$, $R^3$, $R^4$, $R^5$ and $R^6$ are as defined herein.

Scheme E

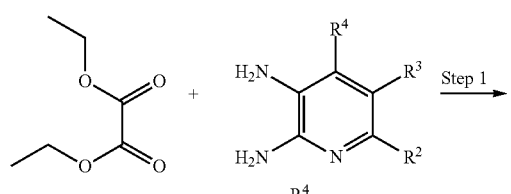

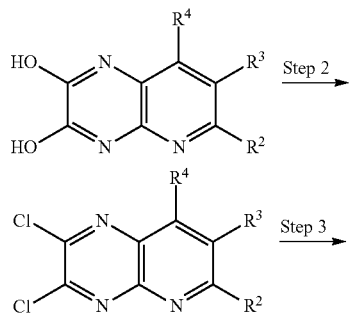

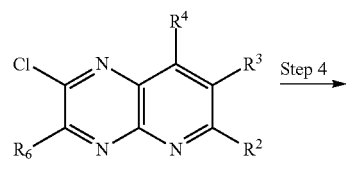

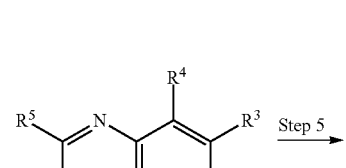

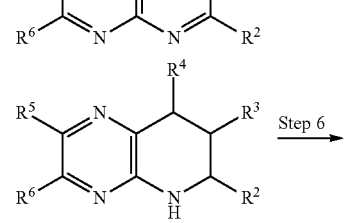

-continued

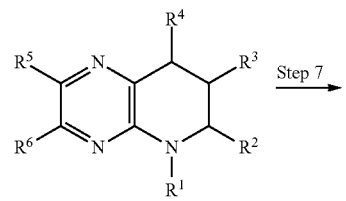

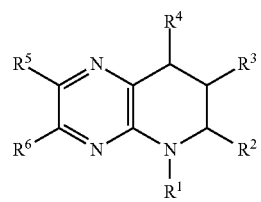

Scheme E begins with a Step 1 reaction taking commercially available starting material or starting material that one skilled in the art can synthesize and condensing the material as shown. Step 2 is a chlorination. Step 3 and Step 4 are Suzuki cross-coupling reactions. Step 5 is a hydrogenation. Step 6 is either an alkylation or reductive amination depending on the desired product. Step 7 of Scheme E is a hydrolysis to form a free acid, if an ester is present. $R^1$, $R^2$, $R^3$, $R^4$, $R^5$ and $R^6$ are as defined herein.

Scheme F

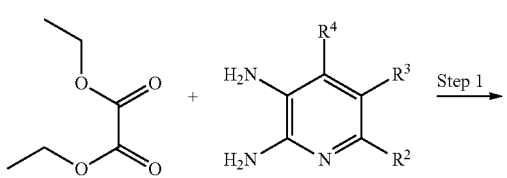

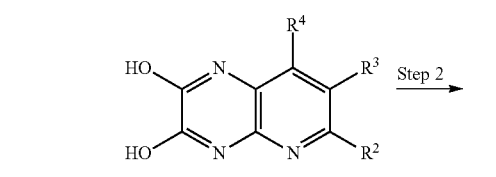

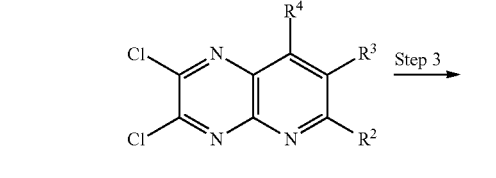

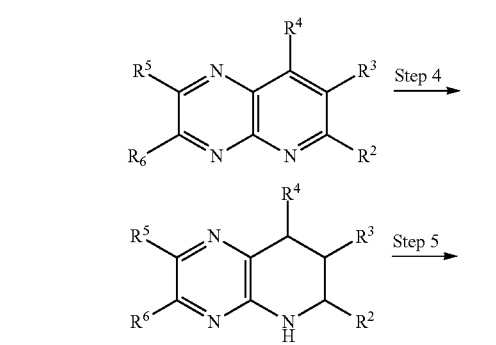

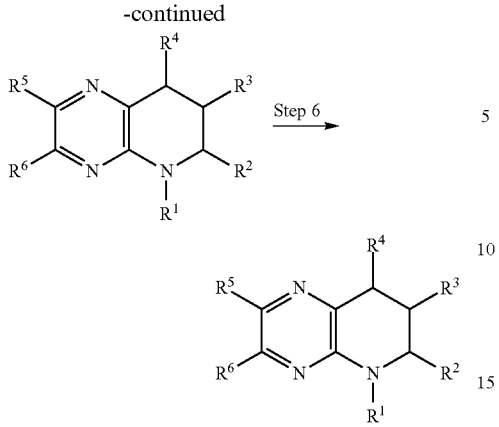

(R5 = R6)

Scheme F begins with a Step 1 reaction taking commercially available starting material or starting material that one skilled in the art can synthesize and condensing the material as shown. Step 2 is a chlorination. Step 3 is a Suzuki cross-coupling reaction. Step 4 is a hydrogenation. Step 5 is either an alkylation or reductive amination depending on the desired product. Step 6 of Scheme F is a hydrolysis to form a free acid, if an ester is present. $R^1$, $R^2$, $R^3$, $R^4$, $R^5$ and $R^6$ are as defined herein.

Scheme G

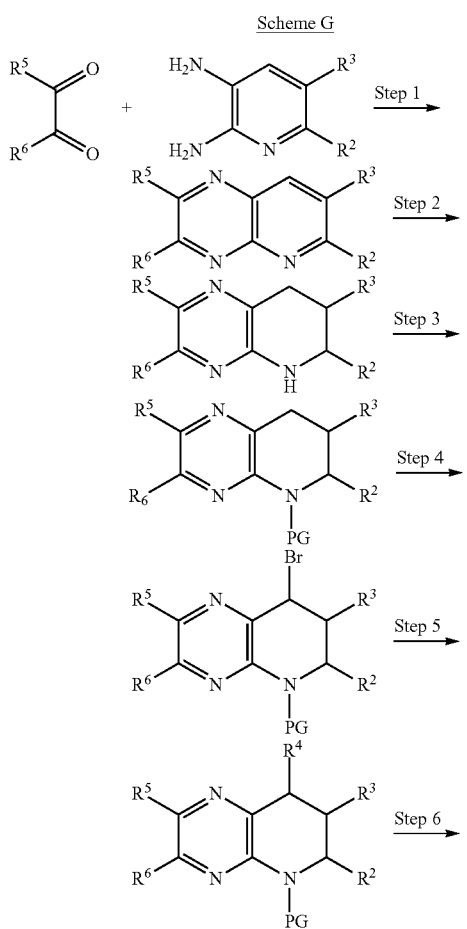

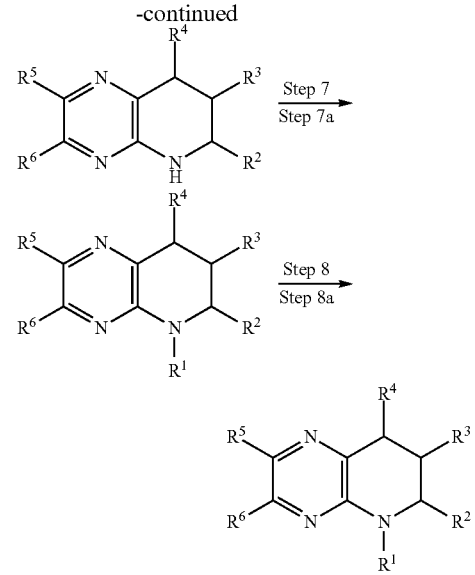

Scheme G begins with a Step 1 reaction taking commercially available starting material or starting material that one skilled in the art can synthesize and condensing the material as shown. Step 2 is a hydrogenation. Step 3 is the introduction of a protecting group (PG). Step 4 is a bromination. Step 5 is either an organometallic reaction or a nucleophilic substitution of a halide derivative depending on the desired product. Step 6 is an optional removal of a protecting group. Step 7 is either an alkylation or reductive amination depending on the desired product. Step 8 of Scheme G is an optional deprotection step and a hydrolysis to form a free acid, if an ester is present. Chiral separation can be done as Step 7a or Step 8a. $R^1$, $R^2$, $R^3$, $R^4$, $R^5$ and $R^6$ are as defined herein.

Scheme H

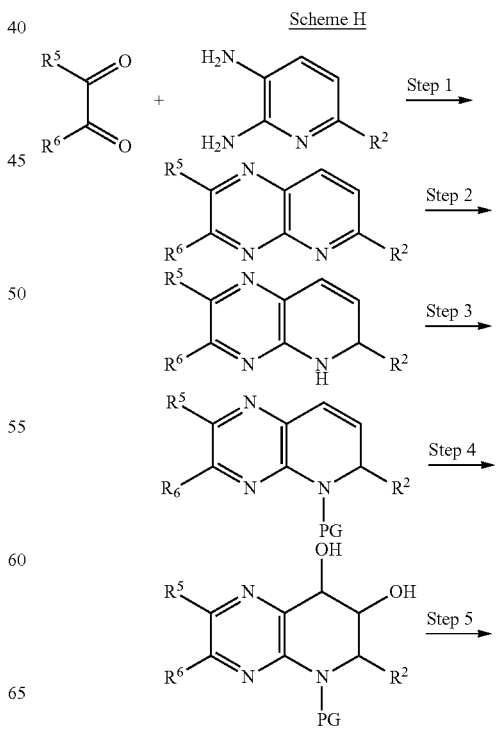

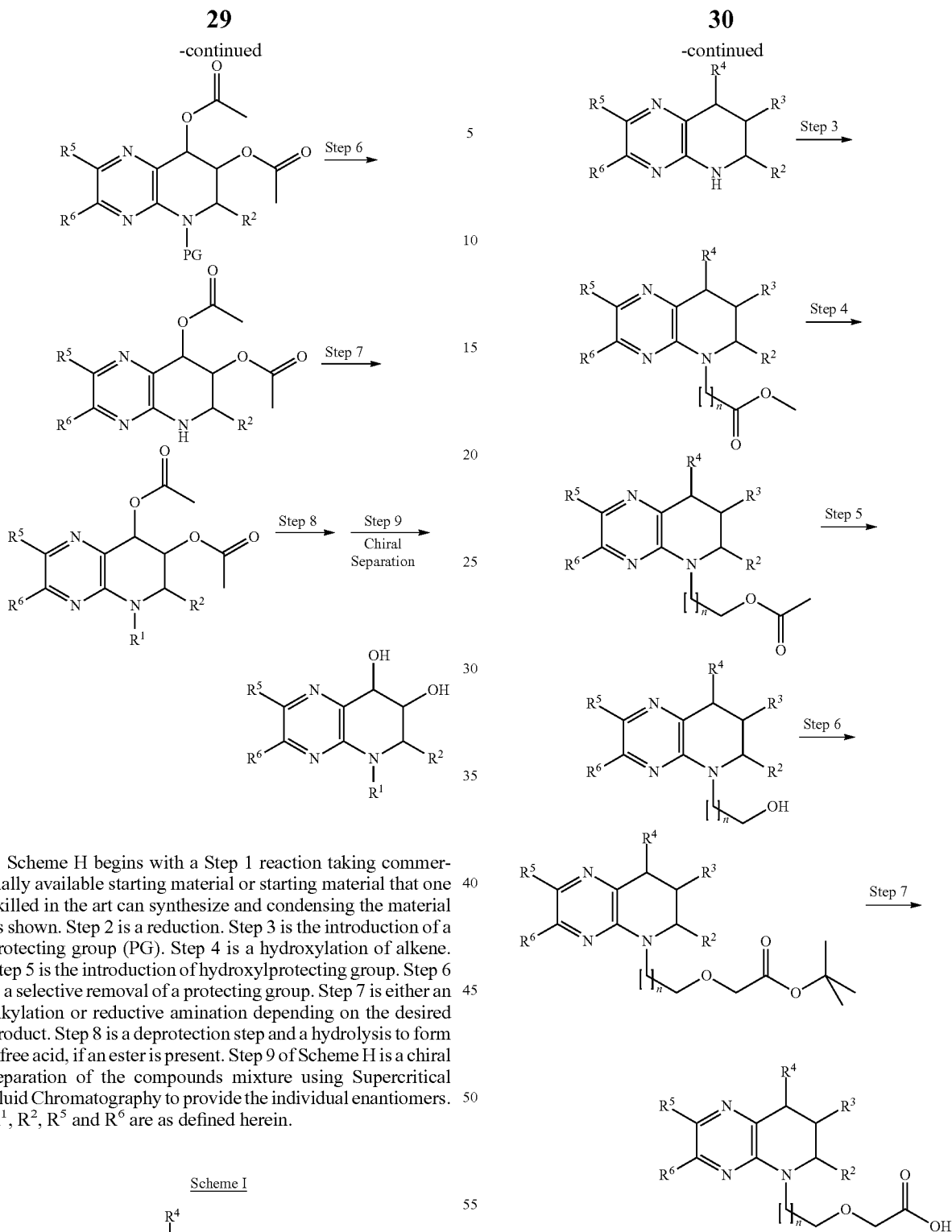

Scheme H begins with a Step 1 reaction taking commercially available starting material or starting material that one skilled in the art can synthesize and condensing the material as shown. Step 2 is a reduction. Step 3 is the introduction of a protecting group (PG). Step 4 is a hydroxylation of alkene. Step 5 is the introduction of hydroxylprotecting group. Step 6 is a selective removal of a protecting group. Step 7 is either an alkylation or reductive amination depending on the desired product. Step 8 is a deprotection step and a hydrolysis to form a free acid, if an ester is present. Step 9 of Scheme H is a chiral separation of the compounds mixture using Supercritical Fluid Chromatography to provide the individual enantiomers. $R^1$, $R^2$, $R^5$ and $R^6$ are as defined herein.

Scheme I begins with a Step 1 reaction taking commercially available starting material or starting material that one skilled in the art can synthesize and condensing the material as shown. Step 2 is a hydrogenation. Step 3 is either an alkylation or reductive amination depending on the desired product. Step 4 is a reduction. Step 5 is an optional hydrolysis. Step 6 is an alkylation. Step 7 of Scheme I is a hydrolysis to form a free acid, if an ester is present. $R^2$, $R^3$, $R^4$, $R^5$ and $R^6$ are as defined herein. n is 0 to 5.

Scheme J
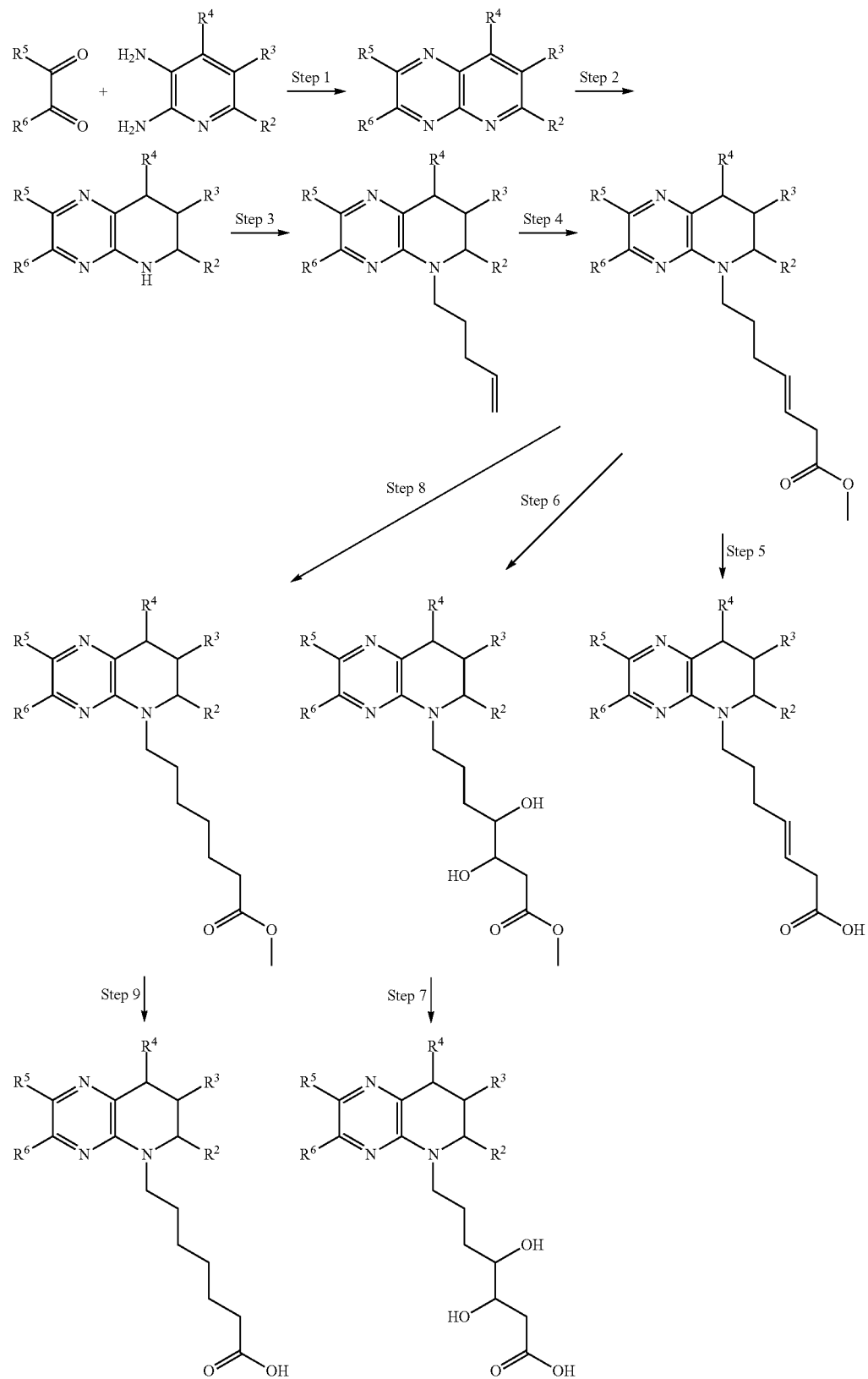

Scheme J begins with a Step 1 reaction taking commercially available starting material or starting material that one skilled in the art can synthesize and condensing the material as shown. Step 2 is a hydrogenation. Step 3 is either an alkylation or reductive amination depending on the desired product. Step 4 is an olefin metathesis reaction. Step 6 is a hydroxylation of an alkene. Step 8 is a hydrogenation. Step 5, 7 and 9 of Scheme J are a hydrolysis to form a free acid if an ester is present. $R^2$, $R^3$, $R^4$, $R^5$ and $R^6$ are as defined herein.

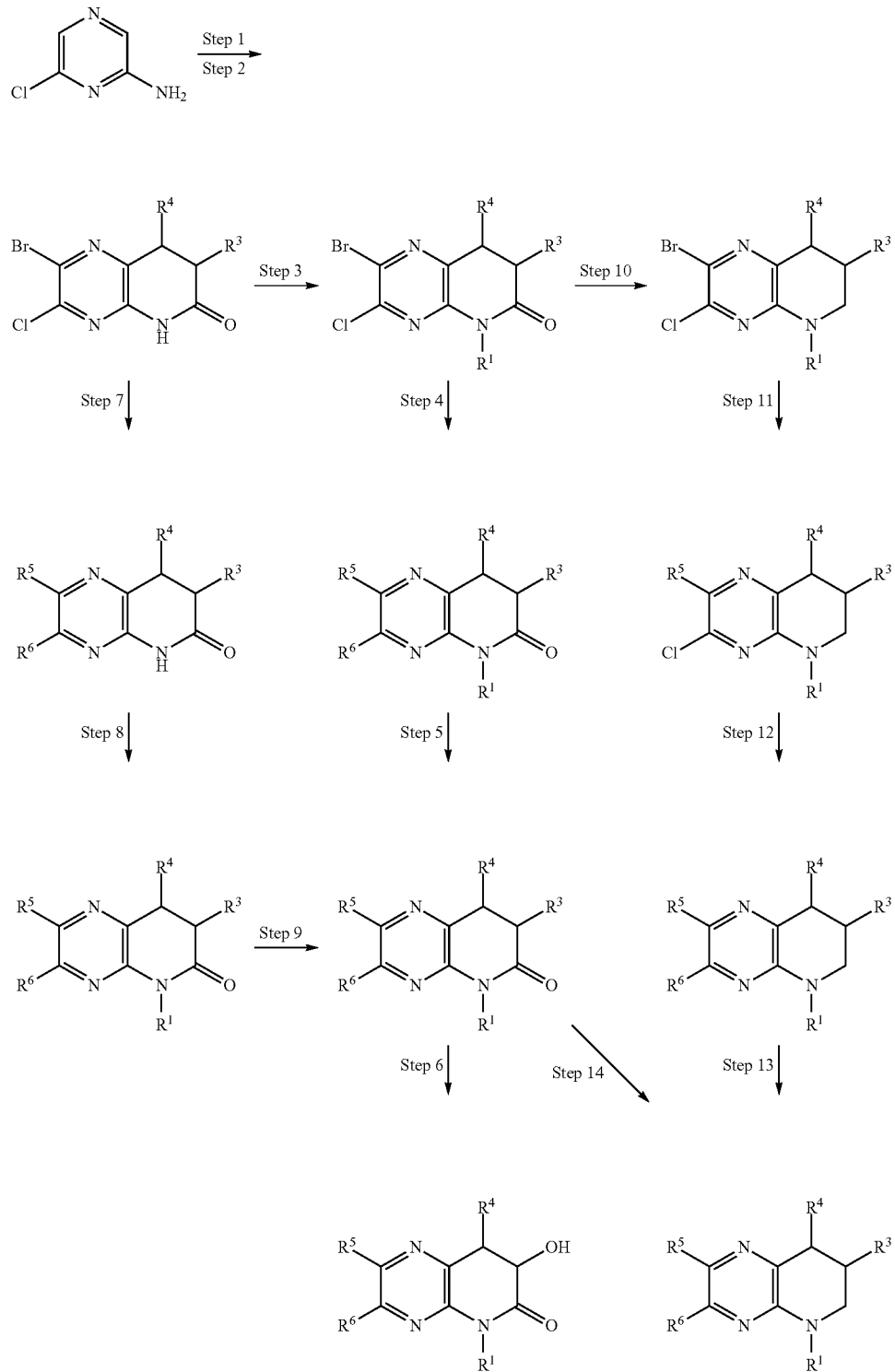

Scheme K

Scheme K begins with a Step 1 reaction taking commercially available starting material or starting material that one skilled in the art can synthesize and dibrominating the material. Step 2 is a Negishi cross-coupling reaction concomitant with an intramolecular cyclisation. Steps 3, 8 is an alkylation. Steps 4, 7, 11 and 12 are Suzuki cross-coupling reactions. Steps 5, 9 and 13 are a hydrolysis to form a free acid. Steps 10 and 14 are a reduction. Step 6 of Scheme K is a hydroxylation. $R^1$, $R^3$, $R^4$, $R^5$ and $R^6$ are as defined herein.

Scheme L

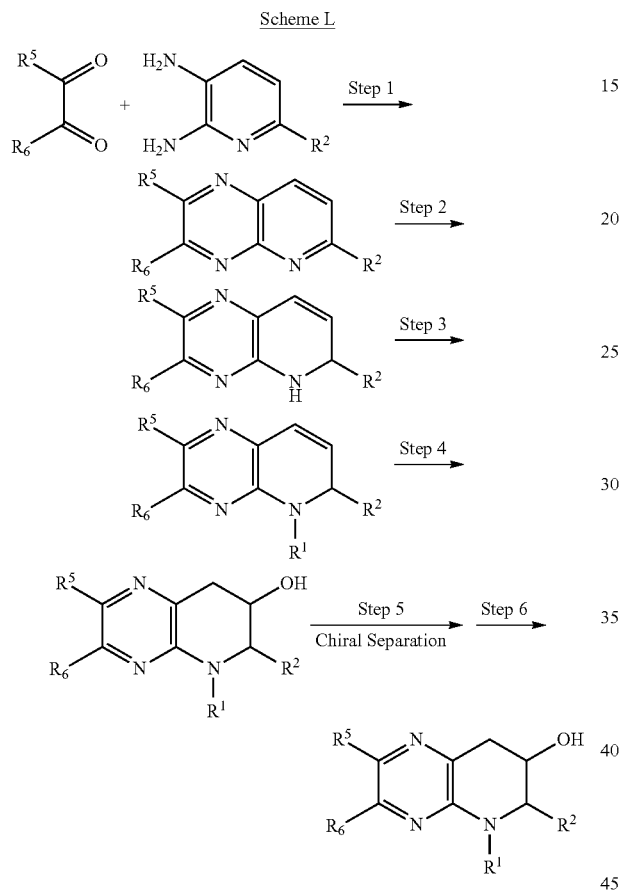

Scheme L begins with a Step 1 reaction taking commercially available starting material or starting material that one skilled in the art can synthesize and condensing the material as shown. Step 2 is a reduction. Step 3 is either an alkylation or reductive amination depending on the desired product. Step 4 is an hydroboration of alkene. Step 5 is a chiral separation of the compounds mixture using Supercritical Fluid Chromatography to provide the individual enantiomers. Step 6 of Scheme L is a hydrolysis to form a free acid if an ester is present. $R^1$, $R^2$, $R^5$ and $R^6$ are as defined herein.

Scheme M

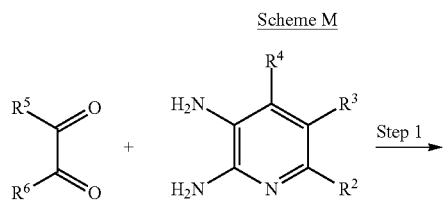

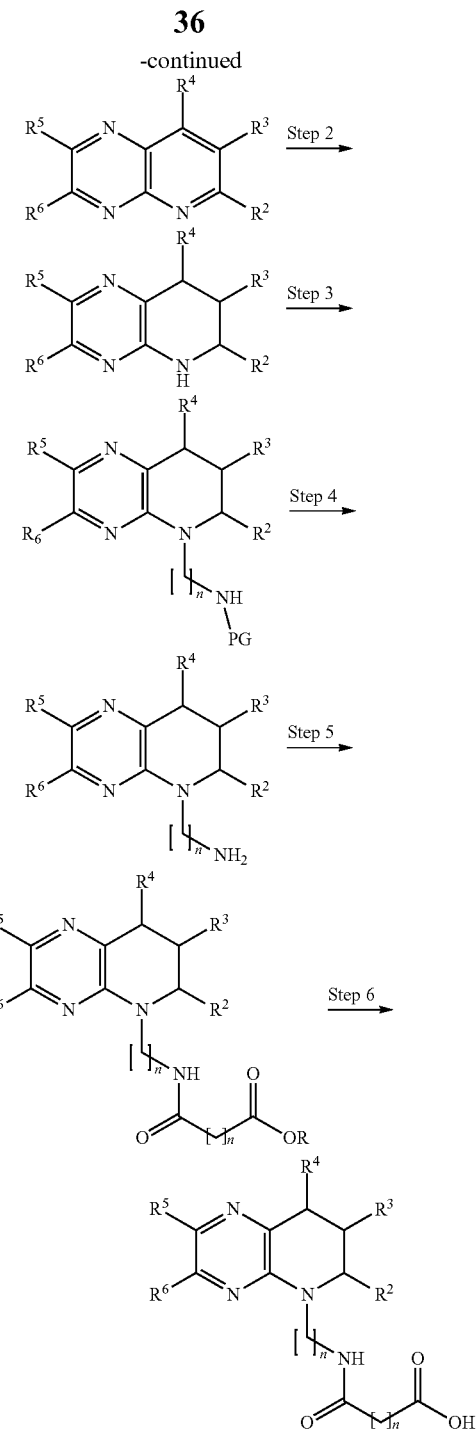

Scheme M begins with a Step 1 reaction taking commercially available starting material or starting material that one skilled in the art can synthesize and condensing the material as shown. Step 2 is a hydrogenation. Step 3 is either an alkylation or reductive amination depending on the desired product. Step 4 is an optional removal of a protecting group. Step 5 is an amide bond formation. Step 6 of Scheme M is a hydrolysis to form a free acid if an ester is present. $R^2$, $R^3$, $R^4$, $R^5$ and $R^6$ are as defined herein. n is 1 to 5. PG is a suitable protecting group.

The skilled person will appreciate that the general synthetic routes detailed above show common reactions to transform the starting materials as required. The specific reaction conditions are not provided, but these are well known to those skilled in the art and appropriate conditions considered to be within the skilled person's common general knowledge.

The starting materials are either commercially available compounds or are known compounds and can be prepared from procedures described in the organic chemistry art.

Compounds of formula I, Ia, II or IIa, in free form, may be converted into salt form, and vice versa, in a conventional manner understood by those skilled in the art. The compounds in free or salt form can be obtained in the form of hydrates or solvates containing a solvent used for crystallisation. Compounds of formula I, Ia, II or IIa can be recovered from reaction mixtures and purified in a conventional manner. Isomers, such as stereoisomers, may be obtained in a conventional manner, e.g., by fractional crystallisation or asymmetric synthesis from correspondingly asymmetrically substituted, e.g., optically active, starting materials.

The compounds of Formula I, Ia, II or IIa or pharmaceutical salts thereof can be prepared, e.g., using the reactions and techniques described below and in the Examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula I, Ia, II or IIa into another compound of formula I, Ia, II or IIa. Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5$^{th}$ Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, *Protective Groups in Organic Synthesis*, Wiley and Sons, 4$^{th}$ Edition (2006).

Pharmacological Activity

The compounds disclosed herein activate the IP receptor and are useful in the treatment of several diseases and disorders, and in the amelioration of symptoms thereof. Without limitation, these include the following:

Pulmonary Arterial Hypertension (PAH)

PAH has a multifactoral pathobiology. Vasoconstriction, remodeling of the pulmonary vessel wall, and thrombosis contribute to increased pulmonary vascular resistance in PAH (Humbert et al, J. Am. Coll. Cardiol., 2004, 43:13 S-24S.). The compounds of the present invention disclosed herein are useful in the treatment of pulmonary arterial hypertension (PAH) and symptoms thereof. PAH shall be understood to encompass the following forms of pulmonary arterial hypertension described in the 2003 World Health Organization (WHO) clinical classification of pulmonary arterial hypertension: idiopathic PAH (BPAH); familial PAH (FPAH); PAH associated with other conditions (APAH), such as PAH associated with collagen vascular disease, PAH associated with congenital systemic-to-pulmonary shunts, PAH associated with portal hypertension, PAH associated with HTV infection, PAH associated with drugs or toxins, or PAH associated with Other; and PAH associated with significant venous or capillary involvement. Idiopathic PAH refers to PAH of undetermined cause. Familial PAH refers to PAH for which hereditary transmission is suspected or documented. PAH associated with collagen vascular disease shall be understood to encompass PAH associated with scleroderma, PAH associated with CREST (calcinosis cutis, Raynaud's phenomenon, esophageal dysfunction, sclerodactyl), and telangiectasias) syndrome, PAH associated with systemic lupus erythematosus (SLE), PAH associated with rheumatoid arthritis, PAH associated with Takayasu's arteritis, PAH associated with polymyositis, and PAH associated with dermatomyositis. PAH associated with congenital systerruc-to-pulmonary shunts shall be understood to encompass PAH associated with atrial septic defect (ASD), PAH associated with ventricular septic defect (VSD) and PAH associated with patent ductus arteriosus.

PAH associated with drugs or toxins shall be understood to encompass PAH associated with ingestion of a minorex, PAH associated with ingestion of a fenfluramine compound (e.g., PAH associated with ingestion of fenfluramine or PAH associated with ingestion of dexfenfluramine), PAH associated with ingestion of certain toxic oils (e g, PAH associated with ingestion of rapeseed oil), PAH associated with ingestion of pyrrolizidine alkaloids (e.g., PAH associated with ingestion of bush tea) and PAH associated with ingestion of monocrotaline. PAH associated with Other shall be understood to encompass PAH associated with a thyroid disorder, PAH associated with glycogen storage disease, PAH associated with Gaucher disease, PAH associated with hereditary hemorrhagic telangiectasia, PAH associated with a hemoglobinopathy, PAH associated with a myeloproliferative disorder, and PAH associated with splenectomy. PAH associated with significant venous or capillary involvement shall be understood to encompass PAH associated with pulmonary veno-occlusive disease (PVOD) and PAH associated with pulmonary capillary hemangiomatosis (PCH). (See, e.g, Simonneau et al, J. Am. Coll. Cardiol., 2004, 43:5 S-12S; McGoon et al., Chest, 2004, 126:14 S-34S; Rabinovitch, Annu. Rev. Pathol. Mech. Dis., 2007, 2:369-399; McLaughlin et al, Circulation, 2006, 114:1417-1431; Strauss et al, Clin. Chest. Med., 2007, 28:127-142; Taichman et al., Clin. Chest. Med., 2007, 28:1-22.).

Evidence for the association of PAH with scleroderma and the beneficial effect of an agonist of the IP receptor on PAH is given by Badesch et al (Badesch et al, Ann. Intern. Med., 2000, 132:425-434). Evidence for the association of PAH with the collagen vascular diseases mixed connective tissue disease (MCTD), systemic lupus erythematosus (SLE), Sjogren's syndrome and CREST syndrome and the beneficial effect of an agonist of the IP receptor on PAH is given by Humbert et al. (Eur. Respir. J., 1999, 13:1351-1356). Evidence for the association of PAH with CREST syndrome and the beneficial effect of an agonist of the IP receptor on PAH is given by Miwa et al. (Int. Heart J., 2007, 48:417-422). Evidence for the association of PAH with SLE and the beneficial effect of an agonist of the IP receptor on PAH is given by Robbins et al (Chest, 2000, 117:14-18). Evidence for the association of PAH with HIV infection and the beneficial of an agonist of the IP receptor on PAH is given by Aguilar et al. (Am. J. Respir. Crit. Care Med., 2000, 162:1846-1850). Evidence for the association of PAH with congenital heart defects (including ASD, VSD and patent ductus arteriosus) and the beneficial effect of an agonist of the IP receptor on PAH is given by Rosenzweig et al. (Circulation, 1999, 99:1858-1865).

Evidence for the association of PAH with fenfluramine and with dexfenfluramine, anorexigens, is given by Archer et al. (Am. J. Respir. Crit. Care Med., 1998, 158: 1061-1067). Evidence for the association of PAH with hereditary hemorrhagic telangiectasia is given by McGoon et al. (Chest, 2004, 126:14-34). Evidence for the association of PAH with splenectomy is given by Hoeper et al. (Ann. Intern. Med., 1999, 130:506-509). Evidence for the association of PAH with portal hypertension and the beneficial effect of an agonist of the IP receptor on PAH is given by Hoeper et al. (Eur. Respir. J., 2005, 25:502-508).

Symptoms of PAH include dyspnea, angina, syncope and edema (McLaughlin et al., Circulation, 2006, 114:1417-1431). The compounds of the present invention disclosed herein are useful in the treatment of symptoms of PAH.

Antiplatelet Therapies (Conditions Related to Platelet Aggregation)

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction, the heart muscle does not receive enough oxygen-rich blood as a result of a blockage in the coronary blood vessels. If taken while an attack is in progress or immediately afterward (preferably within 30 min), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs. Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation of blood clots that cause first or second strokes. Angioplasty is a catheter based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrhythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

There is evidence that an IP receptor agonist will inhibit platelet aggregation and thus be a potential treatment as an antiplatelet therapy (see, e.g., Moncada et al., Lancet, 1977, 1: 18-20). It has been shown that genetic deficiency of the IP receptor in mice leads to an increased propensity towards thrombosis (Murata et al, Nature, 1997, 388:678-682).

IP receptor agonists can be used to treat, for example, claudication or peripheral artery disease as well as cardiovascular complications, arterial thrombosis, atherosclerosis, vasoconstriction caused by serotonin, ischemia-reperfusion injury, and restenosis of arteries following angioplasty or stent placement. (See, e.g., Fetalvero et al, Prostaglandins Other Lipid Mediat., 2007, 82:109-118; Arehart et al, Curr. Med. Chem., 2007, 14:2161-2169; Davi et al, N. Engl. J. Med., 2007, 357:2482-2494; Fetalvero et al, Am. J. Physiol. Heart. Circ. Physiol., 2006, 290:H1337-H1346; Murata et al, Nature, 1997, 388:678-682; Wang et al, Proc. Natl. Acad. Sci. USA, 2006, 103:14507-14512; Xiao et al, Circulation, 2001, 104:2210-2215; McCormick et al, Biochem. Soc. Trans., 2007, 35:910-911; Arehart et al, Circ. Res., 2008, Mar. 6.).

IP receptor agonists can also be used alone or in combination with thrombolytic therapy, for example, tissue-type plasminogen activator (t-PA), to provide cardioprotection following MI or postischemic myocardial dysfunction or protection from ischemic injury during percutaneous coronary intervention, and the like, including complications resulting therefrom. IP receptor agonists can also be used in antiplatelet therapies in combination with, for example, alpha-tocopherol (vitamin E), echistatin (a disintegrin) or, in states of hypercoaguability, heparin. (See, e.g., Chan., J. Nutr., 1998, 128: 1593-1596; Mardla et al, Platelets, 2004, 15:319-324; Bernabei et al, Ann. Thorac. Surg., 1995, 59:149-153; Gainza et al, J. Nephrol., 2006, 19:648-655.)

The IP receptor agonists disclosed herein provide beneficial improvement in microcirculation to patients in need of antiplatelet therapy by antagonizing the vasoconstrictive products of the aggregating platelets in, for example and not limited to the indications described above.

Accordingly, in some embodiments, the present invention provides methods for reducing platelet aggregation in a patient in need thereof, comprising administering to the patient a composition comprising an IP receptor agonist disclosed herein. In further embodiments, the present invention provides methods for treating coronary artery disease, myocardial infarction, transient ischemic attack, angina, stroke, atrial fibrillation, or a symptom of any of the foregoing in a patient in need of the treatment, comprising administering to the patient a composition comprising an IP receptor agonist disclosed herein.

In further embodiments, the present invention provides methods for reducing risk of blood clot formation in an angioplasty or coronary bypass surgery patient, or a patient suffering from atrial fibrillation, comprising administering to the patient a composition comprising an IP receptor agonist disclosed herein at a time where such risk exists.

Atherosclerosis

Atherosclerosis is a complex disease characterized by inflammation, lipid accumulation, cell death and fibrosis. It is the leading cause of mortality in many countries, including the United States. Atherosclerosis, as the term is used herein, shall be understood to encompass disorders of large and medium-sized arteries that result in the progressive accumulation within the intima of smooth muscle cells and lipids.

It has been shown that an agonist of the IP receptor can confer protection from atherosclerosis, such as from atherothrombosis (Arehart et al, Curr. Med. Chem., 2007, 14:2161-2169; Stitham et al, Prostaglandins Other Lipid Mediat., 2007, 82:95-108; Fries et al, Hematology Am. Soc. Hematol. Educ. Program, 2005: 445-451; Egan et al, Science, 2004, 306:1954-1957; Kobayashi et al, J. Clin. Invest, 2004, 114: 784-794; Arehart et al, Circ. Res., 2008, Mar. 6). It has been shown that defective IP receptor signaling appears to accelerate atherothrombosis in humans, i e that an agonist of the IP receptor can confer protection from atherothrombosis in humans (Arehart et al, Circ. Res., 2008, Mar. 6.)

The compounds of the present invention disclosed herein are useful in the treatment of atherosclerosis, and the treatment of the symptoms thereof. Accordingly, in some embodiments, the present invention provides methods for treating atherosclerosis in a patient in need of the treatment, comprising administering to the patient a composition comprising an IP receptor agonist disclosed herein. In further embodiments, methods are provided for treating a symptom of atherosclerosis in a patient in need of the treatment, comprising administering to the patient a composition comprising an IP receptor agonist disclosed herein.

Asthma

Asthma is a lymphocyte-mediated inflammatory airway disorder characterised by airway eosinophilia, increased mucus production by goblet cells, and structural remodeling of the airway wall. The prevalence of asthma has dramatically increased worldwide in recent decades. It has been shown that genetic deficiency of the IP receptor in mice augments allergic airway inflammation (Takahashi et al, Br J Pharmacol, 2002, 137:315-322). It has been shown that an agonist of the IP receptor can suppress not only the development of asthma when given during the sensitization phase, but also the cardinal features of experimental asthma when given during the challenge phase (Idzko et al, J. Clin. Invest., 2007, 117:464-72, Nagao et al, Am. J. Respir. Cell Mol. Biol., 2003, 29:314-320), at least in part through markedly interfering with the function of antigen-presenting dendnuc cells within the airways (Idzko et al., J. Clin. Invest., 2007, 117:464-472; Zhou et al, J. Immunol., 2007, 178:702-710; Jaffar et al., J. Immunol., 2007, 179:6193-6203; Jozefowski et al, Int. Immunopharmacol., 2003, 3:865-878). These cells are crucial for both the initiation and the maintenance phases of allergic asthma, as depletion of airway dendritic cells during secondary challenge in sensitized mice abolished all characteristic features of asthma, an effect that could be completely restored by adoptive transfer of wild-type dendritic cells (van Rijt et al., J. Exp. Med., 2005, 201:981-991). It has also been shown that an agonist of the IP receptor can inhibit proinflammatory cytokine secretion by human alveolar macrophages (Raychaudhuri et al., J. Biol. Chem., 2002, 277:33344-33348). The compounds of the present invention disclosed herein are useful in the treatment of asthma, and the treatment of the symptoms thereof. Accordingly, in some embodiments, the present invention provides methods for treating asthma in a patient in need of the treatment, comprising administering to the patient a composition comprising IP receptor agonist disclosed herein.

In further embodiments, methods are provided for treating a symptom of asthma in a patient in need of the treatment, comprising administering to the patient a composition comprising IP receptor agonist disclosed herein.

Chronic Obstructive Pulmonary Disease

Activation of the IP-receptor may also be beneficial in chronic obstructive pulmonary disease (COPD). Taprostene, an IP-receptor agonist, suppressed the generation of the $CD8^+$ T cell chemoattractants CXCL9 and CXCL10 from human airway epithelial cells in vitro. (Ayer, L. M., S. M. Wilson, S. L. Traves, D. Proud, M. A. Giembycz. 2008. J. Pharmacol. Exp. Ther. 324: 815-826.) Beraprost, an IP-receptor agonist, protected rats against the development of experimental cigarette smoke-induced emphysema, possibly by means of a concerted inhibitory action on alveolar epithelial cell apoptosis, oxidative burden, matrix metalloproteinase expression, and proinflammatory cytokine generation. (Chen, Y., M. Hanaoka, P. Chen, Y. Droma, N. F. Voelkel, K. Kubo. 2009. Am. J. Physiol. 296: L648-L656.)

In further embodiments, methods are provided for treating COPD in a patient in need of the treatment, comprising administering to the patient a composition comprising IP receptor agonist disclosed herein.

Hyperglycemia

Although hyperglycemia is the major cause for the pathogenesis of diabetic complications such as diabetic peripheral neuropathy (DPN), diabetic nephropathy (DN) and diabetic retinopathy (DR), enhanced vasoconstriction and platelet aggregation in diabetic patients has also been implicated to play a role in disease progression (Cameron et al., Naunyn Schmiedebergs Arch. Pharmacol., 2003, 367:607-614). Agonists of the IP receptor promote vasodilation and inhibit platelet aggregation. Improving microvascular blood flow is able to benefit diabetic complications (Cameron, Diabetologia, 2001, 44:1973-1988).

It has been shown that an agonist of the IP receptor can prevent and reverse motor and sensory peripheral nerve conduction abnormalities in streptozotocin-diabetic rats (Cotter et al., Naunyn Schmiedebergs Arch. Pharmacol., 1993, 347: 534-540). Further evidence for the beneficial effect of an agonist of the IP receptor in the treatment of diabetic peripheral neuropathy is given by Hotta et al. (Diabetes, 1996, 45:361-366), Ueno et al. (Jpn. J. Pharmacol., 1996, 70:177-182), Ueno et al. (Life Sci., 1996, 59:PL105-PL110), Hotta et al. (Prostaglandins, 1995, 49:339-349), Shindo et al. (Prostaglandins, 1991, 41:85-96), Okuda et al. (Prostaglandins, 1996, 52:375-384), and Koike et al. (FASEB J., 2003, 17:779-781).

Evidence for the beneficial effect of an agonist of the IP receptor in the treatment of diabetic nephropathy is given by Owada et al. (Nephron, 2002, 92:788-796) and Yamashita et al. (Diabetes Res. Clin. Pract., 2002, 57:149-161). Evidence for the beneficial effect of an agonist of the IP receptor in the treatment of diabetic retinopathy is given by Yamagishi et al. (Mol. Med., 2002, 8:546-550), Burnette et al. (Exp. Eye Res., 2006, 83: 1359-1365), and Hotta et al. (Diabetes, 1996, 45:361-366). It has been shown that an agonist of the IP receptor can reduce increased tumor necrosis factor-[alpha]

(TNF-[alpha]) levels in diabetic patients, implying that an agonist of the IP receptor may contribute to the prevention of progression in diabetic complications (Fujiwara et al, Exp. Clin. Endocrinol. Diabetes, 2004, 112:390-394).

Evidence that topical administration of an agonist of the IP receptor can result in a decrease in intraocular pressure (IOP) in rabbits and dogs and thereby have beneficial effect in the treatment of glaucoma is given by Hoyng et al (Hoyng et al, Invest. Ophthalmol. Vis. Sci., 1987, 28:470-476).

Agonists of the IP receptor have been shown to have activity for regulation of vascular tone, for vasodilation, and for amelioration of pulmonary hypertension (see, e.g., Strauss et al, Clin Chest Med, 2007, 28:127-142; Driscoll et al, Expert Opin. Pharmacother., 2008, 9:65-81). Evidence for a beneficial effect of an agonist of the IP receptor in the treatment of hypertension is given by Yamada et al. (Peptides, 2008, 29:412-418). Evidence that an agonist of the IP receptor can protect against cerebral ischemia is given by Dogan et al. (Gen. Pharmacol., 1996, 27:1163-1166) and Fang et al (J. Cereb. Blood Flow Metab., 2006, 26:491-501).

Anti-Inflammation

Anti-inflammation agents are prescribed for a variety of conditions. For example, in an inflammatory disease they are used to interfere with and thereby reduce an underlying deleterious.

There is evidence that an IP receptor agonist can inhibit inflammation and thus be a potential treatment as an anti-inflammation therapy. It has been shown that an agonist of the IP receptor can inhibit pro-inflammatory cytokine and chemokine (interleukin-12 (IL-12), tumor necrosis factor-[alpha] (TNF-[alpha]), DL-([alpha], EL-6, macrophage inflammatory protein-1 alpha (MIP-I[alpha]), monocyte chemoattractant protein-1 (MCP-I)) production and T cell stimulatory function of dendritic cells (Jozefowski et al, Int. Immunopharmacol., 2003, 865-878; Zhou et al, J. Immunol., 2007, 178:702-710; Nagao et al, Am. J. Respir. Cell Mol. Biol., 2003, 29:314-320; Idzko et al, J. Clin. Invest., 2007, 117:464-472). It has been shown that an agonist of the IP receptor can inhibit pro-inflammatory cytokine (TNF-[alpha], IL-1/3, EL-6, granulocyte macrophage stimulating factor (GM-CSF)) production by macrophages (Raychaudhuri et al, J. Biol. Chem., 2002, 277:33344-33348; Czeslick et al, Eur. J. Clin. Invest., 2003, 33:1013-1017; Di Renzo et al, Prostaglandin Leukot. Essent. Fatty Acids, 2005, 73:405-410; Shinomiya et al, Biochem. Pharmacol., 2001, 61:1153-1160). It has been shown that an agonist of the IP receptor can stimulate anti-inflammatory cytokine (DL-IO) production by dendritic cells (Jozefowski et al, Int. Immunopharmacol., 2003, 865-878; Zhou et al, J. Immunol., 2007, 178:702-710). It has been shown that an agonist of the IP receptor can stimulate anti-inflammatory cytokine (DL-10) production by macrophages (Shinomiya et al, Biochem. Pharmacol., 2001, 61: 1153-1160). It has been shown that an agonist of the IP receptor can inhibit a chemokine (CCL 17)-induced chemotaxis of leukocytes (CD4<+> Th2 T cells) (Jaffar et al, J. Immunol., 2007, 179:6193-6203). It has been shown that an agonist of the IP receptor can confer protection from atherosclerosis, such as from atherothrombosis (Arehart et al, Curr. Med. Chem., 2007, 14:2161-2169; Stitham et al, Prostaglandins Other Lipid Mediat., 2007, 82:95-108; Fries et al, Hematology Am. Soc. Hematol. Educ. Program, 2005: 445-451; Egan et al, Science, 2004, 306:1954-1957; Kobayashi et al, J. Clin. Invest., 2004, 114:784-794; Arehart et al, Circ. Res., 2008, Mar. 6). It has been shown that an agonist of the IP receptor can attenuate asthma (Idzko et al, J. Clin. Invest., 2007, 117:464-472; Jaffar et al, J. Immunol., 2007, 179:6193-6203; Nagao et al, Am. J. Respir. Cell. Mol. Biol., 2003, 29:314-320). It has been shown that an agonist of the IP receptor can decrease TNF-[alpha] production in type 2 diabetes patients (Fujiwara et al, Exp. Clin. Endocrinol. Diabetes, 2004, 112:390-394; Goya et al, Metabolism, 2003, 52: 192-198). It has been shown that an agonist of the IP receptor can inhibit ischemia-reperfusion injury (Xiao et al, Circulation, 2001, 104:2210-2215). It has been shown that an agonist of the IP receptor can inhibit restenosis (Cheng et al, Science, 2002, 296:539-541). It has been shown that an agonist of the IP receptor can attenuate pulmonary vascular injury and shock in a rat model of septic shock (Harada et al, Shock, 2008, Feb. 21). It has been shown that an agonist of the IP receptor can reduce the serum levels of TNF-[alpha] in vivo in patients with rheumatoid arthritis, and this is associated with improvement in the clinical course of the disease (Gao et al, Rheumatol. Int., 2002, 22:45-51; Boehme et al, Rheumatol. Int., 2006, 26:340-347).

The compounds of the present invention disclosed herein provide beneficial reduction of inflammation. The compounds of the present invention disclosed herein provide beneficial reduction of a deleterious inflammatory response associated with an inflammatory disease. Accordingly, in some embodiments, the present invention provides methods for reducing inflammation in a patient in need thereof, comprising administering to the patient a composition comprising an IP receptor agonist disclosed herein. In some embodiments, the present invention provides methods for decreasing IL-12, TNF-[alpha], IL-([alpha], IL-IjS, BL-6, MIP-1α or MCP-I production in a patient in need thereof, comprising administering to the patient a composition comprising an IP receptor agonist disclosed herein. In some embodiments, the present invention provides methods for decreasing TNF-[alpha] production in a patient in need thereof, comprising administering to the patient a composition comprising an IP receptor agonist disclosed herein. In some embodiments, the present invention provides methods for increasing EL-IO production in a patient in need thereof, comprising administering to the patient a composition comprising an IP receptor agonist disclosed herein. In some embodiments, the present invention provides methods for reducing a deleterious inflammatory response associated with an inflammatory disease in a patient in need thereof, comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein, wherein the inflammatory disease is selected from the group consisting of psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, diabetes (including type 1 diabetes and type 2 diabetes), sepsis, chronic obstructive pulmonary disease (COPD), and asthma.

Fibrosis

PGI2 signaling has been shown to play a beneficial role in fibrotic diseases of various organs, including kidney, heart, lung, skin, pancreas and liver, as well as in systemic sclerosis and associated pathologies. It has been shown that an agonist of the IP receptor can ameliorate cardiac fibrosis (Chan E C et al (2010) *J Mol Cell Cardiol*. April 18; Hirata Y et al (2009) *Biomed Pharmacother.* 63(10):781-6; Kaneshige T et al (2007) *J Vet Med Sci.* 69(12):1271-6). It has been shown that an agonist of the IP receptor can attenuate renal fibrosis (Takenaka M et al (2009) Prostaglandins Leukot Essent Fatty Acids. 80(5-6):263-7). It has been shown that an agonist of the IP receptor can protect against pulmonary fibrosis in a bleomycin model (Zhu Y et al (2010) *Respir Res.* 20; 11(1): 34). It has been shown that an agonist of the IP receptor can suppress the production of connective tissue growth factor, a key mediator of fibrosis, in scleroderma patients (Stratton R et al (2001) *J Clin Invest.* 108(2):241-50). It has been shown that an agonist of the IP receptor can reduce the incidence of digital ulcerations in patients with systemic sclerosis M. Vayssairat (1999) *J Rheumatol* 26:2173-2178. It has been shown that an agonist of the IP receptor can reduce fingertip necrosis in infants with refractory Renaud's phenomenon (Shouval D S et al (2008) *Clin Exp Rheumatol.* 26(3 Suppl 49):5105-7). It has been shown that an agonist of the IP receptor can reduce markers of endothelial activation in patients with systemic sclerosis (Rehberger P et al (2009) *Acta Derm Venereol.* 89(3):245-9.). It has been shown that an agonist of the IP receptor can reduce severity, frequency, and duration of Raynaud's attacks in patients with systemic sclerosis (Torlay et al (1991) *Ann Rheum Dis* 50, 800-804). It has been shown that an agonist of the IP receptor can improve portal hemodynamics in patients with systemic sclerosis and Raynaud's phenomenon (Zardi et al (2006) *In Vivo* 20(3):377-80). It has been shown that an agonist of the IP receptor can inhibit the progression of pancreatic fibrosis in obese Zucker rats (Sato et al (2010) *Diabetes* 59(4):1092-100).

The IP receptor agonists disclosed herein provide beneficial anti-fibrotic effects to patients suffering from fibrosis of the kidney, heart, lung, skin, pancreas and liver which can be idiopathic or secondary to chronic inflammation and systemic sclerosis, for example, and are not limited to the indications described above.

In addition, there is substantial evidence that an agonist of the IP receptor can improve kidney function in acute and chronic renal failure. It has been shown that an agonist of the IP receptor can restore kidney function in endotoxemia-related acute renal failure (Johannes T et al (2009) *Crit Care Med.* 37(4):1423-32). It has been shown that an agonist of the IP receptor can improve renal function in a model of renal ischemia/reperfusion injury Sahsivar M O et al (2009) *Shock* 32(5):498-502). It has been shown that an agonist of the IP receptor can prevent contrast agent-induced nephropathy in patients with renal dysfunction undergoing cardiac surgery (Spargias K et al (2009) *Circulation* 3; 120(18):1793-9.) It has been shown that an agonist of the IP receptor can improve renal function, reduce inflammation and sclerotic changes of the kidney in a model for diabetic nephropathy Watanabe M et al (2009) Am J Nephrol. 2009; 30(1):1-11).

The IP receptor agonists disclosed herein provide beneficial improvement of renal function in patients with acute and chronic kidney injury and nephropathies secondary to dye-contrast agents, ischemia-reperfusion injury, systemic inflammation and diabetes for example, and are not limited to the indications described above.

There is considerable evidence for a causal role of Prostacyclin deficiency in the development of preeclampsia (Mills J L et al (1999) *JAMA* 282: 356-362; Walsh SW (2004) *Prostaglandins Leukot Essent Fatty Acids* 70: 223-232). The administration of an agonist of the IP receptor has been shown to lower blood pressure in a rat model of preeclampsia (Zlatnik M G et al (1999) *Am J Obstet Gynecol.* 180(5):1191-5).

The IP receptor agonists disclosed herein provide beneficial improvement of hemodynamics in patients with preeclampsia.

The IP receptor agonist disclosed herein may provide beneficial treatment of cystic fibrosis.

The IP receptor agonists disclosed herein may provide chemoprevention. Chemoprevention is the practice of using of drugs, vitamins, or nutritional supplements to reduce the risk of developing, or having a recurrence of cancer. Oral iloprost (Ventavis), an analogue of prostacyclin, shows promise as a chemopreventive agent for lung cancer. Data supporting IP receptor agonist chemoprevention was presented by Paul Bunn Jr. MD, who is the executive Director of the International Association for the Study of Lung Cancer at the American Association for Cancer Research 102nd Annual Meeting showed that it significantly improved endobronchial dysplasia in former smokers.

PGI2 agonist, including the compounds of formula I, Ia, II or IIa, are also useful as co-therapeutic agents for use in combination with second agents, such as organic nitrates and NO-donors, such as sodium nitroprusside, nitroglycerin, isosorbide mononitrate, isosorbide dinitrate, molsidomine or SIN-1, and inhalational NO; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors such as sildenafil, vardenafil and tadalafil; NO-independent, but haem-dependent stimulators of guanylate cyclase, such as in particular the compounds described in WO 00/06568, WO 00/06569, WO 02/42301 and WO 03/095451; NO- and haem-independent activators of guanylate cyclase, such as in particular the compounds described in WO 01/19355, WO 01/19776, WO 01/19778, WO 01/19780, WO 02/070462 and WO 02/070510; compounds which inhibit human neutrophilic elastase, such as sivelestat or DX-890 (Reltran); compounds inhibiting the signal transduction cascade, such as tyrosine kinase and/or serine/threonine kinase inhibitors, in particular imatinib, gefitinib, erlotinib, sorafenib and sunitinib; compounds influencing the energy metabolism of the heart, for example and preferably etomoxir, dichloroacetate, ranolazine or trimetazidine; anti-thrombotic agents, for example and preferably from the group comprising platelet aggregation inhibitors, anticoagulants or profibrinolytic substances; active substances for lowering blood pressure, for example and preferably from the group comprising calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists, Rho-kinase inhibitors and diuretics; and/or active substances that modify lipid metabolism, for example and preferably from the group comprising thyroid receptor agonists, inhibitors of cholesterol synthesis, for example and preferably HMG-CoA-reductase inhibitors or inhibitors of squalene synthesis, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid absorbers, bile acid reabsorption inhibitors and lipoprotein(a) antagonists, particularly in the treatment of PAH or diseases and disorders such as those mentioned hereinbefore, e.g., as potentiators of therapeutic activity of such drugs or as a means of reducing required dosaging or potential side effects of such drugs.

In particular, an embodiment of this invention is a pharmaceutical combination comprising the compounds of Formula I, Ia, II or IIa or pharmaceutical salts thereof and a second agent wherein the second agent is a PDEV inhibitor or neutral endopeptidase inhibitor.

The compounds of Formula I, Ia, II or IIa or pharmaceutical salts thereof may be mixed with a second agent in a fixed pharmaceutical composition or it may be administered separately, before, simultaneously with or after the other drug substance.

Accordingly, the invention includes as a further aspect a combination of an IP receptor activity with osmotic agents (hypertonic saline, dextran, mannitol, Xylitol), ENaC blockers, an anti-inflammatory, bronchodilatory, antihistamine, anti-tussive, antibiotic and/or DNase drug substance, wherein the IP receptor agonist and the further drug substance may be in the same or different pharmaceutical composition.

Suitable antibiotics include macrolide antibiotics, e.g., tobramycin (TOBI™).

Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Other useful combinations of IP receptor agonist with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-amin-ium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, for example corticosteroids. Suitable steroids include budesonide, beclomethasone (e.g. dipropionate), butixocort (e.g. propionate), CHF5188, ciclesonide, dexamethasone, flunisolide, fluticasone (e.g. propionate or furoate), GSK-685698, GSK-870086, LAS40369, methyl prednisolone, mometasone (e.g. furoate), prednisolone, rofleponide, and triamcinolone (e.g. acetonide). In certain preferred embodiments the steroid is long-acting corticosteroids such as budesonide, ciclesonide, fluticasone or mometasone.

Suitable second active ingredients include $\beta_2$-agonists. Suitable $\beta_2$-agonists include aformoterol (e.g. tartrate), albuterol/salbutamol (e.g. racemate or single enantiomer such as the R-enantiomer, or salt thereof especially sulfate), AZD3199, bambuterol, BI-171800, bitolterol (e.g. mesylate), carmoterol, clenbuterol, etanterol, fenoterol (e.g. racemate or single enantiomer such as the R-enantiomer, or salt thereof especially hydrobromide), flerobuterol, formoterol (e.g. racemate or single diastereomer such as the R,R-diastereomer, or salt thereof especially fumarate or fumarate dihydrate), GSK-159802, GSK-597901, GSK-678007, indacaterol (e.g. racemate or single enantiomer such as the R-enantiomer, or salt thereof especially maleate, acetate or xinafoate), LAS100977, metaproterenol, milveterol (e.g. hydrochloride), naminterol, olodaterol (e.g. racemate or single enantiomer such as the R-enantiomer, or salt thereof especially hydrochloride), PF-610355, pirbuterol (e.g. acetate), procaterol, reproterol, salmefamol, salmeterol (e.g. racemate or single enantiomer such as the R-enantiomer, or salt thereof especially xinafoate), terbutaline (e.g. sulphate) and vilanterol (or a salt thereof especially trifenatate. In certain preferred embodiments the $\beta_2$-agonist is an ultra-long-acting $\beta_2$-agonist such as indacaterol, or potentially carmoterol, LAS-100977, milveterol, olodaterol, PF-610355 or vilanterol. A preferred embodiment one of the second active ingredients is indacaterol (i.e. (R)-5-[2-(5,6-diethyl-indan-2-ylamino)-1-hydroxyethyl]-8-hydroxy-1H-quinolin-2-one) or a salt thereof. This is a $\beta_2$-adrenoceptor agonist that has an especially long duration of action (i.e. over 24 hours) and a short onset of action (i.e. about 10 minutes). This compound is prepared by the processes described in international patent applications WO 2000/75114 and WO 2005/123684. It is capable of forming acid addition salts, particularly pharmaceutically acceptable acid addition salts. A preferred salt of (R)-5-[2-(5,6-diethyl-indan-2-ylamino)-1-hydroxyethyl]-8-hydroxy-1H-quinolin-2-one is the maleate salt. Another preferred salt is (R)-5-[2-(5,6-diethyl-indan-2-ylamino)-1-hydroxyethyl]-8-hydroxy-1H-quinolin-2-one acetate. Another preferred salt is (R)-5-[2-(5,6-diethyl-indan-2-ylamino)-1-hydroxyethyl]-8-hydroxy-1H-quinolin-2-one xinafoate.

Suitable bronchodilatory drugs include anticholinergic or antimuscarinic agents, such as aclidinium (e.g. bromide), BEA-2108 (e.g. bromide), BEA-2180 (e.g. bromide), CHF-5407, darifenacin (e.g. bromide), darotropium (e.g. bromide), glycopyrrolate (e.g. racemate or single enantiomer, or salt thereof especially bromide), dexpirronium (e.g. bromide), iGSK-202405, GSK-203423, GSK-573719, GSK-656398, ipratropium (e.g. bromide), LAS35201, LAS186368, otilonium (e.g. bromide), oxitropium (e.g. bromide), oxybutynin, PF-3715455, PF-3635659, pirenzepine, revatropate (e.g. hydrobromide), solifenacin (e.g. succinate), SVT-40776, TD-4208, terodiline, tiotropium (e.g. bromide), tolterodine (e.g. tartrate), and trospium (e.g. chloride). In certain preferred embodiments the muscarinic antagonists is long-acting muscarinic antagonist such as darotropium bromide, glycopyrrolate or tiotropium bromide.

Suitable dual anti-inflammatory and bronchodilatory drugs include dual beta-2 adrenoceptor agonist/muscarinic antagonists such as GSK-961081 (e.g. succinate). and those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

Accordingly, the invention includes as a further aspect a combination of IP receptor agonist with agents that inhibit ALK5 and/or ALK4 phosphorylation of Smad2 and Smad3.

Accordingly, the invention includes as a further aspect a combination of IP receptor agonist with second agents that are Rho-kinase inhibitors.

Accordingly, the invention includes as a further aspect a combination of IP receptor agonist with second agents that are tryptophan hydroylase 1 (TPH1) inhibitors.

Accordingly, the invention includes as a further aspect a combination of IP receptor agonist with second agents that are multi-kinase inhibitors, such as imatinib mysilate, Gleevec. Imatinib functions as a specific inhibitor of a number of tyrosine kinase enzymes. It occupies the TK active site, leading to a decrease in activity. TK enzymes in the body include the insulin receptor. Imatinib is specific for the TK domain in the Abelson proto-oncogene, c-kit and PDGF-R (platelet-derived growth factor receptor).

In an embodiment of this invention, the IP receptor agonist of this invention are dosed in combination with a second active agent selected from phosphodiesterase V inhibitors, neutral endopeptidase 1 inhibitors, THP1 inhibitors, multi-kinase inhibitors, endothelin antagonist, diuretic, aldosterone receptor blocker, and endothelin receptor blocker.

In an embodiment of this invention, the IP receptor agonist of this invention are dosed in combination with a second active agent selected from phosphodiesterase V inhibitors, neutral endopeptidase 1 inhibitors, THP1 inhibitors, and multi-kinase inhibitors, such as PDGFR or c-Kit.

In another aspect the invention provides a compound of formula I, Ia, II or IIa, in free form or in the form of a pharmaceutically acceptable salt, for use in the manufacture of a medicament for the treatment of a condition responsive to IP receptor agonist activity, particularly in PAH.

The agents of the invention may be administered by any appropriate route, e.g. orally, e.g., in the form of a tablet or capsule; parenterally, e.g., intravenously; by inhalation, e.g., in the treatment of an obstructive airways disease; intranasally, e.g., in the treatment of allergic rhinitis; topically to the skin; or rectally. In a further aspect, the invention also provides a pharmaceutical composition comprising a compound of formula I, Ia, II or IIa, in free form or in the form of a pharmaceutically acceptable salt, optionally together with a pharmaceutically acceptable diluent or carrier therefor. The composition may contain a co-therapeutic agent, such as an anti-inflammatory, broncho-dilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, e.g., the compound of Formula I, Ia, II or IIa or pharmaceutical salts thereof having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulized formulation, it preferably contains, e.g., the compound of Formula I, Ia, II or IIa or pharmaceutical salts thereof either dissolved, or suspended, in a vehicle containing water, a co-solvent, such as ethanol or propylene glycol and a stabilizer, which may be a surfactant.

Further aspects of the invention include:
(a) a compound of Formula I, Ia, II or IIa or pharmaceutical salts thereof in inhalable form, e.g., in an aerosol or other atomisable composition or in inhalable particulate, e.g., micronised form;
(b) an inhalable medicament comprising a compound of Formula I, Ia, II or IIa or pharmaceutical salts thereof in inhalable form;
(c) a pharmaceutical product comprising a compound of formula (I) in inhalable form in association with an inhalation device; and
(d) an inhalation device containing a compound of Formula I, Ia, II or IIa or pharmaceutical salts thereof in inhalable form.

Dosages of compounds of Formula I, Ia, II or IIa or pharmaceutical salts thereof employed in practicing the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

Pharmaceutical Use and Assay

Compounds of and their pharmaceutically acceptable salts, hereinafter referred to alternatively as "agents of the invention", are useful as pharmaceuticals. In particular, the compounds are suitable IP receptor agonist and may be tested in the following assays.

Activity of compounds at the IP receptor (IP receptor) is assessed by measuring cAMP accumulation in CHO cells stably expressing the IP receptor (CHO-IP) using the PerkinElmer AlphaScreen assay. This technology measures the endogenous production of cAMP, in a non-radioactive luminescence proximity homogenous assay. A biological reaction occurs between streptavidin coated donor beads, biotinylated cAMP and anti-cAMP acceptor beads, bringing the donor and acceptor beads close enough together so that upon excitation a fluorescence signal is produced. On production of endogenous cAMP, competition between the biotinylated cAMP and cellular-derived cAMP causes a reduction in the fluorescent signal. The reduction in signal is proportional to the amount of cAMP being produced, thus it is possible to quantify the amount of cAMP being produced on stimulation with agonist.

Test and reference compounds are prepared at 100×[final] in 100% DMSO, and diluted 1:3 using a Biomek Fx (Beckman Coulter). This is followed by an intermediate dilution to give 5×[final] in assay buffer (HBSS containing 5 mM HEPES, 0.1% (w/v) BSA). 5 µL of 5×[final] test compounds, reference compounds and buffer/DMSO control are then transferred to a 384-well white OptiPlate, containing 20 µL CHO-IP cell suspension (15,000 cells/well, prepared from frozen), and plate is incubated at room temperature for 1 hour. A cAMP standard curve is constructed for each experiment (concentration range of 10000 nM to 0.001 nM, in assay buffer) and 25 µL of each concentration added to the last two columns of the assay plate. The incubation is terminated by the addition of lysis buffer (dH$_2$O; 0.3% (v v$^{-1}$) Tween-20) containing 20 units mL$^{-1}$ streptavidin coated donor beads and biotinylated cAMP (pre-incubated for 30 minutes) and 20 units mL$^{-1}$ anti-cAMP acceptor beads, which are added to the lysis buffer just before addition to the assay plate. The assay plate is then incubated at room temperature in the dark, for 60 minutes with gentle shaking, and read on the Envision plate reader (Perkin Elmer).

The raw data of the reference compounds, test compounds and controls are converted into cAMP concentrations, using the cAMP standard curve, in GraphPadPrism (GraphPad Software Inc). EC$_{50}$ as well as maximal values of the agonist curves are determined using a 4-parameter logistic equation. The % maximum response values of all test compounds are determined using the top of the treprostinil concentration-response curve.

Compounds of the Examples, herein below, generally have EC$_{50}$ values in the data measurements described above below 5 µM. Table 1 provides a list of representative compounds with their EC$_{50}$ value.

TABLE 1

| Example | EC$_{50}$/μM |
|---|---|
| 1.1 | 0.0055 |
| 2.1 | 0.03 |
| 2.2 | 0.1 |
| 3.1 | 0.036 |
| 3.2 | 0.245 |
| 4.1 | 0.0012 |
| 4.3 | 0.00011 |
| 4.14 | 0.00013 |
| 4.15 | 0.00048 |
| 5.2 | 0.00008 |
| 6.1 | 0.00032 |
| 8.2a | 0.00049 |
| 8.2b | 0.00089 |
| 9.1 | 0.0056 |
| 9.2 | 0.0086 |
| 9.8 | 0.000296 |
| 9.8a | 0.0004 |
| 9.8b | 0.0018 |
| 12.1 | 0.0000754 |
| 14.1 | 0.0000718 |
| 14.2 | 0.0000627 |
| 15.1 | 0.057 |
| 16.1 | 0.00074 |
| 17.1a | 0.003 |
| 17.1b | 0.0048 |

Compounds listed below are within the scope of the broadest claim; however, the EC$_K$ values in the data measurements described above were above 10 μM:

ethyl 6-(2,3-bis(4-propylphenyl)-7,8-dihydropyrido[2,3-b]pyrazin-5(6H)-yl)hexanoate;

ethyl 7-(2-(m-tolyl)-3-(p-tolyl)-7,8-dihydropyrido[2,3-b]pyrazin-5(6H)-yl)heptanoate; and 5-(6,7-diphenyl-3,4-dihydro-1,8-naphthyridin-1(2H)-yl)pentanoic acid.

The invention is illustrated by the following Examples.

EXAMPLES

General Conditions

Mass spectra were run on LCMS systems using electrospray ionization. These were either Agilent 1100 HPLC/Micromass Platform Mass Spectrometer combinations or Waters Acquity UPLC with SQD Mass Spectrometer. [M+H]$^+$ refers to mono-isotopic molecular weights.

NMR spectra were run on open access Bruker AVANCE 400 NMR spectrometers using ICON-NMR. Spectra were measured at 298K and were referenced using the solvent peak.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

Abbreviations:

| | |
|---|---|
| AcOH | acetic acid |
| br | broad |
| d | doublet |
| DBU | 1,8-diazabicyclo[5.4.0]undec-7-ene |
| DCM | dichloromethane |
| DCE | 1,2-dichloroethane |
| DIPEA | Diisopropylethylamine |
| DMF | N,N-dimethylformamide |
| DMI | 1,3-dimethyl-2-imidazolidinone |
| DMSO | dimethylsulfoxide |
| DSC | differential scanning calorimetry |
| EDCI | 1-ethyl-3-(3'-dimethylaminopropyl) carbodiimide |
| Et$_2$O | diethyl ether |
| EtOAc | ethyl acetate |
| EtOH | ethanol |
| h | hour(s) |
| Grubbs Catalyst 2nd generation | (1,3-bis(2,4,6-trimethylphenyl)-2-imidazolidinylidene)dichloro(phenylmethylene)(tricyclohexylphosphine)ruthenium, Benzylidene[1,3-bis(2,4,6-trimethylphenyl)-2-imidazolidinylidene]dichloro(tricyclohexylphosphine)ruthenium, [1,3-Bis-(2,4,6-trimethylphenyl)-2-imidazolidinylidene]dichloro(phenylmethylene)(tricyclohexylphosphine)ruthenium |
| HPLC | high pressure liquid chromatography |
| LC-MS | liquid chromatography and mass spectrometry |
| MeOH | methanol |
| MeCN | acetonitrile |
| MS | mass spectrometry |
| m | multiplet |
| min | minutes |
| ml | milliliter(s) |
| m/z | mass to charge ratio |
| obs | obscured |
| NBS | N-bromosuccinamide |
| NMR | nuclear magnetic resonance |
| NMP | 1-Methyl-2-pyrrolidone |
| PEPPSi-iPr | Pyridine-Enhanced Precatalyst Preparation Stabilization and Initiation- 2,6-diisopropylphenyllimidazolium chloride |
| ppm | parts per million |
| PS | polymer supported |
| PEAX | PE-anion exchange (e.g. Isolute ® PE-AX columns from |
| Pd(Ph$_3$P)$_4$ | tetrakis(triphenylphosphine)palladium(0) |
| PdCl$_2$(dppf) | [1,1-Bis(diphenylphosphino)ferrocene]dichloropalladium(II) |
| Rt | retention time |
| RT | room temperature |
| s | singlet |
| sat. | saturated |
| SFC | Supercritical Fluid Chromatography |
| SCX-2 | strong cation exchange (e.g. Isolute ® SCX-2 columns from Biotage) |
| t | triplet |
| TBME | methyl-tert-butyl ether |
| THF | tetrahydrofuran |

Referring to the examples that follow, compounds of the preferred embodiments were synthesized using the methods described herein, or other methods, which are known in the art. The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

If not indicated otherwise, the analytical HPLC conditions are as follows:

Method 2minLC_v001

| | |
|---|---|
| Column | Waters BEH C18 100 × 2.1 mm, 1.7 μm |
| Column Temp. | 50° C. |
| Eluents | A: $H_2O$, B: acetonitrile, both containing 0.1% TFA |
| Flow Rate | 0.7 ml/min |
| Gradient | 0.25 min 5% B; 5% to 95% B in 1.00 min, 0.25 min 95% B |

Method 2minLC_v002

| | |
|---|---|
| Column | Waters BEH C18 50 × 2.1 mm, 1.7 μm |
| Column Temperature | 50° C. |
| Eluents | A: $H_2O$, B: methanol, both containing 0.1% TFA |
| Flow Rate | 0.8 ml/min |
| Gradient | 0.20 min 5% B; 5% to 95% B in 1.30 min, 0.25 min 95% B |

Method 2minLC_v003

| | |
|---|---|
| Column | Waters BEH C18 50 × 2.1 mm, 1.7 μm |
| Column Temperature | 50° C. |
| Eluents | A: $H_2O$, B: acetonitrile, both containing 0.1% TFA |
| Flow Rate | 0.8 ml/min |
| Gradient | 0.20 min 5% B; 5% to 95% B in 1.30 min, 0.25 min 95% B |

Method LowpH_30_v001

| | |
|---|---|
| Column | Phenomenex Gemini C18 50 × 4.6 mm, 3.0 μm |
| Column Temperature | 40° C. |
| Eluents | A: $H_2O$, B: acetonitrile, both containing 0.1% TFA |
| Flow Rate | 1.2 ml/min |
| Gradient | 30% to 95% B in 2.0 min, 0.2 min 95% B |

Method 2minLC_30_v003

| | |
|---|---|
| Column | Waters BEH C18 50 × 2.1 mm, 1.7 μm |
| Column Temperature | 50° C. |
| Eluents | A: $H_2O$, B: acetonitrile, both containing 0.1% TFA |
| Flow Rate | 0.8 ml/min |
| Gradient | 0.25 min 30% B; 30% to 95% B in 1.00 min, 0.25 min 95% B |

2minLowpH

| | |
|---|---|
| Column: | Waters Acquity CSH 17 μm, 2.1 × 50 mm |
| Temperature: | 50° C. |
| Mobile Phase: | A: Water +0.1% Formic Acid B: Acetonitrile + 0.1% Formic Acid |
| Flow rate: | 1.0 mL/min |
| Gradient: | 0.0 min 5% B, 0.2-1.3 min 5-98% B, 1.3-1.55 min 98% B, 1.55-1.6 min 98-5% B |

Method 10minLC_v003

| | |
|---|---|
| Column | Waters BEH C18 50 × 2.1 mm, 1.7 μm |
| Column Temperature | 50° C. |
| Eluents | A: $H_2O$, B: acetonitrile, both containing 0.1% TFA |
| Flow Rate | 0.8 ml/min |
| Gradient | 0.20 min 5% B; 5% to 95% B in 7.80 min, 1.00 min 95% B |

Method A

| | |
|---|---|
| Column: | HSS T3 1.8 um 2.1 × 50 mm |
| Column Temperature: | 50° C. |
| Eluents: | A: $H_2O$ + 0.05% formic acid + 3.75 mM ammonium acetate, B: acetonitrile + 0.04% formic acid |
| Flow rate: | 1.2 ml/min |
| Gradient: | 0.0 min 2% B, 2-98% B in 1.40 min, 1.40 min-2.15 min 98% B |

Method OJ20MeOH

| | |
|---|---|
| Column: | Chiralcel OJ-H 250 × 10 mm, 5 um |
| Mobile phase: | 20% methanol/80% CO2 |
| Flow: | 10 ml/min |
| Detection: | UV @ 220 nm |

Method AS25IPA

| | |
|---|---|
| Column: | Chirapak AS-H 250 × 1 0 mm, 5 um |
| Mobile phase: | 25% IPA/75% CO2 |
| Flow: | 10 ml/min |
| Detection: | UV @ 220 nm |

Method AD40IPA

| | |
|---|---|
| Column | Chirapak AD-H 250 × 10 mm i.d., 5 um |
| Mobile phase: | 10% methanol/90% CO2 |
| Flow Rate | 10 ml/min |
| Detection: | UV @ 220 nm |

Method B

| | |
|---|---|
| Column | Zorbax Eclipse XDB-C18 4.6 × 50 mm, 1.8 um |
| Column Temperature | 35° C. |
| Eluents | A: $H_2O$ + 0.1% TFA, B: acetonitrile + 0.1% TFA |
| Flow Rate | 1 ml/min |
| Gradient | 5-100% MeCN (6 min), 100 MeCN (1.5 min), 100-5% MeCN (0.5 min) |

Method C

| | |
|---|---|
| Column: | Chiralcel OJ-H 250 × 10 mm, 5 um |
| Mobile phase: | 15% methanol/85% CO2 |
| Flow: | 10 ml/min |
| Detection: | UV @ 220 nm |

Example compounds of the present invention include:

Preparation of Final Compounds

Example 1.1

7-(6,7-Diphenyl-3,4-dihydro-1,8-naphthyridin-1(2H)-yl)heptanoic acid

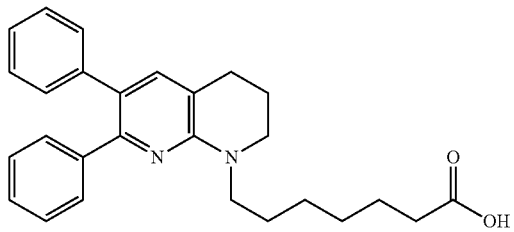 [SMILES: O=C(O)CCCCCCN1CCCc2cc(-c3ccccc3)c(-c3ccccc3)nc21]

Step 1: Ethyl 7-(6,7-diphenyl-3,4-dihydro-1,8-naphthyridin-1(2H)-yl)heptanoate

A solution of 6,7-diphenyl-1,2,3,4-tetrahydro-[1,8]naphthyridine (Intermediate B) (200 mg, 0.698 mmol) in dry NMP (1 ml) under $N_2$ was treated with cesium carbonate (910 mg, 2.79 mmol) and ethyl 7-bromoheptanoate (0.544 ml, 2.79 mmol). The reaction mixture was stirred at 120° C. for 1 h and a further 3 h at 140° C. After cooling to room temperature, the mixture was partitioned between EtOAc and water. The organic portion was washed with brine, dried over $MgSO_4$, filtered and concentrated in vacuo. Purification of the crude product by chromatography on silica eluting with 4:1 iso-hexane/EtOAc afforded a pink oil residue.

The residue was loaded onto an Isolute™ SCX-2 cartridge and eluted with MeOH followed by 2M $NH_3$ in MeOH. The methanolic ammonia fractions were concentrated in vacuo and dried under vacuum at 40° C. to afford the title compound as a colourless oil.

LC-MS Rt=1.54 mins; $[M+H]^+$443.4, Method 2min-LC_v001.

$^1$H NMR (400 MHz, DMSO-d6) δ 7.3 (9H, m), 7.0 (2H, m), 4.0 (2H, q), 3.6 (2H, m), 3.4 (2H, m), 2.75 (2H, m), 2.2 (2H, t), 1.9 (2H, m), 1.6 (2H, m), 1.45 (2H, m), 1.3 (4H, m), 1.1 (3H, t).

Step 2: 7-(6,7-diphenyl-3,4-dihydro-1,8-naphthyridin-1(2H)-yl)heptanoic acid

A solution of Ethyl 7-(6,7-diphenyl-3,4-dihydro-1,8-naphthyridin-1(2H)-yl)heptanoate (step 1) (100 mg, 0.226 mmol) and lithium hydroxide (37.9 mg, 0.904 mmol) in THF (2 ml) was heated at 75° C. for 6 h. The reaction was quenched with water and the pH was adjusted to pH 3-4 by addition of 1M HCl. The mixture was partitioned between EtOAc and water. The organic portion was separated and washed with brine, dried over $MgSO_4$, filtered and concentrated in vacuo. Purification of the crude product by chromatography on silica eluting with 3:2 iso-hexane/EtOAc afforded the title compound.

LC-MS Rt=1.98 mins; $[M+H]^+$ 415.5, Method LowpH_30_v001.

$^1$H NMR (400 MHz, DMSO-d6) δ 12.03 (1H, br s), 7.2 (9H, m), 7.05 (2H, m), 3.6 (2H, t), 3.4 (2H, m), 2.8 (2H, m), 2.15 (2H, t), 1.9 (2H, m), 1.6 (2H, m), 1.4 (2H, m), 1.3 (4H, m).

The compounds of the following tabulated Examples (Table 2) were prepared by a similar method to that of Example 1.1 by replacing ethyl 7-bromoheptanoate with the appropriate bromoester.

TABLE 2

| Ex. | Structure | Name | $[M + H]^+$/NMR |
|---|---|---|---|
| 1.2 | 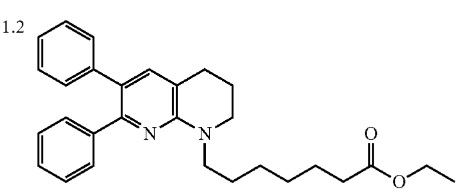 | Ethyl 7-(6,7-diphenyl-3,4-dihydro-1,8-naphthyridin-1-(2H)-yl)heptanoate | Rt = 1.54 mins; $[M + H]^+$ 443.4, Method 2minLC_v002 $^1$H NMR (400 MHz, DMSO-d6) δ 7.3 (9H, m), 7.0 (2H, m), 4.0 (2H, q), 3.6 (2H, m), 3.4 (2H, m), 2.75 (2H, m), 2.2 (2H, t), 1.9 (2H, m), 1.6 (2H, m), 1.45 (2H, m), 1.3 (4H, m), 1.1 (3H, t) |
| 1.3 | 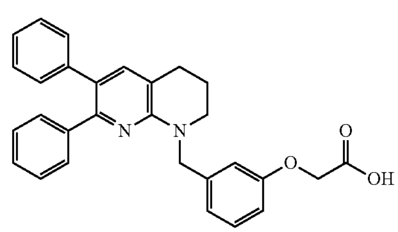 [SMILES: O=C(O)COc1cccc(CN2CCCc3cc(-c4ccccc4)c(-c4ccccc4)nc32)c1] | 2-(3-((6,7-Diphenyl-3,4-dihydro-1,8-naphthyridin-1(2H)-yl)methyl)phenoxy)acetic acid | Rt = 1.41 mins; $[M + H]^+$ 451.3, Method 2minLC_v002 $^1$H NMR (400 MHz, DMSO-d6) δ 13.02 (1H, br s), 7.3-7.2 (10H, m), 7.14 (2H, m), 6.96 (1H, m), 6.91 (1H, m), 6.83 (1H, m), 4.91 (2H, s), 4.71 (2H, s), 3.42 (2H, m), 2.88 (2H, m), 1.97 (2H, m). |

TABLE 2-continued

| Ex. | Structure | Name | [M + H]+/NMR |
|---|---|---|---|
| 1.4 | 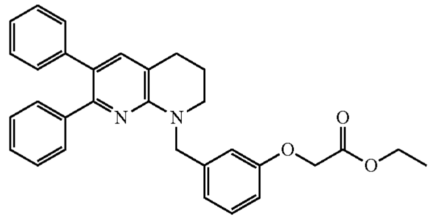 [SMILES: CCOC(=O)COc1cccc(CN2CCCc3cc(-c4ccccc4)c(-c4ccccc4)nc32)c1] | Ethyl 2-(3-((6,7-diphenyl-3,4-dihydro-1,8-naphthyridin-1(2H)-yl)methyl)phenoxy)acetate | Rt = 1.53 mins; [M + H]+ 479.3, Method 2minLC_v002 <br> 1H NMR (400 MHz, DMSO-d6) δ 7.35 (2H, m), 7.3-7.1 (10 H, m), 7.03 (2H, m), 6.8 (1H, m), 5.0 (2H, s), 4.56 (2H, s), 4.26 (2H, q), 3.41 (2H, m), 2.85 (2H, m), 2.02 (2H, m), 1.29 (3H, t). |
| 1.5 | 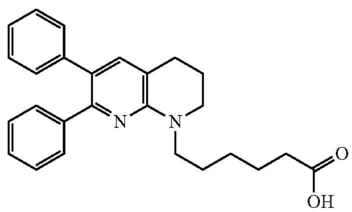 [SMILES: O=C(O)CCCCCN1CCCc2cc(-c3ccccc3)c(-c3ccccc3)nc21] | 6-(6,7-Diphenyl-3,4-dihydro-1,8-naphthyridin-1(2H)-yl)hexanoic acid | Rt = 1.01 mins; [M + H]+ 401, Method 2minLC_v001 <br> 1H NMR (400 MHz, DMSO-d6) δ 12.1 (1H, br s), 7.3 (9H, m), 7.1 (2H, d), 3.65 (2H, m), 3.45 (2H, m), 2.82 (2H, t), 2.25 (2H, t), 1.95 (2H, m), 1.65 (4H, m), 1.4 (2H, m). |

Example 2.1 and 2.2

Enantiomer 1 and Enantiomer 2 of 6-(1-Methyl-6,7-diphenyl-1,2,3,4-tetrahydro-1,8-naphthyridin-2-yl)hexanoic acid Step 1: 7-Chloro-2,3-diphenyl-1,8-naphthyridine POCl₃ (10 ml, 107 mmol) was added dropwise to a mixture of 6,7-diphenyl-1,8-naphthyridine 1-oxide and 2,3-diphenyl-1,8-naphthyridine 1-oxide (Intermediates C) (3 g, 10.06 mmol) at 0° C. The reaction mixture was allowed to warm at room temperature and heated at 100° C. for 2 h. The mixture was poured carefully onto ice/water and the pH was adjusted to pH 8-9 by addition of Na₂CO₃ (solid) portionwise. The aqueous layer was separated and extracted with DCM (3×150 ml). The organic portions were combined and washed with brine, dried over MgSO₄, filtered and concentrated in vacuo to afford a brown oil. Purification of the crude oil by chromatography on silica eluting with 0-50% EtOAc in iso-hexane afforded 7-chloro-2,3-diphenyl-1,8-naphthyridine and 5-chloro-2,3-diphenyl-1,8-naphthyridine:

7-Chloro-2,3-diphenyl-1,8-naphthyridine

Yellow Solid

LC-MS Rt=1.58 mins, [M+H]+317.1, Method 2minLC_v002
¹H NMR (400 MHz, DMSO-d₆) δ 8.63 (1H, d), 8.6 (1H, s), 7.78 (1H d), 7.28-7.7.43 (10H, m).

5-Chloro-2,3-diphenyl-1,8-naphthyridine

Beige Solid

LC-MS Rt=1.64 mins, [M+H]+317.1, Method 2minLC_v002
¹H NMR (400 MHz, DMSO-d6) δ 9.09 (1H, d), 8.52 (1H, s), 7.93 (1H, d), 7.37-7.5 (10H, m). 7-Chloro-2,3-diphenyl-1,8-naphthyridine, the desired product, was used in the next step.

Step 2: Ethyl 6-(6,7-diphenyl-1,8-naphthyridin-2-yl)hexanoate

A mixture comprising lithium bromide (307 mg, 3.54 mmol) and PEPPSi-iPr catalyst (75 mg, 0.110 mmol) in THF (2 ml) was stirred at room temperature for 15 minutes until a solution formed. (6-Ethoxy-6-oxohexyl)zinc(II) bromide (13.26 ml of a 0.5M solution in THF, 6.62 mmol) was added and the mixture was cooled to 0° C. A solution of 7-chloro-2,3-diphenyl-1,8-naphthyridine (step 1) (350 mg, 1.105 mmol) in THF (3 ml)/DMI (1 ml) was added and the resulting mixture was stirred at room temperature for 24 h. The reaction mixture was partitioned between EtOAc and water and the organic portion was washed with brine, dried over MgSO₄, filtered and concentrated in vacuo. Purification of the crude product by chromatography on silica eluting with 0-50% EtOAc in iso-hexane afforded the title product as a yellow oil; LC-MS Rt=1.54 mins; [M+H]+425.3, Method 2minLC_v002

Step 3: rac-Ethyl 6-(6,7-diphenyl-1,2,3,4-tetrahydro-1,8-naphthyridin-2-yl)hexanoate A stirred solution of ethyl 6-(6,7-diphenyl-1,8-naphthyridin-2-yl)hexanoate (step 2)(280 mg, 0.660 mmol) in EtOH (10 ml) under an atmosphere of argon was treated with 10% palladium on carbon (70.2 mg), purged three times with nitrogen and placed under an atmosphere of hydrogen overnight. The mixture was filtered through Celite® (filter material) and the catalyst was washed with EtOAc (100 ml). The filtrate was concentrated in vacuo to yield the title compound as an off white solid. Purification of the crude product by chromatography on silica eluting with 0-100% EtOAc in iso-hexane afforded the title compound as a yellow oil. LC-MS Rt=1.46 mins; [M+H]+429.3, Method 2minLC_v002.
¹H NMR (400 MHz, DMSO-d6) δ 7.25-7.15 (9H, m), 7.04 (2H, m), 6.54 (1H, s, NH), 4.04 (2H, q), 3.36 (1H, m), 2.74 (2H, m), 2.29 (2H, t), 1.99 (1H, m), 1.57 (4H, m), 1.3-1.4 (5H, m), 1.17 (3H, t)

Step 4: Enantiomer 1 and Enantiomer 2 of Methyl 6-(1-methyl-6,7-diphenyl-1,2,3,4-tetrahydro-1,8-naphthyridin-2-yl)hexanoate A suspension of sodium hydride (61.1 mg of a 60% mixture in mineral oil, 1.528 mmol) in dry DMF (5 ml) under N₂ was treated with a solution of rac-ethyl 6-(6,7-diphenyl-1,2,3,4-tetrahydro-1,8-naphthyridin-2-yl)hexanoate (step 3) (131 mg, 0.306 mmol) in DMF (5 ml). After 30 mins at room temperature iodomethane (0.096 ml, 1.528 mmol) was added and stirring continued for 5 h. The mixture was partitioned between DCM (50 ml) and water (50 ml) and the aqueous portion was separated and extracted with DCM (3×). The combined organic extracts were washed with brine, dried over MgSO$_4$, filtered and concentrated in vacuo. Purification of the crude product by chromatography on silica eluting with 0-30% EtOAc in iso-hexane afforded a mixture of the title products as a colourless oil;

LC-MS Rt=1.43 mins; [M+H]$^+$429.3, Method 2min-LC_v002.

$^1$H NMR (400 MHz, DMSO-d6) δ 7.2-7.3 (9H, m), 7.04 (2H, m), 3.6 (3H, s), 3.43 (1H, m), 3.12 (3H, s), 2.75 (2H, m), 2.31 (2H, t), 1.92 (1H, m), 1.81 (1H, m), 1.63 (1H, m), 1.52 (2H, m), 1.4-1.5 (5H, m).

Chiral separation of the mixture using Supercritical Fluid Chromatography afforded the individual enantiomers:

| | |
|---|---|
| Column: | Chiralcel OJ-H, 250 × 10 mm i.d., 5 μm |
| Injection Volume: | 100 μL |
| Column Loading: | 5.9 mg/injection |
| Mobile Phases | CO$_2$: MeOH (as modifier) |
| Detection: | UV 220 nm |
| Flow rate: | 10 ml/min |

First Eluted Peak; R.t=6.89 mins Enantiomer 1 of Methyl 6-(1-methyl-6,7-diphenyl-1,2,3,4-tetrahydro-1,8-naphthyridin-2-yl)hexanoate

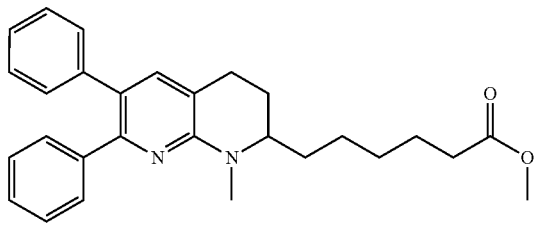 [SMILES: COC(=O)CCCCCC1CCc2cc(-c3ccccc3)c(-c3ccccc3)nc2N1C]

LC-MS Rt=1.43 mins; [M+H]$^+$429.3, Method 2min-LC_v002.

$^1$H NMR (400 MHz, DMSO-d6) δ 7.27 (2H, m), 7.23 (7H, m), 7.18 (2H, m), 3.58 (3H, s), 3.44 (1H, m), 3.12 (3H, s), 2.73 (2H, m), 2.31 (2H, t), 1.92 (1H, m), 1.78 (1H, m), 1.68 (1H, m), 1.56 (2H, m), 1.34 (5H, m)

Second Eluted Peak; Rt=8.72 Mins Enantiomer 2 of Methyl 6-(1-methyl-6,7-diphenyl-1,2,3,4-tetrahydro-1,8-naphthyridin-2-yl)hexanoate

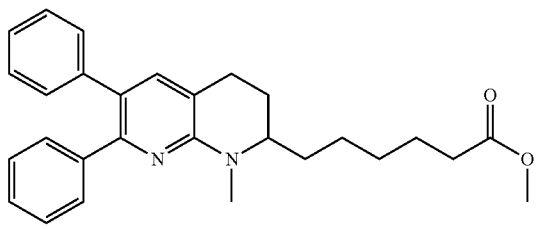 [SMILES: COC(=O)CCCCCC1CCc2cc(-c3ccccc3)c(-c3ccccc3)nc2N1C]

LC-MS Rt=1.43 mins; [M+H]$^+$429.3, Method 2min-LC_v002.

$^1$H NMR (400 MHz, DMSO-d6) δ 7.27 (2H, m), 7.23 (7H, m), 7.09 (2H, m), 3.58 (3H, s), 3.44 (1H, m), 3.12 (3H, s), 2.73 (2H, m), 2.31 (2H, t), 1.92 (1H, m), 1.78 (1H, m), 1.68 (1H, m), 1.56 (2H, m), 1.34 (5H, m)

Step 5: Example 2.1—Enantiomer 1 of 6-(1-methyl-6,7-diphenyl-1,2,3,4-tetrahydro-1,8-naphthyridin-2-yl)hexanoic acid

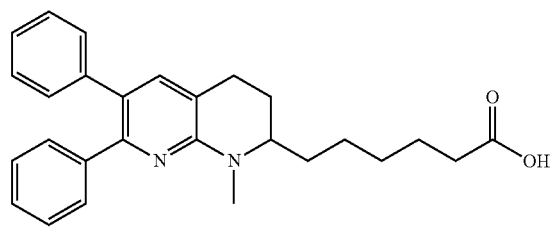 [SMILES: CN1c2nc(-c3ccccc3)c(-c3ccccc3)cc2CCC1CCCCCC(=O)O]

Enantiomer 2 of methyl 6-(1-methyl-6,7-diphenyl-1,2,3,4-tetrahydro-1,8-naphthyridin-2-yl)hexanoate (34 mg, 0.079 mmol) was dissolved in THF/water (2:1) and lithium hydroxide (9.99 mg, 0.238 mmol) was added. The reaction mixture was stirred vigorously at room temperature for 48 h and then diluted with water (20 ml). The pH was adjusted to pH 3-4 by addition of 2M HCl. The aqueous portion was extracted with DCM (3×30 ml) and the combined organic extracts were washed with brine, dried over MgSO$_4$, filtered and concentrated in vacuo to afford the title compound as a yellow oil;

LCMS Rt=1.36 mins, [M+H]$^+$415.3, Method 2min-LC_v002.

$^1$H NMR (400 MHz, DMSO-d6) δ 12.03 (1H, s), 7.35-7.2 (9H, m), 7.14 (2H, m), 3.51 (1H, m), 3.18 (3H, s), 2.8 (2H, m), 2.27 (2H, t), 2.01 (1H, m), 1.82 (1H, m), 1.72 (1H, m), 1.59 (2H, m), 1.4-1.5 (5H, m).

Example 2.2

Enantiomer 2 of 6-(1-methyl-6,7-diphenyl-1,2,3,4-tetrahydro-1,8-naphthyridin-2-yl)hexanoic acid was prepared analogously to Enantiomer 1 from the appropriate starting compound:

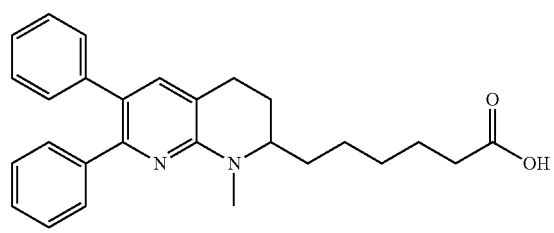 [SMILES: CN1c2nc(-c3ccccc3)c(-c3ccccc3)cc2CCC1CCCCCC(=O)O]

LCMS Rt=1.36 mins, [M+H]$^+$415.3, Method 2min-LC_v002.

$^1$H NMR (400 MHz, DMSO-d6) δ 12.03 (1H, s), 7.35-7.2 (9H, m), 7.14 (2H, m), 3.51 (1H, m), 3.18 (3H, s), 2.8 (2H, m), 2.27 (2H, t), 2.01 (1H, m), 1.82 (1H, m), 1.72 (1H, m), 1.59 (2H, m), 1.4-1.5 (5H, m).

The compounds of the following tabulated Examples (Table 3) were prepared by a similar method to that of Example 2.1 and 2.2 by replacing (6-ethoxy-6-oxohexyl)zinc (II) bromide with the appropriate organozinc derivative.

LC-MS Rt=1.33 mins; [M+H]$^+$297.2, Method 2min-LC_v002

TABLE 3

| Ex. | Structure | Name | [M + H]$^+$/NMR |
|---|---|---|---|
| 2.3 | 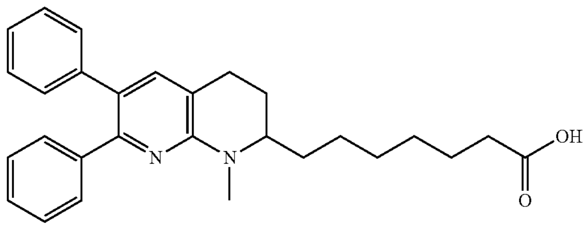 [SMILES: CN1c2nc(-c3ccccc3)c(-c3ccccc3)cc2CCC1CCCCCCC(=O)O] | Enantiomer 1 of 7-(1-Methyl-6,7-diphenyl-1,2,3,4-tetrahydro-[1,8]naphthyridin-2-yl)-heptanoic acid | Rt = 1.4 mins; [M + H]$^+$ 429.3, Method 2minLC.v002 $^1$H NMR (400 MHz, DMSO-d6) δ 7.46 (1H, m), 7.1-7.25 (10H, m), 3.42 (1H, m), 3.23 (3H, m), 2.82 (1H, m), 2.72 (1H, m), 2.36 (2H, m), 1.97 (2H, m), 1.73 (3H, m), 1.3-1.5 (7H, m) SFC Rt 3.32 mins; Method AD40IPA |
| 2.4 | 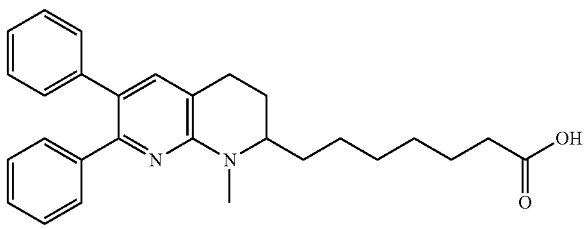 [SMILES: CN1c2nc(-c3ccccc3)c(-c3ccccc3)cc2CCC1CCCCCCC(=O)O] | Enantiomer 2 of 7-(1-Methyl-,67-diphenyl-1,2,3,4-tetrahydro-[1,8]naphthyridin-2-yl)-heptanoic acid | Rt = 1.4 mins; [M + H]$^+$ 429.3, Method 2minLC.v002 $^1$H NMR (400 MHz, DMSO-d6) δ 7.46 (1H, m), 7.1-7.25 (10H, m), 3.42 (1H, m), 3.23 (3H, m), 2.82 (1H, m), 2.72 (1H, m), 2.36 (2H, m), 1.97 (2H, m), 1.73 (3H, m), 1.3-1.5 (7H, m). SFC Rt 3.78 mins; Method AD40IPA |
| 2.5 | 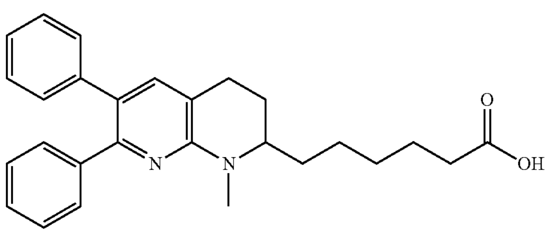 [SMILES: CN1c2nc(-c3ccccc3)c(-c3ccccc3)cc2CCC1CCCCCC(=O)O] | rac-6-(1-Methyl-6,7-diphenyl-1,2,3,4-tetrahydro-[1,8]naphthyridin-2-yl)-hexanoic acid | Rt = 1.38 mins; [M + H]$^+$ 415.3, Method 2minLC.v002 $^1$H NMR (400 MHz, DMSO-d6) δ 7.4 (9H, m), 7.14 (2H, m), 3.55 (2H, m), 3.17 (3H, s), 2.8 (2H, m), 2.07 (2H, m), 1.83 (1H, m), 1.71 (1H, m), 1.3-1.55 (7H, m). |

Example 3.1 and 3.2

Enantiomer 1 and Enantiomer 2 of 7-(2-methyl-6,7-diphenyl-3,4-dihydro-1,8-naphthyridin-1(2H)-yl) heptanoic acid Step 1: 7-Methyl-2,3-diphenyl-1,8-naphthyridine A cooled (0° C.) mixture of 6,7-diphenyl-1,8-naphthyridine 1-oxide and 2,3-diphenyl-1,8-naphthyridine 1-oxide (Intermediates C) (1 g, 3.35 mmol) in dry THF (10 ml) under an atmosphere of N$_2$ was treated dropwise with methylmagnesium chloride (1.676 ml, 5.03 mmol). The resulting mixture was stirred at room temperature for 45 minutes and then partitioned between EtOAc and water. The aqueous portion was extracted with EtOAc (2×100 ml) and the combined organic extracts were washed with brine, dried over MgSO$_4$, filtered and concentrated in vacuo. The crude residue was dissolved in acetic anhydride (5 ml) and heated at 120° C. for 10 mins using microwave radiation. The resulting mixture was partitioned between DCM (150 ml) and water. The organic portion was washed with brine, dried over MgSO$_4$, filtered and concentrated in vacuo. The crude product was loaded onto a Isolute™ SCX-2 cartridge and eluted with MeOH followed by 2M NH$_3$ in MeOH. The methanolic ammonia fractions were concentrated in vacuo to afford a brown oil which was purified by chromatography on silica eluting with 0-50% EtOAc in iso-hexane to afford the title product;

$^1$H NMR (400 MHz, DMSO-d6) δ 8.44 (1H, s), 8.41 (1H, d), 7.57 (1H, d), 7.42 (1H, m), 7.40 (1H, m), 7.33 (8H, m), 2.74 (3H, s).

Step 2: rac-2-Methyl-6,7-diphenyl-1,2,3,4-tetrahydro-1,8-naphthyridine

A stirred solution of 7-methyl-2,3-diphenyl-1,8-naphthyridine (step 1) (352 mg, 1.188 mmol) in ethanol (10 ml) at room temperature under an atmosphere of argon was treated with 10% palladium on carbon (126 mg). The reaction mixture was purged three times with nitrogen and placed under an atmosphere of hydrogen overnight. The mixture was filtered through Celite® (filter material) and the catalyst was washed with EtOAc (200 ml). The solvent was removed in vacuo to afford the title compound as a yellow foam.

LC-MS Rt=1.32 mins; [M+H]$^+$301.2, Method 2min-LC_v002

$^1$H NMR (400 MHz, DMSO-d6) δ 7.4-7.3 (9H, m), 7.12 (2H, m), 6.66 (1H, s), 3.57 (1H, m), 2.81 (2H, m), 1.98 (1H, m), 1.54 (1H, m), 1.25 (3H, d).

Step 3: Enantiomer 1 and Enantiomer 2 of Ethyl 7-(2-methyl-6,7-diphenyl-3,4-dihydro-1,8-naphthyridin-1(2H)-yl)heptanoate To a microwave vial was added 2-methyl-6,7-diphenyl-1,2,3,4-tetrahydro-1,8-naphthyridine (step 2) (345 mg, 1.148 mmol) in NMP (1 ml) followed by ethyl 7-bromoheptanoate (0.671 ml, 3.45 mmol) and cesium carbonate (748 mg, 2.297 mmol). The resulting mixture was heated using microwave radiation at 160° C. for 2 h. Ethyl-7-bromoheptanoate (0.671 ml, 3.45 mmol) was added and heating continued for a further 2 h. The reaction mixture was partitioned between EtOAc and water and the organic portion was washed with brine, dried over $MgSO_4$, filtered and concentrated in vacuo. Purification of the crude product by chromatography on silica eluting with 0-20% EtOAc in iso-hexane afforded a yellow oil which was loaded onto a Isolute™ SCX-2 cartridge and eluted with MeOH followed by 2M $NH_3$ in MeOH. The methanolic ammonia fractions were concentrated in vacuo to afford racemate ethyl 7-(2-methyl-6,7-diphenyl-3,4-dihydro-1,8-naphthyridin-1(2H)-yl)heptanoate. Chiral separation of the mixture using Supercritical Fluid Chromatography afforded the individual enantiomers.

Preparative Chromatography Conditions:

| | |
|---|---|
| Instrumentation: | Gilson Prep HPLC system |
| Injection volume: | 4 ml |
| Mobile phase: | Heptane/2-methyl-2-butanol (98.5:1.5) |
| Flow rate: | 7 ml/min |
| Column: | Chiralpak IC 5 um 1 × 20 × 250 mm + 1 × 30 × 250 mm |
| Detection UV: | 220 nm |

Analytical Conditions:

| | |
|---|---|
| Instrumentation: | Shimadzu Prominence |
| Injection volume: | 15 μl |
| Mobile phase: | Heptane/2-methyl-2-butanol (98.5:1.5) |
| Flow rate: | 0.500 ml/min |
| Column: | Chiralpak IC 5 um 4.6 × 250 mm |
| Detection UV: | 220 nm |

First Eluted Peak; Rt=22.827 mins: Enantiomer 1 of Ethyl 7-(2-methyl-6,7-diphenyl-3,4-dihydro-1,8-naphthyridin-1(2H)-yl)heptanoate LC-MS Rt=1.49 mins; $[M+H]^+$457.5, Method 2min-LC_v002
$^1$H NMR (400 MHz, DMSO-d6) δ 7.21-7.18 (9H, m), 7.08 (2H, m), 4.02 (2H, m), 3.94 (1H, m), 3.68 (1H, m), 3.16 (1H, m), 2.82 (1H, m), 2.70 (1H, m), 2.22 (2H, m), 1.80 (2H, m), 1.72 (2H, m), 1.51 (2H, m), 1.31 (4H, m), 1.24 (6H, m).

Second Eluted Peak. (Rt=25.184 mins): Enantiomer 2 of Ethyl 7-(2-methyl-6,7-diphenyl-3,4-dihydro-1,8-naphthyridin-1(2H)-yl)heptanoate LC-MS Rt=1.49 mins; $[M+H]^+$457.5, Method 2min-LC_v002
1H NMR (400 MHz, DMSO-d6) δ 7.21-7.18 (9H, m), 7.08 (2H, m), 4.02 (2H, m), 3.94 (1H, m), 3.68 (1H, m), 3.16 (1H, m), 2.82 (1H, m), 2.70 (1H, m), 2.22 (2H, m), 1.80 (2H, m), 1.72 (2H, m), 1.51 (2H, m), 1.31 (4H, m), 1.24 (6H, m).

Step 4: Example 3.1 Enantiomer 1 of 7-(2-methyl-6,7-diphenyl-3,4-dihydro-1,8-naphthyridin-1(2H)-yl)heptanoic acid Enantiomer 2 of Ethyl 7-(2-methyl-6,7-diphenyl-3,4-dihydro-1,8-naphthyridin-1(2H)-yl)heptanoate (37 mg, 0.081 mmol) was dissolved in THF/water (1 ml/2:1) and lithium hydroxide (9.70 mg, 0.405 mmol) was added. The mixture was stirred at room temperature for 4 days and then diluted with water (25 ml). The pH was adjusted to pH 5-6 using 1M HCl. The aqueous portion was extracted with EtOAc (2×20 ml) and the combined organics extracts were washed with brine, dried over $MgSO_4$, filtered and evaporated to afford Enantiomer 1 of 7-(2-methyl-6,7-diphenyl-3,4-dihydro-1,8-naphthyridin-1(2H)-yl)heptanoic acid;

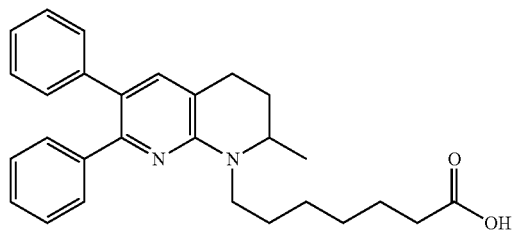 [SMILES: CC1CCc2cc(-c3ccccc3)c(-c3ccccc3)nc2N1CCCCCCC(=O)O]

LC-MS Rt=1.41 mins; $[M+H]^+$429.3, Method 2min-LC_v002
$^1$H NMR (400 MHz, DMSO-d6) δ 12.08 (1H, s), 7.21-7.18 (9H, m), 7.08 (2H, m), 4.02 (1H, m), 3.73 (1H, m), 3.22 (1H, m), 2.83 (1H, m), 2.70 (1H, m), 2.22 (2H, m), 1.84 (2H, m), 1.72 (2H, m), 1.53 (2H, m), 1.43-1.32 (4H, m), 1.24 (3H, d).

Example 3.2

Enantiomer 2 of 7-(2-methyl-6,7-diphenyl-3,4-dihydro-1,8-naphthyridin-1(2H)-yl)heptanoic acid Enantiomer 2 of 7-(2-methyl-6,7-diphenyl-3,4-dihydro-1,8-naphthyridin-1(2H)-yl)heptanoic acid was prepared analogously to Enantiomer 1 using the appropriate starting compound;

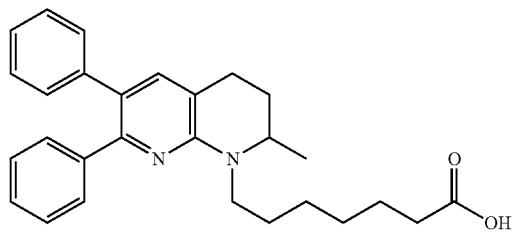 [SMILES: CC1CCc2cc(-c3ccccc3)c(-c3ccccc3)nc2N1CCCCCCC(=O)O]

LC-MS Rt=1.41 mins; $[M+H]^+$429.3, Method 2min-LC_v002
$^1$H NMR (400 MHz, DMSO-d6) δ 12.08 (1H, s), 7.21-7.18 (9H, m), 7.08 (2H, m), 4.02 (1H, m), 3.73 (1H, m), 3.22 (1H, m), 2.83 (1H, m), 2.70 (1H, m), 2.22 (2H, m), 1.84 (2H, m), 1.72 (2H, m), 1.53 (2H, m), 1.45-1.31 (4H, m), 1.23 (3H, d).

Example 4.1

7-(2,3-diphenyl-7,8-dihydropyrido[3,2-b]pyrazin-5(6H)-yl)heptanoic acid

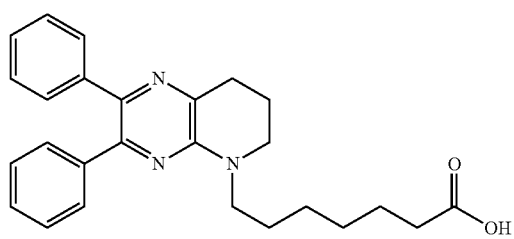 [SMILES: O=C(O)CCCCCCN1CCCc2nc(-c3ccccc3)c(-c3ccccc3)nc21]

Step 1: 2,3-Diphenyl-5,6,7,8-tetrahydropyrido[3,2-b]pyrazine

A suspension of 2,3-diphenylpyrido[3,2-b]pyrazine (Intermediate D) (49.1 g, 143 mmol), triethylamine (20 ml, 143 mmol) and 10% palladium on carbon (19.5 g) in dry THF (410 ml) was placed under an atmosphere of hydrogen (100 mbar) at room temperature for 61 h. After 24 h and 48 h additional palladium catalyst was added (2×4.9 g). The reaction mixture was filtered and the catalyst was washed with THF. The filtrate was concentrated in vacuo and the crude product was dissolved in warm EtOAc (1500 ml) and washed with sat. $Na_2CO_3$ solution (400 ml). The aqueous portion was extracted with EtOAc (200 ml) and the combined organic extracts were washed with water (150 ml), brine (300 ml), dried over sodium sulfate and concentrated in vacuo. This crude product was purified by chromatography on silica eluting with neat DCM followed by DCM (1% MeOH) to afford the title product;
LC-MS Rt=1.13 mins; [M+H]+ 288, Method A

Step 2: Ethyl 7-(2,3-diphenyl-7,8-dihydropyrido[3,2-b]pyrazin-5(6H)-yl)

A mixture comprising 2,3-diphenyl-5,6,7,8-tetrahydropyrido[3,2-b]pyrazine (step 1) (6.6 g, 23.0 mmol), ethyl 7-oxoheptanoate (4.0 g, 23.0 mmol), sodium triacetoxyborohydride (7.3 g, 34.5 mmol) and acetic acid (1.4 g, 23.0 mmol) in DCM (120 ml) was stirred at room temperature. After 2 h, a further portion of ethyl 7-oxoheptanoate (1.9 g, 11.0 mmol) was added and stirring continued for 4 h. The reaction mixture was diluted with water and extracted with EtOAc (3×). The combined organic phases were dried over sodium sulfate, filtered and concentrated in vacuo. The crude product was purified by chromatography on silica eluting with EtOAc/heptane to remove the unreacted starting material. The resulting yellow oil was dissolved in EtOH (80 ml) and treated at <5° C. with a suspension of sodium borohydride (0.5 g) in EtOH (10 g). The reaction mixture was stirred for 10 min and then quenched with acetone (30 ml). After stirring for 15 min at room temperature, the reaction mixture was poured into water (100 ml) and concentrated to a volume of 30 ml. The solution was extracted with EtOAc (3×) and the combined organic extracts were washed with brine, dried over sodium sulfate, filtered and concentrated in vacuo to afford the title compound which was used in the next step without further purification. $R_f$=0.39 in EtOAc/heptane 1:4.

Step 3: 7-(2,3-diphenyl-7,8-dihydropyrido[3,2-b]pyrazin-5(6H)-yl)heptanoic acid Ethyl 7-(2,3-diphenyl-7,8-dihydropyrido[3,2-b]pyrazin-5(6H)-yl)heptanoate (step 2)(6.1 g, 13.8 mmol) in THF (300 ml) and MeOH (100 ml) was treated with a solution of lithium hydroxide monohydrate (3.5 g, 83 mmol) in water (100 ml). The reaction mixture was heated at reflux for 5 h and allowed to cool to room temperature. The pH of the mixture was adjusted to <pH5 using 2M HCl. The volatile solvents were removed in vacuo and the remaining residue was diluted with water (50 ml) and extracted with EtOAc (3×). The combined organic extracts were washed with brine, dried over sodium sulfate, filtered and concentrated in vacuo to yield a greenish grey solid. The crude material was dissolved in MeOH (30 ml) and purified in 2 portions on a cartridge packed with 113 g LiChroprep® RP-18 (40-63 μm, supplier Merck, reverse phase column) eluting with 10-100% MeCN in water. The resulting solid was re-crystallized from a hot mixture of EtOH (120 ml) and water (90 ml). After seeding and stirring for 1 h at 5° C., the crystals were filtered off and the product dried for 2 days at 40° C. in a vacuum oven to afford the title compound;
LC-MS Rt=1.32 mins; [M+H]+ 416, Method A
$^1$H NMR (400 MHz, DMSO-d6) δ 11.95 (1H, br s), 7.32-7.16 (10H, m), 3.59 (2H, t), 3.47 (2H, t), 2.91 (2H, m), 2.16 (2H, m), 2.01 (2H, m), 1.64 (2H, m), 1.52 (2H, m), 1.35 (4H, m).

The compounds of the following tabulated Examples (Table 4) were prepared by a similar method to that of Example 4.1 by replacing 2,3-diphenyl-5,6,7,8-tetrahydropyrido[3,2-b]pyrazine with the appropriate pyrido[3,2-b]pyrazine derivative. Some compounds were obtained by purification carried out by SFC.

TABLE 4

| Ex. | Structure | Name | [M + H]+/NMR |
|---|---|---|---|
| 4.2 | 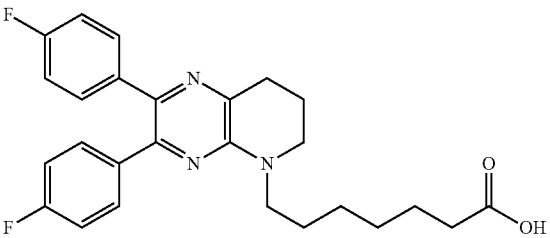 [SMILES: O=C(O)CCCCCCN1CCCc2nc(-c3ccc(F)cc3)c(-c3ccc(F)cc3)nc21] | 7-(2,3-bis(4-fluorophenyl)-7,8-dihydropyrido[2,3-b]pyrazin-5(6H)-yl)heptanoic acid | Rt = 1.26 mins; [M + H]+ 452.4, Method 2minLC_v003 $^1$H NMR (400 MHz, DMSO-d6) δ 11.97 (1H, br s), 7.39-7.30 (2H, m), 7.29-7.21 (2H, m), 7.19-7.02 (4H, m), 3.58 (2H, t), 3.51-3.42 (2H, m), 2.96-2.85 (2H, m), 2.23-2.10 (2H, m), 2.06-1.96 (2H, m), 1.67-1.55 (2H, m), 1.51-1.43 (2H, m), 1.33-1.24 (4H, m). |

TABLE 4-continued

| Ex. | Structure | Name | [M + H]⁺/NMR |
|---|---|---|---|
| 4.3 | 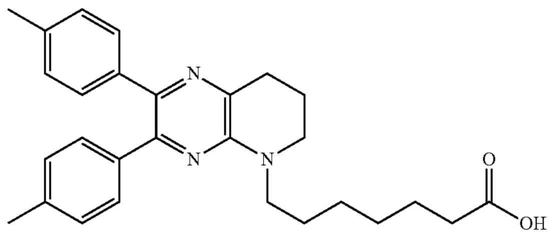 [SMILES: Cc1ccc(-c2nc3c(nc2-c2ccc(C)cc2)N(CCCCCCC(=O)O)CCC3)cc1] | 7-(2,3-dip-tolyl-7,8-dihydropyrido[2,3-b]pyrazin-5(6H)-yl)heptanoic acid | Rt = 4.54 mins; [M + H]⁺ 444.4, Method 10minLC_v003 ¹H NMR (400 MHz, DMSO-d6) δ 11.95 (1H, br s), 7.21 (2H, d), 7.13 (2H, d), 7.07 (2H, d), 7.03 (2H, d), 3.57 (2H, m), 3.44 (2H, m), 2.88 (2H, t), 2.27 (3H, s), 2.26 (3H, s), 2.15 (2H, t), 2.00 (2H, m), 1.59 (2H, m), 1.47 (2H, m), 1.36-1.25 (4H, m). |
| 4.4 | 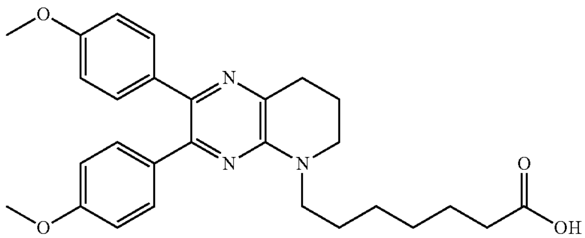 [SMILES: COc1ccc(-c2nc3c(nc2-c2ccc(OC)cc2)N(CCCCCCC(=O)O)CCC3)cc1] | 7-(2,3-bis(4-methoxyphenyl)-7,8-dihydropyrido[2,3-b]pyrazin-5(6H)-yl)heptanoic acid | Rt = 3.92 mins; [M + H]⁺ 476.4, Method 10minLC_v003 ¹H NMR (400 MHz, DMSO-d6) δ 11.96 (1H, br s), 7.30-7.24 (2H, m), 7.20-7.14 (2H, m), 6.87-6.77 (4H, m), 3.74 (3H, s), 3.72 (3H, s), 3.57 (2H, t), 3.48-3.41 (2H, m), 2.93-2.81 (2H, m), 2.20-2.15 (2H, m), 2.07-1.94 (2H, m), 1.67-1.55 (2H, m), 1.53-1.45 (2H, m), 1.33-1.22 (4H, m). |
| 4.5 | 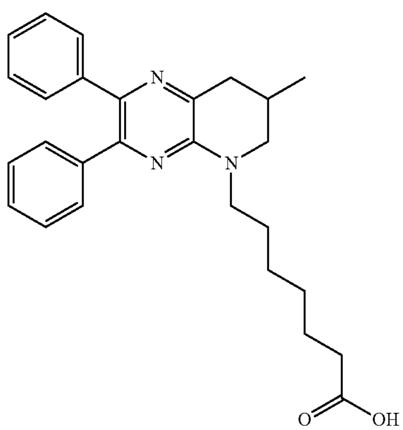 [SMILES: CC1Cc2nc(-c3ccccc3)c(-c3ccccc3)nc2N(CCCCCCC(=O)O)C1] | rac-7-(7-methyl-2,3-diphenyl-7,8-dihydropyrido[2,3-b]pyrazin-5(6H)-yl)heptanoic acid | Rt = 4.56 mins; [M + H]⁺ 430.4, Method 10minLC_v003 |
| 4.6 | 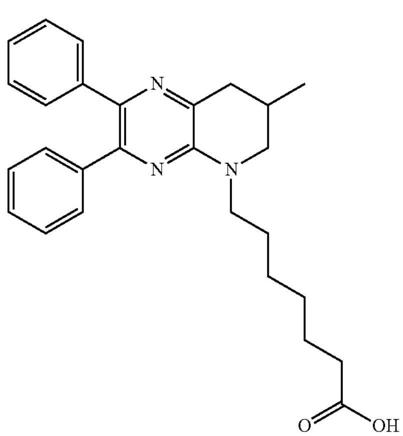 [SMILES: CC1Cc2nc(-c3ccccc3)c(-c3ccccc3)nc2N(CCCCCCC(=O)O)C1] | Enantiomer 1 of 7-(7-methyl-2,3-diphenyl-7,8-dihydropyrido[2,3-b]pyrazin-5(6H)-yl)heptanoic acid | Rt = 4.58 mins; [M + H]⁺ 430.4, Method 10minLC_v003 SFC Rt 4.51 min Method AS25IPA |

TABLE 4-continued

| Ex. | Structure | Name | [M + H]+/NMR |
|---|---|---|---|
| 4.7 | 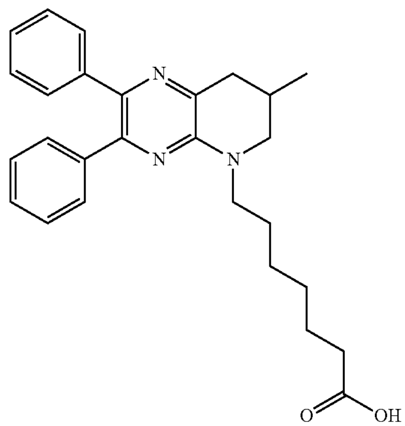 [SMILES: CC1Cc2nc(-c3ccccc3)c(-c3ccccc3)nc2N(CCCCCCC(=O)O)C1] | *Enantiomer 2 of 7-(7-methyl-2,3-diphenyl-7,8-dihydropyrido[2,3-b]pyrazin-5(6H)-yl)heptanoic acid | Rt = 4.81 mins; [M + H]+ 430.6, Method 10minLC_v003 $^1$H NMR (400 MHz, CDCl3) δ: 7.37-7.30 (2H, m), 7.28-7.23 (2H, m), 7.28-7.23, (2H, m), 7.20-7.08 (6H, m), 3.72-3.62 (1H, m), 3.55-3.46, 1H, m), 3.51-3.28 (1H, m), 3.12-2.99 (2H, m), 2.64-2.53 (1H, m), 2.27-2.12 (3H, m), 1.65-1.49 (4H, m), 1.21-1.18, 4H, m) 1.09-1.02 (3H, d). |
| 4.10 | 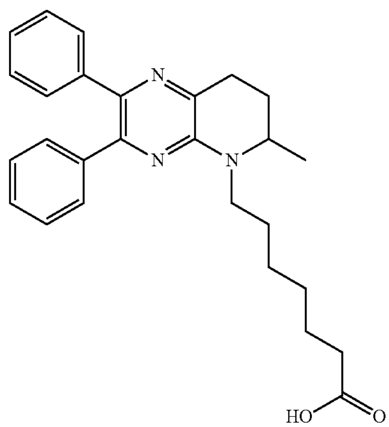 [SMILES: CC1CCc2nc(-c3ccccc3)c(-c3ccccc3)nc2N1CCCCCCC(=O)O] | rac-7-(6-Methyl-2,3-diphenyl-7,8-dihydropyrido[2,3-b]pyrazin-5(6H)-yl)heptanoic acid | Rt = 4.42 mins; [M + H]+ 430, Method 10minLC_v003 |
| 4.11 | 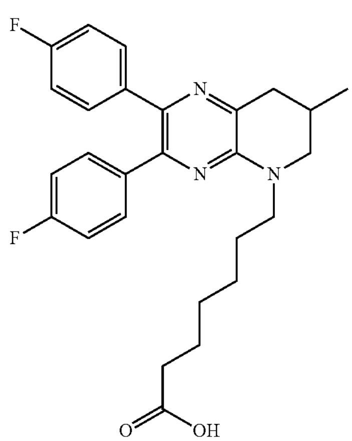 [SMILES: CC1Cc2nc(-c3ccc(F)cc3)c(-c3ccc(F)cc3)nc2N(CCCCCCC(=O)O)C1] | rac-7-(2,3-bis(4-fluorophenyl)-7-methyl-7,8-dihydropyrido[2,3-b]pyrazin-5(6H)-yl)heptanoic acid | Rt = 5.08 mins; [M + H]+ 466, Method 10minLC_v003 |

TABLE 4-continued
| Ex. | Structure | Name | [M + H]⁺/NMR |
|---|---|---|---|
| 4.12 | 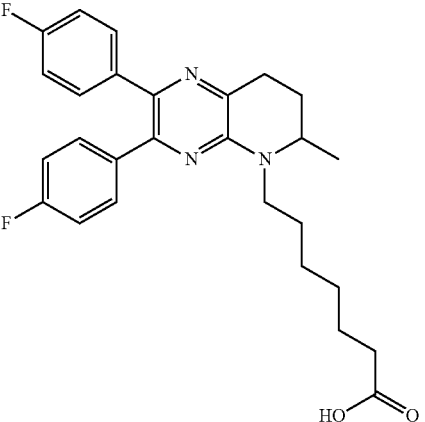 [SMILES: CC1CCc2nc(-c3ccc(F)cc3)c(-c3ccc(F)cc3)nc2N1CCCCCCC(=O)O] | rac-7-(2,3-bis(4-fluorophenyl)-6-methyl-7,8-dihydropyrido[2,3-b]pyrazin-5(6H)-yl)heptanoic acid | Rt = 4.97 mins; [M + H]⁺ 466, Method 10minLC_v003 |
| 4.13 | 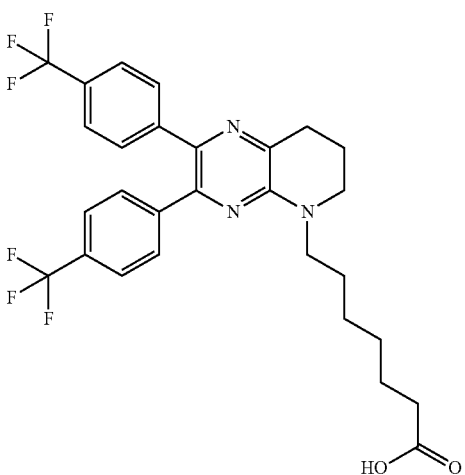 [SMILES: O=C(O)CCCCCCN1CCCc2nc(-c3ccc(C(F)(F)F)cc3)c(-c3ccc(C(F)(F)F)cc3)nc21] | 7-(2,3-bis(4-(trifluoromethyl)phenyl)-7,8-dihydropyrido[2,3-b]pyrazin-5(6H)-yl)heptanoic acid | Rt = 1.48 mins; [M + H]⁺ 552, Method 2minLC_v003 |
| 4.14 | 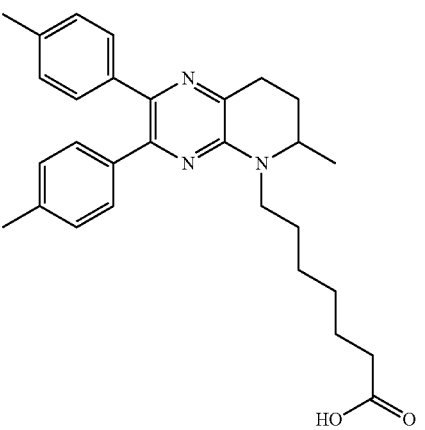 [SMILES: Cc1ccc(-c2nc3c(nc2-c2ccc(C)cc2)N(CCCCCCC(=O)O)C(C)CC3)cc1] | Enantiomer 1 of 7-(6-methyl-2,3-dip-tolyl-7,8-dihydropyrido[2,3-b]pyrazin-5(6H)-yl)heptanoic acid | Rt = 1.38 mins; [M + H]⁺ 458.5, Method 2minLowpH |

TABLE 4-continued

| Ex. | Structure | Name | [M + H]⁺/NMR |
|---|---|---|---|
| 4.15 | 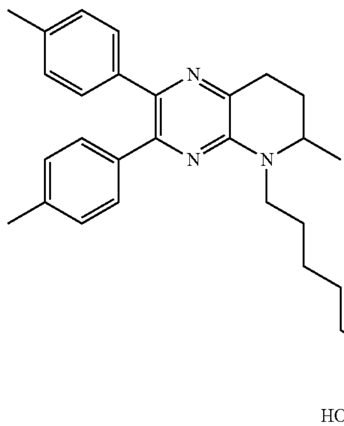 | Enantiomer 2 of 7-(6-methyl-2,3-dip-tolyl-7,8-dihydropyrido[2,3-b]pyrazin-5(6H)-yl)heptanoic acid | Rt = 1.38 mins; [M + H]⁺ 458.2, Method 2minLowpH |

*A second hydrolysis step using LiOH was carried out after chiral separation.

Example 4.3

7-(2,3-Dip-tolyl-7,8-dihydropyrido[2,3-b]pyrazin-5(6H)-yl)heptanoic acid

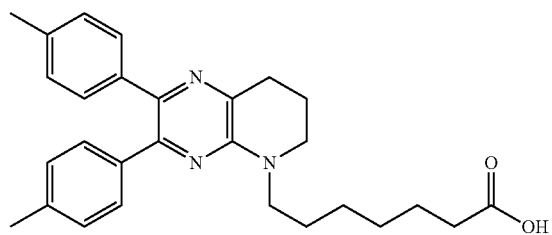 [SMILES: Cc1ccc(-c2nc3c(nc2-c2ccc(C)cc2)N(CCCCCCC(=O)O)CCC3)cc1]

Step 1: Ethyl 7-(2,3-dip-tolyl-7,8-dihydropyrido[2,3-b]pyrazin-5(6H)-yl)heptanoate To a solution of 2,3-Dip-tolyl-5,6,7,8-tetrahydropyrido[2,3-b]pyrazine (Intermediate E) (10 g, 31.7 mmol) in DCE (300 ml) was added DIPEA (6.09 ml, 34.9 mmol) followed by ethyl 7-oxoheptanoate (10.92 g, 63.4 mmol). The mixture was stirred at RT for 10 minutes and sodium triacetoxyborohydride (16.80 g, 79 mmol) was added portionwise. The reaction mixture was heated at 40° C. overnight and then added slowly to water (500 ml) and stirred at RT for 10 minutes. The organic layer was separated and the aqueous layer extracted with dichloromethane (2×200 ml). The combined organics were washed with brine (200 ml), dried over anhydrous sodium sulfate and concentrated in vacuo to give a pale yellow oil. Isolute Separtis SCX-2 (capture/release super cation exchange resin) (222 g, 127 mmol) was added to a column and the product was loaded with MeOH (50 ml). The column was flushed with MeOH (750 L) followed by 2 N NH₃/MeOH (1000 ml, prepared from 280 ml 7 N+720 ml MeOH) to afford the title compound. No further purification was carried out; HPLC (Agilent 1200) Rt 6.38 min, Method B Step 2: 7-(2,3-dip-tolyl-7,8-dihydropyrido[2,3-b]pyrazin-5(6H)-yl)heptanoic acid Ethyl 7-(2,3-dip-tolyl-7,8-dihydropyrido[2,3-b]pyrazin-5(6H)-yl)heptanoate (step 1) was dissolved in THF (94 ml) and lithium hydroxide monohydrate (7.79 g, 186 mmol) in water (94 ml) was added dropwise. The reaction mixture was warmed to 50° C. and stirred for 7.5 hours. The reaction mixture was concentrated in vacuo to remove the THF and diluted with water (500 ml). The pH of the aqueous layer was adjusted to pH 2 with 1 N HCl (100 ml) and extracted with EtOAc (3×500 ml). The combined organic layers were washed with brine (200 ml), dried over anhydrous sodium sulfate and concentrated in vacuo. The crude solid was suspended in TBME/hexane (1:1, 100 ml) and rotated on the rotary evaporator (no vacuum) at RT until crystals formed. The solid was removed by filtration, washed with heptanes (50 ml) and dried at RT overnight. The solid was re-crystallized from a hot mixture of EtOH (211 ml) and water (159 ml). After seeding and stirring for 1 h at 5° C., the crystals were filtered off and the product dried overnight at 40° C. in a vacuum oven to afford the title compound; See Table 4 for characterising data.

Step 3: Mesylate salt of 7-(2,3-dip-tolyl-7,8-dihydropyrido[2,3-b]pyrazin-5(6H)-yl)heptanoic acid To 7-(2,3-dip-tolyl-7,8-dihydropyrido[2,3-b]pyrazin-5(6H)-yl)heptanoic acid (1.97 g, 4.44 mmol) in anhydrous acetone (40 ml) was added methanesulfonic acid (0.288 ml, 4.44 mmol). A clear yellow solution was obtained and almost immediately a yellow precipitate was observed. The reaction mixture was stirred at room temperature for 2 hrs then filtered. The filter bed was washed with acetone and the yellow precipitate was dried in vacuo at room temperature overnight.

¹H NMR (400 MHz, DMSO-d6) δ 12.25-8.77 (2H, br hump), 7.21 (2H, d), 7.15 (2H, d), 7.08 (2H, d), 7.08 (2H, d), 3.59 (2H, m), 3.48 (2H, m), 2.94 (2H, t), 2.37 (3H, s), 2.28 (3H, s), 2.28 (3H, s), 2.15 (2H, t), 2.00 (2H, m), 1.60 (2H, m), 1.47 (2H, m), 1.36-1.25 (4H, complex m).

mp (DSC onset) 206.59° C.

Example 4.8

6-(2,3-Diphenyl-7,8-dihydropyrido[3,2-b]pyrazin-5(6H)-yl)hexanoic acid

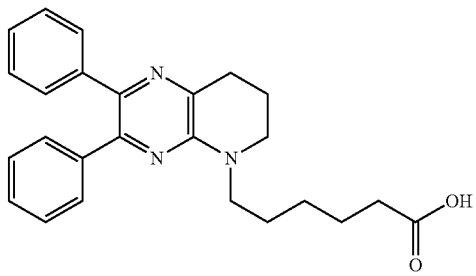 [SMILES: O=C(O)CCCCCN1CCCc2nc(-c3ccccc3)c(-c3ccccc3)nc21]

This compound was prepared from 2,3-diphenyl-5,6,7,8-tetrahydropyrido[3,2-b]pyrazine (Example 4.1 step 1) and ethyl 6-bromohexanoate analogously to 7-(6,7-diphenyl-3,4-dihydro-1,8-naphthyridin-1(2H)-yl)heptanoic acid (Example 1 step 1 and step 2. Step 1 was carried out using microwave radiation).

LC-MS Rt=1.59 mins; [M+H]$^+$402.3, Method 2min-LC_v002.

$^1$H NMR (400 MHz, DMSO-d6) δ 12.03 (1H, s), 7.4-7.2 (10H, m), 3.64 (2H, m), 3.52 (2H, m), 2.97 (2H, t), 2.25 (2H, t), 2.04 (2H, m), 1.74-1.56 (4H, m), 1.39 (2H, m).

Example 4.9

5-(2,3-Diphenyl-7,8-dihydropyrido[3,2-b]pyrazin-5(6H)-yl)pentanoic acid

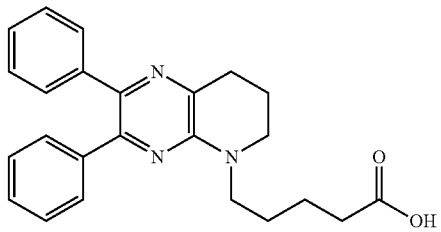 [SMILES: O=C(O)CCCCN1CCCc2nc(-c3ccccc3)c(-c3ccccc3)nc21]

This compound was prepared from 2,3-diphenyl-5,6,7,8-tetrahydropyrido[3,2-b]pyrazine (Example 4.1 step 1) and ethyl 5-bromovalerate analogously to 7-(6,7-diphenyl-3,4-dihydro-1,8-naphthyridin-1(2H)-yl)heptanoic acid (Example 1 step 1 and step 2. Step 1 was carried out using microwave radiation).

LC-MS Rt=1.57 mins; [M+H]$^+$ 388.3, Method 2min-LC_v002.

$^1$H NMR (400 MHz, DMSO-d6) δ 7.33 (2H, m), 7.27 (4H, m), 7.22 (4H, m), 3.6 (2H, m), 3.46 (2H, m), 2.91 (2H, m), 2.23 (2H, t), 2.00 (2H, m), 1.63 (2H, m), 1.54 (2H, m).

Example 5.1

7-(3-Phenyl-2-p-tolyl-7,8-dihydropyrido[2,3-b]pyrazin-5(6H)-yl)heptanoic acid

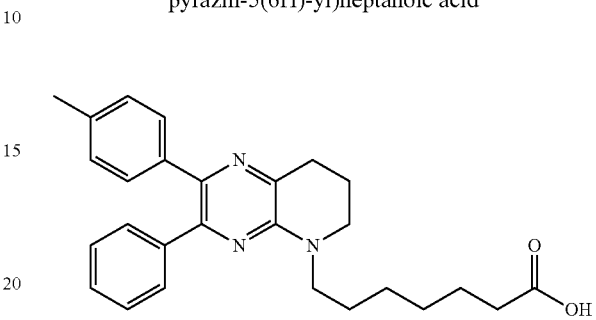

Step 1: Ethyl 7-(3-phenyl-2-p-tolyl-7,8-dihydropyrido[2,3-b]pyrazin-5(6H)-yl)heptanoate 3-Phenyl-2-p-tolyl-5,6,7,8-tetrahydropyrido[2,3-b]pyrazine (Intermediate F) (162 mg, 0.538 mmol) in dry DCE (1 ml) was treated with DIPEA (0.103 ml, 0.591 mmol) followed by ethyl 7-oxoheptanoate (185 mg, 1.075 mmol). The reaction mixture was stirred at RT for 10 minutes and sodium triacetoxyborohydride (570 mg, 2.69 mmol) was added. The resulting mixture was stirred at 60° C. for 16 hours. After cooling to RT, the mixture was slowly added to water (50 ml) and extracted with DCM (3×). The combined organic extracts were passed through a phase separating column and concentrated in vacuo. The resulting crude product was purified by chromatography on silica eluting with 0-10% EtOAc/iso-hexane to afford the title compound; LCMS; Rt 1.38 mins MS m/z 458 [ M+H]+; Method 2minLC_v003

Step 2: 7-(3-Phenyl-2-p-tolyl-7,8-dihydropyrido[2,3-b]pyrazin-5(6H)-yl)heptanoic acid Ethyl 7-(3-phenyl-2-p-tolyl-7,8-dihydropyrido[2,3-b]pyrazin-5(6H)-yl)heptanoate (158 mg, 0.345 mmol) in THF (4 ml) and water (1 ml) at RT was treated with LiOH monohydrate (43.5 mg, 1.036 mmol) and stirred at RT for 16 hours. The organic solvent was removed in vacuo and the residue was diluted with water (20 ml). The pH was adjusted to pH4 with aqueous 10% citric acid solution. The mixture was extracted with DCM (×3) and the organic extracts were passed through a phase separating column and concentrated in vacuo. The resulting crude product was purified by chromatography on silica eluting with 0-40% EtOAc/iso-hexane followed by chiral separation using Supercritical Fluid Chromatography to afford the title compound;

LCMS Rt 1.19 mins MS m/z 430 [ M+H]+; Method 2min-LC_v003

¹H NMR (400 MHz, DMSO-d6) δ 7.35 (2H, m), 7.3 (3H, m), 7.15 (2H, d), 7.05 (2H, d), 3.6 (2H, t), 3.45 (2H, m), 2.9 (2H, t), 2.25 (3H, s), 2.15 (2H, t), 2.0 (2H, m), 1.6 (2H, m), 1.45 (2H, m), 1.3 (4H, m).

Example 5.2

7-(2-Phenyl-3-p-tolyl-7,8-dihydropyrido[2,3-b]pyrazin-5(6H)-yl)heptanoic acid

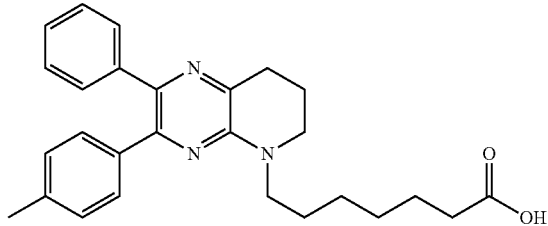 [SMILES: Cc1ccc(-c2nc3c(nc2-c2ccccc2)CCCN3CCCCCCC(=O)O)cc1]

Step 1: Ethyl 7-(2-phenyl-3-p-tolyl-7,8-dihydropyrido[2,3-b]pyrazin-5(6H)-yl)heptanoate A solution of 2-phenyl-3-p-tolyl-5,6,7,8-tetrahydropyrido[2,3-b]pyrazine (Intermediate FA) (1.03 g, 3.42 mmol) in 1,2-dichloroethane (15 ml) was treated with ethyl 7-oxoheptanoate (1.776 g, 10.25 mmol) followed by sodium triacetoxyborohydride (3.62 g, 17.09 mmol). The reaction mixture was stirred at room temperature overnight. The mixture was diluted with saturated NaHCO₃ (70 ml) and was extracted with DCM (×3). The combined organics were dried (MgSO₄), filtered and concentrated in vacuo. The resulting crude product was purified by chromatography on silica eluting with 0-60% EtOAc/iso-hexane to give an oil. The product was loaded onto an Isolute™ SCX-2 cartridge, washed with MeOH and eluted with 2M NH₃ in MeOH. The methanolic ammonia fractions were concentrated in vacuo to afford the title compound;
LCMS; Rt 5.36 mins MS m/z 458.5 [ M+H]+; Method 10 minLC_v003

Step 2: 7-(2-Phenyl-3-p-tolyl-7,8-dihydropyrido[2,3-b]pyrazin-5(6H)-yl)heptanoic acid A solution of ethyl 7-(2-phenyl-3-p-tolyl-7,8-dihydropyrido[2,3-b]pyrazin-5(6H)-yl)heptanoate (1.07 g, 2.338 mmol) in THF (12 ml) and water (6 ml) was treated with LiOH (0.560 g, 23.38 mmol) and stirred at 70° C. for 18 hours. After cooling to RT, the reaction mixture was concentrated in vacuo. The residue was diluted with water (20 ml) and the pH was adjusted to pH~4 using 2M HCl. The aqueous portion was extracted with EtOAc (2×20 ml). The organic extracts were washed with brine, dried (MgSO₄) and evaporated under vacuum. The residue was dissolved in hot (~80° C.) ethanol (20 ml) and water (~15 ml) was added until the solution became turbid. Upon cooling a solid precipitated. The mixture was kept cold for 72 hours. The solid was collected by filtration, washed with water and dried at 40° C. for 5 hours to afford the title compound;
LCMS Rt 4.36 mins MS m/z 430 [ M+H]+; Method 10 minLC_v003
¹H NMR (400 MHz, DMSO-d6) δ 11.94 (1H, s), 7.26-7.15 (5H, m), 7.21 (2H, d), 7.06 (2H, d), 3.57 (2H, m), 3.45 (2H, m), 2.89 (2H, m), 2.27 (3H, s), 2.14 (2H, t), 2.0 (2H, m), 1.6 (2H, m), 1.47 (2H, m), 1.37-1.23 (4H, m).

Example 5.3

7-(2-m-Tolyl-3-p-tolyl-7,8-dihydropyrido[2,3-b]pyrazin-5(6H)-yl)heptanoic acid

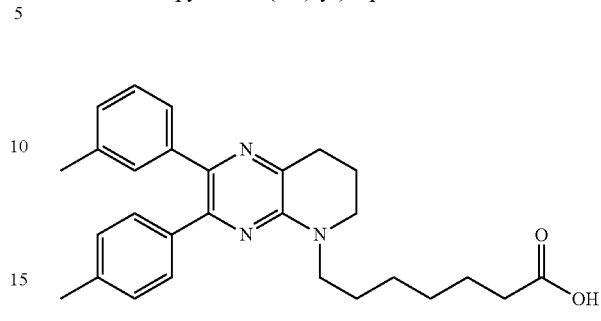

Step 1: Ethyl 7-(2-m-tolyl-3-p-tolyl-7,8-dihydropyrido[2,3-b]pyrazin-5(6H)-yl)heptanoate 2-m-Tolyl-3-p-tolyl-5,6,7,8-tetrahydropyrido[2,3-b]pyrazine (Intermediate FB)(61 mg, 0.193 mmol) in dry DCE (1 ml) at RT was treated with DIPEA (0.037 ml, 0.213 mmol) followed by ethyl 7-oxoheptanoate (66.6 mg, 0.387 mmol). The reaction mixture was stirred at RT for 10 minutes and sodium triacetoxyborohydride (205 mg, 0.967 mmol) was added. The resulting mixture was stirred at 60° C. overnight. After cooling to RT, the mixture was slowly added to water (50 ml) and extracted with DCM (3×). The combined organic extracts were passed through a phase separating column and concentrated in vacuo. The resulting crude product was purified by chromatography on silica eluting with 0-5% EtOAc/iso-hexane to afford the title compound; LCMS Rt 1.61 mins MS m/z 473.4 [ M+H]+; Method 2minLC_v003

Step 2: 7-(2-m-Tolyl-3-p-tolyl-7,8-dihydropyrido[2,3-b]pyrazin-5(6H)-yl)heptanoic acid Ethyl 7-(2-m-tolyl-3-p-tolyl-7,8-dihydropyrido[2,3-b]pyrazin-5(6H)-yl)heptanoate (step 1)(69 mg, 0.146 mmol) in THF (1 ml) and water (0.5 ml) at RT was treated with LiOH monohydrate (18.42 mg, 0.439 mmol) and stirred at RT for 4 hours. MeOH (1 ml) and 2M NaOH (1 ml) were added and the mixture was stirred at RT overnight. The resulting mixture was added to water (20 ml) and the pH was adjusted to pH1 with 2M HCl. The aqueous portion was extracted with DCM (×3) and the organic extracts were passed through a phase separating column. The organic solvent was concentrated in vacuo. The crude product was purified by preparative LC-MS (low pH). The appropriate fraction was collected and extracted with DCM (×3), passing the organics through a phase separating column. The solvent was removed in vacuo to afford the title compound;
LCMS: Rt 1.25 mins MS m/z 444 [ M+H]+; Method 2minLC_v003
¹H NMR (400 MHz, DMSO-d6) δ 11.94 (1H, br s), 7.21 (2H, d), 7.18 (1H, dd), 7.07 (2H, d), 7.05 (1H, dd), 7.00 (1H, ddd), 6.88 (1H, ddd), 3.57 (2H, m), 3.44 (2H, m), 2.88 (2H, t), 2.27 (3H, s), 2.23 (3H, s), 2.14 (2H, t), 2.0 (2H, m), 1.59 (2H, m), 1.47 (2H, m), 1.36-1.25 (4H, m).

The compounds of the following tabulated Examples (Table 5) were prepared by a similar method to that of Example 5.1 by replacing 3-Phenyl-2-p-tolyl-5,6,7,8-tetrahydropyrido[2,3-b]pyrazine (Intermediate F) with the appropriate pyrazine derivative (preparations described hereinafter).

TABLE 5

| Ex. | Structure | Name | [M + H]⁺/NMR |
|---|---|---|---|
| 5.4 | 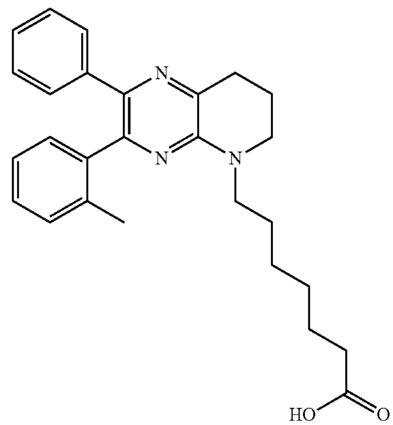 [SMILES: Cc1ccccc1-c1nc2c(nc1-c1ccccc1)CCCN2CCCCCCC(=O)O] | 7-(2-phenyl-3-o-tolyl-7,8-dihydropyrido[2,3-b]pyrazin-5(6H)-yl)heptanoic acid | LC-MS Rt = 4.30 mins; [M + H]+ 430, Method 10minLC_v003. |
| 5.5 | 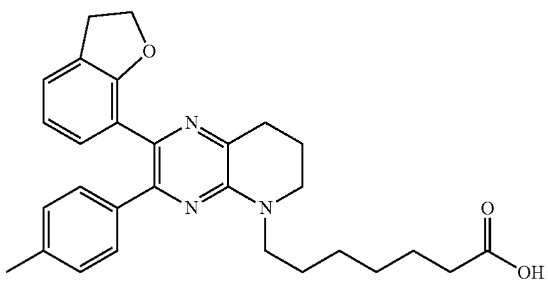 [SMILES: Cc1ccc(-c2nc3c(nc2-c2cccc4c2OCC4)CCCN3CCCCCCC(=O)O)cc1] | 7-(2-(2,3-dihydrobenzofuran-7-yl)-3-p-tolyl-7,8-dihydropyrido[2,3-b]pyrazin-5(6H)-yl)heptanoic acid | LC-MS Rt = 1.13 mins; [M + H]+ 472, Method 2minLC_v003. |
| 5.6 | 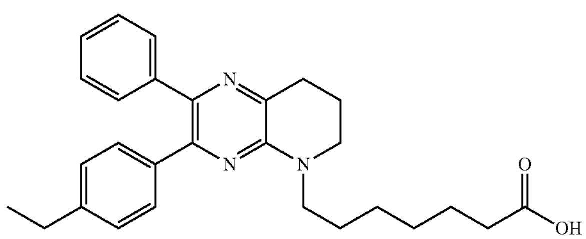 [SMILES: CCc1ccc(-c2nc3c(nc2-c2ccccc2)CCCN3CCCCCCC(=O)O)cc1] | 7-(3-(4-ethylphenyl)-2-phenyl-7,8-dihydropyrido[2,3-b]pyrazin-5(6H)-yl)heptanoic acid | LC-MS Rt = 1.26 mins; [M + H]+ 444, Method 2minLC_v003. |
| 5.7 | 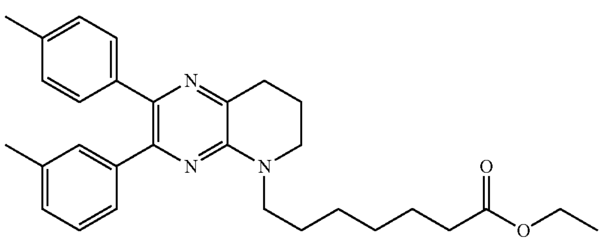 [SMILES: CCOC(=O)CCCCCCN1CCCc2nc(-c3ccc(C)cc3)c(-c3cccc(C)c3)nc21] | ethyl 7-(3-m-tolyl-2-p-tolyl-7,8-dihydropyrido[2,3-b]pyrazin-5(6H)-yl)heptanoate* | LC-MS Rt = 1.41 mins; [M + H]+ 473.2, Method 2minLC_v003. |
| 5.8 | 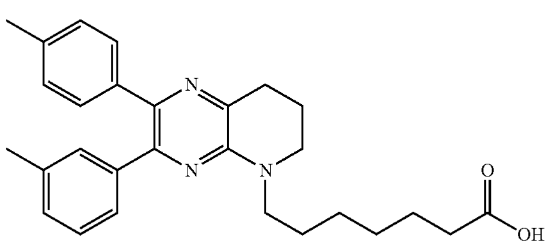 [SMILES: Cc1ccc(-c2nc3c(nc2-c2cccc(C)c2)N(CCCCCCC(=O)O)CCC3)cc1] | 7-(3-m-tolyl-2-p-tolyl-7,8-dihydropyrido[2,3-b]pyrazin-5(6H)-yl)heptanoic acid | LC-MS Rt = 1.23 mins; [M + H]+ 444 Method 2minLC_v003 |

TABLE 5-continued

| Ex. | Structure | Name | [M + H]⁺/NMR |
|---|---|---|---|
| 5.9 | 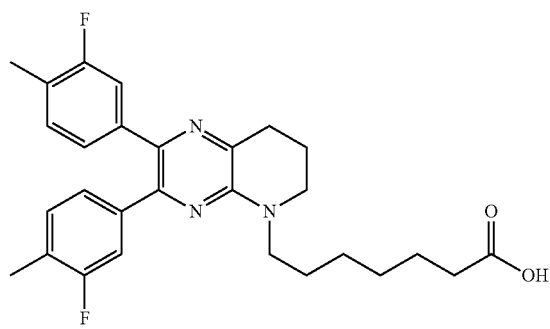 | 7-(2-(4-ethylphenyl)-3-phenyl-7,8-dihydropyrido[2,3-b]pyrazin-5(6H)-yl)heptanoic acid | LC-MS Rt = 1.26 mins; [M + H]+ 444 Method 2minLC_v003 |

*Example 5.7: Hydrolysis step not required

Example 6.1

7-(2,3-bis(3-Fluoro-4-methylphenyl)-7,8-dihydropyrido[2,3-b]pyrazin-5(6H)-yl)heptanoic acid Step 1: Ethyl 7-(2,3-bis(3-fluoro-4-methylphenyl)-7,8-dihydropyrido[2,3-b]pyrazin-5(6H)-yl)heptanoate 2,3-bis(3-Fluoro-4-methylphenyl)-5,6,7,8-tetrahydropyrido[2,3-b]pyrazine (Intermediate G)(256 mg, 0.729 mmol) in DCE (10 ml) was treated with ethyl 7-oxoheptanoate (125 mg, 0.729 mmol) and triethylamine (0.112 ml, 0.801 mmol) and stirred at RT for 15 mins. Sodium triacetoxyborohydride (772 mg, 3.64 mmol) was added and stirring continued at 60° C. for 18 h. The reaction mixture was diluted with water and DCM and the organic portion was separated. The aqueous portion was extracted with DCM and the combined organic extracts were dried (sodium sulphate), filtered and concentrated in vacuo to give a yellow gum. The crude product was purified by chromatography on silica eluting with 0-20% EtOAc in iso-hexane to afford the title compound;

LCMS: Rt 1.56 mins MS m/z 508 [ M+H]+; Method 2min-LC_v003

Step 2: 7-(2,3-bis(3-Fluoro-4-methylphenyl)-7,8-dihydropyrido[2,3-b]pyrazin-5(6H)-yl)heptanoic acid Ethyl 7-(2,3-bis(3-fluoro-4-methylphenyl)-7,8-dihydropyrido[2,3-b]pyrazin-5(6H)-yl)heptanoate (121 mg, 0.238 mmol) in THF (2 ml) and water (2 ml) was treated with LiOH (45.7 mg, 1.907 mmol) and the resulting mixture was stirred at RT for 18 h. The mixture was acidified to pH 4 with HCl and extracted with DCM. The organic extracts were combined, dried (sodium sulphate), filtered and concentrated in vacuo. The residue was azeotroped with ether to afford the title compound;

LCMS: Rt 5.19 mins MS m/z 480.3 [ M+H]+; Method 10 minLC_v003

¹H NMR (400 MHz, MeOH-d₄) δ 7.15-6.91 (6H, m), 3.69 (2H, t), 3.53 (2H, t), 2.97 (2H, t), 2.29-2.20 (8H, m), 2.11 (2H, m), 1.72 (2H, m), 1.59 (2H, m), 1.47-1.36 (4H, m).

The compounds of the following tabulated Examples (Table 6) were prepared by a similar method to that of Example 6.1 by replacing 2,3-bis(3-Fluoro-4-methylphenyl)-5,6,7,8-tetrahydropyrido[2,3-b]pyrazine (Intermediate G) with the appropriate pyrazine derivative (preparations described hereinafter).

TABLE 6

| Ex. | Structure | Name | [M + H]⁺/NMR |
|---|---|---|---|
| 6.2 | 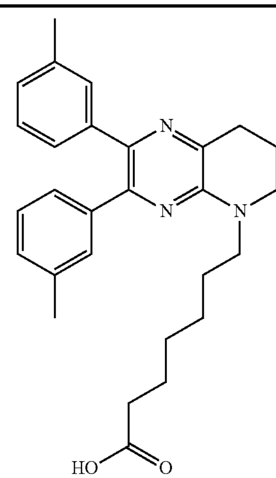 | 7-(2,3-dim-tolyl-7,8-dihydropyrido[2,3-b]pyrazin-5(6H)-yl)heptanoic acid | LC-MS Rt = 1.24 mins; [M + H]+ 444.7, Method 2minLC_v003. |

TABLE 6-continued

| Ex. | Structure | Name | [M + H]+/NMR |
|---|---|---|---|
| 6.3 | 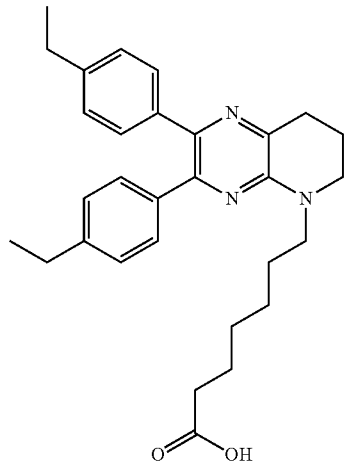 [SMILES: CCc1ccc(-c2nc3c(nc2-c2ccc(CC)cc2)N(CCCCCCC(=O)O)CCC3)cc1] | 7-(2,3-bis(4-ethylphenyl)-7,8-dihydropyrido[2,3-b]pyrazin-5(6H)-yl)heptanoic acid | LC-MS Rt = 1.31 mins; [M + H]+ 473, Method 2minLC_v003. |
| 6.4 | 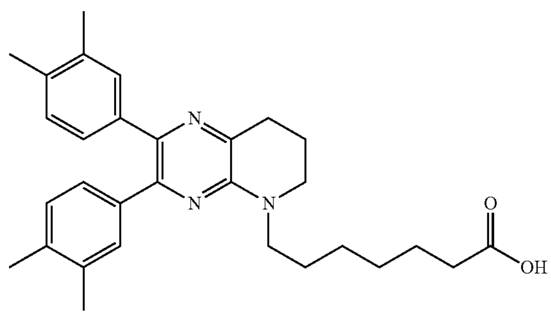 [SMILES: Cc1ccc(-c2nc3c(nc2-c2ccc(C)c(C)c2)N(CCCCCCC(=O)O)CCC3)cc1C] | 7-(2,3-bis(3,4-dimethylphenyl)-7,8-dihydropyrido[2,3-b]pyrazin-5(6H)-yl)heptanoic acid | LC-MS Rt = 4.65 mins; [M + H]+ 472, Method 10minLC_v003. |
| 6.5 | 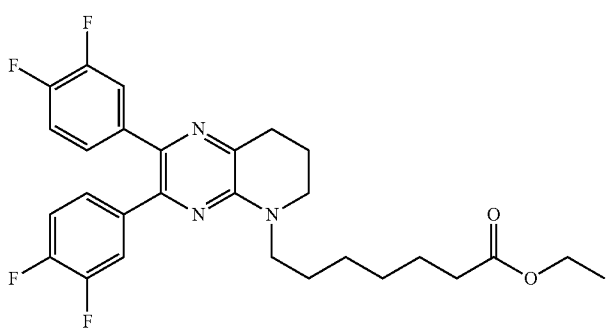 [SMILES: CCOC(=O)CCCCCCN1CCCc2nc(-c3ccc(F)c(F)c3)c(-c3ccc(F)c(F)c3)nc21] | ethyl 7-(2,3-bis(3,4-difluorophenyl)-7,8-dihydropyrido[2,3-b]pyrazin-5(6H)-yl)heptanoate* | LC-MS Rt = 1.56 mins; [M + H]+ 516, Method 2minLC_v003. |
| 6.6 | 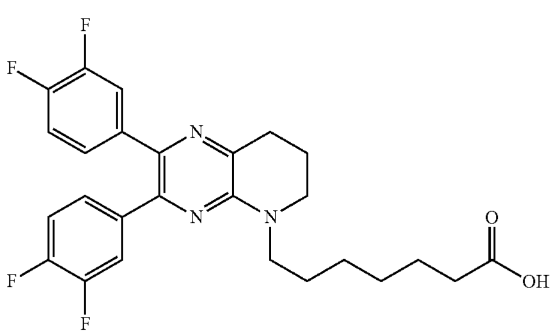 [SMILES: O=C(O)CCCCCCN1CCCc2nc(-c3ccc(F)c(F)c3)c(-c3ccc(F)c(F)c3)nc21] | 7-(2,3-bis(3,4-difluorophenyl)-7,8-dihydropyrido[2,3-b]pyrazin-5(6H)-yl)heptanoic acid | LC-MS Rt = 5.39 mins; [M + H]+ 488, Method 10minLC_v003. |

TABLE 6-continued

| Ex. | Structure | Name | [M + H]+/NMR |
|---|---|---|---|
| 6.7 | 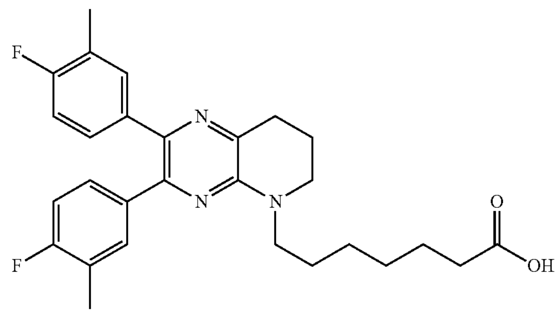 [SMILES: Cc1cc(-c2nc3c(nc2-c2ccc(F)c(C)c2)N(CCCCCCC(=O)O)CCC3)ccc1F] | 7-(2,3-bis(4-fluoro-3-methylphenyl)-7,8-dihydropyrido[2,3-b]pyrazin-5(6H)-yl)heptanoic acid | LC-MS Rt = 4.81 mins; [M + H]+ 480, Method 10minLC_v003. |

*Example 6.5: Hydrolysis step not required

Example 7.1 rac-7-(8-Ethyl-2,3-diphenyl-7,8-dihydropyrido[2,3-b]pyrazin-5(6H)-yl)heptanoic acid

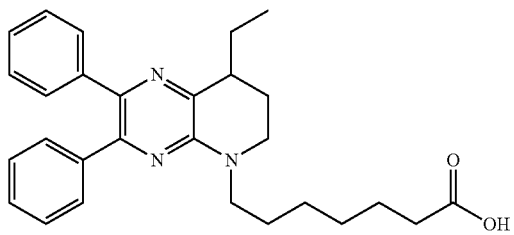 [SMILES: CCC1CCN(CCCCCCC(=O)O)c2nc(-c3ccccc3)c(-c3ccccc3)nc21]

Step 1: rac-Ethyl 7-(8-ethyl-2,3-diphenyl-7,8-dihydropyrido[2,3-b]pyrazin-5(6H)-yl)heptanoate To a solution of rac-8-ethyl-2,3-diphenyl-5,6,7,8-tetrahydropyrido[2,3-b]pyrazine (Intermediate HC)(13 mg, 0.041 mmol) in DCE (2 ml) was added ethyl 7-oxoheptanoate (24.84 mg, 0.144 mmol) followed by sodium triacetoxyborohydride (69.9 mg, 0.330 mmol). The reaction mixture was left to stir at room temperature under an atmosphere of nitrogen. Water (10 ml) was added and the resulting mixture was extracted with EtOAc (3×10 ml). The combined organic extracts were dried over $MgSO_4$, filtered and concentrated in vacuo. The crude product was passed through a pre-conditioned Isolute SCX-2 SPE column loading with MeOH and eluting with 1M ammonia in MeOH (10 ml) to afford the title product;

LC-MS Rt=1.52 mins; [M+H]+ 472, Method 2minLC_v003.

Step 2: rac-7-(8-Ethyl-2,3-diphenyl-7,8-dihydropyrido[2,3-b]pyrazin-5(6H)-yl)heptanoic acid To a solution of rac-ethyl 7-(8-ethyl-2,3-diphenyl-7,8-dihydropyrido[2,3-b]pyrazin-5(6H)-yl)heptanoate (step 1) (15 mg, 0.032 mmol) in THF (4.5 ml) and water (1.5 ml) was added LiOH (4.57 mg, 0.191 mmol). The reaction mixture was heated to reflux for 3.5 hours and stirred at RT overnight. The pH of the reaction mixture was adjusted to pH<5 by addition of 2M HCl. The volatile solvent was removed in vacuo and the crude residue was dissolved in water (10 ml) and extracted with EtOAc (3×10 ml). The combined organic extracts were dried over $MgSO_4$, filtered and concentrated in vacuo to afford the title compound;

LC-MS Rt=1.48 mins; [M+H]+ 444.5, Method 2minLC_v003.

$^1$H NMR (400 MHz, DMSO-d6) δ 7.49-7.41 (2H, dd), 7.40-7.38 (2H, d), 7.30-7.21 (6H, m) 3.75-3.61 (2H, m), 3.57-3.49 (2H, m), 2.98-2.89 (1H, m), 2.33-2.28 (2H, m), 2.19-2.08 (2H, m), 1.98-1.87 (1H, m), 1.75-1.56 (4H, m), 1.48-1.39 (4H, m), 1.29-1.23 (1H, m), 1.12-1.05 (3H, t)

The compounds of the following tabulated Examples (Table 7) were prepared by a similar method to that of Example 7.1 by replacing rac-8-ethyl-2,3-diphenyl-5,6,7,8-tetrahydropyrido[2,3-b]pyrazine (Intermediate HC) with the appropriate pyrazine derivative (prepared analogously to Intermediate HC with the appropriate alkylmagnesium bromide reagent).

TABLE 7

| Ex. | Structure | Name | [M + H]+/NMR |
|---|---|---|---|
| 7.2 | 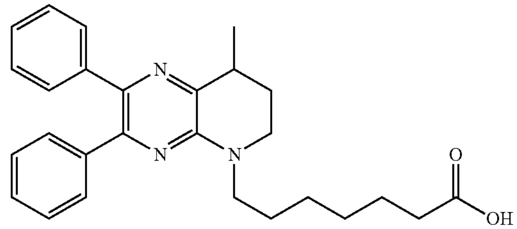 [SMILES: CC1CCN(CCCCCCC(=O)O)c2nc(-c3ccccc3)c(-c3ccccc3)nc21] | rac-7-(8-Methyl-2,3-diphenyl-7,8-dihydropyrido[2,3-b]pyrazin-5(6H)-yl)heptanoic acid | LC-MS RT = 1.44 mins; [M + H]+ 430.5, Method 2minLC_v003. |

TABLE 7-continued

| Ex. | Structure | Name | [M + H]⁺/NMR |
|---|---|---|---|
| 7.3 | 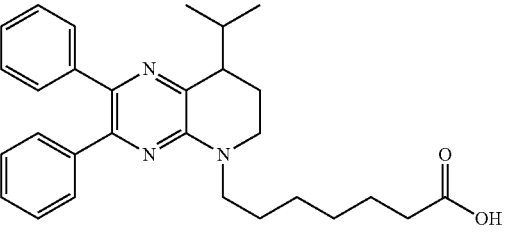 [SMILES: CC(C)C1CCN(CCCCCCC(=O)O)c2nc(-c3ccccc3)c(-c3ccccc3)nc21] | rac-7-(8-Isopropyl-2,3-diphenyl-7,8-dihydro pyrido[2,3-b]pyrazin-5(6H)-yl)heptanoic acid | LC-MS Rt = 1.52 mins; [M + H]+ 458.4, Method 2minLC_v003. |
| 7.4 | 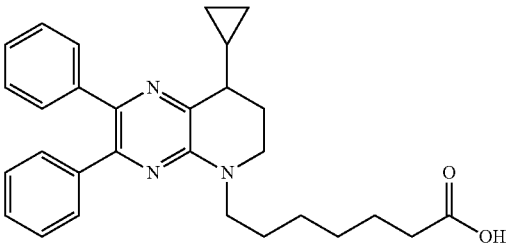 [SMILES: O=C(O)CCCCCCN1CCC(C2CC2)c2nc(-c3ccccc3)c(-c3ccccc3)nc21] | rac-7-(8-Cyclopropyl-2,3-diphenyl-7,8-dihydro pyrido[2,3-b]pyrazin-5(6H)-yl)heptanoic acid | LC-MS Rt = 1.37 mins; [M + H]+ 456.3, Method 2minLC_v003. |
| 7.5 | 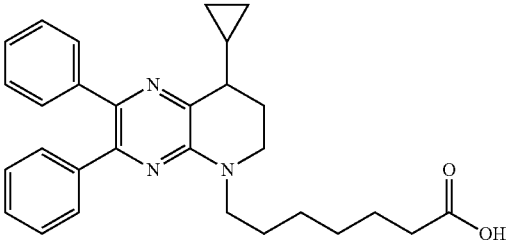 [SMILES: O=C(O)CCCCCCN1CCC(C2CC2)c2nc(-c3ccccc3)c(-c3ccccc3)nc21] | Enantiomer 1 of 7-(8-Cyclopropyl-2,3-diphenyl-7,8-dihydro pyrido[2,3-b]pyrazin-5(6H)-yl)heptanoic acid | LC-MS Rt = 1.35 mins; [M + H]+ 456.3, Method 2minLC_v003. SFC Rt 5.57 min Method C |
| 7.6 | 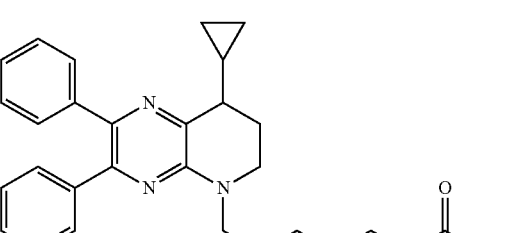 | Enantiomer 2 of 7-(8-Cyclopropyl-2,3-diphenyl-7,8-dihydro pyrido[2,3-b]pyrazin-5(6H)-yl)heptanoic acid | LC-MS Rt = 1.34 mins; [M + H]+ 456.1, Method 2minLC_v003. SFC Rt 7.27 min Method C |
| 7.7 | 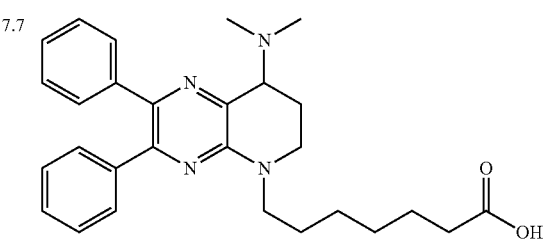 | rac-7-(8-(dimethylamino)-2,3-diphenyl-7,8-dihydropyrido[2,3-b]pyrazin-5(6H)-yl)heptanoic acid | LC-MS Rt = 1.07 mins; [M + H]+ 459.4, Method 2minLC_v003. |

Examples 8.1, 8.1a and 8.1b

Isomer 1 and Isomer 2 of 7-(7,8-dihydroxy-2,3-diphenyl-7,8-dihydropyrido[2,3-b]pyrazin-5(6H)-yl)heptanoic acid

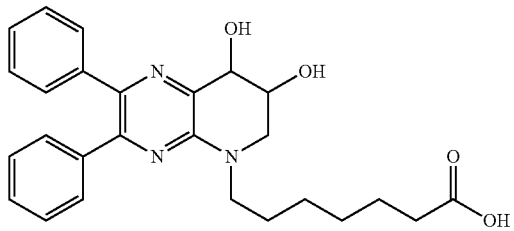 [SMILES: O=C(O)CCCCCCN1CC(O)C(O)c2nc(-c3ccccc3)c(-c3ccccc3)nc21]

| Cis-diol 1 (from peak2) | Cis-diol (from peak 1) |
|---|---|

Step 1: rac-5-(7-Ethoxy-7-oxoheptyl)-2,3-diphenyl-5,6,7,8-tetrahydropyrido[2,3-b]pyrazine-7,8-diyl diacetate To a solution of rac-2,3-diphenyl-5,6,7,8-tetrahydropyrido[2,3-b]pyrazine-7,8-diyl diacetate (Intermediate I) (69 mg, 0.171 mmol) in DCE (3 ml) was added ethyl 7-oxoheptanoate (88 mg, 0.513 mmol) followed by sodium triacetoxyborohydride (109 mg, 0.513 mmol). The reaction was left to stir overnight at room temperature under an atmosphere of nitrogen. To the reaction mixture was added further ethyl 7-oxoheptanoate (88 mg, 0.513 mmol) followed by sodium triacetoxyborohydride (109 mg, 0.513 mmol). The reaction mixture was left to stir at RT under an atmosphere of nitrogen for 4 days. The mixture was diluted with water and extracted with EtOAc (3×20 ml). The combined organic extracts were dried over MgSO$_4$, filtered and concentrated in vacuo. The resulting crude product was purified by chromatography on silica eluting with 0-70% EtOAc/iso-hexane to afford the title compound;

LC-MS Rt=1.46 mins; [M+H]+ 560, Method 2min-LC_v003.

Step 2: Example 8.1 rac-7-(7,8-Dihydroxy-2,3-diphenyl-7,8-dihydropyrido[2,3-b]pyrazin-5(6H)-yl)heptanoic acid To a solution of rac-5-(7-ethoxy-7-oxoheptyl)-2,3-diphenyl-5,6,7,8-tetrahydropyrido[2,3-b]pyrazine-7,8-diyl diacetate (step 1) (30 mg, 0.054 mmol) in THF (3 ml) and water (1.0 ml) was added LiOH (7.70 mg, 0.322 mmol). The suspension was heated to reflux for 1 hour and allowed to stand at RT overnight. The mixture was again heated at reflux for 30 minutes and after cooling to RT, 1M HCl was added to adjust the pH to below pH 5. The volatile solvent was evaporated and the resulting mixture was extracted with EtOAc (10 ml). The organic extract was washed with water, dried over MgSO$_4$, filtered and concentrated in vacuo to afford a mixture of the title products;

LC-MS Rt=1.10 mins; [M+H]+ 448, Method 2min-LC_v003.

Chiral separation of the mixture using Supercritical Fluid Chromatography afforded the individual isomers:
Method Details:

| Column: | Phenomenex LUX C2 250 × 10 mm, 5 um |
|---|---|
| Mobile phase: | 50% methanol/50% CO2 |
| Flow: | 10 ml/min |
| Detection: | UV @ 220 nm |

Example 8.1a

First eluted peak; R.t=6.21 mins Isomer 1 of 7-(7,8-Dihydroxy-2,3-diphenyl-7,8-dihydropyrido[2,3-b]pyrazin-5(6H)-yl)heptanoic acid LC-MS Rt=1.12 mins; [M+H]+448.3, Method 2min-LC_v003
$^1$H NMR (400 MHz, CDCl$_3$) δ 7.45-7.41 (2H, m), 7.37-7.34 (2H, m), 7.29-7.27 (6H, m), 4.81 (1H, d), 4.39 (1H, br d), 3.74-3.58 (4H, m), 2.29 (2H, t), 1.74-1.63 (4H, m), 1.41 (4H, m)

Example 8.1b

Second eluted peak; R.t=9.74 mins Isomer 2 of 7-(7,8-Dihydroxy-2,3-diphenyl-7,8-dihydropyrido[2,3-b]pyrazin-5(6H)-yl)heptanoic acid LC-MS Rt=1.10 mins; [M+H]+448.0, Method 2min-LC_v003
$^1$H NMR (400 MHz, CDCl$_3$) δ 7.45-7.41 (2H, m), 7.37-7.34 (2H, m), 7.29-7.27 (6H, m), 4.81 (1H, d), 4.39 (1H, broad doublet), 3.74-3.58 (4H, m), 2.29 (2H, t), 1.74-1.63 (4H, m), 1.41 (4H, m)

Example 8.2a and 8.2b

Isomer 1 and Isomer 2 of 7-(7,8-dihydroxy-2,3-diptolyl-7,8-dihydropyrido[2,3-b]pyrazin-5(6H)-yl)heptanoic acid

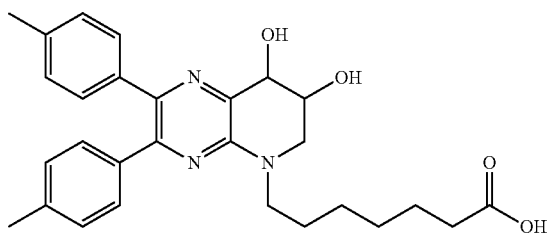 [SMILES: Cc1ccc(-c2nc3c(nc2-c2ccc(C)cc2)N(CCCCCCC(=O)O)CC(O)C3O)cc1]

Step 1: 2,3-Dip-tolyl-5,6-dihydropyrido[2,3-b]pyrazine

To 2,3-Dip-tolylpyrido[2,3-b]pyrazine (Intermediate E, step 1) (6.74 g, 21.65 mmol) in THF (130 ml) was added dropwise at room temperature 2.4 M LiAlH4 in THF (4.51 ml, 10.82 mmol). To the reaction mixture cooled to 0° C. was added dropwise and successively water (0.409 ml), 15% aqueous NaOH (0.409 ml) and water (1.227 ml). The mixture was stirred at 0° C. for 15 min and allowed to warm to RT. Anhydrous MgSO$_4$ was added and the mixture was stirred for 15 min and filtered. The residue was washed with EtOAc (×5) and the filtrate was concentrated in vacuo to afford the title compound:

LC-MS Rt=1.12 mins; [M+H]⁺314, Method 2min-LC_v003.

Step 2: tert-Butyl 2,3-dip-tolylpyrido[2,3-b]pyrazine-5(6H)-carboxylate 2,3-Dip-tolyl-5,6-dihydropyrido[2,3-b]pyrazine (Step 1) (2.9 g, 9.25 mmol) in dry Et₂O (150 ml) cooled to −78° C. was treated dropwise with 2.5M BuLi in hexanes (7.40 ml, 18.51 mmol). After stirring at −78° C. for 10 minutes, di-tert-butyl dicarbonate (2.79 ml, 12.03 mmol) was added and the mixture was allowed to stir and warm to RT. After stirring for 2 days, the reaction mixture was quenched with NH₄Cl (sat.). The phases were separated and the organics were washed with water and brine, dried (sodium sulphate), filtered and concentrated in vacuo. The crude product was purified by chromatography on silica eluting with 0-50% EtOAc in iso-hexane, to afford the title compound:

LC-MS Rt=1.54 mins; [M+H]⁺414, [ M+H-tBu] 358 Method 2minLC_v003.

Step 3: rac-tert-Butyl 7,8-dihydroxy-2,3-dip-tolyl-7,8-dihydropyrido[2,3-b]pyrazine-5(6H)-carboxylate To a solution of tributylmethylammonium chloride (0.970 g, 4.11 mmol) in DCM (15 ml) at RT under nitrogen was added potassium permanganate (0.650 g, 4.11 mmol) portionwise over 10 minutes. The mixture was cooled to 0° C. and treated dropwise with a solution of tert-butyl 2,3-dip-tolylpyrido[2,3-b]pyrazine-5(6H)-carboxylate (step 2) (1 g, 2.418 mmol) in DCM (10 ml). A solution of sodium bisulfite (1.510 g, 14.51 mmol) in water (12.5 ml) was added keeping the temperature <10° C. The mixture was filtered through Celite® (filter material), washing with DCM. The phases were separated and the organic portion was washed with brine, dried (sodium sulphate), filtered and the solvent was removed in vacuo. The crude product was dissolved in DCM and purified by chromatography on silica eluting with 30-50% EtOAc in iso-hexanes to afford the title compound;

LC-MS Rt=1.31 mins; [M+H]⁺448, [ M+H-tBu] 392 Method 2minLC_v003.

Step 4: rac-5-(tert-Butoxycarbonyl)-2,3-dip-tolyl-5,6,7,8-tetrahydropyrido[2,3-b]pyrazine-7,8-diyl diacetate Acetic anhydride (260 μl, 2.76 mmol) was added to a solution of rac-tert-butyl 7,8-dihydroxy-2,3-dip-tolyl-7,8-dihydropyrido[2,3-b]pyrazine-5(6H)-carboxylate (step 3) (411 mg, 0.918 mmol) in pyridine (1783 μl, 22.04 mmol) and stirred at RT for 18 h. The resulting mixture was diluted with DCM and washed with saturated NaHCO₃. The organic portion was dried (sodium sulphate) filtered and concentrated in vacuo. The crude product was purified on silica eluting with 0-65% EtOAc in iso-hexane to afford the title compound;

LC-MS Rt=1.47 mins; [M+H]⁺532, [ M+H-tBu] 476 Method 2minLC_v003.

Step 5: rac-2,3-Dip-tolyl-5,6,7,8-tetrahydropyrido[2,3-b]pyrazine-7,8-diyldiacetate A solution of rac-5-(tert-butoxycarbonyl)-2,3-dip-tolyl-5,6,7,8-tetrahydropyrido[2,3-b]pyrazine-7,8-diyl diacetate (step 4) (430 mg, 0.809 mmol) in 4M HCl in dioxane (4.044 ml, 16.18 mmol) was stirred at RT for 20 minutes. The mixture was washed with saturated sodium bicarbonate solution and extracted with ethyl acetate (2×20 ml). The organic extracts were combined, dried over MgSO₄, filtered and concentrated in vacuo. The crude product was purified by chromatography on silica eluting with 10-100% ethyl acetate in iso-hexane to afford the title compound;

LC-MS Rt=1.29 mins; [M+H]⁺432. Method 2min-LC_v003.

Step 6: rac-5-(7-Ethoxy-7-oxoheptyl)-2,3-dip-tolyl-5,6,7,8-tetrahydropyrido[2,3-b]pyrazine-7,8-diyl diacetate A solution of rac-2,3-dip-tolyl-5,6,7,8-tetrahydropyrido[2,3-b]pyrazine-7,8-diyl diacetate (step 5) (215 mg, 0.498 mmol) in 1,2-dichloroethane (20 ml) was treated with ethyl 7-oxoheptanoate (257 mg, 1.495 mmol) followed by sodium triacetoxyborohydride (634 mg, 2.99 mmol). The resulting suspension was stirred at RT for 18 h. Further portions of ethyl 7-oxoheptanoate (517 mg, 3.386 mmol) was added over the course of 2 days. The mixture was diluted with NaHCO₃ (sat. 50 ml) and extracted with DCM (3×40 ml). The combined organic extracts were dried (MgSO₄) and concentrated in vacuo. The crude product was purified by chromatography on silica eluting with 0-1% THF/DCM to afford the title compound:

LC-MS Rt=6.62 mins; [M+H]⁺588. Method 10min-LC_v003

Step 7: Isomer 1 and Isomer 2 of 7-(7,8-dihydroxy-2,3-dip-tolyl-7,8-dihydropyrido[2,3-b]pyrazin-5(6H)-yl)heptanoic acid To a solution of rac-5-(7-ethoxy-7-oxoheptyl)-2,3-dip-tolyl-5,6,7,8-tetrahydropyrido[2,3-b]pyrazine-7,8-diyl diacetate (step 6) (117 mg, 0.199 mmol) in THF (3 ml) and water (1 ml) was added LiOH (28.6 mg, 1.194 mmol). The mixture was stirred at RT for 18 h followed by heated at 60° C. for 1 h. After cooling to RT, the mixture was acidified to pH 4/5 with 2M HCl and extracted with EtOAc. The combined organic extracts were dried (sodium sulphate), filtered and concentrated in vacuo to afford a mixture of the title products;

Chiral separation of the mixture using Supercritical Fluid Chromatography afforded the individual isomers:

Method Details:
  Column: Phenomenex LUX C2 250×10 mm, 5 um
  Mobile phase: 40% methanol/60% CO₂
  Flow: 10 ml/min
  Detection: UV @ 220 nm Example 8.2a First eluted peak; R.t=6.58 mins Isomer 1 of 7-(7,8-dihydroxy-2,3-dip-tolyl-7,8-dihydropyrido[2,3-b]pyrazin-5(6H)-yl)heptanoic acid LC-MS Rt=4.34 mins; [M+H]⁺476, Method 10min-LC_v003

¹H NMR (400 MHz, MeOH-d₄) δ 7.26 (2H, d), 7.21 (2H, d), 7.07 (4H, m), 4.77 (1H, m), 4.22-4.17 (1H, m), 3.71 (2H, t), 3.63-3.56 (1H, m), 3.53-3.47 (1H, m), 2.33 (6H, s), 2.21 (2H, t) 1.77-1.67 (2H, m), 1.65-1.51 (2H, m) 1.48-1.37 (4H, m)

Example 8.2b

Second eluted peak; R.t=10.23 mins Isomer 2 of 7-(7,8-dihydroxy-2,3-dip-tolyl-7,8-dihydropyrido[2,3-b]pyrazin-5(6H)-yl)heptanoic acid LC-MS Rt=4.28 mins; [M+H]+ 476, Method 10min-LC_v003

¹H NMR (400 MHz, MeOH-d4) δ 7.26 (2H, d), 7.21 (2H, d), 7.07 (4H, m), 4.77 (1H, m), 4.24-4.15 (1H, m), 3.71 (2H, t), 3.64-3.56 (1H, m), 3.54-3.46 (1H, m), 2.33 (6H, s), 2.21 (2H, t), 1.78-1.67 (2H, m), 1.64-1.53 (2H, m), 1.49-1.27 (4H, m)

Example 9.1

(R)-7-(8-Hydroxy-2,3-diphenyl-7,8-dihydropyrido[2,3-b]pyrazin-5(6H)-yl)heptanoic acid

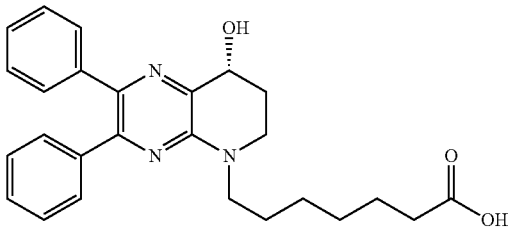 [SMILES: O=C(O)CCCCCCN1CC[C@@H](O)c2nc(-c3ccccc3)c(-c3ccccc3)nc21]

Step 1: (R)-Ethyl 7-(8-acetoxy-2,3-diphenyl-7,8-dihydropyrido[2,3-b]pyrazin-5(6H)-yl)heptanoate To a solution of (R)-2,3-diphenyl-5,6,7,8-tetrahydropyrido[2,3-b]pyrazin-8-yl acetate (Intermediate HBR) in DCE (7 ml) was added ethyl 7-oxoheptanoate (71.8 mg, 0.417 mmol) followed by sodium triacetoxyborohydride (236 mg, 1.112 mmol). The reaction mixture was left to stir at room temperature overnight under an atmosphere of nitrogen. A further portion of ethyl 7-oxoheptanoate (6 equivalents) was added and the reaction mixture was left to stir at RT for 4 days. The mixture was diluted with water (20 ml) and extracted with EtOAc (3×20 ml). The combined organic extracts were dried over MgSO₄, filtered and concentrated in vacuo. The resulting crude product was purified by chromatography on silica eluting with 0-40% EtOAc/iso-hexane to afford the title compound;

LC-MS Rt=1.42 mins; [M+H]+ 503, Method 2min-LC_v003.

Step 2: (R)-7-(8-Hydroxy-2,3-diphenyl-7,8-dihydropyrido[2,3-b]pyrazin-5(6H)-yl)heptanoic acid To a solution of (R)-ethyl 7-(8-acetoxy-2,3-diphenyl-7,8-dihydropyrido[2,3-b]pyrazin-5(6H)-yl)heptanoate (step 1) (24.4 mg, 0.049 mmol) in THF (3 ml) and water (1 ml) was added LiOH (6.99 mg, 0.292 mmol). The reaction mixture was heated to reflux for 1.5 h. A further 6 equivalents of LiOH was added and heated continued at reflux for 1 h. After cooling to RT, the pH of the mixture was adjusted to pH below 5 by addition of 2M HCl. The volatile solvent was removed in vacuo. To the residue was added water (10 ml) and the mixture was extracted with ethyl acetate (3×10 ml). The organic phase were combined, dried over MgSO₄, filtered and concentrated in vacuo. Purification of the crude product was carried out by chromatography on silica eluting with 0-100% EtOAc/iso-hexane followed by 0-100% MeOH/DCM. The residue was passed through a pre-conditioned Isolute SCX-2 SPE column loading with MeOH and eluting with 1M ammonia in MeOH. The basic fraction was concentrated in vacuo and the residue was dissolved in THF (3 ml) and water (1.0 ml) and treated with LiOH (6.99 mg, 0.292 mmol). After stirring at reflux for 1.5 h, the mixture was allowed to cool to RT and acidifed with 2M HCl to pH below 5. The volatile solvent was removed in vacuo. To the residue was added water (10 ml) and the mixture was extracted with ethyl acetate (3×10 ml). The organic phases were combined, dried over MgSO₄, filtered and concentrated in vacuo to afford the title compound;

LC-MS Rt=1.15 mins; [M+H]+ 432, Method 2min-LC_v003.

¹H NMR (400 MHz CDCl3) δ 7.32 (2H, dd), 7.28 (2H, m), 7.21-7.12 (6H, m) 4.75 (1H, dd), 3.60 (2H, t), 3.43 (2H, t), 2.29-2.18 (3H, m), 2.01 (1H, m), 1.61-1.50 (4H, m), 1.35-1.26 (4H, m).

Example 9.2

(S)-7-(8-Hydroxy-2,3-diphenyl-7,8-dihydropyrido[2,3-b]pyrazin-5(6H)-yl)heptanoic acid

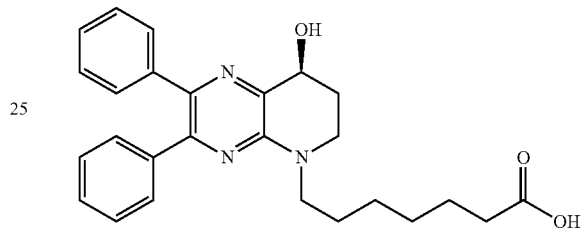

Step 1: (S)-Ethyl 7-(8-acetoxy-2,3-diphenyl-7,8-dihydropyrido[2,3-b]pyrazin-5(6H)-yl)heptanoate To a solution of (S)-2,3-diphenyl-5,6,7,8-tetrahydropyrido[2,3-b]pyrazin-8-yl acetate (Intermediate HBS) (46 mg, 0.133 mmol) in DCE (7 ml) was added ethyl 7-oxoheptanoate (68.8 mg, 0.4 mmol) followed by sodium triacetoxyborohydride (226 mg, 1.065 mmol). The reaction mixture was left to stir at room temperature overnight under an atmosphere of nitrogen. A further portion of ethyl 7-oxoheptanoate (71.8 mg, 0.417 mmol) was added. The reaction mixture was left to stir for a further 5 hours under an atmosphere of nitrogen. Water (20 ml) was added and the resulting mixture was extracted with EtOAc (3×20 ml). The combined organic extracts were dried over MgSO₄, filtered and concentrated to give a crude oil. The resulting crude product was purified by chromatography on silica eluting with 0-40% EtOAc/iso-hexane to afford an oil. The compound was passed through a pre-conditioned Isolute SCX-2 SPE column loading with MeOH and eluting with 1M ammonia in MeOH (20 ml) to afford the title compound;

LC-MS Rt=1.40 mins; [M+H]+ 502, Method 2min-LC_v003.

Step 2: (S)-7-(8-Hydroxy-2,3-diphenyl-7,8-dihydropyrido[2,3-b]pyrazin-5(6H)-yl)heptanoic acid The title compound was prepared from (S)-ethyl 7-(8-acetoxy-2,3-diphenyl-7,8-dihydropyrido[2,3-b]pyrazin-5(6H)-yl)heptanoate (step 1) and LiOH analogously to Example 9.1;

LC-MS Rt=1.16 mins; [M+H]+ 432, Method 2min-LC_v003.

¹H NMR (400 MHz CDCl3) δ 7.32 (2H, dd), 7.28 (2H, m), 7.21-7.12 (6H, m) 4.75 (1H, dd), 3.60 (2H, t), 3.43 (2H, t), 2.29-2.18 (3H, m), 2.01 (1H, m), 1.61-1.50 (4H, m), 1.35-1.26 (4H, m)

Example 9.8, 9.8a and 9.8b

Enantiomer 1 and Enantiomer 2 of 7-(8-Hydroxy-2, 3-dip-tolyl-7,8-dihydropyrido[2,3-b]pyrazin-5(6H)-yl)heptanoic acid

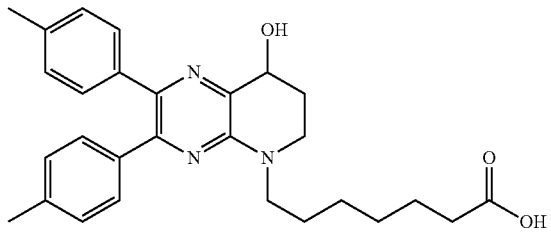 [SMILES: Cc1ccc(-c2nc3c(nc2-c2ccc(C)cc2)N(CCCCCCC(=O)O)CCC3O)cc1]

Step 1: rac-Ethyl 7-(8-acetoxy-2,3-dip-tolyl-7,8-dihydropyrido[2,3-b]pyrazin-5(6H)-yl)heptanoate To rac-2,3-dip-tolyl-5,6,7,8-tetrahydropyrido[2,3-b]pyrazin-8-yl acetate (Intermediate HF)(70 mg, 0.187 mmol) in 1,2-dichloroethane (3 ml) was added ethyl 7-oxoheptanoate (97 mg, 0.562 mmol). The reaction mixture was stirred at room temperature for 20 minutes and sodium triacetoxyborohydride (119 mg, 0.562 mmol) was added. The solution was stirred at room temperature overnight. Water (5 ml) was added and the reaction mixture was stirred vigorously for 15 minutes. The resulting mixture was extracted with DCM (×3). The combined organic extracts were dried over MgSO$_4$, filtered and concentrated. The residue was passed through a pre-conditioned Isolute SCX-2 SPE column loading with MeOH and eluting with 1M ammonia in MeOH (20 ml). The solvent was removed in vacuo and the resulting crude was purified by chromatography on silica eluting with 0-100% EtOAc/iso-hexane to afford the title compound LC-MS Rt=1.58 mins; [M+H]+ 530.4, Method 2minLC_v003.

Step 2: Example 9.8 rac-7-(8-Hydroxy-2,3-dip-tolyl-7,8-dihydropyrido[2,3-b]pyrazin-5(6H)-yl)heptanoic acid To rac-ethyl 7-(8-acetoxy-2,3-dip-tolyl-7,8-dihydropyrido[2,3-b]pyrazin-5(6H)-yl)heptanoate (step 1) (75 mg, 0.142 mmol) in ethanol (2 ml) was added 2M sodium hydroxide (0.283 ml, 0.566 mmol). The reaction mixture was stirred at room temperature for 18 hours. The mixture was acidified with 2M HCl (0.283 ml) and the solvent was removed in vacuo. To the residue was added DCM and water. The organic portion was separated, dried (MgSO$_4$), filtered and concentrated in vacuo to afford the title compound;

LC-MS Rt=1.27 mins; [M+H]+ 460.4, Method 2minLC_v003.

$^1$H NMR (400 MHz, CDCl3) δ 7.33 (2H, d), 7.24 (2H, d), 7.08 (4H, m), 4.86 (1H, m), 3.67 (2H, m), 3.51 (2H, m), 2.36 (3H, s), 2.35 (3H, s) 2.31 (3H, m), 2.09 (1H, m), 1.66 (4H, m), 1.41 (4H, m).

Step 3: Enantiomer 1 and Enantiomer 2 of 7-(8-Hydroxy-2,3-dip-tolyl-7,8-dihydropyrido[2,3-b]pyrazin-5(6H)-yl)heptanoic acid Chiral separation of rac-7-(8-Hydroxy-2,3-dip-tolyl-7,8-dihydropyrido[2,3-b]pyrazin-5(6H)-yl)heptanoic acid (step 2) using Supercritical Fluid Chromatography afforded the individual enantiomers:

Method Details:

| | |
|---|---|
| Column: | Phenomenex LUX C2 250 × 10 mm, 5 um |
| Mobile phase: | 45% methanol/55% CO2 |
| Flow: | 10 ml/min |
| Detection: | UV @ 220 nm |
| System: | Berger Minigram SFC2 |
| Column Temp: | 35 deg C. |

Example 9.8a

First eluted peak; Rt=7.14 mins: Enantiomer 1 of 7-(8-Hydroxy-2,3-dip-tolyl-7,8-dihydropyrido[2,3-b]pyrazin-5(6H)-yl)heptanoic acid LC-MS Rt=1.25 mins; [M+H]+ 460.4, Method 2min-LC_v003

$^1$H NMR (400 MHz, CDCl3) δ 7.34 (2H, d), 7.27 (2H, d), 7.08 (4H, m), 4.84 (1H, m), 3.68 (2H, m), 3.51 (2H, m), 2.36 (3H, s), 2.35 (3H, s) 2.33 (3H, m), 2.09 (1H, m), 1.66 (4H, m), 1.41 (4H, m).

Example 9.8b

Second eluted peak; Rt=8.16 mins: Enantiomer 2 of 7-(8-Hydroxy-2,3-dip-tolyl-7,8-dihydropyrido[2,3-b]pyrazin-5(6H)-yl)heptanoic acid LC-MS Rt=1.25 mins; [M+H]+ 460.4, Method 2min-LC_v003

$^1$H NMR (400 MHz, CDCl3) δ 7.34 (2H, d), 7.27 (2H, d), 7.08 (4H, m), 4.83 (1H, m), 3.67 (2H, m), 3.51 (2H, m), 2.36 (3H, s), 2.35 (3H, S) 2.32 (3H, m), 2.07 (1H, m), 1.66 (4H, m), 1.41 (4H, m).

The compounds of the following tabulated Examples (Table 8) were prepared by a similar method to that of Example 9.1 by replacing (R)-2,3-diphenyl-5,6,7,8-tetrahydropyrido[2,3-b]pyrazin-8-yl acetate (Intermediates HBR) with the appropriate pyrazine derivative. Some compounds are obtained by purification using SFC.

TABLE 8

| Ex. | Structure | Name | [M + H]+/NMR |
|---|---|---|---|
| 9.3 | 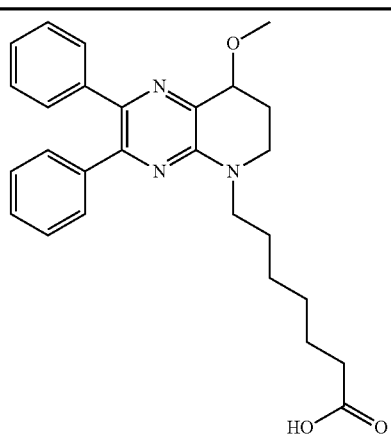 | rac-7-(8-Methoxy-2,3-diphenyl-7,8-dihydropyrido[2,3-b]pyrazin-5(6H)-yl)heptanoic acid | LC-MS Rt = 1.51 mins; [M + H]+ 446, Method 2minLC_v003. |

TABLE 8-continued

| Ex. | Structure | Name | [M + H]⁺/NMR |
|---|---|---|---|
| 9.4 | 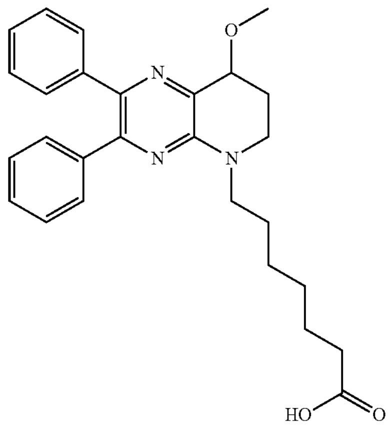 [SMILES: COC1CCN(CCCCCCC(=O)O)c2nc(-c3ccccc3)c(-c3ccccc3)nc21] | Enantiomer 1 of 7-(8-Methoxy-2,3-diphenyl-7,8-dihydropyrido[2,3-b]pyrazin-5(6H)-yl)heptanoic acid | LC-MS Rt = 1.34 mins; [M + H]+ 446, Method 2minLC_v003. SFC Rt 3.91 mins; Method OJ20MEOH |
| 9.5 | 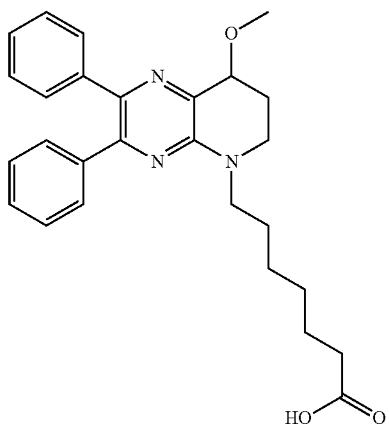 [SMILES: COC1CCN(CCCCCCC(=O)O)c2nc(-c3ccccc3)c(-c3ccccc3)nc21] | Enantiomer 2 of 7-(8-methoxy-2,3-diphenyl-7,8-dihydropyrido[2,3-b]pyrazin-5(6H)-yl)heptanoic | LC-MS Rt = 1.34 mins; [M + H]+ 446, Method 2minLC_v003. SFC Rt 4.63 mins; Method OJ20MEOH |
| 9.6 | 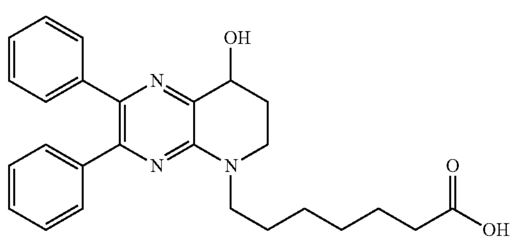 [SMILES: O=C(O)CCCCCCN1CCC(O)c2nc(-c3ccccc3)c(-c3ccccc3)nc21] | rac-7-(8-hydroxy-2,3-diphenyl-7,8-dihydropyrido[2,3-b]pyrazin-5(6H)-yl)heptanoic acid | LC-MS Rt = 1.19 mins; [M + H]+ 432, Method 2minLC_v003. |
| 9.7 | 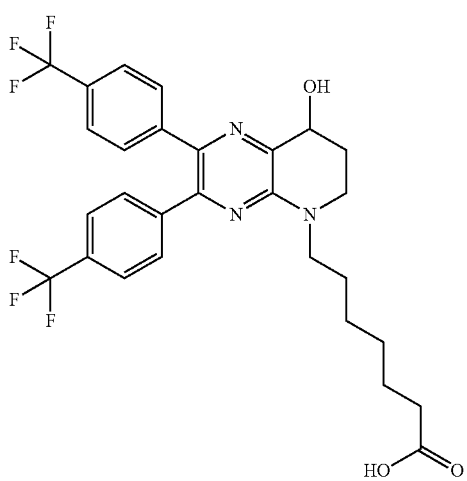 [SMILES: O=C(O)CCCCCCN1CCC(O)c2nc(-c3ccc(C(F)(F)F)cc3)c(-c3ccc(C(F)(F)F)cc3)nc21] | rac-7-(8-hydroxy-2,3-bis(4-(trifluoromethyl)phenyl)-7,8-dihydropyrido[2,3-b]pyrazin-5(6H)-yl)heptanoic acid | LC-MS Rt = 1.39 mins; [M + H]+ 568, Method 2minLC_v003. |

Example 10.1

(E)-7-(2,3-Diphenyl-7,8-dihydropyrido[3,2-b]pyrazin-5(6H)-yl)hept-3-enoic acid

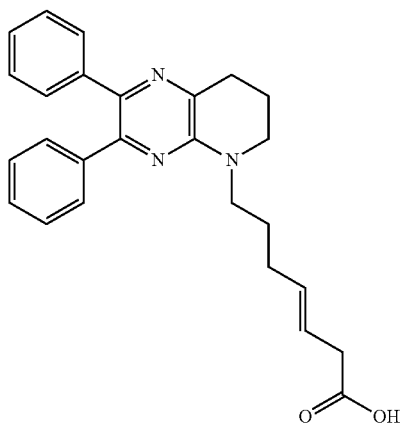 [SMILES: O=C(O)C/C=C/CCCN1CCCc2nc(-c3ccccc3)c(-c3ccccc3)nc21]

Step 1: 5-(Pent-4-enyl)-2,3-diphenyl-5,6,7,8-tetrahydropyrido[3,2-b]pyrazine To a solution of 2,3-diphenyl-5,6,7,8-tetrahydropyrido[3,2-b]pyrazine (Ex. 4.1 step 1) (2 g, 6.96 mmol) in DCE (35 ml) was added pent-4-enal (2.061 ml, 20.88 mmol) and the mixture was stirred at RT overnight. A further portion of sodium triacetoxyborohydride (4.43 g, 20.88 mmol) was added and the mixture was stirred at RT for 2.5 hours under an atmosphere of nitrogen. Water was added and the mixture was extracted with EtOAc (3×60 ml). The combined organic extracts were dried over MgSO$_4$, filtered and concentrated in vacuo. The crude material was purified by chromatography on silica eluting with EtOAc/iso-hexane to afford the title compound;

LC-MS Rt=1.54 mins; [M+H]$^+$357, Method 2min-LC_v003.

Step 2: (E)-Methyl 7-(2,3-diphenyl-7,8-dihydropyrido[3,2-b]pyrazin-5(6H)-yl)hept-3-enoate To a solution of 5-(pent-4-enyl)-2,3-diphenyl-5,6,7,8-tetrahydropyrido[3,2-b]pyrazine (step 1) (200 mg, 0.563 mmol) and methyl but-3-enoate (225 mg, 2.251 mmol) in DCM (300 ml) was added Grubbs Catalyst second generation (5 mol %, 23.88 mg, 0.028 mmol). The reaction was stirred at RT under an atmosphere of nitrogen overnight. An additional portion of Grubbs Catalyst second generation (5 mol %, 23.88 mg, 0.028 mmol) was added and stirring continued for 2.5 h. The solvent was removed in vacuo and the resulting crude was purified by chromatography on silica eluting with EtOAc/iso-hexane to afford the title compound;

LC-MS Rt=1.42 mins; [M+H]$^+$428, Method 2min-LC_v003.

Step 3: (E)-7-(2,3-Diphenyl-7,8-dihydropyrido[3,2-b]pyrazin-5(6H)-yl)hept-3-enoic acid To a solution of (E)-methyl 7-(2,3-diphenyl-7,8-dihydropyrido[3,2-b]pyrazin-5(6H)-yl)hept-3-enoate (step 2) (30 mg, 0.070 mmol) in THF (3 ml):MeOH (1 ml) was added LiOH (10.08 mg, 0.421 mmol) in water (1 ml). The reaction mixture was heated at reflux for 1.5 h. After cooling to RT, 2M HCl was added until the pH of the mixture was below pH 5. The volatile solvent was removed in vacuo and the resulting mixture was extracted with EtOAc (2×15 ml). The combined organic extracts were washed with water, dried over MgSO$_4$ and concentrated in vacuo to afford the title compound;

LC-MS Rt=1.15 mins; [M+H]$^+$414, Method 2min-LC_v003.

Example 10.2

8-(2,3-Dip-tolyl-7,8-dihydropyrido[2,3-b]pyrazin-5(6H)-yl)octanoic acid

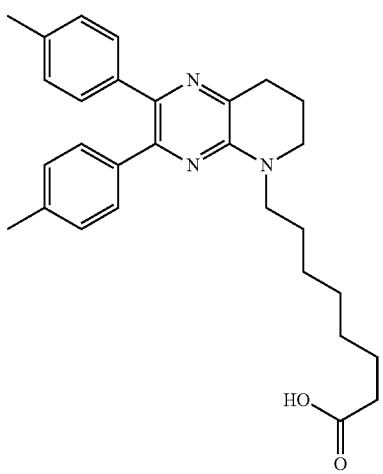 [SMILES: Cc1ccc(-c2nc3c(nc2-c2ccc(C)cc2)N(CCCCCCCC(=O)O)CCC3)cc1]

Step 1: 5-(Hept-6-enyl)-2,3-dip-tolyl-5,6,7,8-tetrahydropyrido[2,3-b]pyrazine The title compound was prepared from 2,3-dip-tolyl-5,6,7,8-tetrahydropyrido[2,3-b]pyrazine (Intermediate E) and hept-6-enal analogously to 5-(pent-4-enyl)-2,3-diphenyl-5,6,7,8-tetrahydropyrido[3,2-b]pyrazine (Example 10.1 step 1).

LC-MS Rt=1.47 mins; [M+H]$^+$412.7, Method 2min-LC_v003.

Step 2: (E)-Ethyl 8-(2,3-dip-tolyl-7,8-dihydropyrido[2,3-b]pyrazin-5(6H)-yl)oct-2-enoate The title compound was prepared from 5-(hept-6-enyl)-2,3-dip-tolyl-5,6,7,8-tetrahydropyrido[2,3-b]pyrazine (step 1) and ethyl acrylate analogously to (E)-Methyl 7-(2,3-diphenyl-7,8-dihydropyrido[3,2-b]pyrazin-5(6H)-yl)hept-3-enoate (Example 10.1 step 2).

LC-MS Rt=1.42 mins; [M+H]$^+$484.4, Method 2min-LC_v003.

Step 3: Ethyl 8-(2,3-dip-tolyl-7,8-dihydropyrido[2,3-b]pyrazin-5(6H)-yl)octanoate A solution of (E)-ethyl 8-(2,3-dip-tolyl-7,8-dihydropyrido[2,3-b]pyrazin-5(6H)-yl)oct-2-enoate (step 1) (60 mg, 0.124 mmol) and 10% Pd/C (66.0 mg, 0.062 mmol) in MeOH (10 ml) placed under an atmosphere of hydrogen at 0.35 bar pressure and stirred at room temperature overnight. The mixture was filtered through Celite® (filter material) and washed through with MeOH. The filtrated was concentrated in vacuo and purification of the crude product by chromatography on silica eluting with iso-hexane/EtOAc afforded the title compound as a pale yellow oil;

LC-MS Rt=1.41 mins; [M+H]⁺486.2, Method 2min-LC_v003.

Step 4: 8-(2,3-Dip-tolyl-7,8-dihydropyrido[2,3-b]pyrazin-5(6H)-yl)octanoic acid The title compound was prepared from ethyl 8-(2,3-dip-tolyl-7,8-dihydropyrido[2,3-b]pyrazin-5(6H)-yl)octanoate (step 1) analogously to (E)-7-(2,3-diphenyl-7,8-dihydropyrido[3,2-b]pyrazin-5(6H)-yl)hept-3-enoic acid (Example 10.1 step 3);

LC-MS Rt=1.27 mins; [M+H]⁺458.1, Method 2min-LC_v003.

¹H NMR (400 MHz, CDCl3) δ 7.34-7.32 (2H, d), 7.25-7.23 (2H, d) 7.07-7.04 (4H, m), 3.67 (2H, t), 3.46 (2H, t), 3.02 (2H, t), 2.34 (3H, s), 2.32 (3H, s), 2.32-2.29 (2H, t), 2.12-2.07 (2H, m), 1.72-1.57 (4H, m), 1.41-1.26 (6H, m)

Example 11.1

2-(4-(2,3-Diphenyl-7,8-dihydropyrido[2,3-b]pyrazin-5(6H)-yl)butoxy)acetic acid

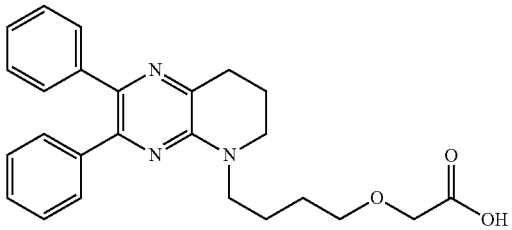 [SMILES: O=C(O)COCCCCN1CCCc2nc(-c3ccccc3)c(-c3ccccc3)nc21]

Step 1: Methyl 4-(2,3-diphenyl-7,8-dihydropyrido[2,3-b]pyrazin-5(6H)-yl)butanoate The title compound was prepared from 2,3-diphenyl-5,6,7,8-tetrahydropyrido[3,2-b]pyrazine (Ex. 4.1 step 1) and methyl 4-oxobutanoate analogously to Example 10, step 1;

LC-MS Rt=1.39 mins; [M+H]⁺388, Method 2min-LC_v003.

Step 2: 4-(2,3-Diphenyl-7,8-dihydropyrido[2,3-b]pyrazin-5(6H)-yl)butyl acetate To a solution of methyl 4-(2,3-diphenyl-7,8-dihydropyrido[2,3-b]pyrazin-5(6H)-yl)butanoate (step 1) (500 mg, 1.290 mmol) in THF (5 ml) was added 1M lithium aluminium hydride in THF (1.290 ml, 1.290 mmol) at 0° C. The reaction was allowed to warm to RT and stirred for 1 h. The mixture was cooled in an ice bath and the reaction was quenched by addition of MeOH. After warming to RT, the solvent was removed in vacuo and the residue was dissolved in EtOAc. The mixture was filtered through Celite® (filter material) and the filtrate was washed with water (3×), dried (MgSO₄) and concentrated in vacuo to afford the title compound;

LC-MS Rt=1.24 mins; [M+H]⁺402, Method 2min-LC_v003.

Step 3: 4-(2,3-Diphenyl-7,8-dihydropyrido[2,3-b]pyrazin-5(6H)-yl)butan-1-ol

To a solution of 4-(2,3-diphenyl-7,8-dihydropyrido[2,3-b]pyrazin-5(6H)-yl)butyl acetate (step 2) (410 mg, 1.021 mmol) in THF (6 ml) and water (3 ml) was added lithium hydroxide (56.9 mg, 2.375 mmol) and the mixture was heated at reflux for 18 h. The reaction mixture was diluted with EtOAc and the combined organic extracts were washed with water (2×), brine, dried (MgSO₄), filtered and concentrated in vacuo to afford the title compound;

LC-MS Rt=1.07 mins; [M+H]⁺360.5, Method 2min-LC_v003.

Step 4: tert-Butyl 2-(4-(2,3-diphenyl-7,8-dihydropyrido[2,3-b]pyrazin-5(6H)-yl)butoxy)acetate To a stirred solution of 4-(2,3-diphenyl-7,8-dihydropyrido[2,3-b]pyrazin-5(6H)-yl)butan-1-ol (step 3) (50 mg, 0.139 mmol) in toluene (1 ml) was added KOH (40% aq, 1 ml, 0.139 mmol) and tetrabutylammonium hydrogen sulfate (47.2 mg, 0.139 mmol) followed after 5 min at RT, by tertiary butyl bromoacetate (90 uL). The reaction mixture was stirred at RT for 24 h. The mixture was diluted with ether and the phases were separated. The aqueous portion was extracted with ether (×2), the combined organics were dried (sodium sulphate), filtered and the solvent removed in vacuo. The residue was dissolved in THF (1 ml) followed by the addition of KOH (40% aq, 1 ml, 0.139 mmol), tetrabutylammonium hydrogen sulfate (47.2 mg, 0.139 mmol) and tertiary butyl bromoacetate (88 uL). The reaction mixture was stirred at RT for 6 h. The mixture was diluted with ether and stirred at RT for 12 h. The phases were separated, the aqueous extracted with ether (×2), the combined organics were dried (sodium sulphate), filtered and the solvent removed in vacuo. The crude material was purified on silica eluting with 0-100% EtOAc/DCM to afford the title compound:

LC-MS Rt=1.36 mins; [M+H]⁺474, Method 2min-LC_v003.

Step 5: 2-(4-(2,3-Diphenyl-7,8-dihydropyrido[2,3-b]pyrazin-5(6H)-yl)butoxy)acetic acid tert-Butyl 2-(4-(2,3-diphenyl-7,8-dihydropyrido[2,3-b]pyrazin-5(6H)-yl)butoxy)acetate (step 4)(20 mg, 0.042 mmol) in DCM (0.5 ml) was treated with TFA (0.5 ml, 6.49 mmol) and stirred at RT for 1 h. The solvent was removed in vacuo and the crude product was dissolved in DCM (with <10% MeOH) and basified with saturated sodium bicarbonate solution. The organic portion was separated and the aqueous was extracted with 10% MeOH/DCM. The combined organic extracts were washed with brine, dried (Na₂SO₄), filtered and concentrated in vacuo to afford the title compound;

LC-MS Rt=3.82 mins; [M+H]⁺418, Method 10min-LC_v003.

¹H NMR (MeOD) δ 7.40-7.20 (10H, m), 3.90 (2H, S), 3.72 (2H, t), 3.60-3.47 (4H, m), 2.98 (2H, t), 2.13 (2H, m), 1.81 (2H, m), 1.70 (2H, m).

Example 11.2

2-(3-((2,3-Diphenyl-7,8-dihydropyrido[3,2-b]pyrazin-5(6H)-yl)methyl)phenoxy)acetic acid

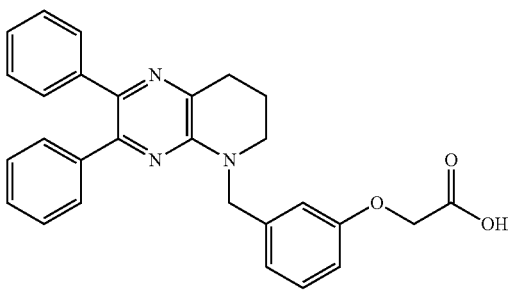 [SMILES: O=C(O)COc1cccc(CN2CCCc3nc(-c4ccccc4)c(-c4ccccc4)nc32)c1]

Step 1: 34(2,3-Diphenyl-7,8-dihydropyrido[3,2-b]pyrazin-5(6H)-yl)methyl)phenol A solution of 2,3-diphenyl-5,6,7,8-tetrahydropyrido[3,2-b]pyrazine (Ex. 4.1 step 1) (287 mg, 0.999 mmol) and 3-hydroxybenzaldehyde (244 mg, 1.998 mmol) in toluene (3 ml) was treated with sodium triacetoxyborohydride (1058 mg, 4.99 mmol) followed by acetic acid (0.057 ml, 0.999 mmol). The resulting suspension was stirred at RT for 3 h. Water was added and stirring continued for 30 min. EtOAc was added and the aqueous portion was acidified with 2M HCl to pH1. The organic layer was separated and concentrated in vacuo. The crude product was purified by chromatography on silica eluting with EtOAc/iso-hexane. A second purification was carried out on silica eluting with water/MeCN to afford the title compound;

$^1$H NMR (400 MHz, DMSO-d6) δ 9.32 (1H, s), 7.30 (2H, m), 7.24 (8H, m), 7.12 (1H, t), 6.73 (2H, m), 6.64 (1H, d), 4.80 (2H, s), 3.42 (2H, t), 2.96 (2H, t), 2.03 (2H, m)

Step 2: Ethyl 2-(3-((2,3-diphenyl-7,8-dihydropyrido[3,2-b]pyrazin-5(6H)-yl)methyl)phenoxy)acetate A mixture comprising 3-((2,3-diphenyl-7,8-dihydropyrido[3,2-b]pyrazin-5(6H)-yl)methyl)phenol (140 mg, 0.356 mmol), potassium carbonate (98 mg, 0.712 mmol) and ethyl 2-bromoacetate (119 mg, 0.712 mmol) in acetone (3 ml) was heated at reflux overnight. The suspension was cooled to room temperature and filtered. The filtrate was evaporated to dryness and the residue was purified by chromatography on silica eluting with EtOAc/iso-hexane to afford the title compound.

Step 3: 2-(3-((2,3-Diphenyl-7,8-dihydropyrido[3,2-b]pyrazin-5(6H)-yl)methyl)phenoxy)acetic acid Ethyl 2-(34(2,3-diphenyl-7,8-dihydropyrido[3,2-b]pyrazin-5(6H)-yl)methyl)phenoxy)acetate (step 2) (163 mg, 0.340 mmol) in EtOH (2 ml) was treated dropwise with 2M NaOH (0.340 ml, 0.680 mmol). The solution was stirred at room temperature for 1 h. The resulting white suspension was collected by filtration, washed with water and dried in a vacuum oven at 40° C. to afford the title compound;

LC-MS Rt=1.18 mins; [M+H]+ 452, Method 2min-LC_v003.

$^1$H NMR (400 MHz, DMSO-d6) δ 7.31 (2H, m), 7.26 (8H, m), 7.16 (1H, t), 6.79 (2H, m), 6.67 (1H, dd), 4.81 (2H, s), 4.04 (2H, s), 3.44 (2H, t), 2.96 (2H, t), 2.03 (2H, m)

Example 11.3

4-(2-(2,3-Dip-tolyl-7,8-dihydropyrido[2,3-b]pyrazin-5(6H)-yl)ethylamino)-4-oxobutanoic acid

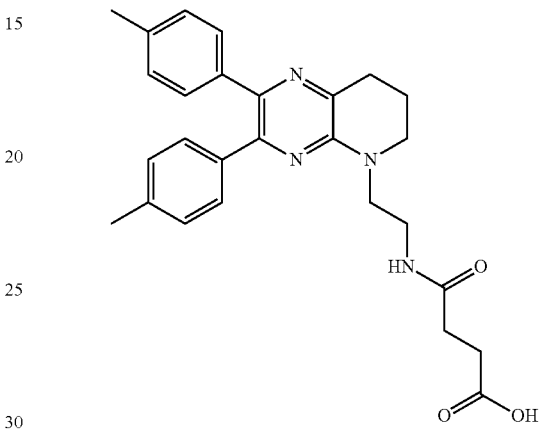

Step 1: tert-Butyl 2-(2,3-dip-tolyl-7,8-dihydropyrido[2,3-b]pyrazin-5(6H)-yl)pethylcarbamate 2,3-Dip-tolyl-5,6,7,8-tetrahydropyrido[2,3-b]pyrazine (Intermediate E) (150 mg, 0.476 mmol) and N-Boc-2-aminoacetaldehyde (151 mg, 0.951 mmol) was suspended in 1,2-dichloroethane (3 ml). After 20 minutes at room temperature, sodium triacetoxyborohydride (252 mg, 1.189 mmol) was added and stirring continued for 2 days at room temperature. A further portion of N-Boc-2-aminoacetaldehyde (100 mg) was added followed by sodium triacetoxyborohydride (252 mg, 1.189 mmol) and the reaction mixture was stirred at room temperature for 3 days. The mixture was partitioned between water and EtOAc and stirring continued for 30 minutes. The organic layer was separated and concentrated in vacuo. The residue was purified by chromatography on silica eluting with 20-60% EtOAc in iso-hexane to afford the title compound;

LC-MS Rt=1.33 mins; [M+H]+ 460, Method 2min-LC_v003

Step 2: 2-(2,3-Dip-tolyl-7,8-dihydropyrido[2,3-b]pyrazin-5(6H)-yl)ethanamine tert-Butyl 2-(2,3-dip-tolyl-7,8-dihydropyrido[2,3-b]pyrazin-5(6H)-yl)ethylcarbamate (step 1)(171 mg, 0.373 mmol) was stirred in 4M HCl in Dioxane (1 ml, 4.00 mmol) for 2 h. The suspension was added to EtOAc and saturated sodium carbonate. The organic layer was separated, dried over (MgSO$_4$), filtered and concentrated in vacuo to afford the title compound;

LC-MS Rt=1.00 mins; [M+H]+ 359, Method 2min-LC_v003.

Step 3: Ethyl 4-(2-(2,3-dip-tolyl-7,8-dihydropyrido [2,3-b]pyrazin-5(6H)-yl)ethylamino)-4-oxobutanoate A mixture comprising 2-(2,3-dip-tolyl-7,8-dihydropyrido [2,3-b]pyrazin-5(6H)-yl)ethanamine (step 2) (108 mg, 0.301 mmol) in ethyl acetate (5 ml) and triethylamine (0.084 ml, 0.603 mmol) at RT was treated dropwise with ethyl succinyl chloride (74.4 mg, 0.452 mmol) and the resulting suspension was stirred at RT for 30 minutes. The mixture was poured into water and extracted with ethyl acetate. The organic layer was separated, dried over and concentrated in vacuo to afford the title compound;

LC-MS Rt=1.15 mins; [M+H]+ 486.8, Method 2min-LC_v003

Step 4: 4-(2-(2,3-Dip-tolyl-7,8-dihydropyrido[2,3-b] pyrazin-5(6H)-yl)ethylamino)-4-oxobutanoic acid Ethyl 4-(2-(2,3-dip-tolyl-7,8-dihydropyrido[2,3-b] pyrazin-5(6H)-yl)ethylamino)-4-oxobutanoate (step 3)(168 mg, 0.345 mmol) was dissolved in EtOH (3 ml). 2M Sodium hydroxide (0.345 ml, 0.690 mmol) was added and the solution stirred for 30 minutes at room temperature. The reaction mixture was concentrated in vacuo and the residue was partitioned between EtOAc and 0.1 M HCl solution. The organic layer was separated and washed with saturated brine, dried (MgSO$_4$) and concentrated in vacuo to a volume of 5 ml. The suspension was filtered and washed with EtOAc to afford the title compound;

LC-MS Rt=1.04 mins; [M+H]+ 459, Method 2min-LC_v003

Example 12.1

7-(6-oxo-2,3-dip-tolyl-7,8-dihydropyrido[2,3-b] pyrazin-5(6H)-yl)heptanoic acid

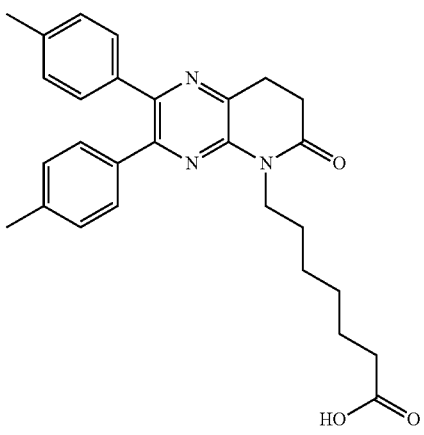 [SMILES: Cc1ccc(-c2nc3c(nc2-c2ccc(C)cc2)N(CCCCCCC(=O)O)C(=O)CC3)cc1]

Step 1: 2,3-Dip-tolyl-7,8-dihydropyrido[2,3-b] pyrazin-6(5H)-one

To a stirrred suspension of 2-bromo-3-chloro-7,8-dihydro-pyrido[2,3-b]pyrazin-6(5H)-one (Intermediate J) (10 g, 38.1 mmol), p-tolylboronic acid (11.39 g, 84 mmol) in MeCN (400 ml) and water (100 ml) under N$_2$ supply, was added solid K$_2$CO$_3$ (fine mesh) (7.90 g, 57.1 mmol) followed by Pd(PPh$_3$)$_2$Cl$_2$ (1.337 g, 1.905 mmol). The yellow RM was heated to 80° C. and was left stirring for 66 hours. The RM was allowed to cool slowly to RT and then placed in the fridge for 3-4 hours. The fine yellow needles were filtered off under suction and were washed with small quantity of acetonitrile, followed by water. After air drying for 10 min, the solid was transferred, dried in vacuo at 40° C. for 2 hours, to afford the title compound as fine crystalline needles;

LC-MS Rt=1.24 mins; [M+H]+ 330.3, Method 2min-LC_v003.

Step 2: Ethyl 7-(6-oxo-2,3-dip-tolyl-7,8-dihydropy-rido[2,3-b]pyrazin-5(6H)-yl)heptanoate A yellow solution of 2,3-dip-tolyl-7,8-dihydropyrido[2,3-b]pyrazin-6(5H)-one (step 1) (1.0 g, 3.04 mmol) and ethyl 7-bromoheptanoate (1.440 g, 6.07 mmol) in DMF (20 ml), under a nitrogen atmosphere, was treated with potassium carbonate (2.098 g, 15.18 mmol) and the resultant suspension was stirred at room temperature for 16 hours. The mixture was diluted with water and extracted with EtOAc (×2). The extracts were washed with water (×2) and brine, dried (MgSO$_4$) and evaporated under vacuum to a brown oil. The crude material was purified by chromatography on silica eluting with 0-100% EtOAc/iso-hexane to afford the title compound as a pale solid;

LC-MS Rt=1.52 mins; [M+H]+ 486.5, Method 2min-LC_v003.

Step 3: 7-(6-oxo-2,3-dip-tolyl-7,8-dihydropyrido[2, 3-b]pyrazin-5(6H)-yl)heptanoic acid A solution of ethyl 7-(6-oxo-2,3-dip-tolyl-7,8-dihydropy-rido[2,3-b]pyrazin-5(6H)-yl)heptanoate (550 mg, 1.133 mmol) in methanol (10 ml) was treated with 1M sodium hydroxide (3.40 ml, 3.40 mmol) and the resultant solution was stirred at 50° C. for 1 hour. The solution was cooled to room temperature and concentrated under vacuum. The residue was diluted with water, acidified to pH ~2 with 1N HCl, giving a white solid which was extracted with DCM (×3). The extracts were dried (MgSO4) and evaporated under vacuum to afford the title compound as a white solid;

LC-MS Rt=1.28 mins; [M+H]+ 458, Method 2minLowpH $^1$H NMR (400 MHz, CDCl$_3$) δ 7.41-7.35 (4H, m), 7.39-7.30 (4H, m), 4.22-4.14 (2H, m), 3.24 (2H, t), 2.90 (2H, t), 2.40-2.29 (8H, m), 1.79-1.69 (2H, m), 1.68-1.60 (2H, m), 1.48-1.35 (4H, m).

Example 13.1

7-(2-(Pyridin-4-yl)-3-p-tolyl-7,8-dihydropyrido[2,3-b]pyrazin-5(6H)-yl)heptanoic acid

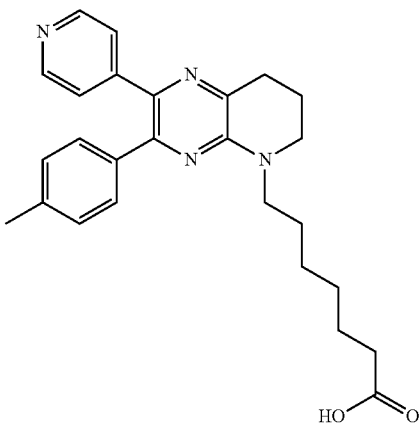 [SMILES: Cc1ccc(-c2nc3c(nc2-c2ccncc2)CCCN3CCCCCCC(=O)O)cc1]

Step 1: Ethyl 7-(2-bromo-3-chloro-6-oxo-7,8-dihydropyrido[2,3-b]pyrazin-5(6H)-yl)heptanoate A solution of 2-bromo-3-chloro-7,8-dihydro-5H-pyrido[2,3-b]pyrazin-6-one (Intermediate J) (3.9 g, 14.86 mmol) and ethyl 7-bromoheptanoate (7.05 g, 29.7 mmol) in DMF (75 ml) under nitrogen was treated with potassium carbonate (10.27 g, 74.3 mmol) and the resultant solution was stirred at room temperature for 96 hours. The mixture was diluted with water and extracted with EtOAc (×2). The combined organic extracts were washed with water, brine, dried (MgSO₄) and concentrated in vacuo. Purification of the crude product by chromatography on silica eluting with 0-60% EtOAc/iso-hexane 0-60% afforded the title compound;

LC-MS Rt=4.91 mins; [M+H]+418/420, Method 10min-LC_v003.

Step 2: Ethyl 7-(2-bromo-3-chloro-7,8-dihydropyrido[2,3-b]pyrazin-5(6H)-yl)heptanoate A solution of ethyl 7-(2-bromo-3-chloro-6-oxo-7,8-dihydropyrido[2,3-b]pyrazin-5(6H)-yl)heptanoate (step 1) (1.0 g, 2.388 mmol) in tetrahydrofuran (10 ml) under a nitrogen atmosphere at 0° C. was treated slowly with 1M borane tetrahydrofuran complex (11.94 ml, 11.94 mmol) and the resultant solution was stirred at 0° C. for 30 minutes and then allowed to warm to room temperature. The mixture was cooled to 0° C. and treated with borane tetrahydrofuran complex borane (2.4 ml, 2.4 mmol). Once the addition was complete the mixture was stirred at 0° C. for 30 minutes and then at RT. The mixture was cooled in ice and carefully treated with MeOH. The mixture was stirred at room temperature for 1 hour and then evaporated under vacuum to give an oil which was purified by chromatography on silica eluting with 0-100% EtOAc/iso-hexane to afford the title compound;

LC-MS Rt=4.91 mins; [M+H]+418/420, Method 10min-LC_v003.

Step 3: Ethyl 7-(3-chloro-2-(pyridin-4-yl)-7,8-dihydropyrido[2,3-b]pyrazin-5(6H)-yl)heptanoate A mixture of ethyl 7-(2-bromo-3-chloro-7,8-dihydropyrido[2,3-b]pyrazin-5(6H)-yl)heptanoate (step 2) (100 mg, 0.247 mmol) and potassium carbonate (102 mg, 0.741 mmol) in dioxane (2 ml) was degassed by bubbling nitrogen through (×3). Pd(Ph₃P)₄ (28.6 mg, 0.025 mmol) was added and the mixture was degassed by bubbling nitrogen through (×3). The mixture was heated at 150° C. for 2 hours using microwave irradiation. The mixture was diluted with water and extracted with EtOAc (×2). The organics were washed with brine, dried (MgSO₄) and evaporated under vacuum to a pale oil. The crude was purified by chromatography on silica eluting with 20-100% EtOAc/iso-hexane to give the title compound as a clear oil;

LC-MS Rt=1.08 mins; [M+H]+ 403, Method 10min-LC_v003.

Step 4: Ethyl 7-(2-(pyridin-4-yl)-3-p-tolyl-7,8-dihydropyrido[2,3-b]pyrazin-5(6H)-yl)heptanoate A mixture of ethyl 7-(3-chloro-2-(pyridin-4-yl)-7,8-dihydropyrido[2,3-b]pyrazin-5(6H)-yl)heptanoate (step 3) (58 mg, 0.144 mmol), p-tolylboronic acid (39.1 mg, 0.288 mmol) and potassium carbonate (59.7 mg, 0.432 mmol) in dioxane (2 ml) was degassed by bubbling nitrogen through (×3). Pd(Ph₃P)₄ (33.3 mg, 0.029 mmol) was added and the mixture was degassed by bubbling nitrogen through (×3). The mixture was heated at 150° C. for 2 hours using microwave irradiation. The mixture was diluted with water and extracted with EtOAc (×2). The combined extracts were washed with brine, dried (MgSO₄) and evaporated under vacuum. The crude product was purified by chromatography on silica eluting with 50-100% EtOAc in iso-hexane followed by 5-10% THF in DCM. The fractions were evaporated under vacuum and the residue was purified by ion exchange using a Isolute SCX-2 cartridge, loading and washing with methanol and eluting with 2M NH₃ in MeOH to afford the title compound;

LC-MS Rt=4.27 mins; [M+H]+ 459, Method 10min-LC_v003.

Step 5: 7-(2-(Pyridin-4-yl)-3-p-tolyl-7,8-dihydropyrido[2,3-b]pyrazin-5(6H)-yl)heptanoic acid A solution of ethyl 7-(2-(pyridin-4-yl)-3-p-tolyl-7,8-dihydropyrido[2,3-b]pyrazin-5(6H)-yl)heptanoate (step 4)(65 mg, 0.142 mmol) in THF (3 ml) and water (1 ml) was treated with LiOH (33.9 mg, 1.417 mmol) and the mixture was stirred at room temperature for 16 hours. The mixture was concentrated under vacuum and the residue was diluted with water and washed with EtOAc (×2). The aqueous was acidified (1 N HCl, pH ~5) and extracted with EtOAc. The combined extracts were washed with brine, dried (MgSO₄) and evaporated under vacuum to a yellow gum which was triturated with ether to afford the title compound;

LC-MS Rt=3.48 mins; [M+H]+ 431, Method 10min-LC_v003.

¹H NMR (400 MHz, CDCl₃-d) δ 8.41 (2H, d), 7.42 (2H, m), 7.30 (2H, d), 7.12 (2H, d), 3.69 (2H, t), 3.50 (2H, t), 3.01 (2H, t), 2.39-2.29 (5H, m), 2.11 (2H, m), 1.71-1.60 (4H, m), 1.43-1.35 (4H, m).

Example 13.2

7-(3-(Pyridin-4-yl)-2-p-tolyl-7,8-dihydropyrido[2,3-b]pyrazin-5(6H)-yl)heptanoic acid

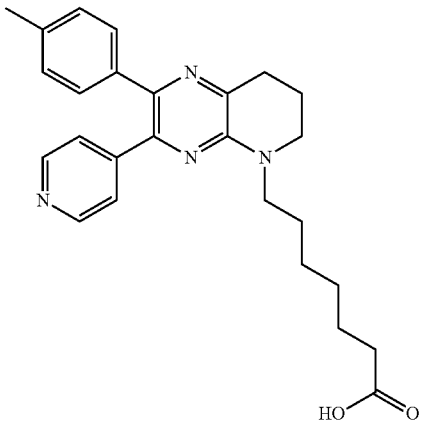 [SMILES: Cc1ccc(-c2nc3c(nc2-c2ccncc2)N(CCCCCCC(=O)O)CCC3)cc1]

Step 1: Ethyl 7-(3-chloro-2-p-tolyl-7,8-dihydropyrido[2,3-b]pyrazin-5(6H)-yl)heptanoate A mixture of ethyl 7-(2-bromo-3-chloro-7,8-dihydropyrido[2,3-b]pyrazin-5(6H)-yl)heptanoate (Example 13.1 step 2)(50 mg, 0.124 mmol), p-tolylboronic acid (16.80 mg, 0.124 mmol), potassium carbonate (51.2 mg, 0.371 mmol) in dioxane (2 ml) was degassed by bubbling nitrogen through (×3). Pd(Ph₃P)₄ (14.28 mg, 0.012 mmol) was added and the mixture was degassed by bubbling nitrogen through (×3). The reaction mixture was heated using microwave radiation at 150° C. for 3 hours. The mixture was diluted with water and extracted with EtOAc (×2). The organic extracts were combined and washed with brine, dried (MgSO₄) and evaporated under vacuum. The crude product was purified by chromatography on silica eluting with 10-50% EtOAc in iso-hexane to afford a (3:1) mixture of ethyl 7-(3-chloro-2-p-tolyl-7,8-dihydropyrido[2,3-b]pyrazin-5(6H)-yl)heptanoate and ethyl 7-(2-bromo-3-chloro-7,8-dihydropyrido[2,3-b]pyrazin-5(6H)-yl)heptanoate (Example 13.1, step 2).

LC-MS Rt=6.05 mins; [M+H]+ 416/418, Method 10min-LC_v003.

Step 2: Ethyl 7-(3-(pyridin-4-yl)-2-p-tolyl-7,8-dihydropyrido[2,3-b]pyrazin-5(6H)-yl)heptanoate A (3:1) mixture of ethyl 7-(3-chloro-2-p-tolyl-7,8-dihydropyrido[2,3-b]pyrazin-5(6H)-yl)heptanoate (Example 13.2, step 1) (30 mg, 0.072 mmol) and ethyl 7-(2-bromo-3-chloro-7,8-dihydropyrido[2,3-b]pyrazin-5(6H)-yl)heptanoate (Example 13.1, step 2)(10 mg, 0.025 mmol), 4-(4,4,5,5-tetramethyl-1,3,2-dioxaborolan-2-yl)pyridine (39.4 mg, 0.192 mmol) and potassium carbonate (39.9 mg, 0.288 mmol) in dioxane (2 ml) was degassed by bubbling nitrogen through (×3). Pd(Ph₃P)₄ (22.22 mg, 0.019 mmol) was added and the mixture was degassed by bubbling nitrogen through (×3). The reaction mixture was heated using microwave radiation at 150° C. for 2 hours. The mixture was diluted with water and extracted with EtOAc (×2). The combined extracts were washed with brine, dried (MgSO₄) and evaporated under vacuum. The crude material was purified by ion exchange [Isolute SCX-2 washing with MeOH and eluting with 2M NH₃ in MeOH] to give a brown residue. The crude residue was purified by chromatography on silica eluting with 0-100% EtOAc in iso-hexane followed by 10% MeOH/DCM to afford the title compound;

LC-MS Rt=1.18 mins; [M+H]+ 459, Method 2min-LC_v003.

Step 3: 7-(3-(Pyridin-4-yl)-2-p-tolyl-7,8-dihydropyrido[2,3-b]pyrazin-5(6H)-yl)heptanoic acid A solution of ethyl 7-(3-(pyridin-4-yl)-2-p-tolyl-7,8-dihydropyrido[2,3-b]pyrazin-5(6H)-yl)heptanoate (step 2) (15 mg, 0.033 mmol) in THF (2 ml) and water (1 ml) was treated with LiOH (7.83 mg, 0.327 mmol) and stirred at 70° C. for 4 hours. The mixture was cooled to room temperature and concentrated under vacuum. The residue was acidified (1N HCl, pH ~5) and extracted with DCM (×3). The combined extracts were washed with brine, dried (MgSO₄) and evaporated under vacuum to a yellow gum which was triturated with ether and dried under vacuum at 40° C. for 2.5 hours to afford the title compound;

LC-MS Rt=1.03 mins; [M+H]+ 431, Method 2min-LC_v003.

¹H NMR (400 MHz, CDCl₃-d) δ 8.53 (2H, d), 7.53 (2H, d), 7.21 (2H, d), 7.10 (2H, d), 3.66-3.60 (2H, m), 3.52-3.46 (2H, m), 3.03 (2H, t), 2.36-2.28 (5H, m), 2.15-2.08 (2H, m), 1.73-1.60 (4H, m), 1.42 (4H, m).

Examples 14.1 and 14.2

Enantiomer 1 and Enantiomer 2 of 7-(7-hydroxy-2,3-dip-tolyl-7,8-dihydropyrido[2,3-b]pyrazin-5(6H)-yl)heptanoic acid

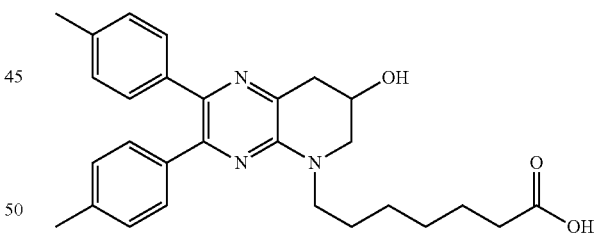

Step 1: Ethyl 7-(2,3-dip-tolylpyrido[2,3-b]pyrazin-5(6H)-yl)heptanoate

To a solution of 2,3-dip-tolyl-5,6-dihydropyrido[2,3-b]pyrazine (Example 8.2 step 1) (3.88 g, 12.38 mmol) in DCE (70 ml) was added ethyl 7-oxoheptanoate (6.40 g, 37.1 mmol) followed by sodium triacetoxyborohydride (10.4 g, 49.1 mmol). The reaction mixture was stirred for 2 days at room temperature under an atmosphere of nitrogen. The reaction mixture was diluted with water (70 ml) and extracted with EtOAc (3×70 ml). The combined organic extracts were dried over MgSO₄, filtered and concentrated in vacuo. The crude product was purified by chromatography on silica eluting with EtOAc/iso-hexane, followed by further purification using reverse phase chromatography eluting with MeCN/water (0.1% TFA) to afford the title compound;
LC-MS Rt=1.46 mins; [M+H]+ 470.5, Method 2min-LC_v003.

Step 2: rac-Ethyl 7-(7-hydroxy-2,3-dip-tolyl-7,8-dihydropyrido[2,3-b]pyrazin-5(6H)-yl)heptanoate A solution of 1M $BH_3$.THF in THF (3.66 ml, 3.66 mmol) was added dropwise to Ethyl 7-(2,3-dip-tolylpyrido[2,3-b]pyrazin-5(6H)-yl)heptanoate (step 1) (1.145 g, 2.438 mmol) under an atmosphere of nitrogen. The reaction mixture was stirred at room temperature for 1 hour and then cooled to 0-5° C. using an ice bath. The mixture was treated with 35% $H_2O_2$ (1.067 ml, 12.19 mmol) followed by 2M NaOH (6.10 ml, 12.19 mmol). The mixture was allowed to warm to room temperature and stirred overnight under an atmosphere of nitrogen. The reaction mixture was washed with water (25 ml) and extracted with ethyl acetate (2×25 ml). The organic extracts were combined, dried over $MgSO_4$, filtered and the filtrate concentrated in vacuo to give an orange oil. The crude product was purified by chromatography on silica eluting with EtOAc/iso-hexane, followed by further purification by chromatography on silica eluting with DCM/MeOH to afford the title compound;
LC-MS Rt=1.37 mins; [M+H]+ 488.6, Method 2min-LC_v003.

Step 3: Enantiomer 1 and Enantiomer 2 of ethyl 7-(7-hydroxy-2,3-dip-tolyl-7,8-dihydropyrido[2,3-b]pyrazin-5(6H)-yl)heptanoate Chiral separation of rac-ethyl 7-(7-hydroxy-2,3-dip-tolyl-7,8-dihydropyrido[2,3-b]pyrazin-5(6H)-yl)heptanoate (step 2) using Supercritical Fluid Chromatography afforded the individual enantiomers:
Method Details:

| Column: | Phenomenex LUX C2 250 × 10 mm, 5 um |
|---|---|
| Mobile phase: | 45% methanol + 0.1% DEA/55% CO2 |
| Flow: | 10 ml/min |
| Detection: | UV @ 220 nm |
| System: | Berger Minigram SFC2 |
| Column Temp: | 35 deg C. |

First eluted peak; Rt=3.73 mins: Enantiomer 1 of ethyl 7-(7-hydroxy-2,3-dip-tolyl-7,8-dihydropyrido[2,3-b]pyrazin-5(6H)-yl)heptanoate LC-MS Rt=1.31 mins; [M+H]+ 488.7, Method 2minLC_v003

$^1$H NMR (400 MHz, $CDCl_3$) δ 7.35-7.33 (2H, m), 7.26-7.24 (2H, m), 7.09-7.07 (4H, m), 4.44 (1H, broad m), 4.17-4.11 (2H, m), 3.79-3.61 (2H, br m), 3.61 (1H, complex m), 3.43 (1H, complex m), 3.28 (1H, m), 3.11 (1H, m), 2.36 (3H, s), 2.33 (3H, s), 2.28 (2H, m), 2.01 (1H, br m), 1.70-1.51 (4H, m), 1.41 (4H, m), 1.27 (3H, m)

Second eluted peak; Rt=4.71 mins: Enantiomer 2 of ethyl 7-(7-hydroxy-2,3-dip-tolyl-7,8-dihydropyrido[2,3-b]pyrazin-5(6H)-yl)heptanoate LC-MS Rt=1.32 mins; [M+H]+ 488.6, Method 2minLC_v003

$^1$H NMR (400 MHz, CDCl3) δ 7.34 (2H, d), 7.25 (2H, d), 7.09-7.06 (4H, m), 4.44 (1H, br m), 4.14 (2H, q), 3.78-3.61 (2H, complex m), 3.61 (1H, complex m), 3.43 (1H, complex m), 3.27 (1H, m), 3.11 (1H, m), 2.35 (3H, s), 2.33 (3H, s), 2.28 (2H, t), 2.02 (1H, br m), 1.74-1.53 (4H, m), 1.41 (4H, m), 1.27 (3H, t)

Example 14.1

Enantiomer 1 of 7-(7-hydroxy-2,3-dip-tolyl-7,8-dihydropyrido[2,3-b]pyrazin-5(6H)-yl)heptanoic acid Enantiomer 1 of ethyl 7-(7-hydroxy-2,3-dip-tolyl-7,8-dihydropyrido[2,3-b]pyrazin-5(6H)-yl)heptanoate (step 3) (5.6 mg, 0.011 mmol) was dissolved in ethanol (0.5 ml) and 2M NaOH (0.023 ml, 0.046 mmol) was added. The solution was stirred at room temperature overnight under an atmosphere of nitrogen. To the reaction mixture was added 2M HCl until the pH was below pH5. The volatile solvent was removed by distillation. To the residue was added water (10 ml) and the mixture was extracted with ethyl acetate (3×10 ml). The organic extracts were combined, dried over $MgSO_4$, filtered and concentrated in vacuo to afford the title compound as an oil which was dried in a vacuum oven at 40° C. overnight;
LC-MS Rt=1.15 mins; [M+H]+ 460.5, Method 2min-LC_v003
$^1$H NMR (400 MHz, $CDCl_3$) δ 7.24 (2H, d), 7.15 (2H, d), 7.01-6.93 (4H, m), 4.33 (1H, br m), 3.66-3.54 (2H, m), 3.51 (1H, complex m), 3.43 (1H, complex m), 3.17 (1H, m), 3.01 (1H, m), 2.25 (3H, s), 2.27 (3H, s), 2.23 (2H, m), 1.63-1.52 (4H, m), 1.36-1.29 (4H, m)

Example 14.2

Enantiomer 2 of 7-(7-hydroxy-2,3-dip-tolyl-7,8-dihydropyrido[2,3-b]pyrazin-5(6H)-yl)heptanoic acid

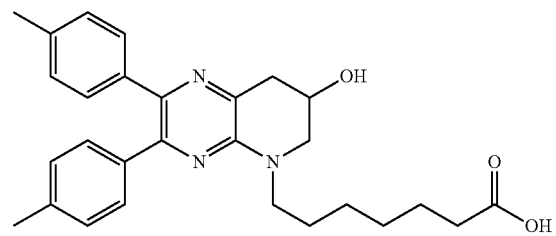 [SMILES: Cc1ccc(-c2nc3c(nc2-c2ccc(C)cc2)N(CCCCCCC(=O)O)CC(O)C3)cc1]

Enantiomer 2 of ethyl 7-(7-hydroxy-2,3-dip-tolyl-7,8-dihydropyrido[2,3-b]pyrazin-5(6H)-yl)heptanoate (step 3) (5.6 mg, 0.011 mmol) was dissolved in ethanol (0.5 ml) and 2M NaOH (0.023 ml, 0.046 mmol) was added. The solution was stirred at room temperature overnight under an atmosphere of nitrogen. 2M NaOH (0.023 ml, 0.046 mmol) was added to the mixture and the reaction was left to stir for a further hour at room temperature under an atmosphere of nitrogen. To the reaction mixture was added 2M HCl until the pH was below pH5. The volatile solvent was removed by distillation. To the residue was added water (10 ml) and the mixture was extracted with ethyl acetate (3×10 ml). The organic extracts were combined, dried over $MgSO_4$, filtered and concentrated in vacuo to afford the title compound as an oil which was dried in a vacuum oven at 40° C. overnight;
LC-MS Rt=1.15 mins; [M+H]+ 460.4, Method 2min-LC_v003
$^1$H NMR (400 MHz, $CDCl_3$) δ 7.33 (2H, d), 7.25 (2H, d), 7.11-7.03 (4H, m), 4.42 (1H, br m), 3.77-3.62 (2H, m), 3.59

(1H, m), 3.43 (1H, m), 3.26 (1H, m), 3.10 (1H, m), 2.35 (3H, s), 2.33 (3H, s), 2.32 (2H, m), 1.75-1.58 (4H, m), 1.48-1.35 (4H, m)

Example 15.1 rac-7-(2,3-Dip-tolyl-7,8-dihydropyrido[2,3-b]pyrazin-5(6H)-yl)-3,4-dihydroxyheptanoic acid

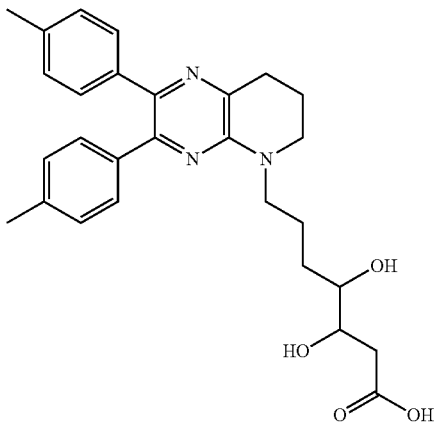 [SMILES: Cc1ccc(-c2nc3c(nc2-c2ccc(C)cc2)N(CCCC(O)C(O)CC(=O)O)CCC3)cc1]

Step 1: (E)-Methyl 7-(2,3-dip-tolyl-7,8-dihydropyrido[2,3-b]pyrazin-5(6H)-yl)hept-3-enoate The title compound was prepared from 2,3-dip-tolyl-5,6,7,8-tetrahydropyrido[2,3-b]pyrazine (Intermediate E) analogously to (E)-Methyl 7-(2,3-diphenyl-7,8-dihydropyrido[3,2-b]pyrazin-5(6H)-yl)hept-3-enoate (Example 10.1 step 1 and step 2).

LC-MS Rt=1.32 mins; [M+H]$^+$457.4, Method 2min-LC_v003.

Step 2: rac-Methyl 7-(2,3-dip-tolyl-7,8-dihydropyrido[2,3-b]pyrazin-5(6H)-yl)-3,4-dihydroxyheptanoate To methyltributylammonium chloride (141 mg, 0.597 mmol) (hygroscopic) in dichloromethane (5 ml) was added potassium permanganate (94 mg, 0.597 mmol) and the purple solution was stirred at room temperature for 45 minutes. The solution was cooled to 0° C. with an ice bath and a solution of (E)-methyl 7-(2,3-dip-tolyl-7,8-dihydropyrido[2,3-b]pyrazin-5(6H)-yl)hept-3-enoate (Step 1) (160 mg, 0.351 mmol) in dichloromethane (1 ml) was added dropwise. The solution was stirred at 0-5° C. for 2 h. Sodium metabisulfite (500 mg, 2.63 mmol) in water (5 ml) was added dropwise at 0-5° C. to the reaction mixture. The purple suspension turned to a white suspension after 15 minutes. The organic layer was separated from the suspension using a phase separator cartridge. The organic layer was evaporated to dryness. The crude product was purified by chromatography on silica eluting with 0-100% EtOAc/iso-hexane to afford the title compound;

LC-MS Rt=1.12 mins; [M+H]$^+$490.5, Method 2min-LC_v003.

Step 3: rac-7-(2,3-Dip-tolyl-7,8-dihydropyrido[2,3-b]pyrazin-5(6H)-yl)-3,4-dihydroxyheptanoic acid To rac-Methyl 7-(2,3-dip-tolyl-7,8-dihydropyrido[2,3-b]pyrazin-5(6H)-yl)-3,4-dihydroxyheptanoate (Step 2) (30 mg, 0.061 mmol) in methanol (1 ml) was added 2M NaOH (0.061 ml, 0.123 mmol). The solution was stirred at room temperature for 3 h. 2M HCl (0.061 ml) was added and the solution was evaporated to dryness. The crude product was purified by chromatography on silica eluting with 0-15% DCM/MeOH to afford the title compound;

LC-MS Rt=1.04 mins; [M+H]$^+$476.5, Method 2min-LC_v003.

$^1$H NMR (400 MHz, DMSO-d6) δ 7.23 (2H, d), 7.13 (2H, d), 7.08 (2H, d), 7.03 (2H, d), 3.32 (1H, obs m), 3.68 (1H, m), 3.58 (2H, m), 3.46 (2H, m), 2.89 (2H, t), 2.28 (3H, s), 2.27 (3H, s), 2.25 (1H, m), 2.12 (1H, m), 2.01 (2H, m), 1.76 (1H, br m), 1.59 (1H, br m), 1.47 (1H, br m), 1.29 (1H, br m).

Example 16.1

7-(7-Hydroxy-6-oxo-2,3-dip-tolyl-7,8-dihydropyrido[2,3-b]pyrazin-5(6H)-yl)heptanoic acid

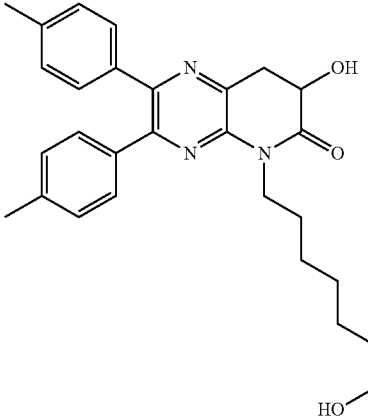

To a solution of 7-(6-oxo-2,3-dip-tolyl-7,8-dihydropyrido[2,3-b]pyrazin-5(6H)-yl)heptanoic acid (Ex. 12.1) (100 mg, 0.219 mmol) in THF (2 ml), under a nitrogen atmosphere at −78° C., was treated dropwise with 1M lithium bis trimethylsilylamide in THF (0.5 ml, 0.500 mmol). Once the addition was complete, the mixture was stirred at −78° C. for 1 hour before a solution of (+)-(8,8-dichlorocamphorylsulfonyl)oxaziridine (78 mg, 0.262 mmol) in THF (2 ml) was added. The resultant solution was stirred at −78° C. for 60 minutes. The cooling was removed and the mixture allowed to warm to around −10° C. The mixture was allowed to slowly warm to room temperature overnight. The mixture was cooled to −78° C., quenched with sat. NH$_4$Cl (3 ml) and allowed to slowly warm to room temperature. The yellow solution was diluted with water and extracted with EtOAc (×2). The aqueous layer (pH-9) was acidified to pH ~2 with 1M HCl and extracted with DCM (×2). The combined organic extracts were dried (MgSO$_4$) and evaporated under vacuum to give a yellow gum. The residue was purified by chromatography on silica eluting with 1% MeOH/DCM followed by 10% MeOH/DCM to afford the title compound;

LC-MS Rt=0.84 mins; [M+H]$^+$474, Method 2minLowpH.

$^1$H NMR (400 MHz, CDCl$_3$) δ 7.89 (1H, d), 7.26 (2H, d), 7.24 (2H, d), 7.03 (4H, m), 4.44 (1H, m), 4.20 (1H, d), 4.02

(1H, m), 3.54 (1H, m), 3.10 (1H, m), 2.28 (3H, s), 2.28 (3H, s), 2.24 (2H, m), 1.66 (2H, m), 1.56 (2H, m), 1.43-1.25 (4H, m).

Example 17.1a and 17.1b

Enantiomer 1 and Enantiomer 2 of 7-(7-Methoxy-2,3-dip-tolyl-7,8-dihydropyrido[2,3-b]pyrazin-5(6H)-yl)heptanoic acid

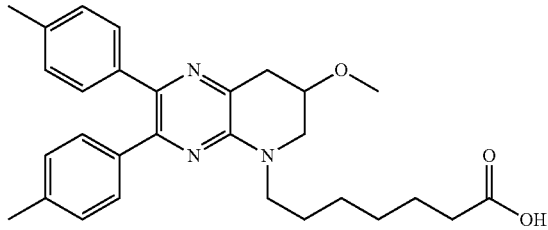 [SMILES: COC1Cc2nc(-c3ccc(C)cc3)c(-c3ccc(C)cc3)nc2N(CCCCCCC(=O)O)C1]

Step 1: rac-Ethyl 7-(7-methoxy-2,3-dip-tolyl-7,8-dihydropyrido[2,3-b]pyrazin-5(6H)-yl)heptanoate rac-7-Methoxy-2,3-dip-tolyl-5,6,7,8-tetrahydropyrido[2,3-b]pyrazine (Intermediate K) (80 mg, 0.232 mmol) in dry DCE (4 ml) at RT under nitrogen was treated with DIPEA (0.044 ml, 0.255 mmol) followed by ethyl 7-oxoheptanoate (80 mg, 0.463 mmol). The resulting mixture was stirred at RT for 10 minutes and treated with sodium triacetoxyborohydride (245 mg, 1.158 mmol). The mixture was heated at 60° C. for 16 hours. A further portion of sodium triacetoxyborohydride (245 mg, 1.158 mmol) was added and the mixture was heated at 50° C. for 3 days. After cooling to RT, the reaction mixture was diluted with DCM (50 ml) and washed with water (×2). The organic portion was isolated using a phase separating cartridge and the solvent was removed in vacuo. Purification of the crude product by chromatography on silica eluting with 0-20% EtOAc/iso-hexane afforded the title compound.

LCMS Rt 1.43 mins MS m/z 502 [ M+H]+Method 2min-LC_v003.

Step 2: rac-7-(7-Methoxy-2,3-dip-tolyl-7,8-dihydropyrido[2,3-b]pyrazin-5(6H)-yl)heptanoic acid rac-Ethyl 7-(7-methoxy-2,3-dip-tolyl-7,8-dihydropyrido[2,3-b]pyrazin-5(6H)-yl)heptanoate (step 1) (139 mg, 0.277 mmol) in MeOH (3 ml) at RT was treated with 2M NaOH (416 µL, 0.831 mmol) and the mixture was stirred at RT for 4 hours. A further portion of 2M NaOH (416 µL, 0.831 mmol) was added the reaction mixture was stirred at RT overnight. The organic solvent was removed in vacuo and the resulting aqueous portion was diluted with water (20 ml). The pH was adjusted to pH1 using 2M HCl and the mixture was extracted with DCM (×3). The combined organic extracts were isolated using a phase separating cartridge and the solvent was removed in vacuo. Purification of the crude product by chromatography on silica eluting with 0-30% EtOAc/iso-hexane followed by 10% MeOH in EtOAc afforded the title compound.

LCMS: Rt 1.30 mins MS m/z 474/475 [ M+H]+Method 2minLowpH.

Chiral separation of the mixture using Supercritical Fluid Chromatography afforded the individual enantiomers:

Method Details:

| Column: | Chiralcel OJ-H 250 × 10 mm, 5 um |
|---|---|
| Mobile phase: | 25% methanol/75% CO2 |
| Flow: | 10 ml/min |
| Column temperature: | 35° C. |
| Detection: | UV @ 220 nm |
| System: | Berger Minigram SFC2 |

Example 17.1a

First eluted peak; R.t=3.51 mins Enantiomer 1 of 7-(7-methoxy-2,3-dip-tolyl-7,8-dihydropyrido[2,3-b]pyrazin-5(6H)-yl)heptanoic acid LCMS: Rt 1.29 mins MS m/z 474 [ M+H]+; Method 2min-LowpH
1H NMR (400 MHz, CDCl$_3$) δ 7.32 (2H, d), 7.24 (2H, d), 7.06 (4H, m), 3.91 (1H, m), 3.74-3.62 (2H, m), 3.58 (1H, m), 3.47 (3H, s), 3.43 (1H, m), 3.24 (1H, m), 3.13 (1H, m), 2.34 (3H, s), 2.32 (3H, s), 2.29 (2H, m), 1.70-1.55 (4H, m), 1.41 (4H, m).

Example 17.1b

Second eluted peak; R.t=4.69 mins Enantiomer 2 of 7-(7-methoxy-2,3-dip-tolyl-7,8-dihydropyrido[2,3-b]pyrazin-5(6H)-yl)heptanoic acid LCMS: Rt 1.29 mins MS m/z 474 [ M+H]+; Method 2min-LowpH
1H NMR (400 MHz, CDCl$_3$) δ 7.32 (2H, d), 7.24 (2H, d), 7.06 (4H, m), 3.91 (1H, m), 3.73-3.62 (2H, m), 3.58 (1H, m), 3.47 (3H, s), 3.43 (1H, m), 3.24 (1H, m), 3.13 (1H, m), 2.34 (3H, s), 2.32 (3H, s), 2.29 (2H, m), 1.71-1.55 (4H, m), 1.40 (4H, m)

Preparation of Intermediate Compounds

Intermediate A 2,3-Diphenyl-[1,8]naphthyridine

A suspension comprising 2-amino-pyridine-3-carbaldehyde (5 g, 40.9 mmol) and deoxybenzoin (8.03 g, 40.9 mmol) in piperidine (4.46 ml, 45.0 mmol) was heated at 120° C. overnight. The resulting solution was partitioned between DCM (200 ml) and water (200 ml). The organic layer was separated and washed with water (2×150 ml), brine, dried over MgSO$_4$, filtered and concentrated in vacuo. The crude product was purified by chromatography on silica eluting with 0-50% EtOAc in iso-hexane to afford the title product as a yellow solid;
LC-MS Rt=1.41 mins; [M+H]$^+$283.1, Method 2min-LC_v002.
$^1$H NMR (400 MHz, DMSO-d6) δ 9.12 (1H, dd), 8.56 (2H, dd), 7.68 (1H, dd), 7.44 (2H, m), 7.34 (8H, m).

Intermediate B 6,7-Diphenyl-1,2,3,4-tetrahydro-[1,8]naphthyridine

A solution of 2,3-diphenyl-[1,8]naphthyridine (Intermediate A) (2 g, 7.08 mmol) in EtOH (50 ml) was purged with N$_2$ and 10% palladium on carbon (0.754 g, 0.708 mmol) was added. The reaction mixture was placed under an atmosphere of hydrogen overnight. The mixture was filtered through Celite® (filter material) and the catalyst was washed with EtOAc (400 ml). The filtrate was concentrated in vacuo to yield the title compound as an off white solid;

LC-MS: Rt=1.33 mins; [M+H$_2$O]$^+$=303.3, Method 2min-LC_v001

$^1$H NMR (400 MHz, DMSO-d6) δ 7.3 (9H, m), 7.1 (2H, m), 6.7 (1H, s), 3.4 (2H, m), 2.7 (2H, t), 1.8 (2H, m)

Intermediates C

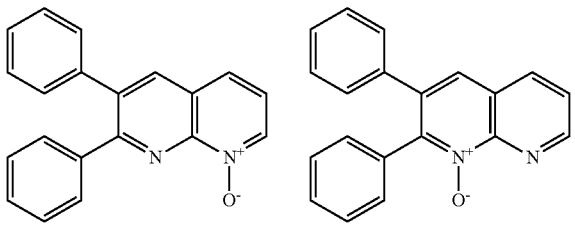

A solution of 2,3-diphenyl-[1,8]naphthyridine (Intermediate A) (5.3 g, 18.77 mmol) in DCM (60 ml) was treated with hydrogen peroxide (6.58 ml, 75 mmol) and methyltrioxorhenium(VII) (0.468 g, 1.878 mmol) and the resulting mixture was stirred at room temperature overnight. The mixture was partitioned between DCM (250 ml) and water (250 ml) and the organic portion was washed with brine, dried over MgSO$_4$, filtered and concentrated in vacuo. The resulting yellow foam was dried in vacuo at 40° C. overnight to afford a mixture of the title compounds. This mixture was used crude without further purification;

LC-MS 2 peaks: Rt=1.31 mins, 18%, [M+H]$^+$299.2; Rt=1.36 mins, 82%, [M+H]$^+$299.2, Method 2minLC_v002.

Intermediate D 2,3-Diphenylpyrido[3,2-b]pyrazine

A solution of benzil (45.7 g, 217 mmol) and pyridine-2,3-diamine (23.7 g, 217 mmol) in methanol (514 ml) and acetic acid (57 ml) was heated at 160° C. for 10 mins using microwave radiation. The reaction mixture was concentrated in vacuo. To the crude residue in methanol (510 ml) was added activated charcoal (25 g) and the suspension was stirred at 60° C. for 1 h. The suspension was filtered hot, cooled and then was stirred in an ice bath. The solid was filtered, washed with cold methanol (50 ml) and dried in vacuo at 40° C. overnight to afford the title compound as pale brown crystals.

LC-MS Rt=1.07 mins; [M+H]+ 284, Method A

Intermediate E 2,3-Dip-tolyl-5,6,7,8-tetrahydropyrido[2,3-b]pyrazine

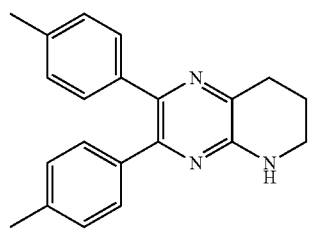 [SMILES: Cc1ccc(-c2nc3c(nc2-c2ccc(C)cc2)NCCC3)cc1]

Step 1: 2,3-Dip-tolylpyrido[2,3-b]pyrazine

A solution of 1,2-dip-tolylethane-1,2-dione (commercially available)(175 g, 733 mmol) and pyridine-2,3-diamine (80 g, 733 mmol) in EtOH (1609 ml) and AcOH (179 ml) was heated to reflux (bath at 85° C.) for 1.5 h. The mixture was allowed to cool and concentrated in vacuo. The crude material was dissolved in DCM (500 ml) and filtered through silica to remove baseline impurities. The silica was washed with EtOAc (2 L). The combined filtrate layers were concentrated in vacuo to give a brown solid. The material was triturated in 1:1 TBME/heptane (300 ml). The solid was removed by filtration and washed with 1:1 TBME/heptane (200 ml) before drying at RT over 2 days to afford the title compound as an AcOH salt (1 eq).

HPLC (Agilent 1200), Rt 5.37 min, Method B.

Step 2: 2,3-Dip-tolyl-5,6,7,8-tetrahydropyrido[2,3-b]pyrazine

A solution of 2,3-dip-tolylpyrido[2,3-b]pyrazine (step 1)(181 g, 487 mmol) in EtOH/THF (1:2, 2100 ml) was treated with 10% palladium on carbon (30 g, 28.8 mmol) and the reaction mixture was placed under 0.1 bar of hydrogen at RT. After 2 days and 4 days respectively, additional batches of 10% palladium on carbon (10 g, 9.6 mmol, twice) were added along with Et$_3$N (85 ml, 706 mmol, twice). After 7 days in total, the reaction mixture was filtered through Hyflo (filter material) and washed through with THF (2.5 L in portions). The filtrate was concentrated in vacuo to give a green/yellow solid. The solid was triturated with 1:1 TBME/heptane (500 ml) and filtered. The solid was washed with 1:1 TBME/heptane (200 ml) to give a pale yellow solid which was dried overnight to afford the title compound; HPLC (Agilent 1200), Rt 4.73 min, Method B.

Intermediate EA

7-Methyl-2,3-diphenyl-5,6,7,8-tetrahydropyrido[2,3-b]pyrazine

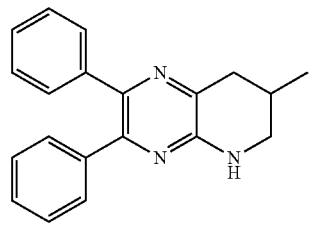 [SMILES: CC1CNc2nc(-c3ccccc3)c(-c3ccccc3)nc2C1]

The title compound was prepared from 5-methyl-pyridine-2,3-diamine and benzil analogously to Intermediate E;

LC-MS Rt=1.21 mins; [M+H]+ 302, Method 2min-LC_v003

Intermediate EB

6-Methyl-2,3-diphenyl-5,6,7,8-tetrahydropyrido[2,3-b]pyrazine

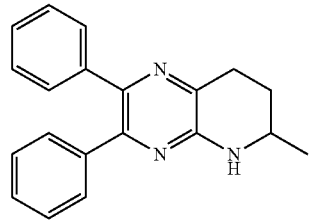 [SMILES: CC1CCc2nc(-c3ccccc3)c(-c3ccccc3)nc2N1]

The title compound was prepared from 6-methyl-pyridine-2,3-diamine benzil analogously to Intermediate E;

LC-MS Rt=1.12 mins; [M+H]+ 302, Method 2min-LC_v003

Intermediate EC 2,3-bis(4-Fluorophenyl)-7-methyl-5,6,7,8-tetrahydropyrido[2,3-b]pyrazine

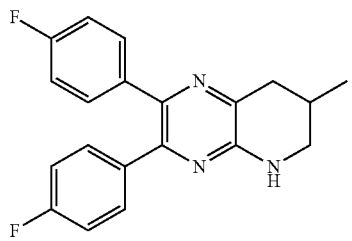 [SMILES: CC1CNc2nc(-c3ccc(F)cc3)c(-c3ccc(F)cc3)nc2C1]

The title compound was prepared from 5-methylpyridine-2,3-diamine and 1,2-bis(4-fluorophenyl)ethane-1,2-dione analogously to Intermediate E;

LC-MS Rt=1.15 mins; [M+H]+ 338, Method 2min-LC_v003.

Intermediate ED 2,3-Bis(4-fluorophenyl)-6-methyl-5,6,7,8-tetrahydropyrido[2,3-b]pyrazine The title compound was prepared from 6-methylpyridine-2,3-diamine and 1,2-bis(4-fluorophenyl)ethane-1,2-dione analogously to Intermediate E;

LC-MS Rt=1.17 mins; [M+H]+ 338, Method 2min-LC_v003.

Intermediate EE 2,3-Bis(4-(trifluoromethyl)phenyl)-5,6,7,8-tetrahydropyrido[2,3-b]pyrazine

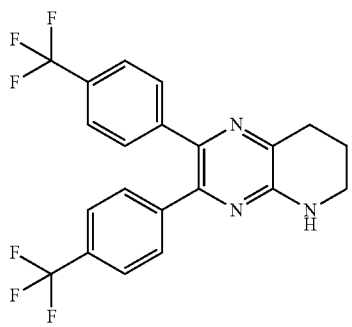 [SMILES: FC(F)(F)c1ccc(-c2nc3c(nc2-c2ccc(C(F)(F)F)cc2)NCCC3)cc1]

The title compound was prepared from 1,2-bis(4-(trifluoromethyl)phenyl)ethane-1,2-dione (this may be prepared according to the procedure of Bioorganic & Medicinal Chemistry Letters (2007), 17(21), 5825-5830) and pyridine-2,3-diamine analogously to Intermediate E;

LC-MS Rt=1.39 mins; [M+H]+ 424, Method 2min-LC_v003.

Intermediate EF

6-Methyl-2,3-dip-tolyl-5,6,7,8-tetrahydropyrido[2,3-b]pyrazine

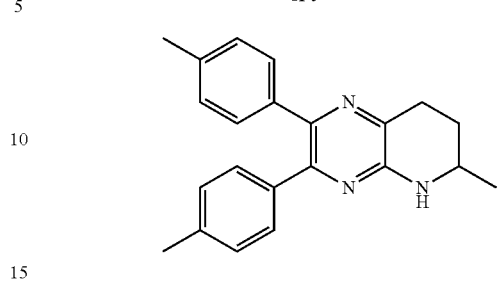

The title compound was prepared analogously to Intermediate E by replacing pyridine-2,3-diamine with 6-methylpyridine-2,3-diamine;

LC-MS Rt=1.17 mins; [M+H]+ 330, Method 2min-LC_v003

Intermediate F

3-Phenyl-2-p-tolyl-5,6,7,8-tetrahydropyrido[2,3-b]pyrazine

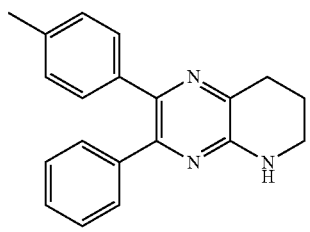 [SMILES: Cc1ccc(-c2nc3c(nc2-c2ccccc2)NCCC3)cc1]

Step 1: Pyrido[3,2-b]pyrazine-2,3(1H,4H)-dione

A stirred suspension of 2,3-diaminopyridine (75 g, 687 mmol) in diethyl oxalate (291 ml, 2131 mmol) under $N_2$ was heated to 120° C. After 1 h, the ethanol was distilled off the reaction mixture and the temperature was elevated to 160° C. for a further 2 hours. The reaction mixture was allowed to cool to RT and diluted with diethyl ether (200 ml). The resulting suspension was stirred for 1 hour and the solid was isolated by filtration and dried in a vacuum oven. The solid was suspended in ethanol (500 ml) and sonicated for 1 hour. The suspension was filtered and dried (vacuum oven overnight) to afford the title compound;

LCMS: Rt 0.29 mins MS m/z 164 [M+H]+; Method 2min-LC_v003

Step 2: 2,3-Dichloropyrido[3,2-b]pyrazine $POCl_3$ (57.1 ml, 613 mmol) was added to pyrido[3,2-b]pyrazine-2,3(1H,4H)-dione (step 1) (20 g, 123 mmol) and the suspension was heated at 110° C. for 8 hours. After cooling to RT, the reaction mixture was added dropwise to stirred water at RT, cooling with ice, if necessary. The aqueous phase was basified by addition of a cooled solution of sat. $NaHCO_3$ (~4 L). The aqueous portion was extracted with EtOAc (2×2.5 L) and the combined organic extracts were dried over $MgSO_4$ and concentrated in vacuo to afford a solid. The crude product was purified by chromatography on silica eluting with 5%-70% EtOAc in iso-hexane to afford the title compound as a yellow solid;

LCMS: Rt 0.53 mins MS m/z 200 [ M+H]+; Method 2minLC_30_v003

Step 3: 2-Chloro-3-phenylpyrido[2,3-b]pyrazine 2,3-Dichloropyrido[2,3-b]pyrazine (step 2) (500 mg, 2.5 mmol) in dry dioxane (10 ml), under nitrogen was treated with phenylboronic acid (305 mg, 2.5 mmol), potassium carbonate (691 mg, 5 mmol) in water (0.5 ml) and tetrakis (triphenylphosphine)palladium(0) (144 mg, 0.125 mmol). The resulting mixture was heated using microwave radiation at 100° C. for 1 hour. After cooling to RT, the mixture was diluted with water (100 ml) and extracted with DCM (×3). The combined organic extracts were washed with brine, dried over MgSO$_4$ and filtered. The solvent was removed in vacuo and the crude product was purified by chromatography on silica eluting with 0-30% EtOAc/iso-hexane to afford the title compound as a solid;

LCMS: Rt 1.03 mins MS m/z 242/244 [ M+H]+; Method 2minLC_v003

1H NMR (400 MHz, DMSO-d6) δ 9.2 (1H, m), 8.6 (1H, dd), 8.0 (1H, m), 7.9 (2H, m), 7.6 (3H, m)

Step 4: 3-Phenyl-2-p-tolylpyrido[2,3-b]pyrazine

2-Chloro-3-phenylpyrido[2,3-b]pyrazine (step 3) (175 mg, 0.724 mmol) in dry dioxane (4 ml) under nitrogen was treated with p-tolylboronic acid (108 mg, 0.797 mmol), potassium carbonate (200 mg, 1.448 mmol) in water (0.5 ml) and tetrakis(triphenylphosphine)palladium(0) (41.8 mg, 0.036 mmol). The resulting mixture was heated using microwave radiation at 150° C. for 1 hour. After cooling to RT, the mixture was diluted with water (100 ml) and extracted with DCM (×3). The combined organic extracts were washed with brine, dried over MgSO$_4$ and filtered. The solvent was removed in vacuo and the crude product was purified by chromatography on silica eluting with 0-30% EtOAc/iso-hexane to afford the title compound as a yellow solid; LCMS; Rt 1.19 mins MS m/z 298 [ M+H]+; Method 2minLC_v003

$^1$H NMR (400 MHz, DMSO-d6) δ 9.2 (1H, m), 8.6 (1H, dd), 7.9 (1H, m), 7.55 (2H, d), 7.4 (5H, m) 7.2 (2H, d), 2.3 (3H, s).

Step 5: 3-Phenyl-2-p-tolyl-5,6,7,8-tetrahydropyrido [2,3-b]pyrazine

3-Phenyl-2-p-tolylpyrido[2,3-b]pyrazine (step 4) (179 mg, 0.602 mmol) under nitrogen in dry MeOH (5 ml) was treated with ammonium formate (190 mg, 3.01 mmol) and 10% palladium on carbon (64.1 mg, 0.060 mmol). The resulting mixture was heated at reflux for 16 hours. After cooling to RT, the mixture was filtered through Celite® (filter material) and the catalyst was washed with MeOH and MeOH/DCM (1:1). The filtrate was concentrated in vacuo and dissolved in DCM (50 ml). The solution was washed with water (×2) and brine (×1). The resulting organic portion was passed through a phase separating column and concentrated in vacuo to afford the title compound;

LCMS; Rt 1.08 mins MS m/z 303 [ M+H]+Method 2minLC_v003

Intermediate FA

2-Phenyl-3-p-tolyl-5,6,7,8-tetrahydropyrido[2,3-b] pyrazine

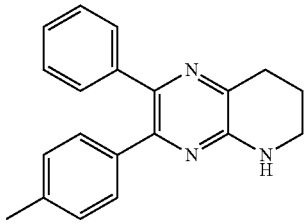 [SMILES: Cc1ccc(-c2nc3c(nc2-c2ccccc2)CCCN3)cc1]

Step 1: 2-Chloro-3-p-tolyl-pyrido[2,3-b]pyrazine

A mixture of 2,3-dichloropyrido[2,3-b]pyrazine (Intermediate F step 2) (5 g, 25 mmol), p-tolylboronic acid (4.08 g, 30.0 mmol), tricyclohexylphosphine (1.682 g, 6.00 mmol), and cesium carbonate (16.29 g, 50.0 mmol) in dry dioxane (60 ml) was degassed by bubbling nitrogen through (×3). Tris(dibenzylideneacetone)dipalladium (0) (2.289 g, 2.5 mmol) was added and the reaction mixture was degassed by bubbling nitrogen through (×3). The resulting mixture was stirred at 70° C. for 16 hours and at room temperature for 2 days. The mixture was diluted with water and EtOAc and filtered through Celite® (filter material). The phases were separated and the aqueous extracted with EtOAc The combined organic extracts were washed with brine, dried over MgSO$_4$ and concentrated in vacuo. The crude product was purified by chromatography on silica eluting with 0-2% THF/ DCM to give a mixture of the mono and bis arylated products. The materials were re-purified by chromatography on silica eluting with 0-2% THF/DCM] to afford the title compound;

LCMS; Rt 1.13 mins MS m/z 256/258 [ M+H]+ Method 2minLC_v003

Step 2: 2-Phenyl-3-p-tolyl-pyrido[2,3-b]pyrazine

A mixture of 2-chloro-3-p-tolyl-pyrido[2,3-b]pyrazine (800 mg, 3.13 mmol), phenylboronic acid (572 mg, 4.69 mmol) and K$_2$CO$_3$ (1297 mg, 9.39 mmol) in dioxane (10 ml) was degassed by bubbling nitrogen through (×3). PdCl$_2$ (dppf) (229 mg, 0.313 mmol) was added and the reaction mixture was degassed by bubbling nitrogen through (×3). The resulting mixture was heated using microwave radiation at 150° C. for 2 hours. PdCl$_2$(dppf) (229 mg, 0.313 mmol) was added and the mixture was heated using microwave radiation at 150° C. for 2 hours. After cooling to RT, the mixture was diluted with water and EtOAc, and filtered through Celite® (filter material). The phases were separated and the aqueous extracted with EtOAc The combined organic extracts were washed with brine, dried over MgSO$_4$ and concentrated in vacuo. The crude product was purified by chromatography on silica eluting with 2-5% THF/DCM to give a contaminated gum. The material was re-purified by chromatography on silica eluting with 0-60% EtOAc/iso-hexane to afford the title compound;

LCMS; Rt 3.93 mins MS m/z 298 [ M+H]+Method 10minLC_v003

Step 3: 2-Phenyl-3-p-tolyl-5,6,7,8-tetrahydropyrido[2,3-b]pyrazine

2-Phenyl-3-p-tolyl-pyrido[2,3-b]pyrazine (1.07 g, 3.60 mmol) under nitrogen in dry MeOH (10 ml) was treated with ammonium formate (2.269 g, 36.0 mmol) and 10% palladium hydroxide on carbon (200 mg, 0.142 mmol). The resulting mixture was heated at reflux for 1 hour. After cooling to RT, the mixture was filtered through Celite® (filter material) and the catalyst was washed with MeOH followed by DCM. The filtrate was concentrated in vacuo to yield a solid which was triturated with MeOH. The resulting solid was dried under vacuum to afford the title compound;

LCMS; Rt 1.04 mins MS m/z 302 [ M+H]+Method 2min-LC_v003

Intermediate FB 2-m-Tolyl-3-p-tolyl-5,6,7,8-tetrahydropyrido[2,3-b]pyrazine

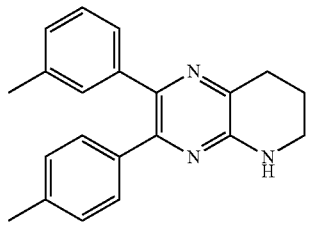 [SMILES: Cc1ccc(-c2nc3c(nc2-c2cccc(C)c2)CCCN3)cc1]

The title compound was prepared analogously to Intermediate FA by replacing phenyl boronic acid with m-tolylboronic acid;

LCMS; Rt 1.10 mins MS m/z 316 [ M+H]+Method 2min-LC_v003 $^1$H NMR (400 MHz, DMSO-d6) δ 7.2 (3H, m), 7.05-7.0 (5H, br m), 6.9 (1H, m), 3.35 (2H, m), 2.9 (2H, m), 2.3 (3H, s), 2.25 (3H, s), 1.95 (2H, m).

The intermediates of the following table (Table 9) were prepared analogously to Intermediate F from 2,3-dichloropyrido[2,3-b]pyrazine (Intermediate F step 2) and the appropriate boronic acid

TABLE 9

| Int. | Structure | Name | [M + H]+/NMR |
|---|---|---|---|
| FC | 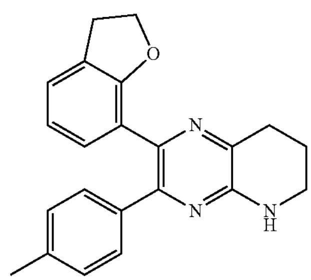 [SMILES: Cc1ccc(-c2nc3c(nc2-c2cccc4c2OCC4)CCCN3)cc1] | 2-(2,3-dihydrobenzofuran-7-yl)-3-p-tolyl-5,6,7,8-tetrahydropyrido[2,3-b]pyrazine | LC-MS Rt = 1.03 mins; [M + H]+ 344, Method 2minLC_v003. |
| FD | 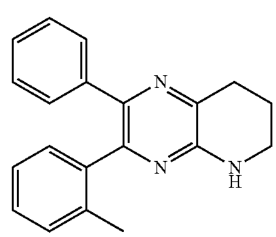 [SMILES: Cc1ccccc1-c1nc2c(nc1-c1ccccc1)CCCN2] | 2-phenyl-3-o-tolyl-5,6,7,8-tetrahydropyrido[3,2-b]pyrazine | LC-MS Rt = 1.02 mins; [M + H]+ 302, Method 2minLC_v003. |
| FE | 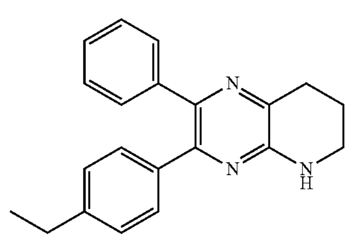 [SMILES: CCc1ccc(-c2nc3c(nc2-c2ccccc2)CCCN3)cc1] | 3-(4-ethylphenyl)-2-phenyl-5,6,7,8-tetrahydropyrido[2,3-b]pyrazine | LC-MS Rt = 1.12 mins; [M + H]+ 316, Method 2minLC_v003. |
| FF | 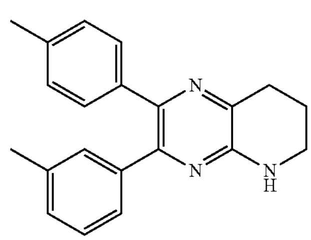 [SMILES: Cc1ccc(-c2nc3c(nc2-c2cccc(C)c2)NCCC3)cc1] | 3-m-tolyl-2-p-tolyl-5,6,7,8-tetrahydropyrido[2,3-b]pyrazine | LC-MS Rt = 1.09 mins; [M + H]+ 316, Method 2minLC_v003. |

TABLE 9-continued

| Int. | Structure | Name | [M + H]⁺/NMR |
|---|---|---|---|
| FG | 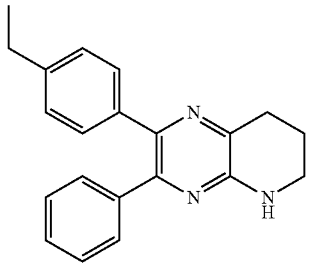 [SMILES: CCc1ccc(-c2nc3c(nc2-c2ccccc2)NCCC3)cc1] | 2-(4-ethylphenyl)-3-phenyl-5,6,7,8-tetrahydropyrido[2,3-b]pyrazine | LC-MS Rt = 1.12 mins; [M + H]+ 316, Method 2minLC_v003. |

Intermediate G 2,3-bis(3-Fluoro-4-methylphenyl)-5,6,7,8-tetrahydropyrido[2,3-b]pyrazine

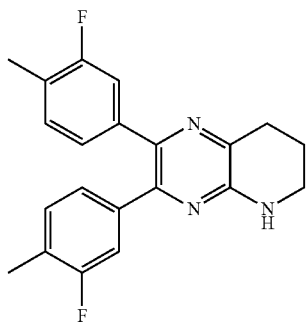 [SMILES: Cc1ccc(-c2nc3c(nc2-c2ccc(C)c(F)c2)NCCC3)cc1F]

Step 1: 2,3-bis(3-Fluoro-4-methylphenyl)pyrido[2,3-b]pyrazine

A slurry of 2,3-Dichloropyrido[2,3-b]pyrazine (Intermediate F step 2) (500 mg, 2.500 mmol), 3-fluoro-4-methylphenylboronic acid (847 mg, 5.50 mmol), tetrakis(triphenylphosphine)palladium(0) (173 mg, 0.150 mmol) and potassium carbonate (1520 mg, 11.00 mmol) in dioxane (20 ml) was degassed by bubbling nitrogen through (×3). The reaction mixture was heated using microwave radiation under nitrogen at 150° C. for 4 h. The resulting mixture was partitioned between EtOAc and water. The organic portion was separated, dried (sodium sulphate), filtered and concentrated in vacuo. The crude product was purified by chromatography on silica eluting with 0-3% THF in DCM to afford the title compound; LCMS; Rt 1.28 mins MS m/z 348 [ M+H]+ Method 2minLC_v003

Step 2: 2,3-bis(3-Fluoro-4-methylphenyl)-5,6,7,8-tetrahydropyrido[2,3-b]pyrazine To Pd(OH)₂ (20% on carbon, 50% water wet) (30 mg, 0.214 mmol) and ammonium formate (557 mg, 8.84 mmol) was added a solution of 2,3-bis(3-fluoro-4-methylphenyl)pyrido[2,3-b]pyrazine (step 1)(307 mg, 0.884 mmol) in MeOH (3 ml) and the reaction mixture was heated to reflux for 5 h. A further portion of Pd(OH)₂ (20% on carbon, 50% water wet) (30 mg, 0.214 mmol) was added and the mixture was heated to reflux for 6 h. The reaction mixture was filtered through Celite® (filter material) and washed with MeOH and EtOAc. The filtrate was concentrated in vacuo to afford the title compound as a yellow solid;
LCMS; Rt 1.07 mins MS m/z 352 [ M+H]+Method 2minLC_v003

The intermediates of the following table (Table 10) were prepared analogously to Intermediate G from 2,3-dichloropyrido[2,3-b]pyrazine (Intermediate F step 2) and the appropriate boronic acid.

TABLE 10

| Int. | Structure | Name | [M + H]⁺/NMR |
|---|---|---|---|
| GA | 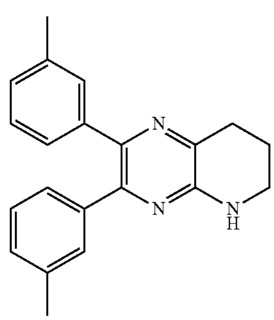 [SMILES: Cc1cccc(-c2nc3c(nc2-c2cccc(C)c2)NCCC3)c1] | 2,3-dim-tolyl-5,6,7,8-tetrahydropyrido[2,3-b]pyrazine | LC-MS Rt = 1.15 mins; [M + H]+ 316, Method 2minLC_v003. |

TABLE 10-continued

| Int. | Structure | Name | [M + H]⁺/NMR |
|---|---|---|---|
| GB | 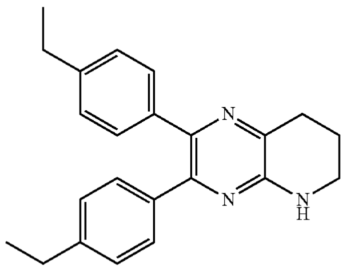 [SMILES: CCc1ccc(-c2nc3c(nc2-c2ccc(CC)cc2)NCCC3)cc1] | 2,3-bis(4-ethylphenyl)-5,6,7,8-tetrahydro pyrido[2,3-b]pyrazine | LC-MS Rt = 1.29 mins; [M + H]+ 343, Method 2minLC_v003. |
| GC | 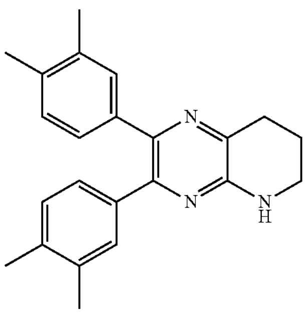 [SMILES: Cc1ccc(-c2nc3c(nc2-c2ccc(C)c(C)c2)NCCC3)cc1C] | 2,3-bis(3,4-dimethylphenyl)-5,6,7,8-tetrahydro pyrido[2,3-b]pyrazine | LC-MS Rt = 1.21 mins; [M + H]+ 344/345, Method 2minLC_v003. |
| GD | 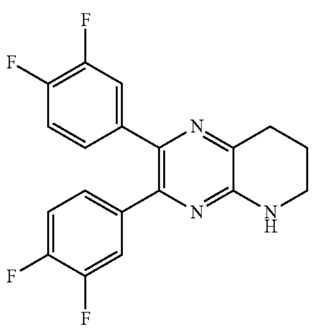 [SMILES: Fc1ccc(-c2nc3c(nc2-c2ccc(F)c(F)c2)NCCC3)cc1F] | 2,3-bis(3,4-difluorophenyl)-5,6,7,8-tetrahydro pyrido[2,3-b]pyrazine | LC-MS Rt = 1.04 mins; [M + H]+ 360, Method 2minLC_30_v003. |
| GE | 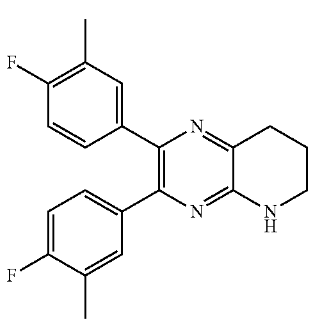 [SMILES: Cc1cc(-c2nc3c(nc2-c2ccc(F)c(C)c2)NCCC3)ccc1F] | 2,3-bis(4-fluoro-3-methylphenyl)-5,6,7,8-tetrahydro pyrido[2,3-b]pyrazine | LC-MS Rt = 1.16 mins; [M + H]+ 352/353, Method 2minLC_v003. |

Intermediate H tert-Butyl 8-bromo-2,3-diphenyl-7,8-dihydropyrido[2,3-b]pyrazine-5(6H)-carboxylate

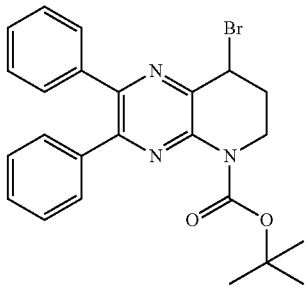 [SMILES: CC(C)(C)OC(=O)N1CCC(Br)c2nc(-c3ccccc3)c(-c3ccccc3)nc21]

Step 1: tert-Butyl 2,3-diphenyl-7,8-dihydropyrido[2,3-b]pyrazine-5(6H)-carboxylate 2,3-Diphenyl-5,6,7,8-tetrahydropyrido[3,2-b]pyrazine (Example 4.1 step 1)(5 g, 17.40 mmol) in THF (75 ml) was treated with di-tert-butyl dicarbonate (4.85 ml, 20.88 mmol) and DMAP (0.425 g, 3.48 mmol) and stirred for 5 h at RT. A further 0.2 equivalents of DMAP was added and the mixture was stirred for 5 days at RT. The mixture was added to water and extracted with EtOAc (×2). The combined organic extracts were washed with brine, dried over MgSO$_4$ and concentrated in vacuo. The product was washed with 0.1 M HCl and extracted with EtOAc. The combined organic extracts were washed with brine, dried over MgSO$_4$ and concentrated in vacuo to afford the title compound;

LC-MS Rt=1.43 mins; [M+H]+ 389, Method 2min-LC_v003.

Step 2: tert-Butyl 8-bromo-2,3-diphenyl-7,8-dihydropyrido[2,3-b]pyrazine-5(6H)-carboxylate To a stirred solution of tert-Butyl 2,3-diphenyl-7,8-dihydropyrido[2,3-b]pyrazine-5(6H)-carboxylate (step 1)(25 g, 64.5 mmol) in carbon tetrachloride (645 ml) at RT under N$_2$ was added NBS (13.78 g, 77 mmol) followed directly by lauroyl peroxide (0.257 g, 0.645 mmol) and the solution was heated at 60° C. for 4 h 15 mins. The mixture was filtered through filter paper and the filtrate was washed with sat. NaHCO$_3$ (300 ml), 2 M Na$_2$SO$_3$ (300 ml) and sat. brine (300 ml). The solution was dried over MgSO$_4$ and filtered, washing MgSO$_4$ bed with DCM (100 ml). The solvent was removed in vacuo. The crude product was dissolved in diethyl ether (300 ml) and was allowed to stand at RT and placed in a fridge overnight. The resulting crystalline solid was isolated by decanting off the mother liquors. The crystals were washed with diethyl ether to afford the title compound. Further product was obtained by chromatography of the mother liquors eluting with iso-hexane/EtOAc to afford the title product;

LC-MS Rt=1.50 mins; [M+H]+ 468, Method 2min-LC_v003.

Intermediate HA

2,3-Diphenyl-5,6,7,8-tetrahydropyrido[2,3-b]pyrazin-8-yl acetate

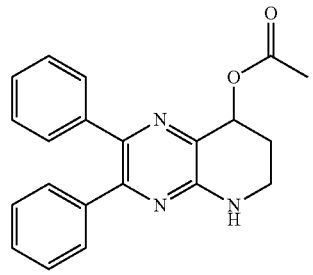 [SMILES: CC(=O)OC1CCNc2nc(-c3ccccc3)c(-c3ccccc3)nc21]

Step 1: tert-Butyl 8-acetoxy-2,3-diphenyl-7,8-dihydropyrido[2,3-b]pyrazine-5(6H)-carboxylate To a solution of tert-butyl 8-bromo-2,3-diphenyl-7,8-dihydropyrido[2,3-b]pyrazine-5(6H)-carboxylate (Intermediate H) (200 mg, 0.429 mmol) in DCM (8 ml) was added silver acetate (143 mg, 0.858 mmol). The reaction mixture was stirred at room temperature overnight under an atmosphere of nitrogen. The mixture was filtered through Celite® (filter material) and washed with DCM (20 ml). The filtrate was then concentrated in vacuo to afford the title compound;

LC-MS Rt=1.54 mins; [M+H]+ 446, Method 2min-LC_v003.

Step 2: 2,3-Diphenyl-5,6,7,8-tetrahydropyrido[2,3-b]pyrazin-8-yl acetate

A solution of tert-butyl 8-acetoxy-2,3-diphenyl-7,8-dihydropyrido[2,3-b]pyrazine-5(6H)-carboxylate (Step 1) (190 mg, 0.426 mmol) in 4M HCl in dioxane (dry) (2.665 ml, 10.66 mmol) was left to stir at room temperature for 1 hour, under an atmosphere of nitrogen. The mixture was concentrated in vacuo and the crude product was purified by chromatography on silica eluting with EtOAc/iso-hexane to afford the title compound;

LC-MS Rt=1.32 mins; [M+H]+ 346, Method 2min-LC_v003.

Intermediates HBR and HBS (R)-2,3-Diphenyl-5,6,7,8-tetrahydropyrido[2,3-b]pyrazin-8-yl acetate (Intermediate HBR) and (S)-2,3-Diphenyl-5,6,7,8-tetrahydropyrido[2,3-b]pyrazin-8-yl acetate (Intermediate HBS)

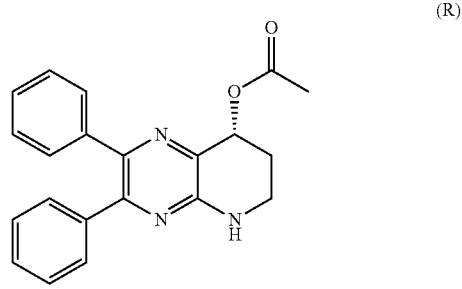

-continued

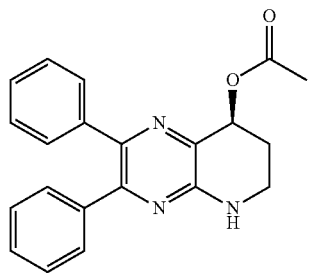

(S)

Step 1: (R)-tert-Butyl 8-acetoxy-2,3-diphenyl-7,8-dihydropyrido[2,3-b]pyrazine-5(6H)-carboxylate and (S)-tert-Butyl 8-acetoxy-2,3-diphenyl-7,8-dihydropyrido[2,3-b]pyrazine-5(6H)-carboxylate tert-Butyl 8-acetoxy-2,3-diphenyl-7,8-dihydropyrido[2,3-b]pyrazine-5(6H)-carboxylate (Intermediate HA step 1) was purified by SFC under the conditions detailed below to afford the following compounds:

| | |
|---|---|
| Column: | Chiralcel OJ-H 250 × 10 mm, 5 um |
| Mobile phase: | 10% isopropanol/90% CO2 |
| Flow: | 10 ml/min |
| Detection: | UV @ 220 nm |

First Eluted Peak: Rt 4.36 mins: (R)-tert-Butyl 8-acetoxy-2,3-diphenyl-7,8-dihydropyrido[2,3-b]pyrazine-5(6H)-carboxylate Second Eluted Peak: Rt 6.76 min (S)-tert-Butyl 8-acetoxy-2,3-diphenyl-7,8-dihydropyrido[2,3-b]pyrazine-5(6H)-carboxylate Step 2: (R)-2,3-Diphenyl-5,6,7,8-tetrahydropyrido[2,3-b]pyrazin-8-yl acetate and (S)-2,3-Diphenyl-5,6,7,8-tetrahydropyrido[2,3-b]pyrazin-8-yl acetate A solution of (R)-tert-butyl 8-acetoxy-2,3-diphenyl-7,8-dihydropyrido[2,3-b]pyrazine-5(6H)-carboxylate (62 mg, 0.139 mmol) in 4M HCl in dioxane (1.252 ml, 5.01 mmol) was left to stir under an atmosphere of nitrogen for 1 hour. The reaction mixture was concentrated in vacuo to afford (R)-2,3-diphenyl-5,6,7,8-tetrahydropyrido[2,3-b]pyrazin-8-yl acetate (Intermediate HBR) which was used without further purification.

LC-MS Rt=0.94 mins; [M+H]+ 346, Method 2min-LC_v003.

Similarly, (S)-2,3-Diphenyl-5,6,7,8-tetrahydropyrido[2,3-b]pyrazin-8-yl acetate (Intermediate HBS) was prepared from (S)-tert-Butyl 8-acetoxy-2,3-diphenyl-7,8-dihydropyrido[2,3-b]pyrazine-5(6H)-carboxylate;

LC-MS Rt=0.94 mins; [M+H]+ 346, Method 2min-LC_v003.

Intermediate HC rac-8-Ethyl-2,3-diphenyl-5,6,7,8-tetrahydropyrido[2,3-b]pyrazine

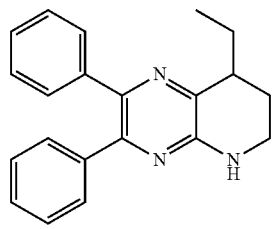 [SMILES: CCC1CCNc2nc(-c3ccccc3)c(-c3ccccc3)nc21]

To a mixture comprising tert-butyl 8-bromo-2,3-diphenyl-7,8-dihydropyrido[2,3-b]pyrazine-5(6H)-carboxylate (Intermediate H) (200 mg, 0.429 mmol) and silver nitrate (0.728 mg, 4.29 μmol) in diethyl ether (4 ml) under nitrogen at RT was added 1-Methylmagnesium bromide in THF (0.557 ml, 0.557 mmol). The reaction mixture was left to stir at RT for 3 h under an atmosphere of nitrogen. The mixture was poured into a saturated ammonium chloride solution (10 ml) and extracted with EtOAc (2×10 ml). The organic extracts were combined, dried over MgSO$_4$, filtered and concentrated in vacuo. The resulting crude product was purified by chromatography on silica eluting with 0-30% EtOAc/iso-hexane to afford the title compound;

LC-MS Rt=1.15 mins; [M+H]+ 316, Method 2min-LC_v003.

Other analogues of this intermediate for example, 8-cyclopropyl-2,3-diphenyl-5,6,7,8-tetrahydropyrido[2,3-b]pyrazine, 8-isopropyl-2,3-diphenyl-5,6,7,8-tetrahydropyrido[2,3-b]pyrazine and 8-methyl-2,3-diphenyl-5,6,7,8-tetrahydropyrido[2,3-b]pyrazine were prepared using a similar method to Intermediate HC by replacing ethylmagnesium bromide with the appropriate alkyl or cycloalkyl magnesium bromide analogue.

Intermediate HD

8-Methoxy-2,3-diphenyl-5,6,7,8-tetrahydropyrido[2,3-b]pyrazine

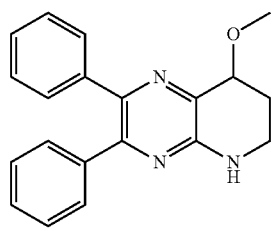 [SMILES: COC1CCNc2nc(-c3ccccc3)c(-c3ccccc3)nc21]

Step 1: tert-Butyl 8-methoxy-2,3-diphenyl-7,8-dihydropyrido[2,3-b]pyrazine-5(6H)-carboxylate To a solution of tert-butyl 8-bromo-2,3-diphenyl-7,8-dihydropyrido[2,3-b]pyrazine-5(6H)-carboxylate (Intermediate H) (200 mg, 0.429 mmol) in dry MeOH (8 ml, 198 mmol) was added silver carbonate (237 mg, 0.858 mmol). The mixture was stirred at RT for 2.5 hours under nitrogen and then filtered through Celite® (filter material) washing through with methanol (25 ml). The filtrate was concentrated in vacuo to afford the title compound;

LC-MS Rt=1.45 mins; [M+H]+ 418, Method 2min-LC_v003.

Step 2: 8-Methoxy-2,3-diphenyl-5,6,7,8-tetrahydropyrido[2,3-b]pyrazine

The title compound was prepared from tert-butyl 8-methoxy-2,3-diphenyl-7,8-dihydropyrido[2,3-b]pyrazine-5(6H)-carboxylate (step 1) analogously to 2,3-diphenyl-5,6,7,8-tetrahydropyrido[2,3-b]pyrazin-8-yl acetate (Intermediate HBR, step 2);

LC-MS Rt=1.17 mins; [M+H]+ 318, Method 2min-LC_v003.

Intermediate HE 2,3-bis(4-(Trifluoromethyl)phenyl)-5,6,7,8-tetrahydropyrido[2,3-b]pyrazin-8-yl acetate

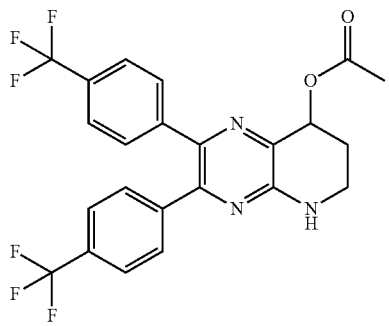 [SMILES: CC(=O)OC1CCNc2nc(-c3ccc(C(F)(F)F)cc3)c(-c3ccc(C(F)(F)F)cc3)nc21]

The title compound is prepared analogously to Intermediate H by replacing 2,3-diphenyl-5,6,7,8-tetrahydropyrido[3,2-b]pyrazine (Example 4.1 step 1) with 2,3-bis(4-(trifluoromethyl)phenyl)-5,6,7,8-tetrahydropyrido[2,3-b]pyrazine (Intermediate EE);

LC-MS Rt=1.40 mins; [M+H]+ 482, Method 2min-LC_v003.

Intermediate HF rac-2,3-Dip-tolyl-5,6,7,8-tetrahydropyrido[2,3-b]pyrazin-8-yl acetate

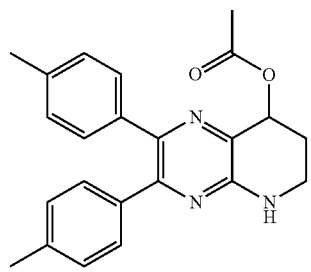 [SMILES: CC(=O)OC1CCNc2nc(-c3ccc(C)cc3)c(-c3ccc(C)cc3)nc21]

Step 1: tert-Butyl 2,3-dip-tolyl-7,8-dihydropyrido[2,3-b]pyrazine-5(6H)-carboxylate To di-tert-butyl dicarbonate (1.104 ml, 4.76 mmol) in THF (50 ml) was added 2,3-dip-tolyl-5,6,7,8-tetrahydropyrido[2,3-b]pyrazine (Intermediate E) (1 g, 3.17 mmol) followed by 4-dimethylaminopyridine (0.039 g, 0.317 mmol). The suspension was stirred at room temperature for 48 hours. The solvent was concentrated in vacuo. The crude product was purified by chromatography on silica eluting with 0-50% EtOAc in iso-hexane to afford the title compound;

LC-MS Rt=1.49 mins; [M+H]+ 416.3, Method 2min-LC_v003.

Step 2: rac-tert-Butyl 8-bromo-2,3-dip-tolyl-7,8-dihydropyrido[2,3-b]pyrazine-5(6H)-carboxylate To a stirred solution of tert-butyl 2,3-dip-tolyl-7,8-dihydropyrido[2,3-b]pyrazine-5(6H)-carboxylate (step1) (530 mg, 1.275 mmol) in chloroform (10 ml) was added N-bromosuccinimide (272 mg, 1.531 mmol) followed by lauroyl peroxide (50.8 mg, 0.128 mmol) and the mixture was heated to reflux for 1 hour. The solvent was concentrated in vacuo. The crude product was purified by chromatography on silica eluting with 0-50% EtOAc in iso-hexane to afford the title compound which was used directly into the next step Step 3: rac-tert-Butyl 8-acetoxy-2,3-dip-tolyl-7,8-dihydropyrido[2,3-b]pyrazine-5(6H)-carboxylate To rac-tert-butyl 8-bromo-2,3-dip-tolyl-7,8-dihydropyrido[2,3-b]pyrazine-5(6H)-carboxylate (step 2) (220 mg, 0.445 mmol) in dichloromethane (10 ml) was added silver acetate (149 mg, 0.890 mmol. The reaction mixture was stirred at room temperature for 30 minutes. The mixture was filtered through Celite® (filter material) and washed with DCM (20 ml). The filtrate was then concentrated in vacuo and the crude product was purified by chromatography on silica eluting with 0-50% EtOAc in iso-hexane to afford the title compound LC-MS Rt=1.61 mins; [M+H]+ 475.3, Method 2minLC_v003.

Step 4: 2,3-Dip-tolyl-5,6,7,8-tetrahydropyrido[2,3-b]pyrazin-8-yl acetate

To rac-tert-Butyl 8-acetoxy-2,3-dip-tolyl-7,8-dihydropyrido[2,3-b]pyrazine-5(6H)-carboxylate (step 3)(110 mg, 0.232 mmol) in dichloromethane (5 ml) was added trifluoroacetic acid (0.089 ml, 1.161 mmol). The solution was stirred at room temperature for 4 hrs. To the reaction mixture was added a saturated aqueous sodium carbonate (2 ml) and the mixture was vigorously stirred for 10 minutes. The organic layer was separated and concentrated in vacuo to afford the title compound;

LC-MS Rt=1.60 mins; [M+H]+ 374.6, Method 2min-LC_v003.

Intermediate HG

N,N-Dimethyl-2,3-diphenyl-5,6,7,8-tetrahydropyrido[2,3-b]pyrazin-8-amine

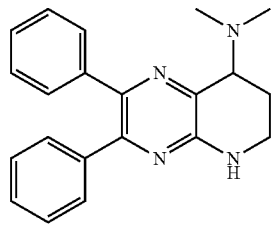 [SMILES: CN(C)C1CCNc2nc(-c3ccccc3)c(-c3ccccc3)nc21]

Step 1: tert-Butyl 8-(dimethylamino)-2,3-diphenyl-7,8-dihydropyrido[2,3-b]pyrazine-5(6H)-carboxylate To a solution of tert-butyl 8-bromo-2,3-diphenyl-7,8-dihydropyrido[2,3-b]pyrazine-5(6H)-carboxylate (Intermediate H) (500 mg, 1.072 mmol) in ethanol (10 ml) was added 40% dimethylamine in water (0.407 ml, 3.22 mmol) and the mixture was left to stir under an atmosphere of nitrogen overnight. The solvent was concentrated in vacuo. The crude product was purified by chromatography on silica eluting with EtOAc in iso-hexane to affore the title compound;

LC-MS Rt=1.13 mins; [M+H]+ 431, Method 2min-LC_v003.

Step 2: N,N-Dimethyl-2,3-diphenyl-5,6,7,8-tetrahydropyrido[2,3-b]pyrazin-8-amine The title compound was prepared from tert-butyl 8-(dimethylamino)-2,3-diphenyl-7,8-dihydropyrido[2,3-b]pyrazine-5(6H)-carboxylate (step 1) analogously to 2,3-diphenyl-5,6,7,8-tetrahydropyrido[2,3-b]pyrazin-8-yl acetate (Intermediate HA step 2);

LC-MS Rt=0.93 mins; [M+H]+ 331, Method 2min-LC_v003.

Intermediate I rac-2,3-diphenyl-5,6,7,8-tetrahydropyrido[2,3-b]pyrazine-7,8-diyl diacetate

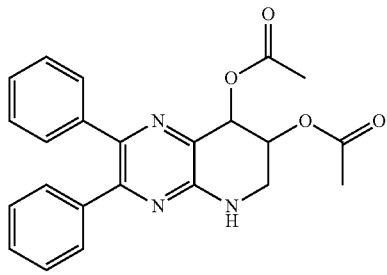 [SMILES: CC(=O)OC1CNc2nc(-c3ccccc3)c(-c3ccccc3)nc2C1OC(C)=O]

Step 1: tert-Butyl 2,3-diphenylpyrido[2,3-b]pyrazine-5(6H)-carboxylate

A solution of tert-Butyl 8-bromo-2,3-diphenyl-7,8-dihydropyrido[2,3-b]pyrazine-5(6H)-carboxylate (Intermediate H) (5 g, 10.72 mmol) in DCM (250 ml) was treated with DBU (1.939 ml, 12.87 mmol) and was stirred at RT under an atmosphere of nitrogen overnight. The solvent was removed in vacuo. The resulting crude product was purified by chromatography on silica eluting with 0-20% EtOAc/iso-hexane to afford the title compound;

LC-MS Rt=1.45 mins; [M+H]+ 386, Method 2min-LC_v003.

Step 2: rac-tert-butyl 7,8-dihydroxy-2,3-diphenyl-7,8-dihydropyrido[2,3-b]pyrazine-5(6H)-carboxylate To a solution of tributylmethylammonium chloride (728 mg, 3.09 mmol) in DCM (10 ml) was added potassium permanganate (488 mg, 3.09 mmol) portionwise over 10 minutes at room temperature. The reaction mixture was allowed to stir under an atmosphere of nitrogen for 30 minutes. The mixture was cooled down to 0° C. and treated dropwise with a solution of tert-butyl 2,3-diphenylpyrido[2,3-b]pyrazine-5(6H)-carboxylate (step 1)(700 mg, 1.816 mmol) in DCM (8 ml). The reaction was then left to stir for a further 2 hours at 0-5° C. under an atmosphere of nitrogen. A solution of sodium bisulfite (1134 mg, 10.90 mmol) in water (9 ml) was added dropwise at 0-5° C. to the reaction mixture. The mixture was filtered through Celite® (filter material) and washed with DCM (20 ml) and water (10 ml). The organic layer was separated and concentrated in vacuo to give a foamy solid. The crude material was purified by chromatography on silica eluting with 0-90% EtOAc/iso-hexane to afford the title compound;

LC-MS Rt=1.19 mins; [M+H]+ 420, Method 2min-LC_v003.

Step 3: rac-5-(tert-Butoxycarbonyl)-2,3-diphenyl-5,6,7,8-tetrahydropyrido[2,3-b]pyrazine-7,8-diyl diacetate A mixture comprising the rac-tert-butyl 7,8-dihydroxy-2,3-diphenyl-7,8-dihydropyrido[2,3-b]pyrazine-5(6H)-carboxylate (step 2) (230 mg, 0.548 mmol), acetic anhydride (155 µl, 1.645 mmol) and pyridine (1064 µl, 13.16 mmol) was stirred at RT under an atmosphere of nitrogen overnight. After standing at RT for 2 days, the mixture was diluted with saturated sodium bicarbonate and extracted with DCM (2×20 ml). The organic extracts were combined and concentrated in vacuo. The crude material was purified by chromatography on silica eluting with 20-100% EtOAc/iso-hexane to afford the title compound;

LC-MS Rt=1.39 mins; [M+H]+ 504, Method 2min-LC_v003.

Step 4: rac-2,3-diphenyl-5,6,7,8-tetrahydropyrido[2,3-b]pyrazine-7,8-diyldiacetate A solution of rac-5-(tert-butoxycarbonyl)-2,3-diphenyl-5,6,7,8-tetrahydropyrido[2,3-b]pyrazine-7,8-diyl diacetate (step 3) (190 mg, 0.377 mmol) in 4M HCl in dioxane (2 ml, 8.00 mmol) was stirred at RT for 30 mins. The mixture was concentrated in vacuo and the residue was dissolved in saturated sodium bicarbonate and extracted with EtOAc (2×20 ml). The combined organic extracts were dried (MgSO$_4$), filtered and concentrated in vacuo. The crude material was purified by chromatography on silica eluting with 0-70% EtOAc/iso-hexane to afford the title compound;

LC-MS Rt=1.21 mins; [M+H]+ 404, Method 2min-LC_v003.

Intermediate J

2-Bromo-3-chloro-7,8-dihydro-5H-pyrido[2,3-b]pyrazin-6-one

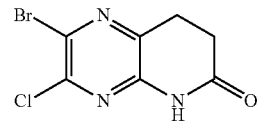

Step 1: 3,5-Dibromo-6-chloro-pyrazin-2-ylamine

A solution of 6-chloropyrazin-2-amine (2 g, 15.44 mmol) and NBS (13.7 g, 77 mmol) in CHCl$_3$ (100 ml) was heated at reflux for 20 hours. The resulting mixture was purified by chromatography on silica eluting with DCM. The relevant fractions were concentrated in vacuo and the crude product was dissolved in EtOAc (~100 ml), washed with 10% sodium thiosulfate (2×100 ml), brine, dried (MgSO$_4$) and were concentrated in vacuo to afford the title compound;

$^1$H NMR (400 MHz, CDCl$_3$) δ 5.4-5.0 (2H, br s).

Step 2: 2-Bromo-3-chloro-7,8-dihydro-5H-pyrido[2,3-b]pyrazin-6-one

A mixture comprising 3,5-dibromo-6-chloropyrazin-2-amine (step 1) (1.0 g, 3.48 mmol) and bistriphenylphosphine-palladium(II)chloride (0.122 g, 0.174 mmol) in THF (15 ml) under nitrogen was treated with (3-ethoxy-3-oxopropyl)zinc (II) bromide 0.5 M in THF (15.31 ml, 7.66 mmol) and the mixture was stirred at room temperature for 3 hours. A further portion of (3-ethoxy-3-oxopropyl)zinc(II) bromide 0.5 M in THF (7.5 mL, 3.8 mmol) was added and stirring continued for 1.5 hours. More (3-ethoxy-3-oxopropyl)zinc(II) bromide 0.5 M in THF (3.8 mL, 1.9 mmol) was added and the mixture was stirred at RT for 65 hours. The mixture was diluted with water (10 ml) and concentrated in vacuo. The residue was diluted with EtOAc (100 ml) the emulsion was filtered through Celite® (filter material). The phases were separated and the aqueous portion was extracted with EtOAc (50 ml). The combined organic extracts were washed with brine, dried (MgSO$_4$) and concentrated in vacuo. The residue was triturated with EtOAc (~10 ml) to afford the title compound as yellow solid.

$^1$H NMR (400 MHz, DMSO-d6) δ 11.15 (1H, br s), 3.1-3.0, (2H, m), 2.75-2.65 (2H, m).

Intermediate K rac-7-Methoxy-2,3-dip-tolyl-5,6,7,8-tetrahydropyrido[2,3-b]pyrazine

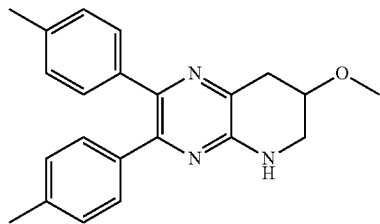

Step 1: 7-Chloro-2,3-dip-tolylpyrido[2,3-b]pyrazine

The title compound was prepared from 1,2-dip-tolylethane-1,2-dione and 5-chloro-pyridine-2,3-diamine analogously to 2,3-dip-tolylpyrido[2,3-b]pyrazine (Intermediate E step 1). Acetic acid is not used in this reaction.

Step 2: 7-Methoxy-2,3-dip-tolylpyrido[2,3-b]pyrazine

A mixture comprising 7-chloro-2,3-dip-tolylpyrido[2,3-b]pyrazine (836 mg, 2.417 mmol) in dry MeOH (10 ml) and DCM (5 ml) bubbled through with nitrogen was treated portionwise with sodium (278 mg, 12.09 mmol). The resulting mixture was heated at reflux overnight. A further portion of sodium (278 mg, 12.09 mmol) was added and refluxing continued overnight. After cooling to RT, the solvent was removed in vacuo and the resulting residue was added to water. The mixture was extracted with DCM (×3) and the combined organic extracts were washed with brine, dried over MgSO$_4$ and concentrated in vacuo. Purification by chromatography on silica eluting with 10-40% EtOAc/iso-hexane afforded the title compound;

LCMS: Rt 1.31 mins MS m/z 342 [M+H]+ Method 2min-LC_v003

Step 3: rac-7-Methoxy-2,3-dip-tolyl-5,6,7,8-tetrahydropyrido[2,3-b]pyrazine

7-Methoxy-2,3-dip-tolylpyrido[2,3-b]pyrazine (94 mg, 0.275 mmol) in dry MeOH (4 ml), under nitrogen was treated with 10% Pd on Carbon (58.6 mg, 0.056 mmol). The suspension was stirred at RT under an atmosphere of hydrogen for 32 hours. The resulting mixture was loaded onto a 2.5 g Celite® column using MeOH and was flushed with 1:1 MeOH:DCM. The filtrate was concentrated in vacuo and the residue was dissolved in DCM (30 ml) and washed with water (×2). The organic portion was isolated and the solvent was removed in vacuo to afford the title compound; LCMS Rt 1.12 mins MS m/z 346 [M+H]+ Method 2minLC_v003

From the foregoing it will be appreciated that, although specific embodiments of the invention have been described herein for purposes of illustration, various modifications may be made without deviating from the spirit and scope of the invention. Accordingly, the invention is not limited except as by the appended claims.

Consistory Clauses

Embodiment 1

A compound represented by Formula I

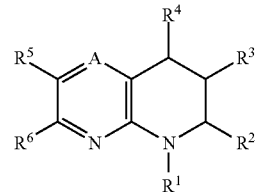

and a pharmaceutically acceptable salt thereof, wherein
A is N or CR';
R' is H, $C_1$-$C_8$ alkyl optionally substituted by one or more halogen atoms;
$R^1$ is H, $C_1$-$C_8$ alkyl optionally substituted by one or more halogen atoms, $C_1$-$C_4$ alkyl, OH, OR', —NR$^{19}$R$^{21}$, CN or $C_3$-$C_7$ cycloalkyl; or
  $R^1$ is —X—Y; or
  $R^1$ is —W—R$^7$—X—Y; or
  $R^1$ is —S(O)$_2$—W—X—Y; or
  $R^1$ is —S(O)$_2$—W—R$^7$—X—Y;
$R^2$ is H, $C_1$-$C_8$ alkyl optionally substituted by one or more halogen atoms, $C_1$-$C_4$ alkyl, OH, OR', —NR$^{19}$R$^{21}$, CN or $C_3$-$C_7$ cycloalkyl; or
  $R^2$ is —X—Y; or
  $R^2$ is —W—R$^7$—X—Y; or
  $R^2$ is —S(O)$_2$—W—X—Y; or
  $R^2$ is —S(O)$_2$—W—R$^7$—X—Y;
  wherein either $R^1$ or $R^2$ must be —X—Y, —S(O)$_2$—W—X—Y; or —S(O)$_2$—W—R$^7$—X—Y;
$R^3$ is H, $C_1$-$C_8$ alkyl optionally substituted by one or more halogen atoms, $C_1$-$C_4$ alkoxy, OH, —NR$^{19}$R$^{21}$, CN or $C_3$-$C_7$ cycloalkyl;

$R^4$ is H, $C_1$-$C_8$ alkyl optionally substituted by one or more halogen atoms, $C_1$-$C_4$ alkoxy, OH, —$NR^{19}R^{21}$, CN or $C_3$-$C_7$ cycloalkyl;

$R^5$ is $C_1$-$C_8$ alkyl optionally substituted by one or more halogen atoms, $C_1$-$C_4$ alkyl, OH, OR', —$NR^{19}R^{21}$, CN or $C_3$-$C_7$ cycloalkyl; $C_1$-$C_8$ alkoxy optionally substituted by one or more halogen atoms; $C_8$-$C_{14}$ aryl; —($C_0$-$C_4$ alkyl)-4 to 14 membered heteroaryl, or —($C_0$-$C_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents;

$R^6$ is $C_8$-$C_{14}$ aryl; —($C_0$-$C_4$ alkyl)-4 to 14 membered heteroaryl, —($C_0$-$C_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents;

W is $C_1$-$C_8$ alkylene optionally substituted by hydroxy, halogens or $C_1$-$C_4$ alkyl;

X is $C_1$-$C_8$ alkylene optionally substituted by hydroxy, halogens or $C_1$-$C_4$ alkyl;

Y is carboxy, alkoxycarbonyl, tetrazolyl, carbamoyl, monoalkylcarbamoyl, dialkylcarbamoyl, or —CONH—S$(O)_q$—$R^x$, wherein $R^x$ is —$C_1$-$C_4$ alkyl or —$NR^{19}R^{21}$;

q is 0, 1 or 2;

$R^7$ is a divalent moiety represented by —$C_6$-$C_{14}$ aryl-D-; –3 to 14 membered heterocyclyl-D-, wherein the heterocyclyl contains at least one heteroatom selected from N, O and S, wherein D is O, S, NH or not present;

Z is independently OH, aryl, O-aryl, benzyl, O-benzyl, $C_1$-$C_6$ alkyl optionally substituted by one or more OH groups or $NH_2$ groups, $C_1$-$C_6$ alkyl optionally substituted by one or more halogen atoms, $C_1$-$C_6$ alkoxy optionally substituted by one or more OH groups, $C_1$-$C_6$ alkoxy optionally substituted by one or more halogen, $C_1$-$C_6$ alkoxy optionally substituted by $C_1$-$C_4$, alkoxy, $NR^{18}(SO_2)R^{21}$, $(SO_2)NR^{19}R^{21}$, $(SO_2)R^{21}$, $NR^{18}C(O)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, $NO_2$, halogen or a 3 to 14 membered heterocyclyl, wherein the heterocyclyl contains at least one heteroatom selected from N, O and S;

$R^{18}$ is independently H or $C_1$-$C_6$ alkyl;

$R^{19}$ and $R^{21}$ are each independently H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclyl, the heterocyclyl including one or more heteroatoms selected from N, O and S, optionally substituted by one or more groups selected from halogen, oxo, $C_1$-$C_6$ alkyl and $C(O)C_1$-$C_8$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or $C(O)C_1$-$C_8$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl)$_2$; or $R^{19}$ and $R^{21}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

Embodiment 2

A compound represented by Formula Ia

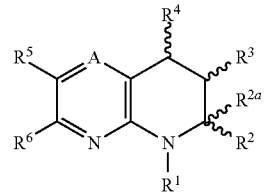

Ia or a pharmaceutically acceptable salt thereof, wherein

A is N or CR';

R' is H, $C_1$-$C_8$ alkyl optionally substituted by one or more halogen atoms;

$R^1$ is H, $C_1$-$C_8$ alkyl optionally substituted by one or more halogen atoms, $C_1$-$C_4$ alkyl, OH, OR', —$NR^{19}R^{21}$, CN or $C_3$-$C_7$ cycloalkyl; or $R^1$ is —X—Y; or $R^1$ is —W—$R^7$—X—Y; or $R^1$ is —$S(O)_2$—W—X—Y; or $R^1$ is —$S(O)_2$—W—$R^7$—X—Y;

$R^2$ is H, $C_1$-$C_8$ alkyl optionally substituted by one or more halogen atoms, $C_1$-$C_4$ alkyl, OH, OR', —$NR^{19}R^{21}$, CN or $C_3$-$C_7$ cycloalkyl; or $R^2$ is —X—Y; or $R^2$ is —W—$R^7$—X—Y; or $R^2$ is —$S(O)_2$—W—X—Y;

$R^2$ is —$S(O)_2$—W—$R^7$—X—Y;

wherein either $R^1$ or $R^2$ is —X—Y, —W—$R^7$—X—Y, —$S(O)_2$—W—X—Y; or —$S(O)_2$—W—$R^7$—X—Y;

$R^{2a}$ is hydrogen;

$R^2$ and $R^{2a}$ taken together are oxo;

$R^3$ is H, $C_1$-$C_4$ alkoxy, OH, —$NR^{19}R^{21}$, CN, halogen, $C_3$-$C_7$ cycloalkyl or $C_1$-$C_8$ alkyl optionally substituted by one or more halogen atoms;

$R^4$ is H, $C_1$-$C_4$ alkoxy, OH, —$NR^{19}R^{21}$, CN, halogen, $C_3$-$C_7$ cycloalkyl or $C_1$-$C_8$ alkyl optionally substituted by one or more halogen atoms;

$R^5$ is $C_1$-$C_8$ alkyl optionally substituted by one or more halogen atoms, $C_1$-$C_4$ alkyl, OH, OR', —$NR^{19}R^{21}$, CN or $C_3$-$C_7$ cycloalkyl; $C_1$-$C_8$ alkoxy optionally substituted by one or more halogen atoms; $C_6$-$C_{14}$ aryl; —($C_0$-$C_4$ alkyl)-4 to 14 membered heteroaryl, or —($C_0$-$C_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents;

$R^6$ is $C_6$-$C_{14}$ aryl; —($C_0$-$C_4$ alkyl)-4 to 14 membered heteroaryl, —($C_0$-$C_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents;

W is $C_1$-$C_8$ alkylene optionally substituted by hydroxy, halogens or $C_1$-$C_4$ alkyl;

X is $C_1$-$C_8$ alkylene optionally substituted by hydroxy, halogens or $C_1$-$C_4$ alkyl;

Y is carboxy, alkoxycarbonyl, tetrazolyl, carbamoyl, monoalkylcarbamoyl, dialkylcarbamoyl, or —CONH—S(O)$_q$—R$^x$, wherein R$^x$ is —C$_1$-C$_4$ alkyl or —NR$^{16}$R$^{21}$;

q is 0, 1 or 2;

R$^7$ is a divalent moiety represented by —O—, —NHC(O)—, —CH$_2$=CH$_2$—, —C$_6$-C$_{14}$ aryl-D-; −3 to 14 membered heterocyclyl-D-, wherein the heterocyclyl contains at least one heteroatom selected from N, O and S, wherein D is O, S, NH or not present;

Z is independently OH, aryl, O-aryl, benzyl, O-benzyl, C$_1$-C$_6$ alkyl optionally substituted by one or more OH groups or NH$_2$ groups, C$_1$-C$_6$ alkyl optionally substituted by one or more halogen atoms, C$_1$-C$_6$ alkoxy optionally substituted by one or more OH groups, C$_1$-C$_6$ alkoxy optionally substituted by one or more halogen, C$_1$-C$_6$ alkoxy optionally substituted by C$_1$-C$_4$ alkoxy, NR$^{18}$(SO$_2$)R$^{21}$, (SO$_2$)NR$^{16}$R$^{21}$, (SO$_2$)R$^{21}$, NR$^{18}$C(O)R$^{21}$, C(O)NR$^{19}$R$^{21}$, NR$^{18}$C(O)NR$^{19}$R$^{21}$, NR$^{18}$C(O)OR$^{19}$, NR$^{19}$R$^{21}$, C(O)OR$^{19}$, C(O)R$^{19}$, SR$^{19}$, OR$^{19}$, oxo, CN, NO$_2$, halogen or a 3 to 14 membered heterocyclyl, wherein the heterocyclyl contains at least one heteroatom selected from N, O and S;

R$^{18}$ is independently H or C$_1$-C$_6$ alkyl;

R$^{19}$ and R$^{21}$ are each independently H; C$_1$-C$_8$ alkyl; C$_3$-C$_8$ cycloalkyl; C$_1$-C$_4$ alkoxy-C$_1$-C$_4$ alkyl; (C$_0$-C$_4$ alkyl)-aryl optionally substituted by one or more groups selected from C$_1$-C$_6$ alkyl, C$_1$-C$_6$ alkoxy and halogen; (C$_0$-C$_4$ alkyl)-3- to 14-membered heterocyclyl, the heterocyclyl including one or more heteroatoms selected from N, O and S, optionally substituted by one or more groups selected from halogen, oxo, C$_1$-C$_6$ alkyl and C(O)C$_1$-C$_8$ alkyl; (C$_0$-C$_4$ alkyl)-O-aryl optionally substituted by one or more groups selected from C$_1$-C$_6$ alkyl, C$_1$-C$_6$ alkoxy and halogen; and (C$_0$-C$_4$ alkyl)-O-3- to 14-membered heterocyclyl, the heterocyclyl including one or more heteroatoms selected from N, O and S, optionally substituted by one or more groups selected from halogen, C$_1$-C$_6$ alkyl or C(O)C$_1$-C$_8$ alkyl; wherein the alkyl groups are optionally substituted by one or more halogen atoms, C$_1$-C$_4$ alkoxy, C(O)NH$_2$, C(O)NHC$_1$-C$_8$ alkyl or C(O)N(C$_1$-C$_8$ alkyl)$_2$; or R$^{19}$ and R$^{21}$ together with the nitrogen atom to which they attached form a 5- to 10-membered heterocyclyl, the heterocyclyl including one or more further heteroatoms selected from N, O and S, the heterocyclyl being optionally substituted by one or more substituents selected from OH; halogen; aryl; 5- to 10-membered heterocyclyl including one or more heteroatoms selected from N, O and S; S(O)$_2$-aryl; S(O)$_2$—C$_1$-C$_8$ alkyl; C$_1$-C$_6$ alkyl optionally substituted by one or more halogen atoms; C$_1$-C$_6$ alkoxy optionally substituted by one or more OH groups or C$_1$-C$_4$ alkoxy; and C(O)OC$_1$-C$_8$ alkyl, wherein the aryl and heterocyclyl substituent groups are themselves optionally substituted by C$_1$-C$_6$ alkyl, C$_1$-C$_6$ haloalkyl or C$_1$-C$_6$ alkoxy.

Embodiment 3

The compound according to embodiment 1 or 2, wherein
R$^1$ is H, C$_1$-C$_8$ alkyl optionally substituted by one or more halogen atoms, C$_1$-C$_4$ alkyl, OH, or OR'; or R$^1$ is —X—Y; or R$^1$ is —W—R$^7$—X—Y; or R$^1$ is —S(O)$_2$—X—Y or R$^2$ is —S(O)$_2$—W—R$^7$—X—Y;
R$^2$ is H, C$_1$-C$_8$ alkyl optionally substituted by one or more halogen atoms, C$_1$-C$_4$ alkyl, OH, or OR'; R$^2$ is —X—Y; or R$^2$ is —W—R$^7$—X—Y; or R$^2$ is —S(O)$_2$—X—Y; R$^2$ is —S(O)$_2$—W—R$^7$—X—Y;
R$^{2a}$ is H; or
R$^2$ and R$^{2a}$ together are oxo;

R$^3$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;

R$^4$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;

wherein either R$^1$ or R$^2$ is —X—Y, —S(O)$_2$—W—X—Y; or —S(O)$_2$—W—R$^7$—X—Y;

W is C$_1$-C$_6$ alkylene optionally substituted by hydroxy, halogens or C$_1$-C$_4$ alkyl;

X is C$_1$-C$_6$ alkylene optionally substituted by hydroxy, halogens or C$_1$-C$_4$ alkyl;

Y is —C(O)OH, —C(O)OR$^x$, tetrazolyl, carbamoyl, monoalkylcarbamoyl, dialkylcarbamoyl, or —CONH—S(O)$_q$—R$^x$, wherein R$^x$ is —C$_1$-C$_4$ alkyl or —NR$^{19}$R$^{21}$;

q is 2;

R' is H, C$_1$-C$_4$ alkyl optionally substituted by one or more halogen atoms;

R$^7$ is a divalent moiety represented by —C$_6$-C$_{14}$ aryl-D-; −3 to 14 membered heterocyclyl-D-, wherein the heterocyclyl contains at least one heteroatom selected from N, O and S, wherein D is O; and R$^{19}$ and R$^{21}$ are each independently H; C$_1$-C$_8$ alkyl.

Embodiment 4

The compound according to any of the preceding embodiment, wherein
R$^1$ is —X—Y; or —W—R$^7$—X—Y;
R$^2$ is H, C$_1$-C$_8$ alkyl optionally substituted by one or more halogen atoms, C$_1$-C$_4$ alkyl, OH, or OR';
R$^3$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;
R$^4$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;
W is C$_1$-C$_6$ alkylene optionally substituted by hydroxy, halogens or C$_1$-C$_4$ alkyl;
X is C$_1$-C$_6$ alkylene optionally substituted by hydroxy, halogens or C$_1$-C$_4$ alkyl;
Y is —C(O)OH, —C(O)OR$^x$, tetrazolyl, carbamoyl, monoalkylcarbamoyl, dialkylcarbamoyl, or —CONH—S(O)$_q$—R$^x$, wherein R$^x$ is —C$_1$-C$_4$ alkyl or —NR$^{19}$R$^{21}$;
q is 2;
R' is H, C$_1$-C$_4$ alkyl optionally substituted by one or more halogen atoms;
R$^7$ is a divalent moiety represented by —C$_6$-C$_{14}$ aryl-D-; −3 to 14 membered heterocyclyl-D-, wherein the heterocyclyl contains at least one heteroatom selected from N, O and S, wherein D is O; and
R$^{19}$ and R$^{21}$ are each independently H; C$_1$-C$_8$ alkyl.

Embodiment 5

The compound according to any of the preceding embodiment, wherein
R$^1$ is —X—Y; or —W—R$^7$—X—Y;
R$^2$ is H, C$_1$-C$_4$ alkyl optionally substituted by one or more halogen atoms;
R$^3$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;
R$^4$ is H, C$_1$-C$_4$ alkoxy, OH, —NR$^{19}$R$^{21}$, CN, halogen, C$_3$-C$_7$ cycloalkyl or C$_1$-C$_4$ alkyl optionally substituted by one or more halogen atoms;

W is $C_1$-$C_6$ alkylene optionally substituted by hydroxy, halogens or $C_1$-$C_4$ alkyl;

X is $C_1$-$C_6$alkylene optionally substituted by hydroxy, halogens or $C_1$-$C_4$ alkyl;

Y is —C(O)OH; and $R^7$ is a divalent moiety represented by —$C_6$-$C_{14}$ aryl-D-; –3 to 14 membered heterocyclyl-D-, wherein the heterocyclyl contains at least one heteroatom selected from N, O and S, wherein D is O.

Embodiment 6

The compound according to any of the preceding embodiment, wherein $R^1$ is $C_1$-$C_4$ alkyl optionally substituted by one or more halogen atoms, —$(CH_2)_m$—C(O)OR", or —$(CH_2)_m$—$R^7$—$(CH_2)_n$—C(O)OR";

$R^2$ is H, $C_1$-$C_4$ alkyl optionally substituted by one or more halogen atoms;

$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;

$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;

m is 1, 2, 3, 4, 5, 6, 7 or 8;

n is 0, 1, 2 or 3;

R" is H or $C_1$-$C_4$ alkyl optionally substituted by one or more halogen atoms; and $R^7$ is a divalent moiety represented by —$C_6$-$C_{14}$ aryl-D-; –3 to 14 membered heterocyclyl-D-, wherein the heterocyclyl contains at least one heteroatom selected from N, O and S, wherein D is O;

Embodiment 7

The compound according to any of the preceding embodiment, wherein $R^1$ is —$(CH_2)$, —C(O)OR", or —$(CH_2)$, —$R^7$—$(CH_2)_n$—C(O)OR";

$R^2$ is H, $C_1$-$C_4$ alkyl optionally substituted by one or more halogen atoms;

$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;

$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;

m is 1, 2, 3, 4, 5, 6, 7 or 8;

n is 0, 1, 2 or 3;

R" is H or $C_1$-$C_4$ alkyl optionally substituted by one or more halogen atoms; and $R^7$ is a divalent moiety represented by —$C_6$-$C_{14}$ aryl-D-; –3 to 14 membered heterocyclyl-D-, wherein the heterocyclyl contains at least one heteroatom selected from N, O and S, wherein D is O.

Embodiment 8

The compound according to any of the preceding embodiment, wherein $R^1$ is —$(CH_2)_m$—C(O)OR";

$R^2$ is H, $C_1$-$C_4$ alkyl optionally substituted by one or more halogen atoms;

$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;

$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;

m is 1, 2, 3, 4, 5, 6, 7 or 8; and

R" is H or $C_1$-$C_4$ alkyl optionally substituted by one or more halogen atoms.

Embodiment 9

The compound according to any of the preceding embodiment, wherein $R^1$ is —$(CH_2)_m$—C(O)OR";

$R^2$ is H;

$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;

$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;

R" is H; and m is 4, 5 or 6.

Embodiment 10

The compound according to embodiment 1 or 2, wherein $R^1$ is X—Y;

$R^2$ is H, or $C_1$-$C_8$ alkyl optionally substituted by one or more halogen atoms;

$R^3$ is H, $C_1$-$C_4$ alkoxy, OH, —$NR^{19}R^{21}$CN, halogen, $C_3$-$C_7$ cycloalkyl or $C_1$-$C_4$ alkyl optionally substituted by one or more halogen atoms;

$R^4$ is H, $C_1$-$C_4$ alkoxy, OH, —$NR^{19}R^{21}$CN, halogen, $C_3$-$C_7$ cycloalkyl or $C_1$-$C_4$ alkyl optionally substituted by one or more halogen atoms;

X is $C_1$-$C_6$ alkylene optionally substituted by hydroxy, halogens or $C_1$-$C_4$ alkyl;

Y is —C(O)OH, —C(O)$OR^x$, or —CONH—S(O)$_q$—$R^x$, wherein $R^x$ is —$C_1$-$C_4$ alkyl; and q is 2.

Embodiment 11

The compound according to embodiment 1 or 2, wherein $R^1$ is

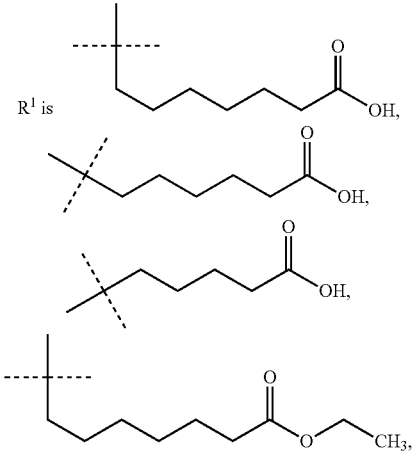

145
-continued

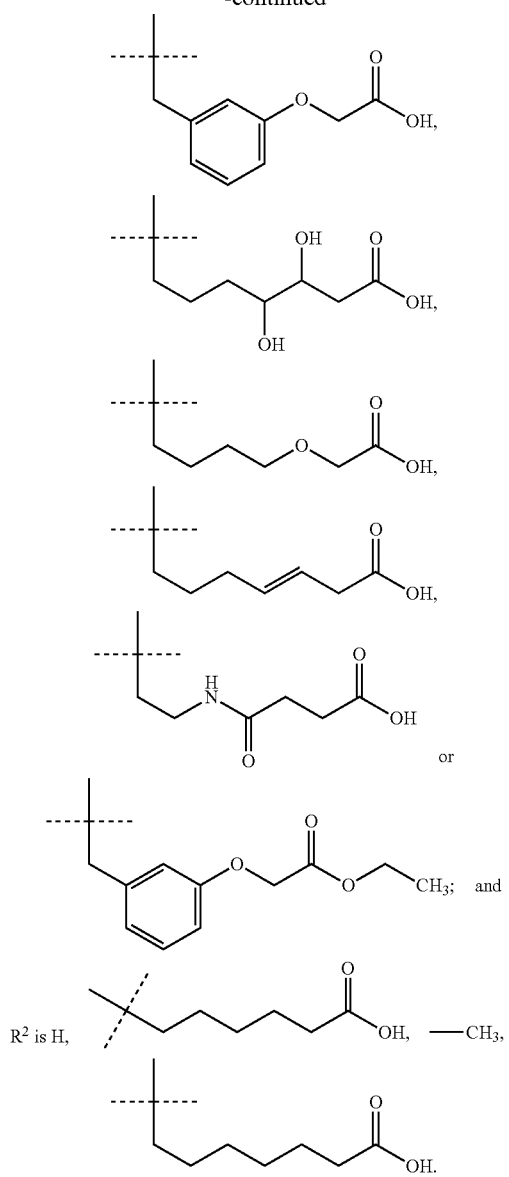

Embodiment 12

The compound according to embodiment 1 or 2, wherein

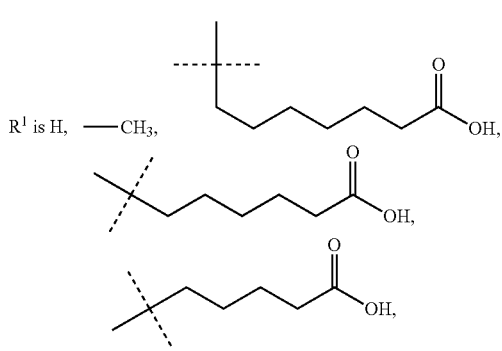

146
-continued

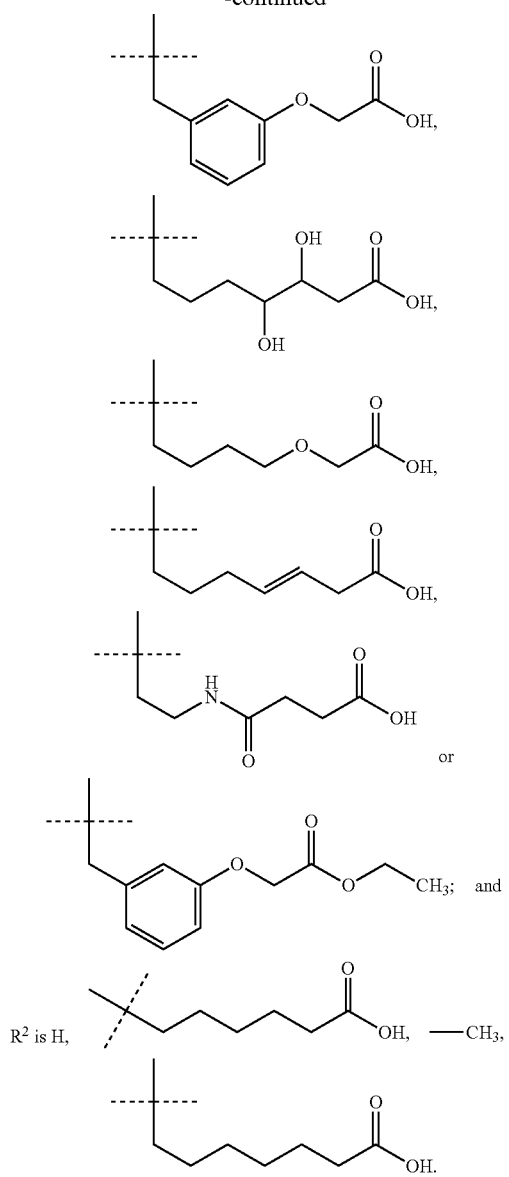

Embodiment 12.1

The compound according to claim 2, wherein
$R^2$ and $R^{2a}$ together are oxo.
$R^1$ is X—Y;
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
X is $C_1$-$C_6$ alkylene optionally substituted by hydroxy, halogens or $C_1$-$C_4$ alkyl;
Y is —C(O)OH, —C(O)$OR^x$, or —CONH—S(O)$_q$—$R^x$, wherein $R^x$ is —$C_1$-$C_4$ alkyl; and
q is 2.

Embodiment 13

The compound according to any of the preceding embodiment, wherein
$R^5$ is $C_6$-$C_{14}$ aryl; —($C_0$-$C_4$ alkyl)-4 to 14 membered heteroaryl, or —($C_0$-$C_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents; and
$R^6$ is $C_6$-$C_{14}$ aryl; —($C_0$-$C_4$ alkyl)-4 to 14 membered heteroaryl, —($C_0$-$C_4$ alkyl)-3 to 14 membered heterocyclyl wherein the heteroaryl and heterocyclyl contain at least one heteroatom selected from N, O and S, wherein the aryl, heteroaryl and heterocyclyl are each optionally substituted by one or more Z substituents.

Embodiment 14

The compound according to any of the preceding embodiment, wherein
$R^5$ is $C_6$-$C_{14}$ aryl; –5 to 6 membered heteroaryl, or -5 to 6 membered heterocyclyl wherein the heteroaryl and heterocyclyl contain at least one heteroatom selected from N, O and S, wherein the aryl, heteroaryl and heterocyclyl are each optionally substituted by one or more Z substituents; and
$R^6$ is $C_6$-$C_{14}$ aryl; –5 to 6 membered heteroaryl, -5 to 6 membered heterocyclyl wherein the heteroaryl and heterocyclyl contain at least one heteroatom selected from N, O and S, wherein the aryl, heteroaryl and heterocyclyl are each optionally substituted by one or more Z substituents.

Embodiment 15

The compound according to any of the preceding embodiment, wherein
$R^5$ is phenyl; 2-pyridyl, 3-pyridyl, or 4-pyridyl, and
$R^6$ is phenyl; 2-pyridyl, 3-pyridyl, or 4-pyridyl,
wherein the phenyl, 2-pyridyl, 3-pyridyl, and 4-pyridyl are each optionally substituted by one or more Z substituents.

Embodiment 16

The compound according to embodiments 1 to 14, wherein
$R^5$ is phenyl optionally substitued by OH, $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; $NR^{19}R^{21}$; $C(O)OR^{19}$; $C(O)R^{19}$; $SR^{19}$; $OR^{19}$; CN; $NO_2$; or halogen; and
$R^6$ is phenyl optionally substituted by OH, $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; $NR^{19}R^{21}$, $C(O)OR^{16}$, $C(O)R^{19}$, $SR^{19}$, $OR^{19}$, CN, $NO_2$, or halogen.

Embodiment 17

The compound according to embodiments 1 to 14 or 16, wherein
$R^5$ is phenyl optionally substituted by $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; or halogen; and $R^6$ is phenyl optionally substituted by $C_1$-$C_4$ alkyl optionally substituted by one or more OH groups or $NH_2$ groups; $C_1$-$C_4$ alkyl optionally substituted by one or more halogen atoms; $C_1$-$C_4$ alkoxy optionally substituted by one or more OH groups or $C_1$-$C_4$ alkoxy; or halogen.

Embodiment 18

The compound according to embodiments 1 to 14 or 16-17, wherein
$R^5$ is phenyl optionally substituted by $C_1$-$C_4$ alkoxy, halogen or $C_1$-$C_4$ alkyl optionally substituted by one or more halogen atoms; and
$R^6$ is phenyl optionally substituted by $C_1$-$C_4$ alkoxy, halogen or $C_1$-$C_4$ alkyl optionally substituted by one or more halogen atoms.

Embodiment 19

The compound according to embodiments 1 to 14 or 16-18, wherein
$R^5$ is phenyl optionally substituted by methyl, trifluoromethyl, methoxy or halogen; and
$R^6$ is phenyl optionally substituted by methyl, trifluoromethyl, methoxy or halogen.

Embodiment 20

The compound according to embodiments 1 to 13, wherein $R^5$ is

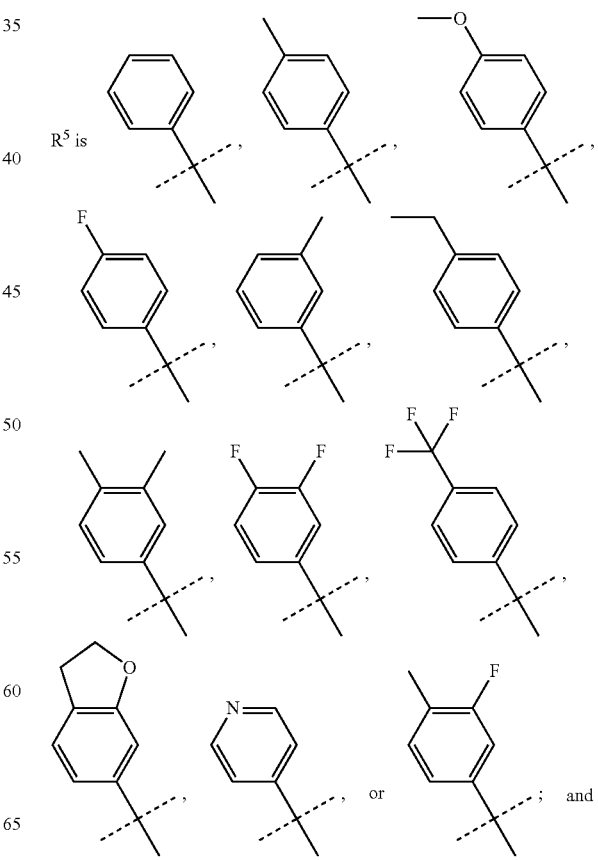

R⁶ is

[structures: various substituted phenyl and related aryl groups shown as R⁶ options]

Embodiment 21

The compound according to embodiment 1 or 2, represented by Formula IIa

[Structure IIa: bicyclic ring system with substituents $(Z)_p$, $R^4$, $R^3$, $R^{2a}$, $R^2$, $R^1$, and ring label A]

wherein, $R^1$ is H, $C_1$-$C_8$ alkyl optionally substituted by one or more halogen atoms, $C_1$-$C_4$ alkyl, OH, or OR'; or $R^1$ is —X—Y; or $R^1$ is —W—$R^7$—X—Y; or $R^1$ is —S(O)$_2$—X—Y or $R^2$ is —S(O)$_2$—W—$R^7$—X—Y;

$R^2$ is H, $C_1$-$C_8$ alkyl optionally substituted by one or more halogen atoms, $C_1$-$C_4$ alkyl, OH, OR', —NR$^{19}$R$^{21}$, CN or $C_3$-$C_7$ cycloalkyl; or $R^2$ is —X—Y; or
$R^2$ is —W—$R^7$—X—Y; or
$R^2$ is —S(O)$_2$—W—X—Y;
$R^2$ is —S(O)$_2$—W—$R^7$—X—Y;
wherein either $R^1$ or $R^2$ is —X—Y, —S(O)$_2$—W—X—Y; or —S(O)$_2$—W—$R^7$—X—Y;

$R^{2a}$ is hydrogen;
$R^2$ and $R^{2a}$ taken together are oxo;
wherein either $R^1$ or $R^2$ is —X—Y, —W—$R^7$—X—Y, —S(O)$_2$—W—X—Y; or —S(O)$_2$—W—$R^7$—X—Y;

$R^3$ is H, $C_1$-$C_4$ alkoxy, OH, —NR$^{19}$R$^{21}$, CN, halogen, $C_3$-$C_7$ cycloalkyl or $C_1$-$C_8$ alkyl optionally substituted by one or more halogen atoms;

$R^4$ is H, $C_1$-$C_4$ alkoxy, OH, —NR$^{19}$R$^{21}$, CN, halogen, $C_3$-$C_7$ cycloalkyl or $C_1$-$C_8$ alkyl optionally substituted by one or more halogen atoms;

W is $C_1$-$C_6$ alkylene optionally substituted by hydroxy, halogens or $C_1$-$C_4$ alkyl;

X is $C_1$-$C_6$ alkylene optionally substituted by hydroxy, halogens or $C_1$-$C_4$ alkyl;

Y is —C(O)OH, —C(O)OR$^x$, tetrazolyl, carbamoyl, monoalkylcarbamoyl, dialkylcarbamoyl, or —CONH—S(O)$_q$—R$^x$, wherein R$^x$ is —$C_1$-$C_4$ alkyl or —NR$^{19}$R$^{21}$;

p is 0, 1, 2, 3, or 4;
q is 2;
R' is H, $C_1$-$C_4$ alkyl optionally substituted by one or more halogen atoms;

$R^7$ is a divalent moiety represented by —O—, —NHC(O)—, —CH$_2$=CH$_2$—, —$C_6$-$C_{14}$ aryl-D-; -3 to 14 membered heterocyclyl-D-, wherein the heterocyclyl contains at least one heteroatom selected from N, O and S, wherein D is O, S, NH or not present; and $R^{19}$ and $R^{21}$ are each independently H; $C_1$-$C_8$ alkyl.

Embodiment 22

The compound according to embodiment 21, wherein
$R^1$ is —X—Y; or —W—$R^7$—X—Y;
$R^2$ is H, $C_1$-$C_8$ alkyl optionally substituted by one or more halogen atoms, $C_1$-$C_4$ alkyl, OH, oxo or OR';
$R^3$ is H, $C_1$-$C_4$ alkoxy, OH, —NR$^{19}$R$^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —NR$^{19}$R$^{21}$, CN, halogen, $C_3$-$C_7$ cycloalkyl or $C_1$-$C_4$ alkyl optionally substituted by one or more halogen atoms;
W is $C_1$-$C_6$ alkylene optionally substituted by hydroxy, halogens or $C_1$-$C_4$ alkyl;
X is $C_1$-$C_6$ alkylene optionally substituted by hydroxy, halogens or $C_1$-$C_4$ alkyl;
Y is —C(O)OH, —C(O)OR$^x$, tetrazolyl, carbamoyl, monoalkylcarbamoyl, dialkylcarbamoyl, or —CONH—S(O)$_q$—R$^x$, wherein R$^x$ is —$C_1$-$C_4$ alkyl or —NR$^{19}$R$^{21}$;
q is 2;
p is 0, 1, 2, 3, or 4;
R' is H, $C_1$-$C_4$ alkyl optionally substituted by one or more halogen atoms; and
$R^7$ is a divalent moiety represented by —O—, —NHC(O)—, —CH$_2$=CH$_2$—, —$C_6$-$C_{14}$ aryl-D-; -3 to 14 membered heterocyclyl-D-, wherein the heterocyclyl contains at least one heteroatom selected from N, O and S, wherein D is O, S, NH or not present.

Embodiment 23

The compound according to embodiment 21 or 22, wherein
$R^1$ is —X—Y; or —W—$R^7$—X—Y;
$R^2$ is H, $C_1$-$C_4$ alkyl optionally substituted by one or more halogen atoms;
$R^3$ is H, $C_1$-$C_4$ alkoxy, OH, —NR$^{19}$R$^{21}$, CN, halogen, $C_3$-$C_7$ cycloalkyl or $C_1$-$C_4$ alkyl optionally substituted by one or more halogen atoms;

151

R⁴ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;

W is $C_1$-$C_6$alkylene optionally substituted by hydroxy, halogens or $C_1$-$C_4$ alkyl;

X is $C_1$-$C_6$alkylene optionally substituted by hydroxy, halogens or $C_1$-$C_4$ alkyl;

Y is —C(O)OH;

p is 0, 1 or 2; and $R^7$ is a divalent moiety represented by —$C_6$-$C_{14}$ aryl-D-; −3 to 14 membered heterocyclyl-D-, wherein the heterocyclyl contains at least one heteroatom selected from N, O and S, wherein D is O.

Embodiment 24

The compound according to embodiment 21 to 23, wherein
$R^1$ is —$(CH_2)_m$—C(O)OR", or —$(CH_2)_m$—$R^7$—$(CH_2)_n$—C(O)OR";
$R^2$ is H, $C_1$-$C_4$ alkyl optionally substituted by one or more halogen atoms;
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
m is 1, 2, 3, 4, 5, 6, 7 or 8;
n is 0, 1, 2 or 3;
p is 0, 1 or 2;
R" is H or $C_1$-$C_4$ alkyl optionally substituted by one or more halogen atoms; and
$R^7$ is a divalent moiety represented by —$C_6$-$C_{14}$ aryl-D-; −3 to 14 membered heterocyclyl-D-, wherein the heterocyclyl contains at least one heteroatom selected from N, O and S, wherein D is O;

Embodiment 25

The compound according to embodiment 21 to 24, wherein
$R^1$ is —$(CH_2)_m$—C(O)OR", or —$(CH_2)_m$—$R^7$—$(CH_2)_n$—C(O)OR";
$R^2$ is H, $C_1$-$C_4$ alkyl optionally substituted by one or more halogen atoms;
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
m is 1, 2, 3, 4, 5, 6, 7 or 8;
n is 0, 1, 2 or 3;
p is 0, 1 or 2;
R" is H or $C_1$-$C_4$ alkyl optionally substituted by one or more halogen atoms; and
$R^7$ is a divalent moiety represented by -phenyl-D-; or -pyridyl-D-, wherein D is O.

Embodiment 26

The compound according to embodiment 21 to 25, wherein
$R^1$ is —$(CH_2)_m$—C(O)OR";
$R^2$ is H, $C_1$-$C_4$ alkyl optionally substituted by one or more halogen atoms;

152

$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
m is 1, 2, 3, 4, 5, 6, 7 or 8;
p is 0, 1 or 2; and
R" is H or $C_1$-$C_4$ alkyl optionally substituted by one or more halogen atoms.

Embodiment 27

The compound according to embodiment 21 to 26, wherein
$R^1$ is —$(CH_2)_m$—C(O)OR";
$R^2$ is H;
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
R" is H;
m is 4, 5 or 6; and
p is 0 or 1.

Embodiment 28

The compound according to embodiment 21 to 27, wherein $R^1$ is

-continued

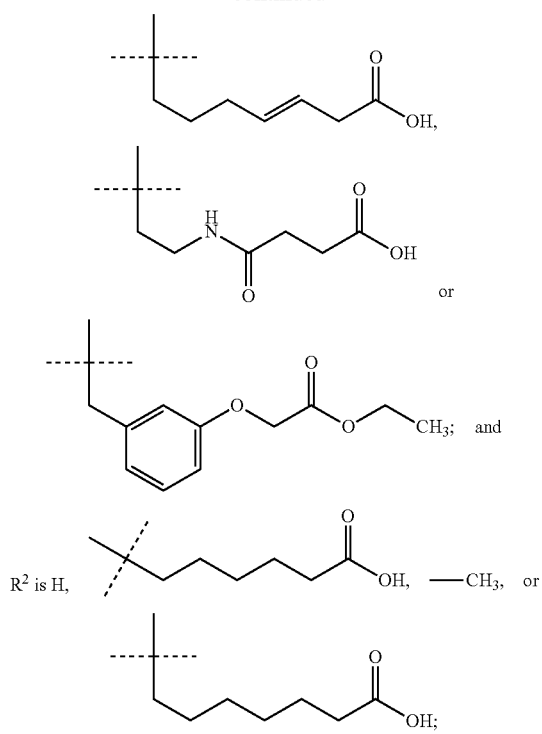

R'' is H;
m is 4, 5 or 6; and
p is 0 or 1.

Embodiment 29

The compound according to embodiment 21 to 27, wherein

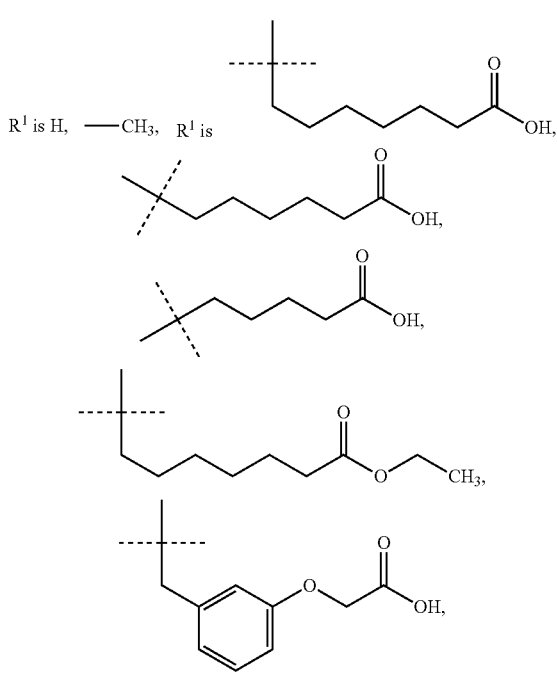

-continued

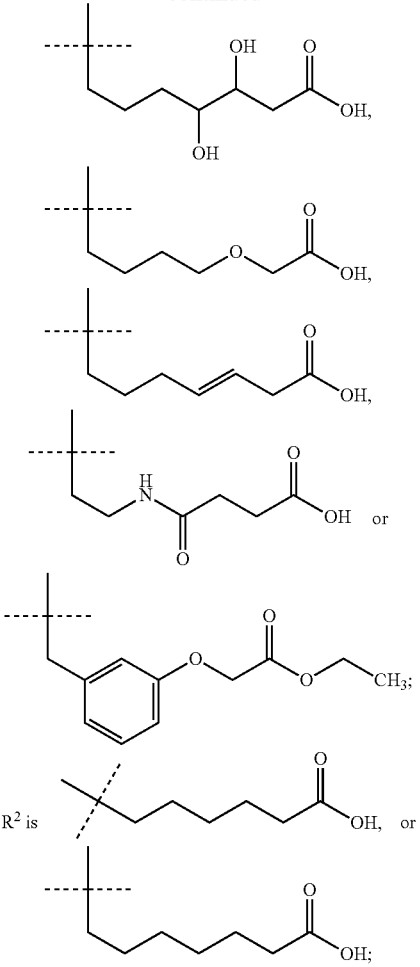

R'' is H;
m is 4, 5 or 6; and
p is 0 or 1.

Embodiment 29.1

The compound according to claim 21, wherein
$R^2$ and $R^{2a}$ together are oxo.
$R^1$ is X—Y;
$R^3$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
$R^4$ is H, $C_1$-$C_4$ alkoxy, OH, —$NR^{19}R^{21}$, CN, halogen, $C_3$-$C_7$ cycloalkyl or $C_1$-$C_4$ alkyl optionally substituted by one or more halogen atoms;
X is $C_1$-$C_6$ alkylene optionally substituted by hydroxy, halogens or $C_1$-$C_4$ alkyl;
Y is —C(O)OH, or —CONH—S(O)$_q$—$R^x$, wherein $R^x$ is —$C_1$-$C_4$ alkyl; and
q is 2.

Embodiment 29

The compound according to any proceeding embodiment, wherein $R^3$ and $R^4$ are independently H, OH, $C_1$-$C_4$ alkyl, $C_1$-$C_4$ alkoxy, $C_3$-$C_6$ cycloalkyl, cyano or halogen.

Embodiment 30

The compound according to any proceeding embodiment, wherein
$R^3$ and $R^4$ are independently H, OH, $C_1$-$C_4$ alkyl, $C_1$-$C_4$ alkoxy, $C_3$-$C_5$ cycloalkyl, or halogen.

Embodiment 31

The compound according to any proceeding embodiment, wherein
$R^3$ and $R^4$ are independently H, OH, methyl, ethyl, isopropyl, tert-butyl, methoxy, ethoxy, propoxy, butoxy, cyclopropyl, fluorine, bromine or chlorine.

Embodiment 32

The compound according to any proceeding embodiment, wherein
Z is independently OH, $C_6$-aryl, O—$C_6$-aryl, benzyl, O-benzyl, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $NR^{18}(SO_2)R^{21}$, $(SO_2)NR^{19}R^{21}$, $(SO_2)R^{21}$, $NR^{18}C(O)R^{21}$, $C(O)NR^{19}R^{21}$, $NR^{18}C(O)NR^{19}R^{21}$, $NR^{18}C(O)OR^{19}$, $NR^{19}R^{21}$, $C(O)OR^{19}$, $C(O)R^{19}$, $SR^{19}$, $OR^{19}$, oxo, CN, $NO_2$, halogen or a 4 to 6 membered heterocyclyl, wherein the heterocyclyl contains at least one heteroatom selected from N, O and S;
$R^{18}$ is H or $C_1$-$C_4$ alkyl;
$R^{19}$ and $R^{21}$ are each independently H; $C_1$-$C_4$ alkyl; $C_3$-$C_6$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_4$ alkyl, $C_1$-$C_4$ alkoxy and halogen; ($C_0$-$C_4$ alkyl)-4- to 6-membered heterocyclyl, the heterocyclyl including one or more heteroatoms selected from N, O and S, optionally substituted by one or more groups selected from halogen, oxo, $C_1$-$C_4$ alkyl and $C(O)C_1$-$C_4$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclyl, the heterocyclyl including one or more heteroatoms selected from N, O and S, optionally substituted by one or more groups selected from halogen, $C_1$-$C_6$ alkyl or $C(O)C_1$-$C_6$ alkyl; wherein the alkyl groups are optionally substituted by one or more halogen atoms, $C_1$-$C_4$ alkoxy, $C(O)NH_2$, $C(O)NHC_1$-$C_6$ alkyl or $C(O)N(C_1$-$C_6$ alkyl)$_2$; or
$R^{19}$ and $R^{21}$ together with the nitrogen atom to which they attached form a 5- to 6-membered heterocyclyl, the heterocyclyl including one or more further heteroatoms selected from N, O and S, the heterocyclyl being optionally substituted by one or more substituents selected from OH; halogen; aryl; 5- to 6-membered heterocyclyl including one or more heteroatoms selected from N, O and S; $S(O)_2$-aryl; $S(O)_2$—$C_1$-$C_6$ alkyl; $C_1$-$C_6$ alkyl optionally substituted by one or more halogen atoms; $C_1$-$C_4$ alkoxy optionally substituted by one or more OH groups or $C_1$-$C_4$ alkoxy; and $C(O)OC_1$-$C_6$ alkyl, wherein the aryl and heterocyclyl substituent groups are themselves optionally substituted by $C_1$-$C_6$ alkyl, $C_1$-$C_6$ haloalkyl or $C_1$-$C_6$ alkoxy.

Embodiment 33

The compound according to any proceeding embodiment, wherein
Z is independently OH, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $NR^{19}R^{21}$, $C(O)OR^{19}$, $C(O)R^{19}$, $SR^{19}$, $OR^{19}$, CN, $NO_2$, or halogen;
$R^{19}$ and $R^{21}$ are each independently H; $C_1$-$C_4$ alkyl; $C_3$-$C_6$ cycloalkyl; or $C_1$-$C_4$ alkoxy-$C_1$-$C_4$ alkyl, wherein all alkyls are optionally substituted with halogens.

Embodiment 34

The compound according to any proceeding embodiment, wherein
Z is independently OH, $C_1$-$C_4$ alkyl optionally substituted by one or more OH groups or $NH_2$ groups, $C_1$-$C_4$ alkyl optionally substituted by one or more halogen atoms, $C_1$-$C_4$ alkoxy optionally substituted by one or more OH groups or $C_1$-$C_4$ alkoxy, $C(O)OR^{19}$, $C(O)R^{19}$, $OR^{19}$, CN, or halogen;
$R^{19}$ is H; $C_1$-$C_4$ alkyl; $C_3$-$C_6$ cycloalkyl; or $C_1$-$C_4$ alkoxy-$C_1$-$C_4$ alkyl, wherein all alkyl are optionally substituted with halogens.

Embodiment 35

The compound according to any proceeding embodiment, wherein
Z is independently, $C_1$-$C_4$ alkyl optionally substituted by one or more halogen atoms, $C_1$-$C_4$ alkoxy or halogen;

Embodiment 36

The compound according to any proceeding embodiment, wherein A is N.

Embodiment 37

The compound according to embodiment 1 to 35, wherein A is CR'.

Embodiment 38

The compound according to embodiment 37, wherein R' is H.

Embodiment 39

The compound according to embodiment 2 to 38, wherein formula Ia has the following stereochemistry:

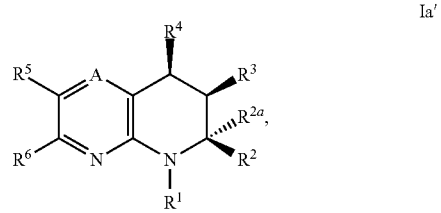

Ia'

-continued

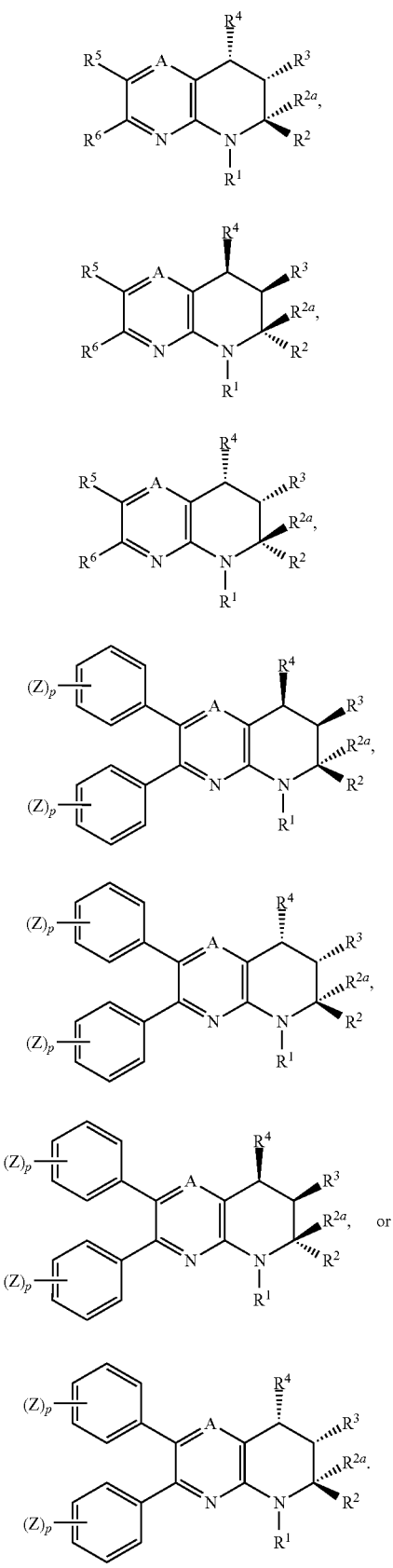

Embodiment 40

The compound according to embodiment 2, the compound is 7-(6,7-Diphenyl-3,4-dihydro-1,8-naphthyridin-1(2H)-yl) heptanoic acid;

Ethyl 7-(6,7-diphenyl-3,4-dihydro-1,8-naphthyridin-1(2H)-yl)heptanoate;

2-(3-((6,7-Diphenyl-3,4-dihydro-1,8-naphthyridin-1 (2H)-yl)methyl)phenoxy)acetic acid;

Ethyl 2-(3-((6,7-diphenyl-3,4-dihydro-1,8-naphthyridin-1 (2H)-yl)methyl)phenoxy)acetate;

6-(6,7-Diphenyl-3,4-dihydro-1,8-naphthyridin-1(2H)-yl) hexanoic acid;

Enantiomer 1 of 6-(1-Methyl-6,7-diphenyl-1,2,3,4-tetrahydro-1,8-naphthyridin-2-yl)hexanoic acid;

Enantiomer 2 of 6-(1-Methyl-6,7-diphenyl-1,2,3,4-tetrahydro-1,8-naphthyridin-2-yl)hexanoic acid;

Enantiomer 1 of 7-(1-Methyl-6,7-diphenyl-1,2,3,4-tetrahydro-[1,8]naphthyridin-2-yl)-heptanoic acid;

Enantiomer 2 of 7-(1-Methyl-6,7-diphenyl-1,2,3,4-tetrahydro-[1,8]naphthyridin-2-yl)-heptanoic acid;

rac-6-(1-Methyl-6,7-diphenyl-1,2,3,4-tetrahydro-[1,8]naphthyridin-2-yl)-hexanoic acid;

Enantiomer 1 of 7-(2-methyl-6,7-diphenyl-3,4-dihydro-1,8-naphthyridin-1(2H)-yl)heptanoic acid;

Enantiomer 2 of 7-(2-methyl-6,7-diphenyl-3,4-dihydro-1,8-naphthyridin-1(2H)-yl)heptanoic acid;

7-(2,3-diphenyl-7,8-dihydropyrido[3,2-b]pyrazin-5(6H)-yl) heptanoic acid;

7-(2,3-bis(4-fluorophenyl)-7,8-dihydropyrido[2,3-b]pyrazin-5(6H)-yl)heptanoic acid;

7-(2,3-dip-tolyl-7,8-dihydropyrido[2,3-b]pyrazin-5(6H)-yl) heptanoic acid;

7-(2,3-bis(4-methoxyphenyl)-7,8-dihydropyrido[2,3-b] pyrazin-5(6H)-yl)heptanoic acid;

rac-7-(7-methyl-2,3-diphenyl-7,8-dihydropyrido[2,3-b] pyrazin-5(6H)-yl)heptanoic acid;

Enantiomer 1 of 7-(7-methyl-2,3-diphenyl-7,8-dihydropyrido[2,3-b]pyrazin-5(6H)-yl)heptanoic acid;

Enantiomer 2 of 7-(7-methyl-2,3-diphenyl-7,8-dihydropyrido[2,3-b]pyrazin-5(6H)-yl)heptanoic acid;

rac-7-(6-Methyl-2,3-diphenyl-7,8-dihydropyrido[2,3-b] pyrazin-5(6H)-yl)heptanoic acid;

rac-7-(2,3-bis(4-fluorophenyl)-7-methyl-7,8-dihydropyrido [2,3-b]pyrazin-5(6H)-yl)heptanoic acid;

rac-7-(2,3-bis(4-fluorophenyl)-6-methyl-7,8-dihydropyrido [2,3-b]pyrazin-5(6H)-yl)heptanoic acid;

7-(2,3-bis(4-(trifluoromethyl)phenyl)-7,8-dihydropyrido[2, 3-b]pyrazin-5(6H)-yl) heptanoic acid;

Enantiomer 1 of 7-(6-methyl-2,3-dip-tolyl-7,8-dihydropyrido[2,3-b]pyrazin-5(6H)-yl)heptanoic acid;

Enantiomer 2 of 7-(6-methyl-2,3-dip-tolyl-7,8-dihydropyrido[2,3-b]pyrazin-5(6H)-yl)heptanoic acid;

6-(2,3-Diphenyl-7,8-dihydropyrido[3,2-b]pyrazin-5(6H)-yl) hexanoic acid;

5-(2,3-Diphenyl-7,8-dihydropyrido[3,2-b]pyrazin-5(6H)-yl) pentanoic acid;

7-(3-Phenyl-2-p-tolyl-7,8-dihydropyrido[2,3-b]pyrazin-5 (6H)-yl)heptanoic acid;

7-(2-Phenyl-3-p-tolyl-7,8-dihydropyrido[2,3-b]pyrazin-5 (6H)-yl)heptanoic acid;

7-(2-m-Tolyl-3-p-tolyl-7,8-dihydropyrido[2,3-b]pyrazin-5 (6H)-yl)heptanoic acid;

7-(2-phenyl-3-o-tolyl-7,8-dihydropyrido[2,3-b]pyrazin-5 (6H)-yl)heptanoic acid;

7-(2-(2,3-dihydrobenzofuran-7-yl)-3-p-tolyl-7,8-dihydropyrido[2,3-b]pyrazin-5(6H)-yl)heptanoic acid;

7-(3-(4-ethylphenyl)-2-phenyl-7,8-dihydropyrido[2,3-b]
pyrazin-5(6H)-yl)heptanoic acid;
ethyl 7-(3-m-tolyl-2-p-tolyl-7,8-dihydropyrido[2,3-b]
pyrazin-5(6H)-yl)heptanoate;
7-(3-m-tolyl-2-p-tolyl-7,8-dihydropyrido[2,3-b]pyrazin-5
(6H)-yl)heptanoic acid;
7-(2-(4-ethylphenyl)-3-phenyl-7,8-dihydropyrido[2,3-b]
pyrazin-5(6H)-yl)heptanoic acid;
7-(2,3-bis(3-Fluoro-4-methylphenyl)-7,8-dihydropyrido[2,
3-b]pyrazin-5(6H)-yl)heptanoic acid;
7-(2,3-dim-tolyl-7,8-dihydropyrido[2,3-b]pyrazin-5(6H)-yl)
heptanoic acid;
7-(2,3-bis(4-ethylphenyl)-7,8-dihydropyrido[2,3-b]pyrazin-
5(6H)-yl)heptanoic acid;
7-(2,3-bis(3,4-dimethylphenyl)-7,8-dihydropyrido[2,3-b]
pyrazin-5(6H)-yl)heptanoic acid;
ethyl 7-(2,3-bis(3,4-difluorophenyl)-7,8-dihydropyrido[2,3-
b]pyrazin-5(6H)-yl)heptanoate;
7-(2,3-bis(3,4-difluorophenyl)-7,8-dihydropyrido[2,3-b]
pyrazin-5(6H)-yl)heptanoic acid;
7-(2,3-bis(4-fluoro-3-methylphenyl)-7,8-dihydropyrido[2,
3-b]pyrazin-5(6H)-yl)heptanoic acid;
rac-7-(8-Ethyl-2,3-diphenyl-7,8-dihydropyrido[2,3-b]
pyrazin-5(6H)-yl)heptanoic acid;
rac-7-(8-Methyl-2,3-diphenyl-7,8-dihydro pyrido[2,3-b]
pyrazin-5(6H)-yl)heptanoic acid;
rac-7-(8-Isopropyl-2,3-diphenyl-7,8-dihydro pyrido[2,3-b]
pyrazin-5(6H)-yl)heptanoic acid;
rac-7-(8-Cyclopropyl-2,3-diphenyl-7,8-dihydro pyrido[2,3-
b]pyrazin-5(6H)-yl)heptanoic acid;
Enantiomer 1 of 7-(8-Cyclopropyl-2,3-diphenyl-7,8-dihydro
pyrido[2,3-b]pyrazin-5(6H)-yl)heptanoic acid;
Enantiomer 2 of 7-(8-Cyclopropyl-2,3-diphenyl-7,8-dihydro
pyrido[2,3-b]pyrazin-5(6H)-yl)heptanoic acid;
rac-7-(8-(dimethylamino)-2,3-diphenyl-7,8-dihydropyrido
[2,3-b]pyrazin-5(6H)-yl)heptanoic acid;
Isomer 1 of 7-(7,8-dihydroxy-2,3-diphenyl-7,8-dihydropy-
rido[2,3-b]pyrazin-5(6H)-yl)heptanoic acid;
Isomer 2 of 7-(7,8-dihydroxy-2,3-diphenyl-7,8-dihydropy-
rido[2,3-b]pyrazin-5(6H)-yl)heptanoic acid;
Isomer 1 7-(7,8-dihydroxy-2,3-dip-tolyl-7,8-dihydropyrido
[2,3-b]pyrazin-5(6H)-yl)heptanoic acid;
Isomer 2 of 7-(7,8-dihydroxy-2,3-dip-tolyl-7,8-dihydropy-
rido[2,3-b]pyrazin-5(6H)-yl)heptanoic acid;
(R)-7-(8-Hydroxy-2,3-diphenyl-7,8-dihydropyrido[2,3-b]
pyrazin-5(6H)-yl)heptanoic acid;
(S)-7-(8-Hydroxy-2,3-diphenyl-7,8-dihydropyrido[2,3-b]
pyrazin-5(6H)-yl)heptanoic acid;
rac-7-(8-Hydroxy-2,3-dip-tolyl-7,8-dihydropyrido[2,3-b]
pyrazin-5(6H)-yl)heptanoic acid;
rac-7-(8-Methoxy-2,3-diphenyl-7,8-dihydropyrido[2,3-b]
pyrazin-5(6H)-yl)heptanoic acid;
Enantiomer 1 of 7-(8-Methoxy-2,3-diphenyl-7,8-dihydropy-
rido[2,3-b]pyrazin-5(6H)-yl)heptanoic acid;
Enantiomer 2 of 7-(8-methoxy-2,3-diphenyl-7,8-dihydropy-
rido[2,3-b]pyrazin-5(6H)-yl)heptanoic;
rac-7-(8-hydroxy-2,3-diphenyl-7,8-dihydropyrido[2,3-b]
pyrazin-5(6H)-yl)heptanoic acid;
rac-7-(8-hydroxy-2,3-bis(4-(trifluoromethyl)phenyl)-7,8-di-
hydropyrido[2,3-b]pyrazin-5(6H)-yl)heptanoic acid;
(E)-7-(2,3-Diphenyl-7,8-dihydropyrido[3,2-b]pyrazin-5
(6H)-yl)hept-3-enoic acid;
8-(2,3-Dip-tolyl-7,8-dihydropyrido[2,3-b]pyrazin-5(6H)-yl)
octanoic acid;
2-(4-(2,3-Diphenyl-7,8-dihydropyrido[2,3-b]pyrazin-5
(6H)-yl)butoxy)acetic acid;
2-(3-((2,3-Diphenyl-7,8-dihydropyrido[3,2-b]pyrazin-5
(6H)-yl)methyl)phenoxy)acetic acid;
4-(2-(2,3-Dip-tolyl-7,8-dihydropyrido[2,3-b]pyrazin-5(6H)-
yl)ethylamino)-4-oxobutanoic acid;
7-(6-oxo-2,3-dip-tolyl-7,8-dihydropyrido[2,3-b]pyrazin-5
(6H)-yl)heptanoic acid;
7-(2-(Pyridin-4-yl)-3-p-tolyl-7,8-dihydropyrido[2,3-b]
pyrazin-5(6H)-yl)heptanoic acid;
7-(3-(Pyridin-4-yl)-2-p-tolyl-7,8-dihydropyrido[2,3-b]
pyrazin-5(6H)-yl)heptanoic acid;
Enantiomer 1 of 7-(7-hydroxy-2,3-dip-tolyl-7,8-dihydropy-
rido[2,3-b]pyrazin-5(6H)-yl)heptanoic acid;
Enantiomer 2 of 7-(7-hydroxy-2,3-dip-tolyl-7,8-dihydropy-
rido[2,3-b]pyrazin-5(6H)-yl)heptanoic acid;
rac-7-(2,3-Dip-tolyl-7,8-dihydropyrido[2,3-b]pyrazin-5
(6H)-yl)-3,4-dihydroxyheptanoic acid;
7-(7-Hydroxy-6-oxo-2,3-dip-tolyl-7,8-dihydropyrido[2,3-b]
pyrazin-5(6H)-yl)heptanoic acid; Enantiomer 1 of 7-(8-
Hydroxy-2,3-dip-tolyl-7,8-dihydropyrido[2,3-b]pyrazin-
5(6H)-yl)heptanoic acid;
Enantiomer 2 of 7-(8-Hydroxy-2,3-dip-tolyl-7,8-dihydropy-
rido[2,3-b]pyrazin-5(6H)-yl)heptanoic acid;
Enantiomer 1 of 7-(7-Methoxy-2,3-dip-tolyl-7,8-dihydropy-
rido[2,3-b]pyrazin-5(6H)-yl)heptanoic acid; and
Enantiomer 2 of 7-(7-Methoxy-2,3-dip-tolyl-7,8-dihydropy-
rido[2,3-b]pyrazin-5(6H)-yl)heptanoic acid.

Embodiment 41

The compound according to embodiments 1 to 38 represented by the name:
7-(2,3-diphenyl-7,8-dihydropyrido[3,2-b]pyrazin-5(6H)-yl)
heptanoic acid;
7-(2,3-bis(4-fluorophenyl)-7,8-dihydropyrido[2,3-b]
pyrazin-5(6H)-yl)heptanoic acid;
7-(2,3-di-p-tolyl-7,8-dihydropyrido[2,3-b]pyrazin-5(6H)-
yl)heptanoic acid;
7-(2,3-bis(4-methoxyphenyl)-7,8-dihydropyrido[2,3-b]
pyrazin-5(6H)-yl)heptanoic acid;
6-(2,3-diphenyl-7,8-dihydropyrido[3,2-b]pyrazin-5(6H)-yl)
hexanoic acid;
5-(2,3-diphenyl-7,8-dihydropyrido[3,2-b]pyrazin-5(6H)-yl)
pentanoic acid;
7-(6,7-diphenyl-3,4-dihydro-1,8-naphthyridin-1(2H)-yl)
heptanoic acid;
Ethyl 7-(6,7-diphenyl-3,4-dihydro-1,8-naphthyridin-1(2H)-
yl)heptanoate;
rac-6-(1-methyl-6,7-diphenyl-1,2,3,4-tetrahydro-1,8-naph-
thyridin-2-yl)hexanoic acid;
Enantiomer 1 of 7-(2-methyl-6,7-diphenyl-3,4-dihydro-1,8-
naphthyridin-1(2H)-yl)heptanoic acid;
Enantiomer 2 of 7-(1-methyl-6,7-diphenyl-1,2,3,4-tetrahy-
dro-1,8-naphthyridin-2-yl)heptanoic acid;
2-(3-((6,7-diphenyl-3,4-dihydro-1,8-naphthyridin-1(2H)-yl)
methyl)phenoxy)acetic acid;
Ethyl 2-(3-((6,7-diphenyl-3,4-dihydro-1,8-naphthyridin-1
(2H)-yl)methyl)phenoxy)acetate;
Enantiomer 2 of 7-(2-methyl-6,7-diphenyl-3,4-dihydro-1,8-
naphthyridin-1(2H)-yl)heptanoic acid;
Enantiomer 1 of 6-(1-methyl-6,7-diphenyl-1,2,3,4-tetrahy-
dro-1,8-naphthyridin-2-yl)hexanoic acid;
Enantiomer 2 of 6-(1-methyl-6,7-diphenyl-1,2,3,4-tetrahy-
dro-1,8-naphthyridin-2-yl)hexanoic acid;
6-(6,7-diphenyl-3,4-dihydro-1,8-naphthyridin-1(2H)-yl)
hexanoic acid; and Enantiomer 1 of 7-(1-methyl-6,7-diphenyl-1,2,3,4-tetrahydro-1,8-naphthyridin-2-yl)heptanoic acid Embodiment 42

The compound according to any one of embodiments 1 to 41, or a pharmaceutically acceptable salt thereof, for use as a medicament for the treatment of a disorder or disease in a subject mediated by activating IP receptor.

Embodiment 43

Use of a compound according to any one of embodiments 1 to 41, or a pharmaceutically acceptable salt thereof for the treatment of a disorder or disease in a subject by activating the IP receptor.

Embodiment 44

The use according to embodiment 43, wherein the disease or disorder is PAH, disorders in need of antiplatlet therapy, atherosclerosis, asthma, COPD, hyperglycemia, inflammatory disease, or fibrotic diseases.

Embodiment 45

The use according to embodiment 43, wherein the disease or disorder is PAH, atherosclerosis, asthma, COPD, hyperglycemia, or fibrotic diseases.

Embodiment 46

The use according to embodiment 43, wherein the disease or disorder is PAH, asthma, COPD, or cystic fibrosis.

Embodiment 47

The use according to embodiment 43, wherein the disease or disorder is PAH or COPD.

Embodiment 48

The use according to embodiment 43, wherein the disease or disorder is PAH or COPD.

Embodiment 49

The use according to embodiment 43, wherein the disease or disorder is PAH.

We claim:
1. A compound, or a pharmaceutically acceptable salt thereof, selected from the group consisting of:
   7-(2,3-diphenyl-7,8-dihydropyrido[3,2-b]pyrazin-5(6H)-yl)heptanoic acid;
   7-(2,3-bis(4-fluorophenyl)-7,8-dihydropyrido[2,3-b]pyrazin-5(6H)-yl)heptanoic acid;
   7-(2,3-di-p-tolyl-7,8-dihydropyrido[2,3-b]pyrazin-5(6H)-yl)heptanoic acid;
   7-(2,3-bis(4-methoxyphenyl)-7,8-dihydropyrido[2,3-b]pyrazin-5(6H)-yl)heptanoic acid;
   6-(2,3-diphenyl-7,8-dihydropyrido[3,2-b]pyrazin-5(6H)-yl)hexanoic acid; and
   5-(2,3-diphenyl-7,8-dihydropyrido[3,2-b]pyrazin-5(6H)-yl)pentanoic acid.
2. A compound, or a pharmaceutically acceptable salt thereof represented by

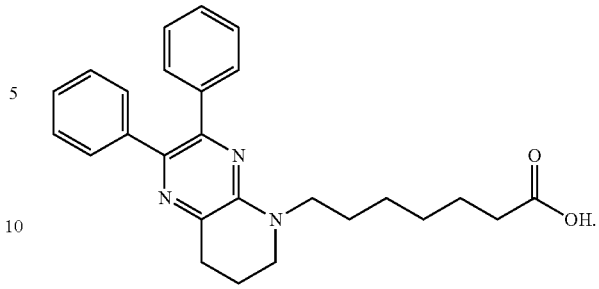

3. A compound, or a pharmaceutically acceptable salt thereof represented by

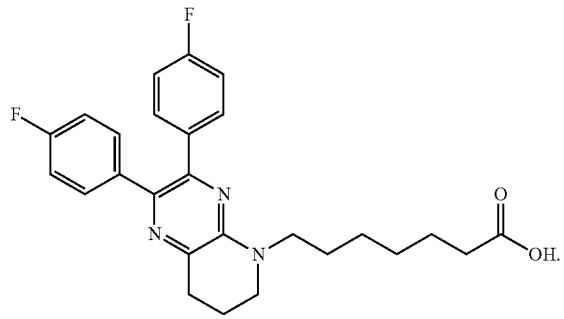 [SMILES: O=C(O)CCCCCCN1CCCc2nc(-c3ccc(F)cc3)c(-c3ccc(F)cc3)nc21]

4. A compound, or a pharmaceutically acceptable salt thereof represented by

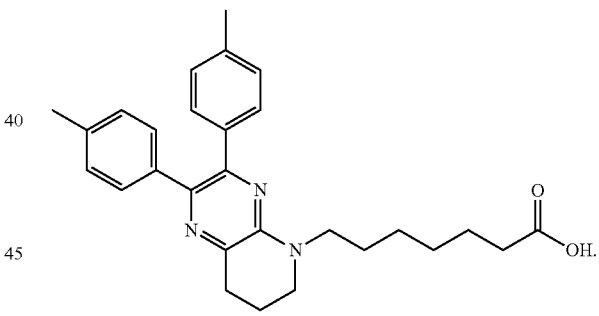

5. A compound, or a pharmaceutically acceptable salt thereof represented by

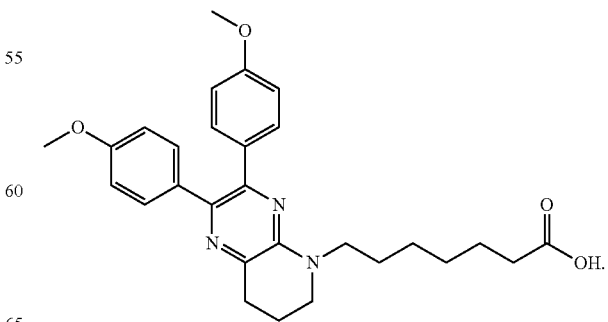

6. A compound, or a pharmaceutically acceptable salt thereof represented by

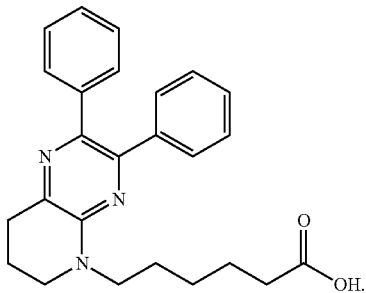 [SMILES: O=C(O)CCCCCN1CCCc2nc(-c3ccccc3)c(-c3ccccc3)nc21]

7. A compound, or a pharmaceutically acceptable salt thereof represented by

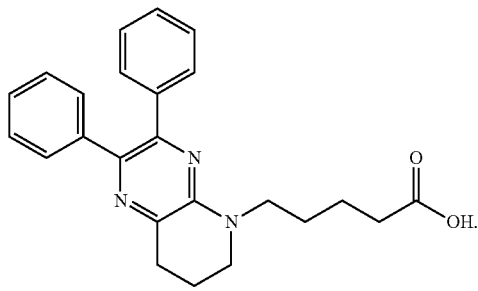 [SMILES: O=C(O)CCCCN1CCCc2nc(-c3ccccc3)c(-c3ccccc3)nc21]

8. The compound according to any one of claims 2 to 7 wherein the pharmaceutically acceptable salt is mesylate.

9. A pharmaceutical composition, comprising:
a therapeutically effective amount of the compound according to claim 2, or a pharmaceutically acceptable salt thereof, and
one or more pharmaceutically acceptable carriers.

10. A pharmaceutical composition, comprising:
a therapeutically effective amount of the compound according to claim 3, or a pharmaceutically acceptable salt thereof, and
one or more pharmaceutically acceptable carriers.

11. A pharmaceutical composition, comprising:
a therapeutically effective amount of the compound according to claim 4, or a pharmaceutically acceptable salt thereof, and
one or more pharmaceutically acceptable carriers.

12. A pharmaceutical composition, comprising:
a therapeutically effective amount of the compound according to claim 5, or a pharmaceutically acceptable salt thereof, and
one or more pharmaceutically acceptable carriers.

13. A pharmaceutical composition, comprising:
a therapeutically effective amount of the compound according to claim 6, or a pharmaceutically acceptable salt thereof, and
one or more pharmaceutically acceptable carriers.

14. A pharmaceutical composition, comprising:
a therapeutically effective amount of the compound according to claim 7, or a pharmaceutically acceptable salt thereof, and
one or more pharmaceutically acceptable carriers.

* * * * *